United States Patent
Bull et al.

(10) Patent No.: US 10,455,783 B2
(45) Date of Patent: Oct. 29, 2019

(54) COMPOSITIONS AND METHODS OF PLANT BREEDING USING HIGH DENSITY MARKER INFORMATION

(75) Inventors: Jason Bull, Wildwood, MO (US); David Butruille, Urbandale, IA (US); Sam Eathington, Ames, IA (US); Marlin Edwards, Woodland, CA (US); Anju Gupta, Ankeny, IA (US); G. Richard Johnson, Urbana, IL (US); Robert Stefan Reiter, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 312 days.

(21) Appl. No.: 13/440,713

(22) Filed: Apr. 5, 2012

(65) Prior Publication Data

US 2013/0276173 A1    Oct. 17, 2013

Related U.S. Application Data

(63) Continuation of application No. 12/376,998, filed as application No. PCT/US2007/018101 on Aug. 15, 2007, now abandoned.

(60) Provisional application No. 60/837,864, filed on Aug. 15, 2006.

(51) Int. Cl.
*A01H 5/10* (2018.01)
*C12Q 1/6895* (2018.01)
*A01H 1/04* (2006.01)

(52) U.S. Cl.
CPC ............ *A01H 1/04* (2013.01); *A01H 5/10* (2013.01); *C12Q 1/6895* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,757,011 A | 7/1988 | Chaleff et al. | |
| 4,769,061 A | 9/1988 | Comai | |
| 4,940,835 A | 7/1990 | Shah et al. | |
| 4,971,908 A | 11/1990 | Kishore et al. | |
| 5,015,580 A * | 5/1991 | Christou | C12N 15/8207 435/317.1 |
| 5,304,719 A | 4/1994 | Segebart | |
| 5,384,253 A | 1/1995 | Krzyzek et al. | |
| 5,437,697 A | 8/1995 | Sebastian et al. | |
| 5,492,547 A | 2/1996 | Johnson | |
| 5,508,184 A | 4/1996 | Negrutiu et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,635,055 A | 6/1997 | Sweet et al. | |
| 5,639,944 A * | 6/1997 | Tinius | 800/312 |
| 5,824,877 A | 10/1998 | Hinchee | |
| 5,981,832 A | 11/1999 | Johnson | |
| 5,981,840 A | 11/1999 | Zhao | |
| 6,160,208 A | 12/2000 | Lundquist | |
| 6,162,971 A * | 12/2000 | Matson | 800/312 |
| 6,207,367 B1 | 3/2001 | Helentjaris et al. | |
| 6,219,964 B1 | 4/2001 | Byrum et al. | |
| 6,225,534 B1 * | 5/2001 | Lussenden | 800/312 |
| 6,384,301 B1 | 5/2002 | Martinell et al. | |
| 6,399,855 B1 | 6/2002 | Beavis | |
| 6,399,861 B1 | 6/2002 | Anderson | |
| 6,403,865 B1 | 6/2002 | Koziel et al. | |
| 6,452,071 B1 * | 9/2002 | Lussenden | 800/312 |
| 6,455,758 B1 | 9/2002 | Johnson | |
| 6,844,154 B2 | 1/2005 | Landers | |
| 6,909,971 B2 | 6/2005 | Toivonen et al. | |
| 6,920,398 B2 | 7/2005 | Liu et al. | |
| 6,931,326 B1 | 8/2005 | Judson et al. | |
| 6,969,589 B2 | 11/2005 | Patil et al. | |
| 7,041,447 B2 | 5/2006 | Evans et al. | |
| 2005/0015827 A1 | 1/2005 | Podlich et al. | |
| 2006/0135758 A1 | 6/2006 | Wu | |
| 2006/0141495 A1 | 6/2006 | Wu | |
| 2006/0200878 A1 | 9/2006 | Lutfiyya et al. | |
| 2007/0011775 A1 | 1/2007 | Allen et al. | |
| 2008/0083042 A1 | 4/2008 | Butruille et al. | |

FOREIGN PATENT DOCUMENTS

| | | |
|---|---|---|
| WO | WO 90/04651 A1 | 5/1990 |
| WO | 99/32661 A | 7/1999 |
| WO | 00/18963 A | 4/2000 |

(Continued)

OTHER PUBLICATIONS

Morgante et al (2003) Current Opinion in Biotechnology 14: 214-219.*
Kuroda et al (2006) Molec. Ecology 15: 959-974.*
Funke et al., 1993, Plant Molecular Biology 22: 437-446.*
King et al., 2013, Transgenic Breeding, In: Plant Breeding in the 21st Century.*
Hyten et al., 2007, Genetics 175: 1937-1944.*
Haun et al., 2011, Plant Physiology 155: 645-655.*
GenBank sequence with accession No. XM_006582273.2, published Nov. 25, 2015.*
GenBank sequence with accession No. XM_003527420.3, published Nov. 25, 2015.*
Wijnker and Jong, 2008, Trends in Plant Science 13: 640-646.*
Buntjer et al., "Haplotype diversity: the link between statistical and biological association," *Trends in Plant Science* 10(10):466-471 (2005).

(Continued)

*Primary Examiner* — Bratislav Stankovic
(74) *Attorney, Agent, or Firm* — Arnold & Porter Kaye Scholer; Jamie Davis

(57) ABSTRACT

The present invention relates to breeding methods to enhance the germplasm of a plant. The methods describe the identification and accumulation of preferred haplotype genomic regions in the germplasm of breeding populations of maize (*Zea mays*) and soybean (*Glycine max*). The invention also relates to maize and soybean plants comprising preferred haplotypes.

12 Claims, 5 Drawing Sheets

Specification includes a Sequence Listing.

(56) References Cited

FOREIGN PATENT DOCUMENTS

WO 00/63432 A 10/2000
WO 01/49104 A 7/2001

OTHER PUBLICATIONS

International Search report dated Dec. 21, 2007 in PCT/US2007/018101.
Peleman et al., "Breeding by Design," *Trends in Plant Science* 8(7):330-334 (2003).
Rafaiski, "Applications of single nucleotide polymorphisms in crop genetics," *Current Opinion in Plant Biology* 5(2):94-100 (2002).
Tost et al., "Molecular haplotyping at high throughput," *Nucleic Acids Research* 30(19):e96-1 (2002).
Griffiths et al., Introduction to Genetic Analysis, pp. 117-118 (2005).
Griffiths et al., Introduction to Genetic Analysis, pp. 124-126 (2005).
Lu et al., "Genetics of cyst nematode resistance in soybean PIs 467312 and 507354,".
Potter et al., "Plant Gene Transfer," Genetic Engineering: Methodology and Analysis, Plant Molecular Biology—A Laboratory Manual, pp. 399-426 (1997).
Shultz et al., "The Soybean Genome Database (SoyGD): a browser for display of duplicated, polyploid, regions and sequence tagged sites on the integrated physical and genetic maps of *Glycine max*," Nucleic Acids Research 34(Database issue): D758-D765 (2006).
Wright et al., "High-frequency homologous recombination in plants mediated by zinc-finger nucleases," *Plant Journal* 44:693-805 (2005).
Benjamin Lewin, *Genes* II 35 (Benjamin Lewin Ed., John Wiley & Sons 1985) 33-38 (1983).
Allard, "Principles of Plant Breeding," John Wiley & Sons, NY, U. of CA, Davis, CA, 50-98, 1960.
Breseghello et al., "Association Analysis as a Strategy for Improvement of Quantitative Traits in Plants," *Crop Science*, 46(3):1323-1330 (2006).
Cheng et al., "Fine Mapping Functional Sites of Regions from Case-Control Data Using Haplotypes of Multiple Linked SNPs," *Annals of Human Genetics*, 69:102-112(2005).
Choi et al., "A Soybean Transcript Map: Gene Distribution, Haplotype and Single-Nucleotide Polymorphism Analysis," *Genetics* 176:685-696 (2007).
Dempster et al., "Maximum Likelihood from Incomplete Data via the EM Algorithm," *Journal of the Royal Statistical Society*, 39:1-38 (1977).
Excoffier et al., "Maximum-Likelihood Estimation of Molecular Haplotype Frequencies in a Diploid Population," *Mol. Biol. Evol.*, 12:921-927 (1995).
Fan et al., "High-Resolution Association Mapping of Quantitative Trait Loci: A Population-Based Approach," *Genetics*, 172-663-686 (2006).

Fehr, In: Soybeans: Improvement, Production and Uses, 2nd Edition, Monograph., 16:249, 1987.
Fehr, "Principles of Cultivar Development," vol. 1, pp. 360-376 (1987).
Fehr, "Principles of Cultivar Development," vol. 2, pp. 533-561 (1987).
Flint-Garcia et al., "Structure of Linkage Disequilibrium in Plants," *Ann. Rev. Plant Biol.*, 54:357-374 (2003).
Frazer et al., "Segmental Phylogenetic Relationships of Inbred Mouse Strains Revealed by Fine-Scale Analysis of Sequence Variation Across 4.6 Mb of Mouse Genome," *Genome Research*, 14:1493-1500 (2004).
Li et al., "Multivariate Survival Models Induced by Genetic Frailties, with Application to Linkage Analysis," *Biostatistics*, 3(1):57-75 (2002).
Li et al., "Haplotype-based quantitative trait mapping using a clustering Algorithm," *BMC Bioinformatics*, 7:258 (2006).
McClurg et al., "Comparative analysis of haplotype association mapping algorithms," *BMC Bioinformatics*, 7:61 (2006).
Nordborg et al., "Linkdage disequilibrium : what history has to tell us," *TRENDS in Genetics*, 18:83-90 (2002).
Paterson, "Molecular dissection of quantitative traits: progress and prospects," *Genome Research*, 5:321-333 (1995).
Pletcher et al., "Use of a Dense Single Nucleotide Polymorphism Map for In Silico Mapping in the Mouse," *PLOS Biology*, 2:e393 (2004).
Schaid et al., "Caution on Pedigree Haplotype Inference with Software That Assumes Linkage Equilibrium," *Am. J. Hum. Genet.*, 71(4):992-995 (2002).
Seltman et al., "Evolutionary-based association analysis using haplotype data," *Genetic Epidemiology*, 25(1):48-58 (2003).
Simmonds, "Principles of crop improvement," Longman, Inc., NY, 369-399, 1979.
Slate, "Quantitative trait locus mapping in natural populations: progress, caveats and future directions," *Molecular Ecology*, 14:363-379 (2005).
Song et al., "A new integrated genetic linkage map of the soybean," *Theor Appl Genet.*, 109(1):122-8 (2004).
Song et al., Supplement 1, "Soybean Consensus Linkage Groups" (2004).
Song et al., Supplement 2, "Soybean SSR Loci, Linkage Group (LG), PCR Primer and Other Associated Information" (2004).
SoyBase and the Soybean Breeder's Toolbox: Integrating Genetics and Molecular Biology for Soybean Researchers, accessed on Oct. 25, 2017, from: https://www.soybase.org/LG2Xsome.php.
Wiltshire et al., "Genome-wide single-nucleotide polymorphism analysis defines haplotype patterns in mouse," *PNAS*, 100:3380-3385 (2003).
Zou et al. "Assignment of molecular linkage groups to soybean chromosomes by primary trisomics," *Theor Appl Genet.*, 107(4):745-50 (2003).

* cited by examiner

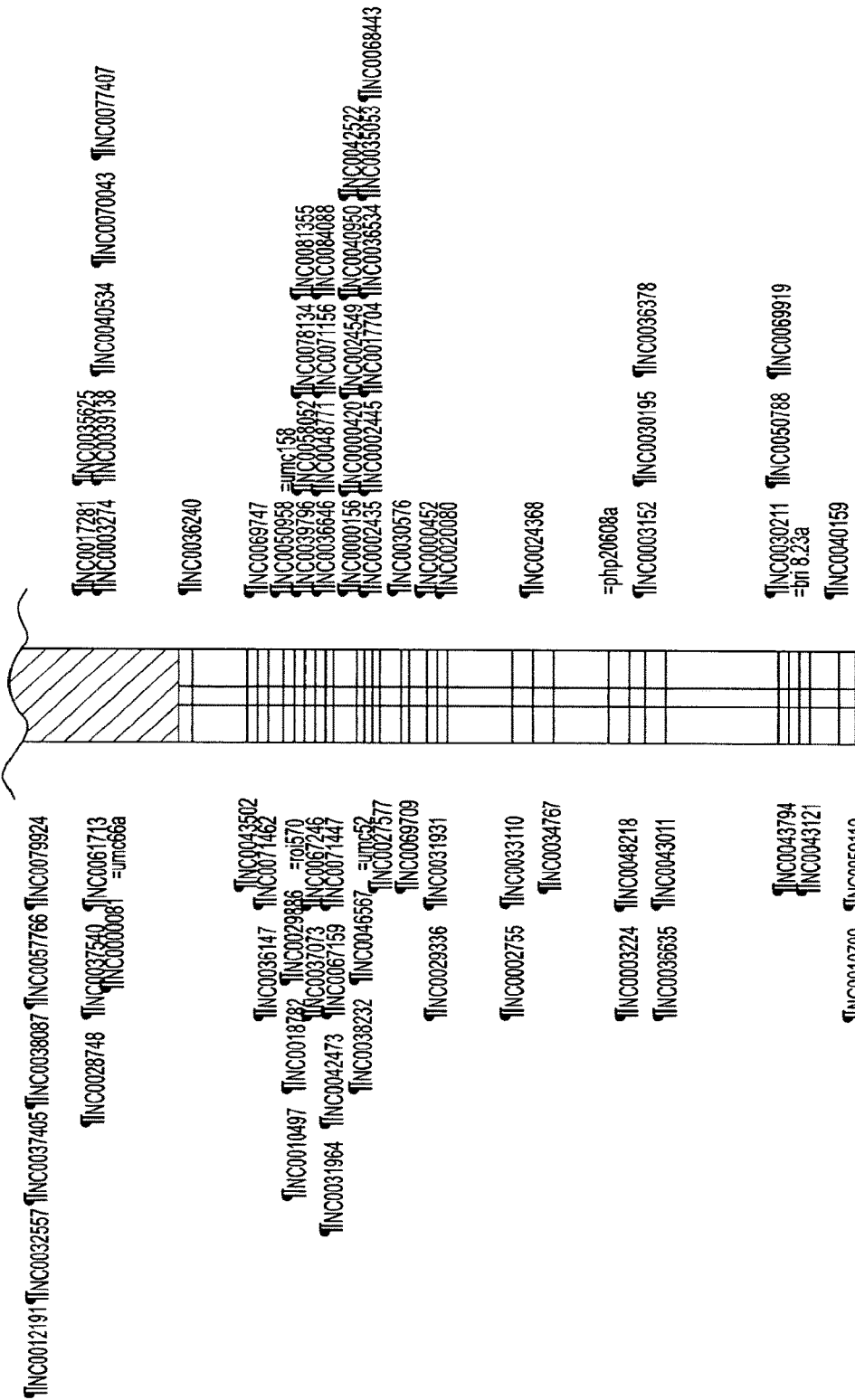
FIG. 1(cont')

FIG. 2

| Marker | Chr # | Chr Pos | 5750 | 3323 | 3140 | 90LDC2 | WQDS7 | 7051 |
|---|---|---|---|---|---|---|---|---|
| NC0003972 | 4 | # | GG | GG | AA | AA | GG | GG |
| NC003847Z | 4 | # | GG | GG | AA | AA | GG | GG |
| NC0058697 | 4 | # | TT | TT | CC | CC | TT | TT |
| NC0077263 | 4 | # | AA | AA | GG | GG | AA | AA |
| NC003413O | 4 | # | CC | CC | GG | GG | CC | CC |
| NC0067577 | 4 | # | CC | CC | GG | GG | CC | CC |
| NC0000785 | 4 | # | GG | GG | AA | AA | GG | GG |
| NC0001122 | 4 | # | CC | CC | CC | CC | TT | TT |
| NC003050Z | 4 | # | TT | TT | CC | CC | TT | TT |
| NC0010671 | 4 | # | CC | CC | AA | AA | CC | CC |
| NC0028441 | 4 | # | CC | CC | CC | CC | CC | CC |
| NC003432Z | 4 | # | AA | AA | AA | AA | TT | TT |
| NC003446Z | 4 | # | CC | CC | CC | CC | CC | CC |
| NC003673O | 4 | # | TT | TT | AA | AA | TT | TT |
| NC004257S | 4 | # | CC | CC | CC | CC | CC | CC |
| NC0070728 | 4 | # | TT | TT | AA | AA | TT | TT |
| NC0010305 | 4 | # | CC | CC | CC | CC | GG | GG |
| NC003179Z | 4 | # | CC | CC | CC | CC | GG | GG |
| NC003568Z | 4 | # | CC | CC | TT | TT | CC | CC |

FIG. 2(cont')

COMPOSITIONS AND METHODS OF PLANT BREEDING USING HIGH DENSITY MARKER INFORMATION

CROSS-REFERENCE TO RELATED APPLICATIONS

This application is a continuation application of U.S. application Ser. No. 12/376,998, filed Feb. 10, 2009, which is a national phase application of International Application No. PCT/US2007/018101, which application claims priority to U.S. Provisional Application No. 60/837,864 (filed Aug. 15, 2006). These applications are incorporated herein by reference in its their entireties.

INCORPORATION OF SEQUENCE LISTING

A sequence listing containing the file named "Revised_Sequence_Listing_2017.txt" which is 79,291 bytes (measured in MS-Windows®) and created on Apr. 11, 2017, comprises 519 nucleotide sequences, is provided herewith via the USPTO's EFS system and is herein incorporated by reference in its entirety.

FIELD OF THE INVENTION

This invention relates to the field of plant breeding, in particular to methods facilitating informed germplasm improvement activities within a breeding program by defining haplotypes within pre-determined chromosomal windows within a genome and associating the haplotypes with haplotype effect estimates for one or more traits, wherein the associations can be made de novo or by leveraging historical marker-trait association data. Accordingly, the methods of the present invention enable decisions related to germplasm improvement activities to be made by ranking haplotypes based on numerical values, wherein the values represent the haplotype effect estimates, haplotype frequency, and/or breeding values. Herein, breeding values are calculated based on haplotype effect estimates and haplotype frequency, wherein the haplotype breeding value represents the effect of fixing a particular haplotype in a population, thus providing the basis for ranking haplotypes.

BACKGROUND OF THE INVENTION

Breeding has advanced from selection for economically important traits in plants and animals based on phenotypic records of an individual and its relatives to the application of molecular genetics to identify genomic regions that contain valuable genetic traits. Inclusion of genetic markers in breeding programs has accelerated the genetic accumulation of valuable traits into a germplasm compared to that achieved based on phenotypic data only. Herein, "germplasm" includes breeding germplasm, breeding populations, collection of elite inbred lines, populations of random mating individuals, and biparental crosses. Genetic marker alleles (an "allele" is an alternative sequence at a locus) are used to identify plants that contain a desired genotype at multiple loci, and that are expected to transfer the desired genotype, along with a desired phenotype to their progeny. Genetic marker alleles are used to identify plants that contain the desired genotype at one marker locus, several loci, or a haplotype, and that would be expected to transfer the desired genotype, along with a desired phenotype to their progeny. This process has been widely referenced and has served to greatly economize plant breeding by accelerating the fixation of advantageous alleles and also eliminating the need for phenotyping every generation.

Recent years have seen tremendous advances in the application of marker-assisted breeding techniques, on both the development of markers and the association of markers with phenotypes, or quantitative trait loci (QTL) mapping. Examples of DNA markers are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Pat. No. 5,437,697; U.S. patent application Ser. Nos. 11/204,780, 11/216,545, 11/218,305, and 11/504,538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis. As a set, polyallelic markers serve as a useful tool for fingerprinting plants to inform the degree of identity of lines or varieties (U.S. Pat. No. 6,207,367). These markers form the basis for determining associations with phenotype and can be used to drive genetic gain. The implementation of marker-assisted selection is dependent on the ability to detect underlying genetic differences between individuals.

Because of ALLELIC differences in these molecular markers, QTL can be identified by statistical evaluation of the genotypes and phenotypes of segregating populations. Processes to map QTL are well-described (WO 90/04651; U.S. Pat. Nos. 5,492,547, 5,981,832, 6,455,758; reviewed in Flint-Garcia et al. 2003 Ann. Rev. Plant Biol. 54:357-374). Using markers to infer phenotype in these cases results in the economization of a breeding program by substitution of costly, time-intensive phenotyping with genotyping. Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (US Patent Application 2005/0015827).

This process has evolved to the application of markers as a tool for the selection of "new and superior plants" via introgression of preferred genomic regions as determined by statistical analyses (U.S. Pat. No. 6,219,964). Marker-assisted introgression involves the transfer of a chromosomal region, defined by one or more markers, from one germplasm to a second germplasm. The initial step in that process is the localization of the genomic region or transgene by gene mapping, which is the process of determining the position of a gene or genomic region relative to other genes and genetic markers through linkage analysis. The basic principle for linkage mapping is that the closer together two genes are on a chromosome, the more likely they are to be inherited together. Briefly, a cross is generally made between two genetically compatible but divergent parents relative to the traits of interest. Genetic markers can then be used to follow the segregation of these traits in the progeny from the cross, often a backcross (BC1), $F_2$, or recombinant inbred population.

It is well recognized that common QTL mapping procedures provide low resolution placement of inferred QTL loci on the genetic map (e.g., Buntjer et al. 2005 Trends Plant Sci. 10:466-471; Morgante et al. 2003 Curr. Op. Biotech. 14:214-219). This is attributable to two, basic underlying facts. First, QTL identification is a low-power activity, requiring that information from a large number of progeny be leveraged to achieve a significant confidence that any observed differences in the expression of a quantitative trait amongst classes of progeny must be due to linkage of a trait locus to the genetic marker that provided the basis for DIFFERENTIATING classes of progeny. Second, the progeny generation usually employed in QTL mapping is of relatively recent derivation from the F1 generation, the point where genetic mechanisms could first act to allow linked alleles to begin the slow approach to linkage EQUILIBRIUM. The consequence of these two facts is that identified QTL can be placed only with a reasonable confidence of existing within a segment of DNA as large as 20-30 cM.

Further, other limitations of traditional QTL mapping research include the fact that inferences are restricted to the particular parents of the mapping population and the genes or gene combinations of these parental varieties. There has long been interest in extrapolating the QTL inferences BEYOND the original mapping population in an attempt to leverage the genetic insight to broad sets of germplasm, including elite and unimproved germplasm sources. However, there are a number of biological reasons why such broad inferences are likely to be invalid (Paterson 1995 Genome Res. 5:321-333; Slate 2005 Mol. Ecol. 14:363-379; Breseghello et al. 2006 Crop Sci. 46:1323-1330), with the major limitation being the lack of knowledge of identity by descent at a specific genomic region (Buntjer et al. 2005 Trends Plant Sci. 10:466-471).

It has long been recognized that genes and genomic sequences may be identical by state (i.e., identical by independent origins) or identical by descent (i.e., through historical inheritance from a common progenitor) which has tremendous bearing on studies of linkage disequilibrium and, ultimately, mapping studies (Nordberg et al. 2002 Trends Gen. 18:83-90). Historically, genetic markers were not appropriate for distinguishing identical in state or by descent. However, newer classes of markers, such as SNPs (single nucleotide polymorphisms), are more diagnostic of origin. The likelihood that a particular SNP allele is derived from independent origins in the extant populations of a particular species is very low. Polymorphisms occurring in linked genes are randomly assorted at a slow, but predictable rate, described by the decay of linkage disequilibrium or, alternatively, the approach of linkage equilibrium. Consequences of this well-established scientific discovery are that long stretches of coding DNA, defined by a specific combination of polymorphisms, are very unique and extremely improbable of existing in duplication except through linkage disequilibrium, which is indicative of recent co-ancestry from a common progenitor. The probability that a particular genomic region, as defined by some combination of alleles, indicates absolute identity of the entire intervening genetic sequence is dependent on the number of linked polymorphisms in this genomic region, barring the occurrence of recent mutations in the interval. Herein, such genomic regions are referred to as haplotype windows. Each haplotype within that window is defined by specific combinations of alleles; the greater the number of alleles, the greater the number of potential haplotypes, and the greater the certainty that identity by state is a result of identity by descent at that region. During the development of new lines, ancestral haplotypes are maintained through the process and are typically thought of as 'linkage blocks' that are inherited as a unit through a pedigree. Further, if a specific haplotype has a known effect, or phenotype, it is possible to extrapolate its effect in other lines with the same haplotype, as determined using one or more diagnostic markers for that haplotype window.

There have been contributions in the public domain around analyses to define haplotype blocks from a plurality of markers and the methodology is well known to anyone skilled in the art (e.g., U.S. Pat. Nos. 6,844,154; 6,909,971; 6,920,398; 6,969,589; 7,041,447). In human populations, statistical analyses, such as association studies, have been employed to determine haplotype-phenotype associations, which is useful for informing clinical decisions (Li et al. 2006 BMC Bioinformatics 7:258; U.S. Pat. Nos. 6,931,326; 6,969,589). In mice, the resolution of haplotype structure (Frazer et al. 2004 Genome Res. 14:1493-1500; Wiltshire et al. 2003 Proc. Natl. Acad. Sci. 100:3380-3385) has also enabled enhanced QTL mapping for inbred lines (Pletcher et al. 2004 PLoS Biol. 2:e393; McClurg et al. 2006 BMC Bioinformatics 7:61).

The present invention allows researchers to address the biological limitations of known methods of QTL mapping and incorporates pedigree information such that the invention enables an improved approach to predictive breeding, based on both an improved approach to traditional QTL mapping coupled with high density fingerprinting. This combination of information allows the correspondence of the deductive inferences about linkage between marker alleles and phenotype with the ability to reliably predict where the same parental linkages exist elsewhere in the germplasm pool. Thus, the present invention provides a means to predict across a broad group of germplasm, comprising multiple populations, where the prior inferences of genotype-phenotype associations are applicable. Further, the present invention allows such inferences to be made for multiple traits, a key feature lacking in previous inventions.

In another aspect, there is a need in the art of plant breeding to identify haplotypes beyond the context of specific traits or regions. In the present invention, haplotype windows are defined across the genome in order to enable comparisons between two or more haplotypes within and between windows, wherein the haplotypes are associated with one or more traits to establish an estimated effect. As a result, haplotypes associated with improved performance with respect to an phenotypic trait or multiple traits are targeted for selection and it is possible to then select for these genomic regions simultaneously. Assessing haplotypes at a genome level generates a greater density of haplotypes and facilitates the identification of preferred haplotypes that might be overlooked with smaller-scale haplotype analyses. Herein, the traits may be nontransgenic or transgenic in nature.

The present invention allows one skilled in the art to estimate haplotype effects using associations, based on historical data or de novo mapping, between genetic markers and one or more phenotypic traits. In conjunction with haplotype frequencies, haplotype effect estimates can also be used to calculate haplotype breeding values for a group of haplotypes. In the context of a specified set of haplotypes, a calculated set of breeding values can be used to ranking haplotypes both within and between windows. In the context of evaluating the effect of substituting a specific region in the genome, either by introgression or a transgenic event, haplotype breeding values provide for comparing haplotypes across windows for substitution effects. Both rankings of haplotype effects and breeding values allow one skilled in the art to make selections for the purpose of germplasm improvement activities.

SUMMARY OF THE INVENTION

The present Invention includes and provides a method for improving plant germplasm by accumulation of haplotypes of interest in a germplasm comprising determining haplotype windows in the genome, defining at least two haplotypes within those windows based on one or more polymorphic markers, and associating the haplotypes with their specific effects, and using the haplotype effect estimates to direct breeding decisions. These haplotype effect estimates can be derived using historical marker-trait associations or de novo from mapping populations. The haplotype effect estimates for one or more traits provide the basis for making decisions in a breeding program. This invention also provides an alternative basis for decision-making using breeding value calculations based on the estimated effect and frequency of haplotypes, within and between haplotype windows, in the germplasm. Haplotype breeding values are used to rank a specified set of haplotypes, either within or across windows. Haplotype breeding values also provide the basis for ranking haplotypes, by evaluating the effect of fixing a haplotype by introgression or a transgenic event.

In the present invention, haplotype effect estimates and/or breeding values for one or more traits of interest provide the basis for determining one or more haplotypes of interest in comparisons of two or more haplotypes. With this a priori information, breeding selections are conducted on a haplotype, rather than marker, basis, wherein a first plant is crossed with a SECOND plant that contains at least one haplotype that is different from the first plant haplotype or haplotypes; and at least one progeny plant is selected by detecting the haplotype or set of haplotypes of the first plant, wherein the progeny plant comprises in its genome one or more haplotypes of interest of the first plant and at least one haplotype of interest of the second plant; and the progeny plant is used in activities related to germplasm improvement, non-limiting examples of which include line development, hybrid development, transgenic event selection, making breeding crosses, testing and advancing a plant through self fertilization, using plant or parts thereof for transformation, using plants or parts thereof for candidates for expression constructs, and using plant or parts thereof for mutagenesis.

The present invention includes a method for breeding of a crop plant, such as maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including indica and *japonica* varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*), members of the genus *Brassica*, broccoli, cabbage, carrot, cauliflower, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut, with enhanced traits comprising at least one sequence of interest, further defined as conferring a preferred property selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other phenotypic traits, traits for industrial uses, or traits for improved consumer appeal, wherein the traits may be nontransgenic or transgenic.

Non-limiting examples of silage quality traits include brown midrib (BMR) traits, in vitro digestability of dry matter, leafiness, horny endosperm, crude protein, neutral detergent fiber, neutral detergent fiber digestability, starch content, starch availability, kernel texture, milk/ton, fat content of milk, readily available energy, soluble carbohydrate digestability, nonsoluble carbohydrate digestability, reduced phytate production, reduced waste production, and silage yield.

Non-limiting examples of grain quality traits for biofuel yield include total biomass, fermentation yield, fermentation kinetics, total starch, extractable starch, starch morphology, phosphorous availability, waxy traits, glucose content, total oil content, germ oil content, endosperm oil content, fatty acid composition, kernel or seed morphology, amylose content, amylopectin content, protein composition and content (in particular, for end-use in animal feed following fractionation).

The present invention also provides for plants and parts thereof with compositions of preferred haplotypes as described herein.

BRIEF DESCRIPTION OF THE DRAWINGS

The drawings described herein are for illustration purposes only and are not intended to limit the scope of the present teachings in any way.

FIG. 2 depicts the marker fingerprint information for the inbreds with the favorable haplotype (5750 (SEQ ID NO. 512) and 3323 (seq id no. 513)) and unfavorable haplotype (3140 (SEQ ID NO. 514) and 90LDC2 (SEQ ID NO.515)). A third haplotype was identified in the two testers (7051 (SEQ ID NO. 516) and WQDS7 (SEQ ID NO. 517)). The markers shown in FIG. 2 were used to screen a corn germplasm set to determine the distribution of these three haplotypes and inform future breeding choices.

DETAILED DESCRIPTION

Figure 1:
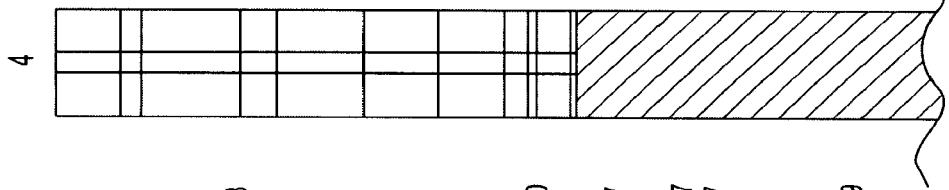
FIG. 1 is an illustration depicting the 30 cM region resolved by high density fingerprinting that mapped to grain yield QTL on chromosome 4 in corn. Both favorable and unfavorable haplotypes were identified in this region, with the favorable haplotype corresponding to a 4.2 Bu/Acre advantage.

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 CFR § 1.822 is used.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism includes a single nucleotide polymorphism (SNP), a simple sequence repeat (SSR) and indels, which are insertions and deletions. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation.

As used herein, "marker" means a polymorphic nucleic acid sequence or nucleic acid feature. A "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (Indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms. In a broader aspect, a "marker" can be a detectable characteristic that can be used to discriminate between heritable differences between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "marker assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, the term "haplotype" means a chromosomal region within a haplotype window defined by at least one polymorphic marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more marker loci located within this region is taken as evidence of identity-by-descent of the entire region. Each haplotype window includes at least one polymorphic marker. Haplotype windows are mapped along each chromosome in the genome.

Haplotype windows are not fixed per se and, given the ever-increasing density of markers, this invention anticipates the number and size of haplotype windows to evolve, with the number of windows increasing and their respective sizes decreasing, thus resulting in an ever-increasing degree confidence in ascertaining identity by descent based on the identity by state at the marker loci.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which are a manifestation of gene expression.

As used herein, "haplotype effect estimate" means a predicted effect estimate for a haplotype reflecting association with one or more phenotypic traits, wherein the associations can be made de novo or by leveraging historical haplotype-trait association data As used herein, "breeding value" means a calculation based on nucleic acid sequence effect estimates and nucleic acid sequence frequency values, the breeding value of a specific nucleic acid sequence relative to other nucleic acid sequences at the same locus (i.e., haplotype window), or across loci (i.e., haplotype windows), can also be determined. In other words, the change in population mean by fixing said nucleic acid sequence is determined. In addition, in the context of evaluating the effect of substituting a specific region in the genome, either by introgression or a transgenic event, breeding values provide the basis for comparing specific nucleic acid sequences for substitution effects. Also, in hybrid crops, the breeding value of nucleic acid sequences can be calculated in the context of the nucleic acid sequence in the tester used to produce the hybrid.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus (QTL)" means a locus that controls to some degree numerically representable traits that are usually continuously distributed.

As used herein, the term "transgene" means nucleic acid molecules in form of DNA, such as cDNA or genomic DNA, and RNA, such as mRNA or microRNA, which may be single or double stranded.

As used herein, the term "inbred" means a line that has been bred for genetic homogeneity. Without limitation, examples of breeding methods to derive inbreds include pedigree breeding, recurrent selection, single-seed descent, backcrossing, and doubled haploids.

As used herein, the term "hybrid" means a progeny of mating between at least two genetically dissimilar parents. Without limitation, examples of mating schemes include single crosses, modified single cross, double modified single cross, three-way cross, modified three-way cross, and double cross, wherein at least one parent in a modified cross is the progeny of a cross between sister lines.

As used herein, the term "tester" means a line used in a testcross with another line wherein the tester and the lines tested are from different germplasm pools. A tester may be isogenic or nonisogenic.

As used herein, the term "corn" means *Zea mays* or maize and includes all plant varieties that can be bred with corn, including wild maize species.

As used herein, the term "soybean" means *Glycine max* and includes all plant varieties that can be bred with soybean, including wild soybean species.

Haplotype Window 13800, corresponding to Haplotype ID No: 1264362, is identifiable using markers Q-NS0125281 and Q-NS0118716 as provided in Table 2 of the present Specification. Markers Q-NS0125281 and Q-NS0118716 are characterized in U.S. patent application Ser. No. 12/395,075, filed Feb. 27, 2009, that is a Division of application Ser. No. 11/204,780, filed Aug. 15, 2005 and incorporated by reference above. U.S. patent application Ser. No. 12/395,075 was published as U.S. Patent Publication No. US2009/0208964 on Aug. 20, 2009 (the '964 Publication)[1]. The '964 Publication identifies markers Q-NS0125281 and Q-NS0118716 at Table 2, the relevant parts of which are reproduced below.

[1] U.S. Patent Publication No. US2009/0208964 corresponds to U.S. application Ser. No. 12/395,075, filed Feb. 27, 2009, that is a division of U.S. application Ser. No. 11/204,780, filed Aug. 15, 2005, and claiming priority to U.S. Provisional Application No. 60/601,756. The present specification incorporates the U.S. application Ser. No. 11/204,780 at page 13, lines 14 to 25 and at page 66, lines 1 to 5.

| Table 2 from US2009/0208964 | | | | |
|---|---|---|---|---|
| Marker | Mutation ID | Sequence ID | Linkage Group | Map Position (cM) |
| Q-NS0125281 | 125281 | 1324605 | C2 | 114.30 |
| Q-NS0118716 | 118716 | 1271420 | C2 | 115.90 |

From U.S. Patent Publication No. US2009/0208964, Table 2

The '964 Publication further identifies SEQ ID NOs:3829 and 2871 corresponding to markers Q-NS0125281 and Q-NS0118716 of Haplotype Window 13800/Haplotype ID No.: 1264362 at Table 1. The relevant parts of Table 1 of the '964 Publication are provided below.

| Table 1.txt from US2009/0208964 | | | | | | | | | |
|---|---|---|---|---|---|---|---|---|---|
| SEQ ID NO: | LOCUS ID | Mutation ID | Start Pos | End Pos | Type | Allele 1 | Strain 1 | Allele 2 | Strain 2 |
| 3829 | 1324605 | 125275 | 146 | 146 | SNP | A | PI507354 | G | Will |
| 3829 | 1324605 | 125279 | 524 | 524 | SNP | G | Will | T | PI507354 |
| 3829 | 1324605 | 125280 | 648 | 648 | SNP | C | Will | T | PI507354 |
| 3829 | 1324605 | 125281 | 834 | 834 | SNP | A | PI507354 | G | Will |
| 2871 | 1271420 | 118716 | 366 | 366 | SNP | C | PI507354 | T | Will |

As used herein, the term "canola" means *Brassica napus* and *B. campestris* and includes all plant varieties than can be bred with canola, including wild *Brassica* species and other agricultural *Brassica* species.

As used herein, the term "elite line" means any line that has resulted from breeding and selection for superior agronomic performance. An elite plant is any plant from an elite line.

In the present invention, haplotypes are defined on the basis of one or more polymorphic markers within a given haplotype window, with haplotype windows being distributed throughout the crop's genome. In another aspect, de novo and/or historical marker-phenotype association data are leveraged to infer haplotype effect estimates for one or more phenotypes for one or more of the haplotypes for a crop. Haplotype effect estimates enable one skilled in the art to make breeding decisions by comparing haplotype effect estimates for two or more haplotypes. Polymorphic markers, and respective map positions, of the present invention are provided in U.S. patent application Ser. Nos. 11/204,780, 11/216,545, 11/218,305, and 11/504,538, which are incorporated herein by reference in their entirety.

In yet another aspect, haplotype effect estimates are coupled with haplotype frequency values to calculate a haplotype breeding value of a specific haplotype relative to other haplotypes at the same haplotype window, or across haplotype windows, for one or more phenotypic traits. In other words, the change in population mean by fixing the haplotype is determined. In still another aspect, in the context of evaluating the effect of substituting a specific region in the genome, either by introgression or a transgenic event, haplotype breeding values are used as a basis in comparing haplotypes for substitution effects. Further, in hybrid crops, the breeding value of haplotypes is calculated in the context of at least one haplotype in a tester used to produce a hybrid. Once the value of haplotypes at a given haplotype window are determined and high density fingerprinting information is available on specific varieties or lines, selection can be applied to these genomic regions using at least one marker in the at least one haplotype.

In the present invention, selection can be applied at one or more stages of a breeding program:

a) Among genetically distinct populations, herein defined as "breeding populations," as a pre-selection method to increase the selection index and drive the frequency of favorable haplotypes among breeding populations, wherein pre-selection is defined as selection among populations based on at least one haplotype for use as parents in breeding crosses, and leveraging of marker-trait association identified in previous breeding crosses.

b) Among segregating progeny from a breeding population, to increase the frequency of the favorable haplotypes for the purpose of line or variety development.

c) Among segregating progeny from a breeding population, to increase the frequency of the favorable haplotypes prior to QTL mapping within this breeding population.

d) For hybrid crops, among parental lines from different heterotic groups to predict the performance potential of different hybrids.

Conversely, mapping can be performed based on haplotypes, versus markers alone (Fan et al. 2006 Genetics). A haplotype is a segment of DNA in the genome of an organism that is assumed to be identical by descent for different individuals when the knowledge of identity by state at one or more loci is the same in the different individuals, and that the regional amount of linkage disequilibrium in the vicinity of that segment on the physical or genetic map is high. A haplotype can be tracked through populations and its statistical association with a given trait can be analyzed. By searching the target space for a QTL association across multiple QTL mapping populations that have parental lines with genomic regions that are identical by descent, the effective population size associated with QTL mapping is increased. The increased sample size results in more recombinant progeny which increases the precision of estimating the QTL position.

Thus, a haplotype association study allows one to define the frequency and the type of the ancestral carrier haplotype. An "association study" is a genetic experiment where one tests the level of departure from randomness between the segregation of alleles at one or more marker loci and the value of individual phenotype for one or more traits. Association studies can be done on quantitative or categorical traits, accounting or not for population structure and/or stratification. In the present invention, associations between haplotypes and phenotypes for the determination of "haplotype effect estimates" can be conducted de novo, using mapping populations for the evaluation of one or more phenotypes, or using historical genotype and phenotype data.

A haplotype analysis is important in that it increases the statistical power of an analysis involving individual biallelic markers. In a first stage of a haplotype frequency analysis, the frequency of the possible haplotypes based on various combinations of the identified biallelic markers of the invention is determined. The haplotype frequency is then compared for distinct populations and a reference population. In general, any method known in the art to test whether a trait and a genotype show a statistically significant correlation may be used.

Methods for determining the statistical significance of a correlation between a phenotype and a genotype, in this case a haplotype, may be determined by any statistical test known in the art and with any accepted threshold of statistical significance being required. The application of particular methods and thresholds of significance are well within the skill of the ordinary practitioner of the art.

In plant breeding populations, linkage disequilibrium (LD) is the level of departure from random association between two or more loci in a population and LD often persists over large chromosomal segments. Although it is possible for one to be concerned with the individual effect of each gene in the segment, for a practical plant breeding purpose the emphasis is typically on the average impact the region has for the trait(s) of interest when present in a line, hybrid or variety.

In the present invention, the amount of pair-wise LD is presented (using the $r^2$ statistic) against the distance in centiMorgan (cM, one hundredth of a Morgan, on average one recombination per meiosis, recombination is the result of the reciprocal exchange of chromatid segments between homologous chromosomes paired at meiosis, and it is usually observed through the association of alleles at linked loci from different grandparents in the progeny) between the markers for a reference germplasm set of 149 soybean elite US varieties and 1168 SNP loci (Table 1), and in 465 corn elite US inbreds and 1231 SNP loci (Table 2). A 200 data points moving average curve is also drawn to indicate the presence of LD between loci as close as 5 cM. Tables 1 and 2 illustrate the set of haplotype windows designated in the genomes of soy and corn, respectively. Also indicated is the set of polymorphic markers that define each window which resolve the haplotypes, based on marker fingerprint. Corn inbreds were divided based on heterotic group: female and male, wherein germplasm used as females in hybrid crosses was developed from B73 and germplasm used as males in hybrid crosses was developed from Iodent. Female inbreds, herein referred to as "females," and male inbreds, herein referred to as "males," when mated with one another create hybrid vigor. In hybrid corn production, females are most commonly used as the recipients of pollen from the males because the females typically produce higher quality ears which result in greater seed set for hybrid seed production; where as males are more commonly used as pollen donors because they are better pollen donors than ear producers.

TABLE 1

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 13051 | Q-NC0111829 | 1 | 0.3 | 0.3 | 2.6 |
| 1 | 13051 | Q-NC0110465 | 2 | 0.9 | 0.3 | 2.6 |
| 1 | 13051 | Q-NC0024027 | 3 | 1 | 0.3 | 2.6 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 13051 | Q-NC0015697 | 4 | 1.4 | 0.3 | 2.6 |
| 1 | 13051 | Q-NC0002640 | 5 | 2.6 | 0.3 | 2.6 |
| 1 | 13051 | Q-NC0021554 | 6 | 2.6 | 0.3 | 2.6 |
| 1 | 13051 | Q-NC0021713 | 7 | 2.6 | 0.3 | 2.6 |
| 1 | 13037 | Q-NC0019086 | 1 | 5.7 | 5.7 | 10.3 |
| 1 | 13037 | Q-NC0033261 | 2 | 5.8 | 5.7 | 10.3 |
| 1 | 13037 | Q-NC0147181 | 3 | 6.7 | 5.7 | 10.3 |
| 1 | 13037 | Q-NC0147202 | 4 | 6.7 | 5.7 | 10.3 |
| 1 | 13037 | Q-NC0148452 | 5 | 6.7 | 5.7 | 10.3 |
| 1 | 13037 | Q-NC0111443 | 6 | 10.3 | 5.7 | 10.3 |
| 1 | 13016 | Q-NC0043992 | 1 | 13.2 | 13.2 | 13.2 |
| 1 | 13031 | Q-NC0154927 | 1 | 18.5 | 18.5 | 23 |
| 1 | 13031 | Q-NC0036199 | 2 | 20.6 | 18.5 | 23 |
| 1 | 13031 | Q-NC0043185 | 3 | 22.6 | 18.5 | 23 |
| 1 | 13031 | Q-NC0068027 | 4 | 23 | 18.5 | 23 |
| 1 | 12941 | Q-NC0001369 | 1 | 24.3 | 24.3 | 27.6 |
| 1 | 12941 | Q-NC0110473 | 2 | 24.6 | 24.3 | 27.6 |
| 1 | 12941 | Q-NC0025418 | 3 | 26.4 | 24.3 | 27.6 |
| 1 | 12941 | Q-NC0147302 | 4 | 27.6 | 24.3 | 27.6 |
| 1 | 12886 | Q-NC0028164 | 1 | 30.1 | 30.1 | 34.5 |
| 1 | 12886 | Q-NC0105051 | 2 | 31.4 | 30.1 | 34.5 |
| 1 | 12886 | Q-NC0107227 | 3 | 34.1 | 30.1 | 34.5 |
| 1 | 12886 | Q-NC0003563 | 4 | 34.5 | 30.1 | 34.5 |
| 1 | 13047 | Q-NC0038710 | 1 | 43.8 | 43.8 | 46 |
| 1 | 13047 | Q-NC0036685 | 2 | 45.8 | 43.8 | 46 |
| 1 | 13047 | Q-NC0029694 | 3 | 46 | 43.8 | 46 |
| 1 | 12911 | Q-NC0003429 | 1 | 49.5 | 49.5 | 51.3 |
| 1 | 12911 | Q-NC0052741 | 2 | 49.5 | 49.5 | 51.3 |
| 1 | 12911 | Q-NC0049734 | 3 | 49.9 | 49.5 | 51.3 |
| 1 | 12911 | Q-NC0000524 | 4 | 50.3 | 49.5 | 51.3 |
| 1 | 12911 | Q-NC0004409 | 5 | 50.3 | 49.5 | 51.3 |
| 1 | 12911 | Q-NC0043571 | 6 | 50.3 | 49.5 | 51.3 |
| 1 | 12911 | Q-NC0038720 | 7 | 50.5 | 49.5 | 51.3 |
| 1 | 12911 | Q-NC0148102 | 8 | 50.5 | 49.5 | 51.3 |
| 1 | 12911 | Q-NC0009213 | 9 | 51.3 | 49.5 | 51.3 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 12911 | Q-NC0035417 | 10 | 51.3 | 49.5 | 51.3 |
| 1 | 12921 | Q-NC0105076 | 1 | 54.1 | 54.1 | 58.4 |
| 1 | 12921 | Q-NC0105856 | 2 | 54.8 | 54.1 | 58.4 |
| 1 | 12921 | Q-NC0152452 | 3 | 56.8 | 54.1 | 58.4 |
| 1 | 12921 | Q-NC0113273 | 4 | 58.2 | 54.1 | 58.4 |
| 1 | 12921 | Q-NC0078549 | 5 | 58.4 | 54.1 | 58.4 |
| 1 | 12921 | Q-NC0080697 | 6 | 58.4 | 54.1 | 58.4 |
| 1 | 13050 | Q-NC0042173 | 1 | 60.2 | 60.2 | 60.2 |
| 1 | 12909 | Q-NC0029329 | 1 | 65.8 | 65.8 | 70.2 |
| 1 | 12909 | Q-NC0039205 | 2 | 65.8 | 65.8 | 70.2 |
| 1 | 12909 | Q-NC0039840 | 3 | 65.8 | 65.8 | 70.2 |
| 1 | 12909 | Q-NC0000116 | 4 | 66 | 65.8 | 70.2 |
| 1 | 12909 | Q-NC0009159 | 5 | 66 | 65.8 | 70.2 |
| 1 | 12909 | Q-NC0040189 | 6 | 66.4 | 65.8 | 70.2 |
| 1 | 12909 | Q-NC0004442 | 7 | 67.7 | 65.8 | 70.2 |
| 1 | 12909 | Q-NC0057022 | 8 | 70.1 | 65.8 | 70.2 |
| 1 | 12909 | Q-NC0014299 | 9 | 70.2 | 65.8 | 70.2 |
| 1 | 12909 | Q-NC0033819 | 10 | 70.2 | 65.8 | 70.2 |
| 1 | 13065 | Q-NC0018320 | 1 | 72.4 | 72.4 | 75.4 |
| 1 | 13065 | Q-NC0018281 | 2 | 72.5 | 72.4 | 75.4 |
| 1 | 13065 | Q-NC0009578 | 3 | 73.5 | 72.4 | 75.4 |
| 1 | 13065 | Q-NC0104670 | 4 | 73.7 | 72.4 | 75.4 |
| 1 | 13065 | Q-NC0146543 | 5 | 73.7 | 72.4 | 75.4 |
| 1 | 13065 | Q-NC0155962 | 6 | 73.7 | 72.4 | 75.4 |
| 1 | 13065 | Q-NC0016876 | 7 | 74.9 | 72.4 | 75.4 |
| 1 | 13065 | Q-NC0039067 | 8 | 75.4 | 72.4 | 75.4 |
| 1 | 13066 | Q-NC0039812 | 1 | 77.8 | 77.8 | 82.1 |
| 1 | 13066 | Q-NC0105022 | 2 | 79.5 | 77.8 | 82.1 |
| 1 | 13066 | Q-NC0077749 | 3 | 79.6 | 77.8 | 82.1 |
| 1 | 13066 | Q-NC0077750 | 4 | 79.6 | 77.8 | 82.1 |
| 1 | 13066 | Q-NC0110365 | 5 | 81.9 | 77.8 | 82.1 |
| 1 | 13066 | Q-NC0009449 | 6 | 82 | 77.8 | 82.1 |
| 1 | 13066 | Q-NC0033372 | 7 | 82 | 77.8 | 82.1 |
| 1 | 13066 | Q-NC0105925 | 8 | 82.1 | 77.8 | 82.1 |
| 1 | 13066 | Q-NC0113462 | 9 | 82.1 | 77.8 | 82.1 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 12964 | Q-NC0148156 | 1 | 83.2 | 83.2 | 84.6 |
| 1 | 12964 | Q-NC0033533 | 2 | 84.3 | 83.2 | 84.6 |
| 1 | 12964 | Q-NC0036506 | 3 | 84.6 | 83.2 | 84.6 |
| 1 | 12964 | Q-NC0043559 | 4 | 84.6 | 83.2 | 84.6 |
| 1 | 13070 | Q-NC0111854 | 1 | 91.4 | 91.4 | 96.4 |
| 1 | 13070 | Q-NC0035579 | 2 | 94.5 | 91.4 | 96.4 |
| 1 | 13070 | Q-NC0019256 | 3 | 96.4 | 91.4 | 96.4 |
| 1 | 12929 | Q-NC0025863 | 1 | 96.7 | 96.7 | 101.6 |
| 1 | 12929 | Q-NC0069524 | 2 | 99.9 | 96.7 | 101.6 |
| 1 | 12929 | Q-NC0016873 | 3 | 101 | 96.7 | 101.6 |
| 1 | 12929 | Q-NC0015205 | 4 | 101.5 | 96.7 | 101.6 |
| 1 | 12929 | Q-NC0109095 | 5 | 101.6 | 96.7 | 101.6 |
| 1 | 13056 | Q-NC0057735 | 1 | 102.5 | 102.5 | 103.7 |
| 1 | 13056 | Q-NC0011522 | 2 | 103.1 | 102.5 | 103.7 |
| 1 | 13056 | Q-NC0005280 | 3 | 103.2 | 102.5 | 103.7 |
| 1 | 13056 | Q-NC0053351 | 4 | 103.3 | 102.5 | 103.7 |
| 1 | 13056 | Q-NC0153831 | 5 | 103.5 | 102.5 | 103.7 |
| 1 | 13056 | Q-NC0028351 | 6 | 103.7 | 102.5 | 103.7 |
| 1 | 13056 | Q-NC0038741 | 7 | 103.7 | 102.5 | 103.7 |
| 1 | 13056 | Q-NC0039702 | 8 | 103.7 | 102.5 | 103.7 |
| 1 | 13056 | Q-NC0066981 | 9 | 103.7 | 102.5 | 103.7 |
| 1 | 13056 | Q-NC0069188 | 10 | 103.7 | 102.5 | 103.7 |
| 1 | 12985 | Q-NC0043901 | 1 | 104.2 | 104.2 | 109.2 |
| 1 | 12985 | Q-NC0005215 | 2 | 104.8 | 104.2 | 109.2 |
| 1 | 12985 | Q-NC0008984 | 3 | 105.5 | 104.2 | 109.2 |
| 1 | 12985 | Q-NC0110353 | 4 | 105.5 | 104.2 | 109.2 |
| 1 | 12985 | Q-NC0014644 | 5 | 107.8 | 104.2 | 109.2 |
| 1 | 12985 | Q-NC0029829 | 6 | 108 | 104.2 | 109.2 |
| 1 | 12985 | Q-NC0107044 | 7 | 108 | 104.2 | 109.2 |
| 1 | 12985 | Q-NC0144090 | 8 | 108.6 | 104.2 | 109.2 |
| 1 | 12985 | Q-NC0111828 | 9 | 109.2 | 104.2 | 109.2 |
| 1 | 12938 | Q-NC0053983 | 1 | 109.4 | 109.4 | 113.6 |
| 1 | 12938 | Q-NC0113263 | 2 | 110.1 | 109.4 | 113.6 |
| 1 | 12938 | Q-NC0008901 | 3 | 110.8 | 109.4 | 113.6 |
| 1 | 12938 | Q-NC0143254 | 4 | 110.9 | 109.4 | 113.6 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 12938 | Q-NC0030198 | 5 | 111 | 109.4 | 113.6 |
| 1 | 12938 | Q-NC0080733 | 6 | 111 | 109.4 | 113.6 |
| 1 | 12938 | Q-NC0104474 | 7 | 111 | 109.4 | 113.6 |
| 1 | 12938 | Q-NC0033728 | 8 | 113.3 | 109.4 | 113.6 |
| 1 | 12938 | Q-NC0029506 | 9 | 113.6 | 109.4 | 113.6 |
| 1 | 12861 | Q-NC0002688 | 1 | 114.6 | 114.6 | 118.8 |
| 1 | 12861 | Q-NC0060430 | 2 | 114.8 | 114.6 | 118.8 |
| 1 | 12861 | Q-NC0004176 | 3 | 116.3 | 114.6 | 118.8 |
| 1 | 12861 | Q-NC0106144 | 4 | 116.3 | 114.6 | 118.8 |
| 1 | 12861 | Q-NC0145573 | 5 | 116.3 | 114.6 | 118.8 |
| 1 | 12861 | Q-NC0050366 | 6 | 118.7 | 114.6 | 118.8 |
| 1 | 12861 | Q-NC0039351 | 7 | 118.8 | 114.6 | 118.8 |
| 1 | 12861 | Q-NC0143864 | 8 | 118.8 | 114.6 | 118.8 |
| 1 | 12861 | Q-NC0146461 | 9 | 118.8 | 114.6 | 118.8 |
| 1 | 13081 | Q-NC0107701 | 1 | 121 | 121 | 126 |
| 1 | 13081 | Q-NC0035132 | 2 | 121.5 | 121 | 126 |
| 1 | 13081 | Q-NC0036448 | 3 | 124.4 | 121 | 126 |
| 1 | 13081 | Q-NC0034627 | 4 | 126 | 121 | 126 |
| 1 | 13081 | Q-NC0035547 | 5 | 126 | 121 | 126 |
| 1 | 13081 | Q-NC0039531 | 6 | 126 | 121 | 126 |
| 1 | 12989 | Q-NC0111780 | 1 | 126.1 | 126.1 | 130.7 |
| 1 | 12989 | Q-NC0107077 | 2 | 130.7 | 126.1 | 130.7 |
| 1 | 13018 | Q-NC0111987 | 1 | 132.8 | 132.8 | 137.4 |
| 1 | 13018 | Q-NC0108768 | 2 | 132.9 | 132.8 | 137.4 |
| 1 | 13018 | Q-NC0008719 | 3 | 137.1 | 132.8 | 137.4 |
| 1 | 13018 | Q-NC0154883 | 4 | 137.4 | 132.8 | 137.4 |
| 1 | 13091 | Q-NC0024096 | 1 | 145.2 | 145.2 | 146.1 |
| 1 | 13091 | Q-NC0155887 | 2 | 145.3 | 145.2 | 146.1 |
| 1 | 13091 | Q-NC0023774 | 3 | 146.1 | 145.2 | 146.1 |
| 1 | 12895 | Q-NC0147024 | 1 | 153.2 | 153.2 | 154.5 |
| 1 | 12895 | Q-NC0107621 | 2 | 153.5 | 153.2 | 154.5 |
| 1 | 12895 | Q-NC0012090 | 3 | 154.5 | 153.2 | 154.5 |
| 1 | 12940 | Q-NC0036863 | 1 | 159.8 | 159.8 | 164 |
| 1 | 12940 | Q-NC0041280 | 2 | 161.4 | 159.8 | 164 |
| 1 | 12940 | Q-NC0050719 | 3 | 161.4 | 159.8 | 164 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 12940 | Q-NC0081537 | 4 | 161.4 | 159.8 | 164 |
| 1 | 12940 | Q-NC0111027 | 5 | 161.4 | 159.8 | 164 |
| 1 | 12940 | Q-NC0111052 | 6 | 162.2 | 159.8 | 164 |
| 1 | 12940 | Q-NC0109328 | 7 | 162.9 | 159.8 | 164 |
| 1 | 12940 | Q-NC0042754 | 8 | 164 | 159.8 | 164 |
| 1 | 13011 | Q-NC0033373 | 1 | 166.5 | 166.5 | 171.5 |
| 1 | 13011 | Q-NC0070305 | 2 | 166.5 | 166.5 | 171.5 |
| 1 | 13011 | Q-NC0021568 | 3 | 167.1 | 166.5 | 171.5 |
| 1 | 13011 | Q-NC0070702 | 4 | 167.1 | 166.5 | 171.5 |
| 1 | 13011 | Q-NC0038475 | 5 | 168.3 | 166.5 | 171.5 |
| 1 | 13011 | Q-NC0004453 | 6 | 169.3 | 166.5 | 171.5 |
| 1 | 13011 | Q-NC0009626 | 7 | 169.6 | 166.5 | 171.5 |
| 1 | 13011 | Q-NC0113254 | 8 | 170.7 | 166.5 | 171.5 |
| 1 | 13011 | Q-NC0072095 | 9 | 171.5 | 166.5 | 171.5 |
| 1 | 12866 | Q-NC0069565 | 1 | 172.1 | 172.1 | 176.9 |
| 1 | 12866 | Q-NC0105648 | 2 | 172.2 | 172.1 | 176.9 |
| 1 | 12866 | Q-NC0067728 | 3 | 173.7 | 172.1 | 176.9 |
| 1 | 12866 | Q-NC0109882 | 4 | 174.1 | 172.1 | 176.9 |
| 1 | 12866 | Q-NC0004981 | 5 | 174.6 | 172.1 | 176.9 |
| 1 | 12866 | Q-NC0036410 | 6 | 175.6 | 172.1 | 176.9 |
| 1 | 12866 | Q-NC0034903 | 7 | 175.9 | 172.1 | 176.9 |
| 1 | 12866 | Q-NC0069344 | 8 | 176.9 | 172.1 | 176.9 |
| 1 | 12971 | Q-NC0108030 | 1 | 179.2 | 179.2 | 183.9 |
| 1 | 12971 | Q-NC0027567 | 2 | 179.4 | 179.2 | 183.9 |
| 1 | 12971 | Q-NC0040039 | 3 | 180.6 | 179.2 | 183.9 |
| 1 | 12971 | Q-NC0016724 | 4 | 180.8 | 179.2 | 183.9 |
| 1 | 12971 | Q-NC0106296 | 5 | 181 | 179.2 | 183.9 |
| 1 | 12971 | Q-NC0004909 | 6 | 182.1 | 179.2 | 183.9 |
| 1 | 12971 | Q-NC0005098 | 7 | 183.9 | 179.2 | 183.9 |
| 1 | 12998 | Q-NC0032240 | 1 | 185.3 | 185.3 | 185.3 |
| 1 | 13046 | Q-NC0039502 | 1 | 195.5 | 195.5 | 200 |
| 1 | 13046 | Q-NC0111626 | 2 | 196.4 | 195.5 | 200 |
| 1 | 13046 | Q-NC0008982 | 3 | 198.4 | 195.5 | 200 |
| 1 | 13046 | Q-NC0031993 | 4 | 199.4 | 195.5 | 200 |
| 1 | 13046 | Q-NC0040427 | 5 | 199.4 | 195.5 | 200 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 13046 | Q-NC0033427 | 6 | 199.8 | 195.5 | 200 |
| 1 | 13046 | Q-NC0148362 | 7 | 200 | 195.5 | 200 |
| 1 | 13015 | Q-NC0113311 | 1 | 201.5 | 201.5 | 205.9 |
| 1 | 13015 | Q-NC0016674 | 2 | 202.2 | 201.5 | 205.9 |
| 1 | 13015 | Q-NC0035891 | 3 | 202.2 | 201.5 | 205.9 |
| 1 | 13015 | Q-NC0066464 | 4 | 202.2 | 201.5 | 205.9 |
| 1 | 13015 | Q-NC0147205 | 5 | 202.2 | 201.5 | 205.9 |
| 1 | 13015 | Q-NC0013584 | 6 | 204.4 | 201.5 | 205.9 |
| 1 | 13015 | Q-NC0111792 | 7 | 205.8 | 201.5 | 205.9 |
| 1 | 13015 | Q-NC0031264 | 8 | 205.9 | 201.5 | 205.9 |
| 1 | 12878 | Q-NC0035961 | 1 | 206.7 | 206.7 | 208.9 |
| 1 | 12878 | Q-NC0039896 | 2 | 207.6 | 206.7 | 208.9 |
| 1 | 12878 | Q-NC0009701 | 3 | 207.9 | 206.7 | 208.9 |
| 1 | 12878 | Q-NC0014038 | 4 | 207.9 | 206.7 | 208.9 |
| 1 | 12878 | Q-NC0016059 | 5 | 207.9 | 206.7 | 208.9 |
| 1 | 12878 | Q-NC0039486 | 6 | 207.9 | 206.7 | 208.9 |
| 1 | 12878 | Q-NC0153437 | 7 | 207.9 | 206.7 | 208.9 |
| 1 | 12878 | Q-NC0110452 | 8 | 208.9 | 206.7 | 208.9 |
| 1 | 12880 | Q-NC0009082 | 1 | 212.7 | 212.7 | 212.7 |
| 1 | 12992 | Q-NC0015344 | 1 | 221.1 | 221.1 | 221.1 |
| 1 | 12923 | Q-NC0111218 | 1 | 229.4 | 229.4 | 229.4 |
| 1 | 13045 | Q-NC0146570 | 1 | 237 | 237 | 240.7 |
| 1 | 13045 | Q-NC0008996 | 2 | 238.1 | 237 | 240.7 |
| 1 | 13045 | Q-NC0013490 | 3 | 240.7 | 237 | 240.7 |
| 1 | 12910 | Q-NC0030840 | 1 | 245.1 | 245.1 | 245.1 |
| 1 | 12945 | Q-NC0002635 | 1 | 254.8 | 254.8 | 256.5 |
| 1 | 12945 | Q-NC0016137 | 2 | 256.3 | 254.8 | 256.5 |
| 1 | 12945 | Q-NC0005177 | 3 | 256.5 | 254.8 | 256.5 |
| 2 | 12905 | Q-NC0031064 | 1 | 2.9 | 2.9 | 7 |
| 2 | 12905 | Q-NC0009867 | 2 | 3.3 | 2.9 | 7 |
| 2 | 12905 | Q-NC0015766 | 3 | 7 | 2.9 | 7 |
| 2 | 12882 | Q-NC0005133 | 1 | 9.7 | 9.7 | 10.1 |
| 2 | 12882 | Q-NC0009766 | 2 | 10.1 | 9.7 | 10.1 |
| 2 | 13012 | Q-NC0033786 | 1 | 15.2 | 15.2 | 19.7 |
| 2 | 13012 | Q-NC0104447 | 2 | 15.2 | 15.2 | 19.7 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 2 | 13012 | Q-NC0106295 | 3 | 15.2 | 15.2 | 19.7 |
| 2 | 13012 | Q-NC0143411 | 4 | 15.4 | 15.2 | 19.7 |
| 2 | 13012 | Q-NC0106352 | 5 | 15.8 | 15.2 | 19.7 |
| 2 | 13012 | Q-NC0106678 | 6 | 18.3 | 15.2 | 19.7 |
| 2 | 13012 | Q-NC0082235 | 7 | 19.7 | 15.2 | 19.7 |
| 2 | 12879 | Q-NC0003388 | 1 | 27.5 | 27.5 | 30.7 |
| 2 | 12879 | Q-NC0076912 | 2 | 27.5 | 27.5 | 30.7 |
| 2 | 12879 | Q-NC0002814 | 3 | 27.9 | 27.5 | 30.7 |
| 2 | 12879 | Q-NC0024116 | 4 | 28.3 | 27.5 | 30.7 |
| 2 | 12879 | Q-NC0002945 | 5 | 30.7 | 27.5 | 30.7 |
| 2 | 12879 | Q-NC0016074 | 6 | 30.7 | 27.5 | 30.7 |
| 2 | 12968 | Q-NC0080031 | 1 | 33.1 | 33.1 | 35.9 |
| 2 | 12968 | Q-NC0080035 | 2 | 33.1 | 33.1 | 35.9 |
| 2 | 12968 | Q-NC0004265 | 3 | 33.9 | 33.1 | 35.9 |
| 2 | 12968 | Q-NC0050315 | 4 | 34 | 33.1 | 35.9 |
| 2 | 12968 | Q-NC0019127 | 5 | 35.5 | 33.1 | 35.9 |
| 2 | 12968 | Q-NC0009706 | 6 | 35.9 | 33.1 | 35.9 |
| 2 | 12884 | Q-NC0107479 | 1 | 42.3 | 42.3 | 46.8 |
| 2 | 12884 | Q-NC0109140 | 2 | 44.8 | 42.3 | 46.8 |
| 2 | 12884 | Q-NC0048553 | 3 | 46.8 | 42.3 | 46.8 |
| 2 | 13042 | Q-NC0078243 | 1 | 48.8 | 48.8 | 48.8 |
| 2 | 12893 | Q-NC0020105 | 1 | 64.6 | 64.6 | 68.5 |
| 2 | 12893 | Q-NC0106391 | 2 | 65.8 | 64.6 | 68.5 |
| 2 | 12893 | Q-NC0002812 | 3 | 65.9 | 64.6 | 68.5 |
| 2 | 12893 | Q-NC0080704 | 4 | 68.5 | 64.6 | 68.5 |
| 2 | 12893 | Q-NC0080705 | 5 | 68.5 | 64.6 | 68.5 |
| 2 | 13032 | Q-NC0009364 | 1 | 71.6 | 71.6 | 74.8 |
| 2 | 13032 | Q-NC0032200 | 2 | 71.6 | 71.6 | 74.8 |
| 2 | 13032 | Q-NC0004697 | 3 | 74.8 | 71.6 | 74.8 |
| 2 | 13032 | Q-NC0104946 | 4 | 74.8 | 71.6 | 74.8 |
| 2 | 13054 | Q-NC0042242 | 1 | 77 | 77 | 81.8 |
| 2 | 13054 | Q-NC0015022 | 2 | 77.3 | 77 | 81.8 |
| 2 | 13054 | Q-NC0111617 | 3 | 78.2 | 77 | 81.8 |
| 2 | 13054 | Q-NC0036323 | 4 | 80.4 | 77 | 81.8 |
| 2 | 13054 | Q-NC0148248 | 5 | 81.4 | 77 | 81.8 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 2 | 13054 | Q-NC0153250 | 6 | 81.8 | 77 | 81.8 |
| 2 | 12927 | Q-NC0016297 | 1 | 85 | 85 | 89.6 |
| 2 | 12927 | Q-NC0110133 | 2 | 85 | 85 | 89.6 |
| 2 | 12927 | Q-NC0011466 | 3 | 86.2 | 85 | 89.6 |
| 2 | 12927 | Q-NC0049430 | 4 | 87.7 | 85 | 89.6 |
| 2 | 12927 | Q-NC0105002 | 5 | 88.6 | 85 | 89.6 |
| 2 | 12927 | Q-NC0108493 | 6 | 88.6 | 85 | 89.6 |
| 2 | 12927 | Q-NC0146518 | 7 | 89.4 | 85 | 89.6 |
| 2 | 12927 | Q-NC0104479 | 8 | 89.6 | 85 | 89.6 |
| 2 | 12932 | Q-NC0053463 | 1 | 93.1 | 93.1 | 94.7 |
| 2 | 12932 | Q-NC0027319 | 2 | 93.2 | 93.1 | 94.7 |
| 2 | 12932 | Q-NC0021092 | 3 | 93.4 | 93.1 | 94.7 |
| 2 | 12932 | Q-NC0107090 | 4 | 93.4 | 93.1 | 94.7 |
| 2 | 12932 | Q-NC0057604 | 5 | 94 | 93.1 | 94.7 |
| 2 | 12932 | Q-NC0005467 | 6 | 94.3 | 93.1 | 94.7 |
| 2 | 12932 | Q-NC0105696 | 7 | 94.3 | 93.1 | 94.7 |
| 2 | 12932 | Q-NC0082768 | 8 | 94.4 | 93.1 | 94.7 |
| 2 | 12932 | Q-NC0146130 | 9 | 94.6 | 93.1 | 94.7 |
| 2 | 12932 | Q-NC0019874 | 10 | 94.7 | 93.1 | 94.7 |
| 2 | 13004 | Q-NC0002468 | 1 | 94.9 | 94.9 | 99.2 |
| 2 | 13004 | Q-NC0032601 | 2 | 94.9 | 94.9 | 99.2 |
| 2 | 13004 | Q-NC0013347 | 3 | 96 | 94.9 | 99.2 |
| 2 | 13004 | Q-NC0079826 | 4 | 96 | 94.9 | 99.2 |
| 2 | 13004 | Q-NC0060879 | 5 | 97.7 | 94.9 | 99.2 |
| 2 | 13004 | Q-NC0000066 | 6 | 98.3 | 94.9 | 99.2 |
| 2 | 13004 | Q-NC0107911 | 7 | 99.2 | 94.9 | 99.2 |
| 2 | 13004 | Q-NC0107948 | 8 | 99.2 | 94.9 | 99.2 |
| 2 | 13071 | Q-NC0106729 | 1 | 100.2 | 100.2 | 103.9 |
| 2 | 13071 | Q-NC0106407 | 2 | 101.3 | 100.2 | 103.9 |
| 2 | 13071 | Q-NC0112226 | 3 | 101.5 | 100.2 | 103.9 |
| 2 | 13071 | Q-NC0112229 | 4 | 101.5 | 100.2 | 103.9 |
| 2 | 13071 | Q-NC0108607 | 5 | 102.1 | 100.2 | 103.9 |
| 2 | 13071 | Q-NC0153941 | 6 | 102.1 | 100.2 | 103.9 |
| 2 | 13071 | Q-NC0053097 | 7 | 102.6 | 100.2 | 103.9 |
| 2 | 13071 | Q-NC0107736 | 8 | 102.8 | 100.2 | 103.9 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 2 | 13071 | Q-NC0000551 | 9 | 103.6 | 100.2 | 103.9 |
| 2 | 13071 | Q-NC0059782 | 10 | 103.9 | 100.2 | 103.9 |
| 2 | 12865 | Q-NC0057210 | 1 | 104.1 | 104.1 | 107.6 |
| 2 | 12865 | Q-NC0000366 | 2 | 104.9 | 104.1 | 107.6 |
| 2 | 12865 | Q-NC0151288 | 3 | 107.6 | 104.1 | 107.6 |
| 2 | 12949 | Q-NC0082458 | 1 | 112.4 | 112.4 | 116.7 |
| 2 | 12949 | Q-NC0031289 | 2 | 114.8 | 112.4 | 116.7 |
| 2 | 12949 | Q-NC0108013 | 3 | 115.3 | 112.4 | 116.7 |
| 2 | 12949 | Q-NC0111475 | 4 | 115.7 | 112.4 | 116.7 |
| 2 | 12949 | Q-NC0044080 | 5 | 116.7 | 112.4 | 116.7 |
| 2 | 12907 | Q-NC0022775 | 1 | 118.1 | 118.1 | 120.4 |
| 2 | 12907 | Q-NC0104954 | 2 | 120.4 | 118.1 | 120.4 |
| 2 | 12907 | Q-NC0107850 | 3 | 120.4 | 118.1 | 120.4 |
| 2 | 12988 | Q-NC0084632 | 1 | 124.1 | 124.1 | 128.8 |
| 2 | 12988 | Q-NC0084633 | 2 | 124.6 | 124.1 | 128.8 |
| 2 | 12988 | Q-NC0000069 | 3 | 125.1 | 124.1 | 128.8 |
| 2 | 12988 | Q-NC0082265 | 4 | 125.8 | 124.1 | 128.8 |
| 2 | 12988 | Q-NC0109393 | 5 | 127.1 | 124.1 | 128.8 |
| 2 | 12988 | Q-NC0029138 | 6 | 127.6 | 124.1 | 128.8 |
| 2 | 12988 | Q-NC0147676 | 7 | 127.6 | 124.1 | 128.8 |
| 2 | 12988 | Q-NC0040472 | 8 | 128.8 | 124.1 | 128.8 |
| 2 | 12988 | Q-NC0041850 | 9 | 128.8 | 124.1 | 128.8 |
| 2 | 13087 | Q-NC0009102 | 1 | 130 | 130 | 130 |
| 2 | 13087 | Q-NC0024089 | 2 | 130 | 130 | 130 |
| 2 | 12873 | Q-NC0009818 | 1 | 136.5 | 136.5 | 141.4 |
| 2 | 12873 | Q-NC0105556 | 2 | 139.5 | 136.5 | 141.4 |
| 2 | 12873 | Q-NC0031474 | 3 | 141.4 | 136.5 | 141.4 |
| 2 | 13022 | Q-NC0002878 | 1 | 145.1 | 145.1 | 147.6 |
| 2 | 13022 | Q-NC0005088 | 2 | 147.6 | 145.1 | 147.6 |
| 2 | 13043 | Q-NC0035297 | 1 | 150.7 | 150.7 | 151.1 |
| 2 | 13043 | Q-NC0155994 | 2 | 151.1 | 150.7 | 151.1 |
| 2 | 12891 | Q-NC0019267 | 1 | 157.5 | 157.5 | 157.5 |
| 2 | 13027 | Q-NC0043579 | 1 | 163.8 | 163.8 | 167.3 |
| 2 | 13027 | Q-NC0147548 | 2 | 163.8 | 163.8 | 167.3 |
| 2 | 13027 | Q-NC0005214 | 3 | 164.3 | 163.8 | 167.3 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 2 | 13027 | Q-NC0014467 | 4 | 167.3 | 163.8 | 167.3 |
| 2 | 12947 | Q-NC0003241 | 1 | 169.8 | 169.8 | 174.2 |
| 2 | 12947 | Q-NC0008930 | 2 | 174.2 | 169.8 | 174.2 |
| 2 | 12947 | Q-NC0029041 | 3 | 174.2 | 169.8 | 174.2 |
| 2 | 13062 | Q-NC0023748 | 1 | 181.9 | 181.9 | 185.5 |
| 2 | 13062 | Q-NC0104359 | 2 | 182.5 | 181.9 | 185.5 |
| 2 | 13062 | Q-NC0035238 | 3 | 185.5 | 181.9 | 185.5 |
| 2 | 13062 | Q-NC0110974 | 4 | 185.5 | 181.9 | 185.5 |
| 2 | 12997 | Q-NC0107149 | 1 | 190.1 | 190.1 | 191.5 |
| 2 | 12997 | Q-NC0076792 | 2 | 190.8 | 190.1 | 191.5 |
| 2 | 12997 | Q-NC0011740 | 3 | 190.9 | 190.1 | 191.5 |
| 2 | 12997 | Q-NC0000735 | 4 | 191.5 | 190.1 | 191.5 |
| 2 | 12997 | Q-NC0077782 | 5 | 191.5 | 190.1 | 191.5 |
| 3 | 12904 | Q-NC0020971 | 1 | 13.9 | 13.9 | 18.5 |
| 3 | 12904 | Q-NC0106389 | 2 | 14.2 | 13.9 | 18.5 |
| 3 | 12904 | Q-NC0002719 | 3 | 18.5 | 13.9 | 18.5 |
| 3 | 12870 | Q-NC0008911 | 1 | 19.9 | 19.9 | 24.6 |
| 3 | 12870 | Q-NC0051614 | 2 | 19.9 | 19.9 | 24.6 |
| 3 | 12870 | Q-NC0106276 | 3 | 20 | 19.9 | 24.6 |
| 3 | 12870 | Q-NC0104528 | 4 | 24.6 | 19.9 | 24.6 |
| 3 | 12946 | Q-NC0048700 | 1 | 31.3 | 31.3 | 31.3 |
| 3 | 12919 | Q-NC0032137 | 1 | 40.2 | 40.2 | 40.6 |
| 3 | 12919 | Q-NC0019963 | 2 | 40.6 | 40.2 | 40.6 |
| 3 | 13084 | Q-NC0000423 | 1 | 49.9 | 49.9 | 54.4 |
| 3 | 13084 | Q-NC0106329 | 2 | 53.9 | 49.9 | 54.4 |
| 3 | 13084 | Q-NC0004821 | 3 | 54.4 | 49.9 | 54.4 |
| 3 | 12897 | Q-NC0049293 | 1 | 69.9 | 69.9 | 69.9 |
| 3 | 13036 | Q-NC0108727 | 1 | 77.4 | 77.4 | 77.4 |
| 3 | 12996 | Q-NC0004599 | 1 | 82.9 | 82.9 | 83.5 |
| 3 | 12996 | Q-NC0021154 | 2 | 82.9 | 82.9 | 83.5 |
| 3 | 12996 | Q-NC0147768 | 3 | 82.9 | 82.9 | 83.5 |
| 3 | 12996 | Q-NC0028923 | 4 | 83.1 | 82.9 | 83.5 |
| 3 | 12996 | Q-NC0147511 | 5 | 83.1 | 82.9 | 83.5 |
| 3 | 12996 | Q-NC0024631 | 6 | 83.2 | 82.9 | 83.5 |
| 3 | 12996 | Q-NC0105291 | 7 | 83.2 | 82.9 | 83.5 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 3 | 12996 | Q-NC0106515 | 8 | 83.2 | 82.9 | 83.5 |
| 3 | 12996 | Q-NC0110326 | 9 | 83.2 | 82.9 | 83.5 |
| 3 | 12996 | Q-NC0021190 | 10 | 83.5 | 82.9 | 83.5 |
| 3 | 13007 | Q-NC0010220 | 1 | 83.6 | 83.6 | 88 |
| 3 | 13007 | Q-NC0012017 | 2 | 85.7 | 83.6 | 88 |
| 3 | 13007 | Q-NC0008685 | 3 | 86.5 | 83.6 | 88 |
| 3 | 13007 | Q-NC0143268 | 4 | 86.5 | 83.6 | 88 |
| 3 | 13007 | Q-NC0016729 | 5 | 86.8 | 83.6 | 88 |
| 3 | 13007 | Q-NC0145322 | 6 | 87.1 | 83.6 | 88 |
| 3 | 13007 | Q-NC0002207 | 7 | 87.9 | 83.6 | 88 |
| 3 | 13007 | Q-NC0009468 | 8 | 88 | 83.6 | 88 |
| 3 | 12913 | Q-NC0031647 | 1 | 89.5 | 89.5 | 94.5 |
| 3 | 12913 | Q-NC0144001 | 2 | 91.9 | 89.5 | 94.5 |
| 3 | 12913 | Q-NC0040104 | 3 | 92.2 | 89.5 | 94.5 |
| 3 | 12913 | Q-NC0106440 | 4 | 92.3 | 89.5 | 94.5 |
| 3 | 12913 | Q-NC0035187 | 5 | 93.9 | 89.5 | 94.5 |
| 3 | 12913 | Q-NC0039003 | 6 | 94 | 89.5 | 94.5 |
| 3 | 12913 | Q-NC0146158 | 7 | 94 | 89.5 | 94.5 |
| 3 | 12913 | Q-NC0039785 | 8 | 94.5 | 89.5 | 94.5 |
| 3 | 12913 | Q-NC0082153 | 9 | 94.5 | 89.5 | 94.5 |
| 3 | 12913 | Q-NC0082160 | 10 | 94.5 | 89.5 | 94.5 |
| 3 | 12982 | Q-NC0146230 | 1 | 96.2 | 96.2 | 100.6 |
| 3 | 12982 | Q-NC0008900 | 2 | 97.6 | 96.2 | 100.6 |
| 3 | 12982 | Q-NC0010933 | 3 | 99.3 | 96.2 | 100.6 |
| 3 | 12982 | Q-NC0031720 | 4 | 99.7 | 96.2 | 100.6 |
| 3 | 12982 | Q-NC0107671 | 5 | 100.6 | 96.2 | 100.6 |
| 3 | 13092 | Q-NC0009739 | 1 | 102.2 | 102.2 | 106.3 |
| 3 | 13092 | Q-NC0022590 | 2 | 104 | 102.2 | 106.3 |
| 3 | 13092 | Q-NC0104504 | 3 | 104 | 102.2 | 106.3 |
| 3 | 13092 | Q-NC0013092 | 4 | 105.4 | 102.2 | 106.3 |
| 3 | 13092 | Q-NC0108089 | 5 | 106.3 | 102.2 | 106.3 |
| 3 | 13038 | Q-NC0154505 | 1 | 109.3 | 109.3 | 112.4 |
| 3 | 13038 | Q-NC0154509 | 2 | 109.3 | 109.3 | 112.4 |
| 3 | 13038 | Q-NC0154511 | 3 | 109.3 | 109.3 | 112.4 |
| 3 | 13038 | Q-NC0155689 | 4 | 109.3 | 109.3 | 112.4 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 3 | 13038 | Q-NC0155708 | 5 | 109.3 | 109.3 | 112.4 |
| 3 | 13038 | Q-NC0153431 | 6 | 110.6 | 109.3 | 112.4 |
| 3 | 13038 | Q-NC0144126 | 7 | 111.6 | 109.3 | 112.4 |
| 3 | 13038 | Q-NC0055894 | 8 | 112.4 | 109.3 | 112.4 |
| 3 | 13038 | Q-NC0144823 | 9 | 112.4 | 109.3 | 112.4 |
| 3 | 13038 | Q-NC0145616 | 10 | 112.4 | 109.3 | 112.4 |
| 3 | 12948 | Q-NC0024395 | 1 | 116 | 116 | 120.6 |
| 3 | 12948 | Q-NC0079081 | 2 | 117.1 | 116 | 120.6 |
| 3 | 12948 | Q-NC0111959 | 3 | 117.6 | 116 | 120.6 |
| 3 | 12948 | Q-NC0023890 | 4 | 119.5 | 116 | 120.6 |
| 3 | 12948 | Q-NC0106349 | 5 | 120.6 | 116 | 120.6 |
| 3 | 12942 | Q-NC0002905 | 1 | 123.9 | 123.9 | 128.2 |
| 3 | 12942 | Q-NC0009173 | 2 | 124.2 | 123.9 | 128.2 |
| 3 | 12942 | Q-NC0011320 | 3 | 124.2 | 123.9 | 128.2 |
| 3 | 12942 | Q-NC0144788 | 4 | 125.7 | 123.9 | 128.2 |
| 3 | 12942 | Q-NC0008922 | 5 | 128.2 | 123.9 | 128.2 |
| 3 | 12990 | Q-NC0040232 | 1 | 139.8 | 139.8 | 141 |
| 3 | 12990 | Q-NC0031450 | 2 | 139.9 | 139.8 | 141 |
| 3 | 12990 | Q-NC0015954 | 3 | 141 | 139.8 | 141 |
| 3 | 12990 | Q-NC0034494 | 4 | 141 | 139.8 | 141 |
| 3 | 13000 | Q-NC0039763 | 1 | 145.4 | 145.4 | 150.2 |
| 3 | 13000 | Q-NC0041040 | 2 | 145.4 | 145.4 | 150.2 |
| 3 | 13000 | Q-NC0077118 | 3 | 145.9 | 145.4 | 150.2 |
| 3 | 13000 | Q-NC0015865 | 4 | 147.5 | 145.4 | 150.2 |
| 3 | 13000 | Q-NC0004013 | 5 | 148.1 | 145.4 | 150.2 |
| 3 | 13000 | Q-NC0036694 | 6 | 148.1 | 145.4 | 150.2 |
| 3 | 13000 | Q-NC0036695 | 7 | 148.1 | 145.4 | 150.2 |
| 3 | 13000 | Q-NC0017494 | 8 | 148.4 | 145.4 | 150.2 |
| 3 | 13000 | Q-NC0147952 | 9 | 150.2 | 145.4 | 150.2 |
| 3 | 12931 | Q-NC0043810 | 1 | 151.9 | 151.9 | 155.3 |
| 3 | 12931 | Q-NC0028736 | 2 | 152.7 | 151.9 | 155.3 |
| 3 | 12931 | Q-NC0029390 | 3 | 152.7 | 151.9 | 155.3 |
| 3 | 12931 | Q-NC0021772 | 4 | 154.1 | 151.9 | 155.3 |
| 3 | 12931 | Q-NC0105966 | 5 | 154.6 | 151.9 | 155.3 |
| 3 | 12931 | Q-NC0146188 | 6 | 154.6 | 151.9 | 155.3 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 3 | 12931 | Q-NC0054742 | 7 | 155.3 | 151.9 | 155.3 |
| 3 | 13085 | Q-NC0111204 | 1 | 161.4 | 161.4 | 164.2 |
| 3 | 13085 | Q-NC0143174 | 2 | 161.4 | 161.4 | 164.2 |
| 3 | 13085 | Q-NC0071496 | 3 | 161.7 | 161.4 | 164.2 |
| 3 | 13085 | Q-NC0069529 | 4 | 163.2 | 161.4 | 164.2 |
| 3 | 13085 | Q-NC0108630 | 5 | 163.5 | 161.4 | 164.2 |
| 3 | 13085 | Q-NC0004371 | 6 | 164.2 | 161.4 | 164.2 |
| 3 | 13085 | Q-NC0040437 | 7 | 164.2 | 161.4 | 164.2 |
| 3 | 12951 | Q-NC0009473 | 1 | 168.4 | 168.4 | 171.3 |
| 3 | 12951 | Q-NC0031216 | 2 | 171.3 | 168.4 | 171.3 |
| 3 | 12875 | Q-NC0021603 | 1 | 175.6 | 175.6 | 177.1 |
| 3 | 12875 | Q-NC0110780 | 2 | 176.8 | 175.6 | 177.1 |
| 3 | 12875 | Q-NC0055817 | 3 | 177.1 | 175.6 | 177.1 |
| 3 | 12860 | Q-NC0112487 | 1 | 182.9 | 182.9 | 187.5 |
| 3 | 12860 | Q-NC0112491 | 2 | 182.9 | 182.9 | 187.5 |
| 3 | 12860 | Q-NC0056939 | 3 | 183.6 | 182.9 | 187.5 |
| 3 | 12860 | Q-NC0032026 | 4 | 183.9 | 182.9 | 187.5 |
| 3 | 12860 | Q-NC0154169 | 5 | 184.3 | 182.9 | 187.5 |
| 3 | 12860 | Q-NC0146497 | 6 | 187.4 | 182.9 | 187.5 |
| 3 | 12860 | Q-NC0155987 | 7 | 187.4 | 182.9 | 187.5 |
| 3 | 12860 | Q-NC0028145 | 8 | 187.5 | 182.9 | 187.5 |
| 3 | 12860 | Q-NC0143969 | 9 | 187.5 | 182.9 | 187.5 |
| 3 | 13044 | Q-NC0009079 | 1 | 194.2 | 194.2 | 198.7 |
| 3 | 13044 | Q-NC0110756 | 2 | 197.4 | 194.2 | 198.7 |
| 3 | 13044 | Q-NC0010232 | 3 | 198.7 | 194.2 | 198.7 |
| 3 | 13033 | Q-NC0019414 | 1 | 204.2 | 204.2 | 208 |
| 3 | 13033 | Q-NC0040000 | 2 | 207.1 | 204.2 | 208 |
| 3 | 13033 | Q-NC0003970 | 3 | 208 | 204.2 | 208 |
| 3 | 12978 | Q-NC0104796 | 1 | 212.1 | 212.1 | 212.1 |
| 3 | 13055 | Q-NC0014041 | 1 | 217.6 | 217.6 | 218.7 |
| 3 | 13055 | Q-NC0077802 | 2 | 218.7 | 217.6 | 218.7 |
| 4 | 13019 | Q-NC0012340 | 1 | 0.5 | 0.5 | 1.8 |
| 4 | 13019 | Q-NC0009523 | 2 | 0.9 | 0.5 | 1.8 |
| 4 | 13019 | Q-NC0055502 | 3 | 1.8 | 0.5 | 1.8 |
| 4 | 13079 | Q-NC0002739 | 1 | 11.8 | 11.8 | 11.8 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 13024 | Q-NC0009057 | 1 | 21.7 | 21.7 | 21.9 |
| 4 | 13024 | Q-NC0069221 | 2 | 21.9 | 21.7 | 21.9 |
| 4 | 12912 | Q-NC0105666 | 1 | 30.4 | 30.4 | 34.4 |
| 4 | 12912 | Q-NC0110069 | 2 | 34.4 | 30.4 | 34.4 |
| 4 | 12912 | Q-NC0111464 | 3 | 34.4 | 30.4 | 34.4 |
| 4 | 13029 | Q-NC0019003 | 1 | 45.3 | 45.3 | 49.9 |
| 4 | 13029 | Q-NC0034133 | 2 | 49.8 | 45.3 | 49.9 |
| 4 | 13029 | Q-NC0034130 | 3 | 49.9 | 45.3 | 49.9 |
| 4 | 12888 | Q-NC0024647 | 1 | 52.5 | 52.5 | 53 |
| 4 | 12888 | Q-NC0143419 | 2 | 53 | 52.5 | 53 |
| 4 | 12974 | Q-NC0037062 | 1 | 59.7 | 59.7 | 64.3 |
| 4 | 12974 | Q-NC0001122 | 2 | 61.4 | 59.7 | 64.3 |
| 4 | 12974 | Q-NC0012012 | 3 | 61.4 | 59.7 | 64.3 |
| 4 | 12974 | Q-NC0034325 | 4 | 63.7 | 59.7 | 64.3 |
| 4 | 12974 | Q-NC0023529 | 5 | 64.3 | 59.7 | 64.3 |
| 4 | 13083 | Q-NC0015735 | 1 | 65.5 | 65.5 | 68.4 |
| 4 | 13083 | Q-NC0069795 | 2 | 65.5 | 65.5 | 68.4 |
| 4 | 13083 | Q-NC0042575 | 3 | 65.9 | 65.5 | 68.4 |
| 4 | 13083 | Q-NC0028441 | 4 | 67.1 | 65.5 | 68.4 |
| 4 | 13083 | Q-NC0038855 | 5 | 67.1 | 65.5 | 68.4 |
| 4 | 13083 | Q-NC0034462 | 6 | 67.8 | 65.5 | 68.4 |
| 4 | 13083 | Q-NC0040371 | 7 | 67.8 | 65.5 | 68.4 |
| 4 | 13083 | Q-NC0070730 | 8 | 67.8 | 65.5 | 68.4 |
| 4 | 13083 | Q-NC0010305 | 9 | 68.4 | 65.5 | 68.4 |
| 4 | 13083 | Q-NC0035683 | 10 | 68.4 | 65.5 | 68.4 |
| 4 | 12987 | Q-NC0008936 | 1 | 68.6 | 68.6 | 73.5 |
| 4 | 12987 | Q-NC0038900 | 2 | 69.3 | 68.6 | 73.5 |
| 4 | 12987 | Q-NC0009603 | 3 | 69.5 | 68.6 | 73.5 |
| 4 | 12987 | Q-NC0033483 | 4 | 69.5 | 68.6 | 73.5 |
| 4 | 12987 | Q-NC0031791 | 5 | 70.1 | 68.6 | 73.5 |
| 4 | 12987 | Q-NC0020481 | 6 | 71 | 68.6 | 73.5 |
| 4 | 12987 | Q-NC0108120 | 7 | 71.5 | 68.6 | 73.5 |
| 4 | 12987 | Q-NC0034464 | 8 | 73.5 | 68.6 | 73.5 |
| 4 | 12987 | Q-NC0151401 | 9 | 73.5 | 68.6 | 73.5 |
| 4 | 12963 | Q-NC0033667 | 1 | 73.7 | 73.7 | 76 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 12963 | Q-NC0036528 | 2 | 74 | 73.7 | 76 |
| 4 | 12963 | Q-NC0002585 | 3 | 74.4 | 73.7 | 76 |
| 4 | 12963 | Q-NC0015574 | 4 | 74.4 | 73.7 | 76 |
| 4 | 12963 | Q-NC0005451 | 5 | 74.8 | 73.7 | 76 |
| 4 | 12963 | Q-NC0015096 | 6 | 74.8 | 73.7 | 76 |
| 4 | 12963 | Q-NC0003351 | 7 | 76 | 73.7 | 76 |
| 4 | 12963 | Q-NC0015247 | 8 | 76 | 73.7 | 76 |
| 4 | 12963 | Q-NC0037514 | 9 | 76 | 73.7 | 76 |
| 4 | 12963 | Q-NC0153424 | 10 | 76 | 73.7 | 76 |
| 4 | 12900 | Q-NC0004924 | 1 | 76.3 | 76.3 | 79.8 |
| 4 | 12900 | Q-NC0113163 | 2 | 76.3 | 76.3 | 79.8 |
| 4 | 12900 | Q-NC0014666 | 3 | 77.8 | 76.3 | 79.8 |
| 4 | 12900 | Q-NC0020374 | 4 | 77.8 | 76.3 | 79.8 |
| 4 | 12900 | Q-NC0068131 | 5 | 77.8 | 76.3 | 79.8 |
| 4 | 12900 | Q-NC0078135 | 6 | 77.8 | 76.3 | 79.8 |
| 4 | 12900 | Q-NC0000415 | 7 | 78.9 | 76.3 | 79.8 |
| 4 | 12900 | Q-NC0040351 | 8 | 78.9 | 76.3 | 79.8 |
| 4 | 12900 | Q-NC0153429 | 9 | 78.9 | 76.3 | 79.8 |
| 4 | 12900 | Q-NC0106099 | 10 | 79.8 | 76.3 | 79.8 |
| 4 | 12959 | Q-NC0039640 | 1 | 81 | 81 | 82.7 |
| 4 | 12959 | Q-NC0003532 | 2 | 81.3 | 81 | 82.7 |
| 4 | 12959 | Q-NC0003533 | 3 | 81.3 | 81 | 82.7 |
| 4 | 12959 | Q-NC0037473 | 4 | 81.3 | 81 | 82.7 |
| 4 | 12959 | Q-NC0080475 | 5 | 82 | 81 | 82.7 |
| 4 | 12959 | Q-NC0084527 | 6 | 82 | 81 | 82.7 |
| 4 | 12959 | Q-NC0027345 | 7 | 82.5 | 81 | 82.7 |
| 4 | 12959 | Q-NC0143732 | 8 | 82.5 | 81 | 82.7 |
| 4 | 12959 | Q-NC0104667 | 9 | 82.7 | 81 | 82.7 |
| 4 | 12959 | Q-NC0104906 | 10 | 82.7 | 81 | 82.7 |
| 4 | 13061 | Q-NC0106797 | 1 | 82.9 | 82.9 | 85.2 |
| 4 | 13061 | Q-NC0104785 | 2 | 83.9 | 82.9 | 85.2 |
| 4 | 13061 | Q-NC0035294 | 3 | 85.2 | 82.9 | 85.2 |
| 4 | 13082 | Q-NC0037873 | 1 | 88.3 | 88.3 | 92.4 |
| 4 | 13082 | Q-NC0038782 | 2 | 90.4 | 88.3 | 92.4 |
| 4 | 13082 | Q-NC0069570 | 3 | 92.4 | 88.3 | 92.4 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 12862 | Q-NC0002474 | 1 | 93.6 | 93.6 | 95.2 |
| 4 | 12862 | Q-NC0005018 | 2 | 94.8 | 93.6 | 95.2 |
| 4 | 12862 | Q-NC0038087 | 3 | 94.8 | 93.6 | 95.2 |
| 4 | 12862 | Q-NC0105550 | 4 | 94.8 | 93.6 | 95.2 |
| 4 | 12862 | Q-NC0106845 | 5 | 94.8 | 93.6 | 95.2 |
| 4 | 12862 | Q-NC0032557 | 6 | 95.1 | 93.6 | 95.2 |
| 4 | 12862 | Q-NC0040744 | 7 | 95.2 | 93.6 | 95.2 |
| 4 | 13006 | Q-NC0105197 | 1 | 99.9 | 99.9 | 104.7 |
| 4 | 13006 | Q-NC0003695 | 2 | 104.2 | 99.9 | 104.7 |
| 4 | 13006 | Q-NC0077408 | 3 | 104.3 | 99.9 | 104.7 |
| 4 | 13006 | Q-NC0003964 | 4 | 104.4 | 99.9 | 104.7 |
| 4 | 13006 | Q-NC0040117 | 5 | 104.4 | 99.9 | 104.7 |
| 4 | 13006 | Q-NC0107840 | 6 | 104.4 | 99.9 | 104.7 |
| 4 | 13006 | Q-NC0003274 | 7 | 104.7 | 99.9 | 104.7 |
| 4 | 13006 | Q-NC0009280 | 8 | 104.7 | 99.9 | 104.7 |
| 4 | 13006 | Q-NC0040534 | 9 | 104.7 | 99.9 | 104.7 |
| 4 | 13060 | Q-NC0070043 | 1 | 105.7 | 105.7 | 109.2 |
| 4 | 13060 | Q-NC0009620 | 2 | 109.2 | 105.7 | 109.2 |
| 4 | 13105 | Q-NC0036240 | 1 | 112 | 112 | 115.7 |
| 4 | 13105 | Q-NC0036239 | 2 | 112.1 | 112 | 115.7 |
| 4 | 13105 | Q-NC0110078 | 3 | 115.7 | 112 | 115.7 |
| 4 | 12976 | Q-NC0039511 | 1 | 121.5 | 121.5 | 125.9 |
| 4 | 12976 | Q-NC0106491 | 2 | 125.9 | 121.5 | 125.9 |
| 4 | 12881 | Q-NC0023289 | 1 | 126.7 | 126.7 | 130.2 |
| 4 | 12881 | Q-NC0030070 | 2 | 127 | 126.7 | 130.2 |
| 4 | 12881 | Q-NC0151518 | 3 | 127 | 126.7 | 130.2 |
| 4 | 12881 | Q-NC0112809 | 4 | 127.5 | 126.7 | 130.2 |
| 4 | 12881 | Q-NC0028933 | 5 | 127.6 | 126.7 | 130.2 |
| 4 | 12881 | Q-NC0029886 | 6 | 127.8 | 126.7 | 130.2 |
| 4 | 12881 | Q-NC0008979 | 7 | 127.9 | 126.7 | 130.2 |
| 4 | 12881 | Q-NC0050947 | 8 | 127.9 | 126.7 | 130.2 |
| 4 | 12881 | Q-NC0037471 | 9 | 128.7 | 126.7 | 130.2 |
| 4 | 12881 | Q-NC0070533 | 10 | 130.2 | 126.7 | 130.2 |
| 4 | 13088 | Q-NC0081351 | 1 | 131.7 | 131.7 | 136.7 |
| 4 | 13088 | Q-NC0035451 | 2 | 133.5 | 131.7 | 136.7 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 13088 | Q-NC0084088 | 3 | 134.5 | 131.7 | 136.7 |
| 4 | 13088 | Q-NC0036646 | 4 | 134.7 | 131.7 | 136.7 |
| 4 | 13088 | Q-NC0005295 | 5 | 135.1 | 131.7 | 136.7 |
| 4 | 13088 | Q-NC0071156 | 6 | 136.7 | 131.7 | 136.7 |
| 4 | 13088 | Q-NC0071158 | 7 | 136.7 | 131.7 | 136.7 |
| 4 | 13088 | Q-NC0147097 | 8 | 136.7 | 131.7 | 136.7 |
| 4 | 13088 | Q-NC0147712 | 9 | 136.7 | 131.7 | 136.7 |
| 4 | 13088 | Q-NC0147919 | 10 | 136.7 | 131.7 | 136.7 |
| 4 | 12972 | Q-NC0039477 | 1 | 137.5 | 137.5 | 141.5 |
| 4 | 12972 | Q-NC0040357 | 2 | 137.5 | 137.5 | 141.5 |
| 4 | 12972 | Q-NC0067159 | 3 | 137.6 | 137.5 | 141.5 |
| 4 | 12972 | Q-NC0030877 | 4 | 138 | 137.5 | 141.5 |
| 4 | 12972 | Q-NC0031964 | 5 | 138 | 137.5 | 141.5 |
| 4 | 12972 | Q-NC0071447 | 6 | 138.3 | 137.5 | 141.5 |
| 4 | 12972 | Q-NC0030745 | 7 | 139 | 137.5 | 141.5 |
| 4 | 12972 | Q-NC0004170 | 8 | 139.4 | 137.5 | 141.5 |
| 4 | 12972 | Q-NC0108170 | 9 | 141.1 | 137.5 | 141.5 |
| 4 | 12972 | Q-NC0028162 | 10 | 141.5 | 137.5 | 141.5 |
| 4 | 12936 | Q-NC0038447 | 1 | 141.8 | 141.8 | 144.7 |
| 4 | 12936 | Q-NC0104901 | 2 | 142 | 141.8 | 144.7 |
| 4 | 12936 | Q-NC0104975 | 3 | 142 | 141.8 | 144.7 |
| 4 | 12936 | Q-NC0110764 | 4 | 142 | 141.8 | 144.7 |
| 4 | 12936 | Q-NC0079199 | 5 | 144.3 | 141.8 | 144.7 |
| 4 | 12936 | Q-NC0009491 | 6 | 144.6 | 141.8 | 144.7 |
| 4 | 12936 | Q-NC0012711 | 7 | 144.7 | 141.8 | 144.7 |
| 4 | 12936 | Q-NC0017828 | 8 | 144.7 | 141.8 | 144.7 |
| 4 | 12936 | Q-NC0038053 | 9 | 144.7 | 141.8 | 144.7 |
| 4 | 12936 | Q-NC0054601 | 10 | 144.7 | 141.8 | 144.7 |
| 4 | 12950 | Q-NC0048567 | 1 | 146.9 | 146.9 | 148.9 |
| 4 | 12950 | Q-NC0104484 | 2 | 147.3 | 146.9 | 148.9 |
| 4 | 12950 | Q-NC0020933 | 3 | 147.5 | 146.9 | 148.9 |
| 4 | 12950 | Q-NC0020934 | 4 | 147.5 | 146.9 | 148.9 |
| 4 | 12950 | Q-NC0024422 | 5 | 147.5 | 146.9 | 148.9 |
| 4 | 12950 | Q-NC0018439 | 6 | 147.9 | 146.9 | 148.9 |
| 4 | 12950 | Q-NC0036534 | 7 | 147.9 | 146.9 | 148.9 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 12950 | Q-NC0111505 | 8 | 148.2 | 146.9 | 148.9 |
| 4 | 12950 | Q-NC0109767 | 9 | 148.9 | 146.9 | 148.9 |
| 4 | 13005 | Q-NC0027877 | 1 | 152.5 | 152.5 | 156.4 |
| 4 | 13005 | Q-NC0035950 | 2 | 153.3 | 152.5 | 156.4 |
| 4 | 13005 | Q-NC0030576 | 3 | 153.8 | 152.5 | 156.4 |
| 4 | 13005 | Q-NC0028579 | 4 | 155.7 | 152.5 | 156.4 |
| 4 | 13005 | Q-NC0105818 | 5 | 155.8 | 152.5 | 156.4 |
| 4 | 13005 | Q-NC0034250 | 6 | 156.3 | 152.5 | 156.4 |
| 4 | 13005 | Q-NC0031931 | 7 | 156.4 | 152.5 | 156.4 |
| 4 | 13005 | Q-NC0051079 | 8 | 156.4 | 152.5 | 156.4 |
| 4 | 12903 | Q-NC0037175 | 1 | 161.2 | 161.2 | 165.1 |
| 4 | 12903 | Q-NC0008860 | 2 | 162 | 161.2 | 165.1 |
| 4 | 12903 | Q-NC0037601 | 3 | 162.2 | 161.2 | 165.1 |
| 4 | 12903 | Q-NC0032049 | 4 | 162.6 | 161.2 | 165.1 |
| 4 | 12903 | Q-NC0104453 | 5 | 163.2 | 161.2 | 165.1 |
| 4 | 12903 | Q-NC0034767 | 6 | 165.1 | 161.2 | 165.1 |
| 4 | 12903 | Q-NC0112744 | 7 | 165.1 | 161.2 | 165.1 |
| 4 | 12930 | Q-NC0110455 | 1 | 169.4 | 169.4 | 173.6 |
| 4 | 12930 | Q-NC0009398 | 2 | 173.5 | 169.4 | 173.6 |
| 4 | 12930 | Q-NC0003224 | 3 | 173.6 | 169.4 | 173.6 |
| 4 | 12930 | Q-NC0003226 | 4 | 173.6 | 169.4 | 173.6 |
| 4 | 13069 | Q-NC0003152 | 1 | 176.6 | 176.6 | 181 |
| 4 | 13069 | Q-NC0004445 | 2 | 176.6 | 176.6 | 181 |
| 4 | 13069 | Q-NC0017900 | 3 | 179.3 | 176.6 | 181 |
| 4 | 13069 | Q-NC0036635 | 4 | 179.7 | 176.6 | 181 |
| 4 | 13069 | Q-NC0009066 | 5 | 181 | 176.6 | 181 |
| 4 | 12995 | Q-NC0030985 | 1 | 181.9 | 181.9 | 186.7 |
| 4 | 12995 | Q-NC0148181 | 2 | 183 | 181.9 | 186.7 |
| 4 | 12995 | Q-NC0050788 | 3 | 184.1 | 181.9 | 186.7 |
| 4 | 12995 | Q-NC0043794 | 4 | 186.2 | 181.9 | 186.7 |
| 4 | 12995 | Q-NC0147037 | 5 | 186.2 | 181.9 | 186.7 |
| 4 | 12995 | Q-NC0112943 | 6 | 186.4 | 181.9 | 186.7 |
| 4 | 12995 | Q-NC0030211 | 7 | 186.7 | 181.9 | 186.7 |
| 4 | 12995 | Q-NC0043121 | 8 | 186.7 | 181.9 | 186.7 |
| 4 | 13040 | Q-NC0040159 | 1 | 190 | 190 | 190.6 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 13040 | Q-NC0035338 | 2 | 190.6 | 190 | 190.6 |
| 5 | 12887 | Q-NC0024265 | 1 | 1.8 | 1.8 | 1.8 |
| 5 | 12887 | Q-NC0031790 | 2 | 1.8 | 1.8 | 1.8 |
| 5 | 12887 | Q-NC0143354 | 3 | 1.8 | 1.8 | 1.8 |
| 5 | 13048 | Q-NC0015899 | 1 | 10.1 | 10.1 | 14.8 |
| 5 | 13048 | Q-NC0143251 | 2 | 11.6 | 10.1 | 14.8 |
| 5 | 13048 | Q-NC0014633 | 3 | 11.7 | 10.1 | 14.8 |
| 5 | 13048 | Q-NC0004808 | 4 | 12.3 | 10.1 | 14.8 |
| 5 | 13048 | Q-NC0036565 | 5 | 14.7 | 10.1 | 14.8 |
| 5 | 13048 | Q-NC0069592 | 6 | 14.8 | 10.1 | 14.8 |
| 5 | 12863 | Q-NC0104988 | 1 | 15.9 | 15.9 | 17.1 |
| 5 | 12863 | Q-NC0105613 | 2 | 16.6 | 15.9 | 17.1 |
| 5 | 12863 | Q-NC0107858 | 3 | 17.1 | 15.9 | 17.1 |
| 5 | 12889 | Q-NC0011193 | 1 | 29.3 | 29.3 | 32.1 |
| 5 | 12889 | Q-NC0108373 | 2 | 29.5 | 29.3 | 32.1 |
| 5 | 12889 | Q-NC0000091 | 3 | 30.2 | 29.3 | 32.1 |
| 5 | 12889 | Q-NC0079071 | 4 | 30.7 | 29.3 | 32.1 |
| 5 | 12889 | Q-NC0055976 | 5 | 32.1 | 29.3 | 32.1 |
| 5 | 12958 | Q-NC0153131 | 1 | 34.4 | 34.4 | 36.2 |
| 5 | 12958 | Q-NC0030023 | 2 | 35.6 | 34.4 | 36.2 |
| 5 | 12958 | Q-NC0005275 | 3 | 36 | 34.4 | 36.2 |
| 5 | 12958 | Q-NC0020668 | 4 | 36.2 | 34.4 | 36.2 |
| 5 | 12920 | Q-NC0038726 | 1 | 40.1 | 40.1 | 40.2 |
| 5 | 12920 | Q-NC0079943 | 2 | 40.2 | 40.1 | 40.2 |
| 5 | 12977 | Q-NC0012935 | 1 | 45.7 | 45.7 | 49 |
| 5 | 12977 | Q-NC0109403 | 2 | 46.7 | 45.7 | 49 |
| 5 | 12977 | Q-NC0020401 | 3 | 48 | 45.7 | 49 |
| 5 | 12977 | Q-NC0030899 | 4 | 48 | 45.7 | 49 |
| 5 | 12977 | Q-NC0016527 | 5 | 49 | 45.7 | 49 |
| 5 | 12973 | Q-NC0037588 | 1 | 60.1 | 60.1 | 63.5 |
| 5 | 12973 | Q-NC0016762 | 2 | 60.6 | 60.1 | 63.5 |
| 5 | 12973 | Q-NC0009490 | 3 | 61 | 60.1 | 63.5 |
| 5 | 12973 | Q-NC0109342 | 4 | 61.7 | 60.1 | 63.5 |
| 5 | 12973 | Q-NC0054720 | 5 | 62 | 60.1 | 63.5 |
| 5 | 12973 | Q-NC0018546 | 6 | 63.5 | 60.1 | 63.5 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 5 | 13001 | Q-NC0009668 | 1 | 65.2 | 65.2 | 70 |
| 5 | 13001 | Q-NC0019333 | 2 | 65.8 | 65.2 | 70 |
| 5 | 13001 | Q-NC0111388 | 3 | 66.6 | 65.2 | 70 |
| 5 | 13001 | Q-NC0111398 | 4 | 67.7 | 65.2 | 70 |
| 5 | 13001 | Q-NC0143216 | 5 | 67.7 | 65.2 | 70 |
| 5 | 13001 | Q-NC0113139 | 6 | 68.6 | 65.2 | 70 |
| 5 | 13001 | Q-NC0077545 | 7 | 69.4 | 65.2 | 70 |
| 5 | 13001 | Q-NC0030270 | 8 | 70 | 65.2 | 70 |
| 5 | 12933 | Q-NC0106912 | 1 | 71.2 | 71.2 | 75.3 |
| 5 | 12933 | Q-NC0146546 | 2 | 71.2 | 71.2 | 75.3 |
| 5 | 12933 | Q-NC0108957 | 3 | 71.9 | 71.2 | 75.3 |
| 5 | 12933 | Q-NC0109411 | 4 | 71.9 | 71.2 | 75.3 |
| 5 | 12933 | Q-NC0008797 | 5 | 72 | 71.2 | 75.3 |
| 5 | 12933 | Q-NC0057859 | 6 | 72.4 | 71.2 | 75.3 |
| 5 | 12933 | Q-NC0023808 | 7 | 73.8 | 71.2 | 75.3 |
| 5 | 12933 | Q-NC0051419 | 8 | 73.8 | 71.2 | 75.3 |
| 5 | 12933 | Q-NC0019187 | 9 | 74.1 | 71.2 | 75.3 |
| 5 | 12933 | Q-NC0028807 | 10 | 75.3 | 71.2 | 75.3 |
| 5 | 12896 | Q-NC0082146 | 1 | 75.4 | 75.4 | 79.8 |
| 5 | 12896 | Q-NC0080028 | 2 | 76.6 | 75.4 | 79.8 |
| 5 | 12896 | Q-NC0105612 | 3 | 79 | 75.4 | 79.8 |
| 5 | 12896 | Q-NC0107061 | 4 | 79 | 75.4 | 79.8 |
| 5 | 12896 | Q-NC0107549 | 5 | 79 | 75.4 | 79.8 |
| 5 | 12896 | Q-NC0110919 | 6 | 79 | 75.4 | 79.8 |
| 5 | 12896 | Q-NC0111346 | 7 | 79 | 75.4 | 79.8 |
| 5 | 12896 | Q-NC0147574 | 8 | 79 | 75.4 | 79.8 |
| 5 | 12896 | Q-NC0154691 | 9 | 79 | 75.4 | 79.8 |
| 5 | 12896 | Q-NC0146415 | 10 | 79.8 | 75.4 | 79.8 |
| 5 | 12961 | Q-NC0031886 | 1 | 80.4 | 80.4 | 85 |
| 5 | 12961 | Q-NC0077644 | 2 | 80.4 | 80.4 | 85 |
| 5 | 12961 | Q-NC0105854 | 3 | 81.2 | 80.4 | 85 |
| 5 | 12961 | Q-NC0018230 | 4 | 81.3 | 80.4 | 85 |
| 5 | 12961 | Q-NC0048328 | 5 | 81.3 | 80.4 | 85 |
| 5 | 12961 | Q-NC0022796 | 6 | 81.5 | 80.4 | 85 |
| 5 | 12961 | Q-NC0027874 | 7 | 81.5 | 80.4 | 85 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 5 | 12961 | Q-NC0078535 | 8 | 83.9 | 80.4 | 85 |
| 5 | 12961 | Q-NC0040366 | 9 | 84.1 | 80.4 | 85 |
| 5 | 12961 | Q-NC0033249 | 10 | 85 | 80.4 | 85 |
| 5 | 12991 | Q-NC0035956 | 1 | 85.1 | 85.1 | 88.4 |
| 5 | 12991 | Q-NC0154498 | 2 | 85.2 | 85.1 | 88.4 |
| 5 | 12991 | Q-NC0145634 | 3 | 85.4 | 85.1 | 88.4 |
| 5 | 12991 | Q-NC0110554 | 4 | 87.4 | 85.1 | 88.4 |
| 5 | 12991 | Q-NC0040571 | 5 | 88.4 | 85.1 | 88.4 |
| 5 | 13058 | Q-NC0028110 | 1 | 90.2 | 90.2 | 93.9 |
| 5 | 13058 | Q-NC0027864 | 2 | 93.9 | 90.2 | 93.9 |
| 5 | 13058 | Q-NC0053792 | 3 | 93.9 | 90.2 | 93.9 |
| 5 | 12908 | Q-NC0111999 | 1 | 96.9 | 96.9 | 99.4 |
| 5 | 12908 | Q-NC0018153 | 2 | 97 | 96.9 | 99.4 |
| 5 | 12908 | Q-NC0051711 | 3 | 97 | 96.9 | 99.4 |
| 5 | 12908 | Q-NC0048616 | 4 | 98.2 | 96.9 | 99.4 |
| 5 | 12908 | Q-NC0033305 | 5 | 98.9 | 96.9 | 99.4 |
| 5 | 12908 | Q-NC0108101 | 6 | 98.9 | 96.9 | 99.4 |
| 5 | 12908 | Q-NC0036432 | 7 | 99.2 | 96.9 | 99.4 |
| 5 | 12908 | Q-NC0012480 | 8 | 99.4 | 96.9 | 99.4 |
| 5 | 13035 | Q-NC0104850 | 1 | 102.8 | 102.8 | 106.6 |
| 5 | 13035 | Q-NC0017678 | 2 | 103.8 | 102.8 | 106.6 |
| 5 | 13035 | Q-NC0009297 | 3 | 104.1 | 102.8 | 106.6 |
| 5 | 13035 | Q-NC0003338 | 4 | 106.2 | 102.8 | 106.6 |
| 5 | 13035 | Q-NC0038972 | 5 | 106.2 | 102.8 | 106.6 |
| 5 | 13035 | Q-NC0003054 | 6 | 106.6 | 102.8 | 106.6 |
| 5 | 13035 | Q-NC0106000 | 7 | 106.6 | 102.8 | 106.6 |
| 5 | 13035 | Q-NC0106300 | 8 | 106.6 | 102.8 | 106.6 |
| 5 | 13035 | Q-NC0154432 | 9 | 106.6 | 102.8 | 106.6 |
| 5 | 12925 | Q-NC0107238 | 1 | 114.7 | 114.7 | 118.8 |
| 5 | 12925 | Q-NC0008807 | 2 | 118.8 | 114.7 | 118.8 |
| 5 | 13063 | Q-NC0005480 | 1 | 120 | 120 | 125 |
| 5 | 13063 | Q-NC0016868 | 2 | 122.6 | 120 | 125 |
| 5 | 13063 | Q-NC0017125 | 3 | 122.6 | 120 | 125 |
| 5 | 13063 | Q-NC0083876 | 4 | 124 | 120 | 125 |
| 5 | 13063 | Q-NC0106716 | 5 | 125 | 120 | 125 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 5 | 13104 | Q-NC0009434 | 1 | 125.2 | 125.2 | 129.7 |
| 5 | 13104 | Q-NC0010131 | 2 | 129.7 | 125.2 | 129.7 |
| 5 | 13014 | Q-NC0105970 | 1 | 132.7 | 132.7 | 133.4 |
| 5 | 13014 | Q-NC0035377 | 2 | 132.8 | 132.7 | 133.4 |
| 5 | 13014 | Q-NC0031731 | 3 | 133.4 | 132.7 | 133.4 |
| 5 | 13106 | Q-NC0081212 | 1 | 138.2 | 138.2 | 139.5 |
| 5 | 13106 | Q-NC0154899 | 2 | 138.6 | 138.2 | 139.5 |
| 5 | 13106 | Q-NC0085514 | 3 | 139.5 | 138.2 | 139.5 |
| 5 | 12980 | Q-NC0002353 | 1 | 144.7 | 144.7 | 148.1 |
| 5 | 12980 | Q-NC0041824 | 2 | 144.7 | 144.7 | 148.1 |
| 5 | 12980 | Q-NC0111944 | 3 | 148.1 | 144.7 | 148.1 |
| 5 | 12980 | Q-NC0143380 | 4 | 148.1 | 144.7 | 148.1 |
| 5 | 13008 | Q-NC0000390 | 1 | 159.5 | 159.5 | 159.8 |
| 5 | 13008 | Q-NC0110484 | 2 | 159.5 | 159.5 | 159.8 |
| 5 | 13008 | Q-NC0104963 | 3 | 159.8 | 159.5 | 159.8 |
| 5 | 12965 | Q-NC0104717 | 1 | 171.2 | 171.2 | 175.8 |
| 5 | 12965 | Q-NC0109853 | 2 | 173.9 | 171.2 | 175.8 |
| 5 | 12965 | Q-NC0012417 | 3 | 175.2 | 171.2 | 175.8 |
| 5 | 12965 | Q-NC0000015 | 4 | 175.3 | 171.2 | 175.8 |
| 5 | 12965 | Q-NC0146137 | 5 | 175.8 | 171.2 | 175.8 |
| 5 | 13074 | Q-NC0025270 | 1 | 177.8 | 177.8 | 181.5 |
| 5 | 13074 | Q-NC0111504 | 2 | 181 | 177.8 | 181.5 |
| 5 | 13074 | Q-NC0031084 | 3 | 181.5 | 177.8 | 181.5 |
| 6 | 13013 | Q-NC0014417 | 1 | 25 | 25 | 29.5 |
| 6 | 13013 | Q-NC0105014 | 2 | 28.8 | 25 | 29.5 |
| 6 | 13013 | Q-NC0106341 | 3 | 29.5 | 25 | 29.5 |
| 6 | 13010 | Q-NC0066735 | 1 | 34.3 | 34.3 | 38.4 |
| 6 | 13010 | Q-NC0079529 | 2 | 34.3 | 34.3 | 38.4 |
| 6 | 13010 | Q-NC0013985 | 3 | 35.4 | 34.3 | 38.4 |
| 6 | 13010 | Q-NC0003284 | 4 | 36.4 | 34.3 | 38.4 |
| 6 | 13010 | Q-NC0069630 | 5 | 36.5 | 34.3 | 38.4 |
| 6 | 13010 | Q-NC0105714 | 6 | 36.7 | 34.3 | 38.4 |
| 6 | 13010 | Q-NC0029780 | 7 | 38.3 | 34.3 | 38.4 |
| 6 | 13010 | Q-NC0002870 | 8 | 38.4 | 34.3 | 38.4 |
| 6 | 13010 | Q-NC0003210 | 9 | 38.4 | 34.3 | 38.4 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 6 | 13010 | Q-NC0025657 | 10 | 38.4 | 34.3 | 38.4 |
| 6 | 12944 | Q-NC0110607 | 1 | 38.7 | 38.7 | 43.2 |
| 6 | 12944 | Q-NC0027095 | 2 | 38.8 | 38.7 | 43.2 |
| 6 | 12944 | Q-NC0110850 | 3 | 39.3 | 38.7 | 43.2 |
| 6 | 12944 | Q-NC0025201 | 4 | 39.4 | 38.7 | 43.2 |
| 6 | 12944 | Q-NC0147740 | 5 | 39.4 | 38.7 | 43.2 |
| 6 | 12944 | Q-NC0000439 | 6 | 39.9 | 38.7 | 43.2 |
| 6 | 12944 | Q-NC0036067 | 7 | 41 | 38.7 | 43.2 |
| 6 | 12944 | Q-NC0036073 | 8 | 41 | 38.7 | 43.2 |
| 6 | 12944 | Q-NC0147437 | 9 | 41.2 | 38.7 | 43.2 |
| 6 | 12944 | Q-NC0070260 | 10 | 43.2 | 38.7 | 43.2 |
| 6 | 12979 | Q-NC0108586 | 1 | 43.5 | 43.5 | 48 |
| 6 | 12979 | Q-NC0037981 | 2 | 44.2 | 43.5 | 48 |
| 6 | 12979 | Q-NC0030176 | 3 | 48 | 43.5 | 48 |
| 6 | 13002 | Q-NC0106121 | 1 | 49.2 | 49.2 | 53.4 |
| 6 | 13002 | Q-NC0038040 | 2 | 52.1 | 49.2 | 53.4 |
| 6 | 13002 | Q-NC0067323 | 3 | 52.1 | 49.2 | 53.4 |
| 6 | 13002 | Q-NC0034523 | 4 | 53.2 | 49.2 | 53.4 |
| 6 | 13002 | Q-NC0034054 | 5 | 53.4 | 49.2 | 53.4 |
| 6 | 12966 | Q-NC0106527 | 1 | 56.4 | 56.4 | 60.5 |
| 6 | 12966 | Q-NC0004463 | 2 | 56.5 | 56.4 | 60.5 |
| 6 | 12966 | Q-NC0060751 | 3 | 56.6 | 56.4 | 60.5 |
| 6 | 12966 | Q-NC0057758 | 4 | 57.5 | 56.4 | 60.5 |
| 6 | 12966 | Q-NC0108212 | 5 | 57.5 | 56.4 | 60.5 |
| 6 | 12966 | Q-NC0069870 | 6 | 57.8 | 56.4 | 60.5 |
| 6 | 12966 | Q-NC0011591 | 7 | 60.5 | 56.4 | 60.5 |
| 6 | 13101 | Q-NC0110712 | 1 | 64.8 | 64.8 | 69.7 |
| 6 | 13101 | Q-NC0146195 | 2 | 66 | 64.8 | 69.7 |
| 6 | 13101 | Q-NC0059008 | 3 | 66.2 | 64.8 | 69.7 |
| 6 | 13101 | Q-NC0009134 | 4 | 66.3 | 64.8 | 69.7 |
| 6 | 13101 | Q-NC0105586 | 5 | 66.3 | 64.8 | 69.7 |
| 6 | 13101 | Q-NC0105497 | 6 | 67.6 | 64.8 | 69.7 |
| 6 | 13101 | Q-NC0015059 | 7 | 69.1 | 64.8 | 69.7 |
| 6 | 13101 | Q-NC0003277 | 8 | 69.4 | 64.8 | 69.7 |
| 6 | 13101 | Q-NC0030942 | 9 | 69.7 | 64.8 | 69.7 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 6 | 12871 | Q-NC0148039 | 1 | 70.2 | 70.2 | 75.1 |
| 6 | 12871 | Q-NC0008833 | 2 | 70.9 | 70.2 | 75.1 |
| 6 | 12871 | Q-NC0151453 | 3 | 75.1 | 70.2 | 75.1 |
| 6 | 12999 | Q-NC0008838 | 1 | 77.7 | 77.7 | 79.6 |
| 6 | 12999 | Q-NC0014694 | 2 | 77.8 | 77.7 | 79.6 |
| 6 | 12999 | Q-NC0005064 | 3 | 78.1 | 77.7 | 79.6 |
| 6 | 12999 | Q-NC0005066 | 4 | 78.1 | 77.7 | 79.6 |
| 6 | 12999 | Q-NC0019518 | 5 | 78.5 | 77.7 | 79.6 |
| 6 | 12999 | Q-NC0014128 | 6 | 78.8 | 77.7 | 79.6 |
| 6 | 12999 | Q-NC0077031 | 7 | 78.8 | 77.7 | 79.6 |
| 6 | 12999 | Q-NC0005081 | 8 | 79.3 | 77.7 | 79.6 |
| 6 | 12999 | Q-NC0000557 | 9 | 79.6 | 77.7 | 79.6 |
| 6 | 12999 | Q-NC0082021 | 10 | 79.6 | 77.7 | 79.6 |
| 6 | 13030 | Q-NC0108196 | 1 | 79.8 | 79.8 | 83.8 |
| 6 | 13030 | Q-NC0066737 | 2 | 81.9 | 79.8 | 83.8 |
| 6 | 13030 | Q-NC0070996 | 3 | 81.9 | 79.8 | 83.8 |
| 6 | 13030 | Q-NC0084789 | 4 | 82.2 | 79.8 | 83.8 |
| 6 | 13030 | Q-NC0145427 | 5 | 82.2 | 79.8 | 83.8 |
| 6 | 13030 | Q-NC0013638 | 6 | 83.5 | 79.8 | 83.8 |
| 6 | 13030 | Q-NC0113381 | 7 | 83.8 | 79.8 | 83.8 |
| 6 | 12952 | Q-NC0037517 | 1 | 84.9 | 84.9 | 85.5 |
| 6 | 12952 | Q-NC0028203 | 2 | 85 | 84.9 | 85.5 |
| 6 | 12952 | Q-NC0004030 | 3 | 85.5 | 84.9 | 85.5 |
| 6 | 12952 | Q-NC0040364 | 4 | 85.5 | 84.9 | 85.5 |
| 6 | 13102 | Q-NC0019772 | 1 | 92.4 | 92.4 | 96.7 |
| 6 | 13102 | Q-NC0110972 | 2 | 93.2 | 92.4 | 96.7 |
| 6 | 13102 | Q-NC0019588 | 3 | 96.7 | 92.4 | 96.7 |
| 6 | 13003 | Q-NC0037947 | 1 | 97.6 | 97.6 | 102.4 |
| 6 | 13003 | Q-NC0067075 | 2 | 98.9 | 97.6 | 102.4 |
| 6 | 13003 | Q-NC0005319 | 3 | 99.1 | 97.6 | 102.4 |
| 6 | 13003 | Q-NC0081445 | 4 | 101.8 | 97.6 | 102.4 |
| 6 | 13003 | Q-NC0030771 | 5 | 102.4 | 97.6 | 102.4 |
| 6 | 12994 | Q-NC0017860 | 1 | 103.5 | 103.5 | 106.6 |
| 6 | 12994 | Q-NC0146215 | 2 | 106.6 | 103.5 | 106.6 |
| 6 | 13023 | Q-NC0029924 | 1 | 109.2 | 109.2 | 109.2 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 6 | 13068 | Q-NC0031684 | 1 | 114.5 | 114.5 | 118.1 |
| 6 | 13068 | Q-NC0031026 | 2 | 118 | 114.5 | 118.1 |
| 6 | 13068 | Q-NC0107449 | 3 | 118.1 | 114.5 | 118.1 |
| 6 | 13100 | Q-NC0017761 | 1 | 120.6 | 120.6 | 120.8 |
| 6 | 13100 | Q-NC0023358 | 2 | 120.8 | 120.6 | 120.8 |
| 6 | 12894 | Q-NC0003201 | 1 | 127.9 | 127.9 | 132.9 |
| 6 | 12894 | Q-NC0016017 | 2 | 128.4 | 127.9 | 132.9 |
| 6 | 12894 | Q-NC0028185 | 3 | 130.1 | 127.9 | 132.9 |
| 6 | 12894 | Q-NC0060514 | 4 | 131.2 | 127.9 | 132.9 |
| 6 | 12894 | Q-NC0032509 | 5 | 132.9 | 127.9 | 132.9 |
| 6 | 12918 | Q-NC0002782 | 1 | 133.5 | 133.5 | 136 |
| 6 | 12918 | Q-NC0053636 | 2 | 136 | 133.5 | 136 |
| 6 | 12981 | Q-NC0009667 | 1 | 139.1 | 139.1 | 140.5 |
| 6 | 12981 | Q-NC0021433 | 2 | 140.5 | 139.1 | 140.5 |
| 6 | 12917 | Q-NC0032368 | 1 | 144.3 | 144.3 | 145.8 |
| 6 | 12917 | Q-NC0032370 | 2 | 144.3 | 144.3 | 145.8 |
| 6 | 12917 | Q-NC0037555 | 3 | 144.7 | 144.3 | 145.8 |
| 6 | 12917 | Q-NC0043724 | 4 | 145 | 144.3 | 145.8 |
| 6 | 12917 | Q-NC0021734 | 5 | 145.4 | 144.3 | 145.8 |
| 6 | 12917 | Q-NC0037790 | 6 | 145.4 | 144.3 | 145.8 |
| 6 | 12917 | Q-NC0027223 | 7 | 145.8 | 144.3 | 145.8 |
| 7 | 13034 | Q-NC0143819 | 1 | 7.1 | 7.1 | 7.1 |
| 7 | 13034 | Q-NC0147609 | 2 | 7.1 | 7.1 | 7.1 |
| 7 | 12902 | Q-NC0143514 | 1 | 29 | 29 | 33.3 |
| 7 | 12902 | Q-NC0058637 | 2 | 33.3 | 29 | 33.3 |
| 7 | 13052 | Q-NC0011865 | 1 | 43.5 | 43.5 | 43.9 |
| 7 | 13052 | Q-NC0003924 | 2 | 43.9 | 43.5 | 43.9 |
| 7 | 13052 | Q-NC0107497 | 3 | 43.9 | 43.5 | 43.9 |
| 7 | 13096 | Q-NC0016644 | 1 | 48.6 | 48.6 | 51.3 |
| 7 | 13096 | Q-NC0009409 | 2 | 51.2 | 48.6 | 51.3 |
| 7 | 13096 | Q-NC0084006 | 3 | 51.2 | 48.6 | 51.3 |
| 7 | 13096 | Q-NC0060906 | 4 | 51.3 | 48.6 | 51.3 |
| 7 | 13096 | Q-NC0070341 | 5 | 51.3 | 48.6 | 51.3 |
| 7 | 12864 | Q-NC0009304 | 1 | 56 | 56 | 58.5 |
| 7 | 12864 | Q-NC0108168 | 2 | 56 | 56 | 58.5 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 7 | 12864 | Q-NC0066143 | 3 | 57.1 | 56 | 58.5 |
| 7 | 12864 | Q-NC0042164 | 4 | 57.4 | 56 | 58.5 |
| 7 | 12864 | Q-NC0031370 | 5 | 57.7 | 56 | 58.5 |
| 7 | 12864 | Q-NC0146122 | 6 | 57.8 | 56 | 58.5 |
| 7 | 12864 | Q-NC0107775 | 7 | 58.3 | 56 | 58.5 |
| 7 | 12864 | Q-NC0002225 | 8 | 58.5 | 56 | 58.5 |
| 7 | 12864 | Q-NC0033755 | 9 | 58.5 | 56 | 58.5 |
| 7 | 12864 | Q-NC0147613 | 10 | 58.5 | 56 | 58.5 |
| 7 | 12969 | Q-NC0030674 | 1 | 60.2 | 60.2 | 62.5 |
| 7 | 12969 | Q-NC0056253 | 2 | 60.4 | 60.2 | 62.5 |
| 7 | 12969 | Q-NC0146556 | 3 | 60.4 | 60.2 | 62.5 |
| 7 | 12969 | Q-NC0027428 | 4 | 60.8 | 60.2 | 62.5 |
| 7 | 12969 | Q-NC0033507 | 5 | 61.8 | 60.2 | 62.5 |
| 7 | 12969 | Q-NC0035633 | 6 | 61.8 | 60.2 | 62.5 |
| 7 | 12969 | Q-NC0036486 | 7 | 61.8 | 60.2 | 62.5 |
| 7 | 12969 | Q-NC0028094 | 8 | 61.9 | 60.2 | 62.5 |
| 7 | 12969 | Q-NC0000558 | 9 | 62.2 | 60.2 | 62.5 |
| 7 | 12969 | Q-NC0050490 | 10 | 62.5 | 60.2 | 62.5 |
| 7 | 13041 | Q-NC0030511 | 1 | 62.8 | 62.8 | 64.4 |
| 7 | 13041 | Q-NC0039064 | 2 | 62.8 | 62.8 | 64.4 |
| 7 | 13041 | Q-NC0105086 | 3 | 62.8 | 62.8 | 64.4 |
| 7 | 13041 | Q-NC0108360 | 4 | 62.8 | 62.8 | 64.4 |
| 7 | 13041 | Q-NC0034215 | 5 | 63.1 | 62.8 | 64.4 |
| 7 | 13041 | Q-NC0155984 | 6 | 63.1 | 62.8 | 64.4 |
| 7 | 13041 | Q-NC0033769 | 7 | 64 | 62.8 | 64.4 |
| 7 | 13041 | Q-NC0034121 | 8 | 64.1 | 62.8 | 64.4 |
| 7 | 13041 | Q-NC0078294 | 9 | 64.2 | 62.8 | 64.4 |
| 7 | 13041 | Q-NC0004299 | 10 | 64.4 | 62.8 | 64.4 |
| 7 | 12883 | Q-NC0155766 | 1 | 65.6 | 65.6 | 70.1 |
| 7 | 12883 | Q-NC0009073 | 2 | 65.9 | 65.6 | 70.1 |
| 7 | 12883 | Q-NC0019507 | 3 | 65.9 | 65.6 | 70.1 |
| 7 | 12883 | Q-NC0106910 | 4 | 65.9 | 65.6 | 70.1 |
| 7 | 12883 | Q-NC0110477 | 5 | 65.9 | 65.6 | 70.1 |
| 7 | 12883 | Q-NC0068424 | 6 | 66.2 | 65.6 | 70.1 |
| 7 | 12883 | Q-NC0068426 | 7 | 66.5 | 65.6 | 70.1 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 7 | 12883 | Q-NC0034688 | 8 | 69.4 | 65.6 | 70.1 |
| 7 | 12883 | Q-NC0066422 | 9 | 69.4 | 65.6 | 70.1 |
| 7 | 12883 | Q-NC0147598 | 10 | 70.1 | 65.6 | 70.1 |
| 7 | 13025 | Q-NC0033620 | 1 | 75.7 | 75.7 | 80.7 |
| 7 | 13025 | Q-NC0068434 | 2 | 76.5 | 75.7 | 80.7 |
| 7 | 13025 | Q-NC0039598 | 3 | 77.9 | 75.7 | 80.7 |
| 7 | 13025 | Q-NC0029362 | 4 | 78.4 | 75.7 | 80.7 |
| 7 | 13025 | Q-NC0145922 | 5 | 80.5 | 75.7 | 80.7 |
| 7 | 13025 | Q-NC0057013 | 6 | 80.7 | 75.7 | 80.7 |
| 7 | 13020 | Q-NC0048425 | 1 | 88.3 | 88.3 | 91.3 |
| 7 | 13020 | Q-NC0035408 | 2 | 89.5 | 88.3 | 91.3 |
| 7 | 13020 | Q-NC0005051 | 3 | 91.3 | 88.3 | 91.3 |
| 7 | 12939 | Q-NC0038914 | 1 | 96.6 | 96.6 | 99.7 |
| 7 | 12939 | Q-NC0009240 | 2 | 98.5 | 96.6 | 99.7 |
| 7 | 12939 | Q-NC0022958 | 3 | 98.5 | 96.6 | 99.7 |
| 7 | 12939 | Q-NC0028932 | 4 | 99 | 96.6 | 99.7 |
| 7 | 12939 | Q-NC0068149 | 5 | 99 | 96.6 | 99.7 |
| 7 | 12939 | Q-NC0155829 | 6 | 99 | 96.6 | 99.7 |
| 7 | 12939 | Q-NC0033952 | 7 | 99.4 | 96.6 | 99.7 |
| 7 | 12939 | Q-NC0105642 | 8 | 99.4 | 96.6 | 99.7 |
| 7 | 12939 | Q-NC0034583 | 9 | 99.5 | 96.6 | 99.7 |
| 7 | 12939 | Q-NC0031547 | 10 | 99.7 | 96.6 | 99.7 |
| 7 | 12890 | Q-NC0004302 | 1 | 99.8 | 99.8 | 104.6 |
| 7 | 12890 | Q-NC0070392 | 2 | 99.8 | 99.8 | 104.6 |
| 7 | 12890 | Q-NC0070402 | 3 | 99.8 | 99.8 | 104.6 |
| 7 | 12890 | Q-NC0081460 | 4 | 99.8 | 99.8 | 104.6 |
| 7 | 12890 | Q-NC0004093 | 5 | 100 | 99.8 | 104.6 |
| 7 | 12890 | Q-NC0031157 | 6 | 100 | 99.8 | 104.6 |
| 7 | 12890 | Q-NC0153856 | 7 | 101.7 | 99.8 | 104.6 |
| 7 | 12890 | Q-NC0078828 | 8 | 102 | 99.8 | 104.6 |
| 7 | 12890 | Q-NC0015995 | 9 | 104.6 | 99.8 | 104.6 |
| 7 | 12890 | Q-NC0016008 | 10 | 104.6 | 99.8 | 104.6 |
| 7 | 13076 | Q-NC0144299 | 1 | 104.9 | 104.9 | 107 |
| 7 | 13076 | Q-NC0145260 | 2 | 104.9 | 104.9 | 107 |
| 7 | 13076 | Q-NC0018284 | 3 | 105.8 | 104.9 | 107 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 7 | 13076 | Q-NC0039773 | 4 | 106.1 | 104.9 | 107 |
| 7 | 13076 | Q-NC0015161 | 5 | 106.4 | 104.9 | 107 |
| 7 | 13076 | Q-NC0040335 | 6 | 107 | 104.9 | 107 |
| 7 | 13028 | Q-NC0009674 | 1 | 112.1 | 112.1 | 116.1 |
| 7 | 13028 | Q-NC0030029 | 2 | 112.7 | 112.1 | 116.1 |
| 7 | 13028 | Q-NC0018565 | 3 | 115.2 | 112.1 | 116.1 |
| 7 | 13028 | Q-NC0027069 | 4 | 116.1 | 112.1 | 116.1 |
| 7 | 12898 | Q-NC0003218 | 1 | 117.9 | 117.9 | 117.9 |
| 7 | 12922 | Q-NC0009872 | 1 | 123.8 | 123.8 | 126.9 |
| 7 | 12922 | Q-NC0148208 | 2 | 126.9 | 123.8 | 126.9 |
| 7 | 12935 | Q-NC0112796 | 1 | 130.1 | 130.1 | 131.2 |
| 7 | 12935 | Q-NC0004953 | 2 | 131.2 | 130.1 | 131.2 |
| 7 | 12934 | Q-NC0015974 | 1 | 135.9 | 135.9 | 138.5 |
| 7 | 12934 | Q-NC0110771 | 2 | 138.5 | 135.9 | 138.5 |
| 7 | 12915 | Q-NC0009843 | 1 | 149.2 | 149.2 | 154.2 |
| 7 | 12915 | Q-NC0011659 | 2 | 150.9 | 149.2 | 154.2 |
| 7 | 12915 | Q-NC0011664 | 3 | 150.9 | 149.2 | 154.2 |
| 7 | 12915 | Q-NC0146593 | 4 | 152.9 | 149.2 | 154.2 |
| 7 | 12915 | Q-NC0155473 | 5 | 152.9 | 149.2 | 154.2 |
| 7 | 12915 | Q-NC0155475 | 6 | 154.2 | 149.2 | 154.2 |
| 7 | 12960 | Q-NC0143371 | 1 | 156.6 | 156.6 | 161.1 |
| 7 | 12960 | Q-NC0151568 | 2 | 161.1 | 156.6 | 161.1 |
| 7 | 12962 | Q-NC0078091 | 1 | 164.6 | 164.6 | 169.3 |
| 7 | 12962 | Q-NC0146620 | 2 | 165.7 | 164.6 | 169.3 |
| 7 | 12962 | Q-NC0038317 | 3 | 165.8 | 164.6 | 169.3 |
| 7 | 12962 | Q-NC0036490 | 4 | 166.9 | 164.6 | 169.3 |
| 7 | 12962 | Q-NC0028596 | 5 | 168.9 | 164.6 | 169.3 |
| 7 | 12962 | Q-NC0038499 | 6 | 169.3 | 164.6 | 169.3 |
| 7 | 12867 | Q-NC0106258 | 1 | 170.9 | 170.9 | 173.9 |
| 7 | 12867 | Q-NC0021038 | 2 | 171.4 | 170.9 | 173.9 |
| 7 | 12867 | Q-NC0071624 | 3 | 171.7 | 170.9 | 173.9 |
| 7 | 12867 | Q-NC0004142 | 4 | 173.9 | 170.9 | 173.9 |
| 7 | 12867 | Q-NC0019704 | 5 | 173.9 | 170.9 | 173.9 |
| 8 | 12924 | Q-NC0024672 | 1 | 33.6 | 33.6 | 38.1 |
| 8 | 12924 | Q-NC0019198 | 2 | 38.1 | 33.6 | 38.1 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 8 | 12892 | Q-NC0038724 | 1 | 39.6 | 39.6 | 41.7 |
| 8 | 12892 | Q-NC0040299 | 2 | 41.2 | 39.6 | 41.7 |
| 8 | 12892 | Q-NC0003792 | 3 | 41.7 | 39.6 | 41.7 |
| 8 | 12954 | Q-NC0029842 | 1 | 51.6 | 51.6 | 56.5 |
| 8 | 12954 | Q-NC0027580 | 2 | 51.7 | 51.6 | 56.5 |
| 8 | 12954 | Q-NC0008934 | 3 | 51.8 | 51.6 | 56.5 |
| 8 | 12954 | Q-NC0034552 | 4 | 51.8 | 51.6 | 56.5 |
| 8 | 12954 | Q-NC0107937 | 5 | 52.6 | 51.6 | 56.5 |
| 8 | 12954 | Q-NC0105809 | 6 | 53.4 | 51.6 | 56.5 |
| 8 | 12954 | Q-NC0005266 | 7 | 56.5 | 51.6 | 56.5 |
| 8 | 12914 | Q-NC0111628 | 1 | 57.3 | 57.3 | 60.1 |
| 8 | 12914 | Q-NC0026720 | 2 | 58.7 | 57.3 | 60.1 |
| 8 | 12914 | Q-NC0037392 | 3 | 60 | 57.3 | 60.1 |
| 8 | 12914 | Q-NC0027485 | 4 | 60.1 | 57.3 | 60.1 |
| 8 | 12885 | Q-NC0079080 | 1 | 65.8 | 65.8 | 70.7 |
| 8 | 12885 | Q-NC0053899 | 2 | 65.9 | 65.8 | 70.7 |
| 8 | 12885 | Q-NC0154174 | 3 | 69 | 65.8 | 70.7 |
| 8 | 12885 | Q-NC0010347 | 4 | 69.2 | 65.8 | 70.7 |
| 8 | 12885 | Q-NC0104368 | 5 | 70 | 65.8 | 70.7 |
| 8 | 12885 | Q-NC0104862 | 6 | 70 | 65.8 | 70.7 |
| 8 | 12885 | Q-NC0105974 | 7 | 70 | 65.8 | 70.7 |
| 8 | 12885 | Q-NC0151503 | 8 | 70 | 65.8 | 70.7 |
| 8 | 12885 | Q-NC0020099 | 9 | 70.5 | 65.8 | 70.7 |
| 8 | 12885 | Q-NC0081269 | 10 | 70.7 | 65.8 | 70.7 |
| 8 | 13078 | Q-NC0029015 | 1 | 71.1 | 71.1 | 72.9 |
| 8 | 13078 | Q-NC0051919 | 2 | 71.1 | 71.1 | 72.9 |
| 8 | 13078 | Q-NC0107396 | 3 | 71.1 | 71.1 | 72.9 |
| 8 | 13078 | Q-NC0022765 | 4 | 72.4 | 71.1 | 72.9 |
| 8 | 13078 | Q-NC0009659 | 5 | 72.9 | 71.1 | 72.9 |
| 8 | 12937 | Q-NC0051048 | 1 | 78.9 | 78.9 | 83.9 |
| 8 | 12937 | Q-NC0082612 | 2 | 78.9 | 78.9 | 83.9 |
| 8 | 12937 | Q-NC0027361 | 3 | 79.6 | 78.9 | 83.9 |
| 8 | 12937 | Q-NC0011760 | 4 | 80.3 | 78.9 | 83.9 |
| 8 | 12937 | Q-NC0145200 | 5 | 80.3 | 78.9 | 83.9 |
| 8 | 12937 | Q-NC0145999 | 6 | 80.3 | 78.9 | 83.9 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 8 | 12937 | Q-NC0108315 | 7 | 80.4 | 78.9 | 83.9 |
| 8 | 12937 | Q-NC0009254 | 8 | 83.9 | 78.9 | 83.9 |
| 8 | 13053 | Q-NC0013946 | 1 | 84 | 84 | 88.5 |
| 8 | 13053 | Q-NC0015146 | 2 | 84 | 84 | 88.5 |
| 8 | 13053 | Q-NC0077568 | 3 | 84 | 84 | 88.5 |
| 8 | 13053 | Q-NC0147465 | 4 | 84 | 84 | 88.5 |
| 8 | 13053 | Q-NC0009835 | 5 | 84.5 | 84 | 88.5 |
| 8 | 13053 | Q-NC0018342 | 6 | 84.9 | 84 | 88.5 |
| 8 | 13053 | Q-NC0020912 | 7 | 85.2 | 84 | 88.5 |
| 8 | 13053 | Q-NC0110378 | 8 | 85.5 | 84 | 88.5 |
| 8 | 13053 | Q-NC0155968 | 9 | 87.9 | 84 | 88.5 |
| 8 | 13053 | Q-NC0108631 | 10 | 88.5 | 84 | 88.5 |
| 8 | 12975 | Q-NC0110331 | 1 | 89.1 | 89.1 | 93.9 |
| 8 | 12975 | Q-NC0144363 | 2 | 91.1 | 89.1 | 93.9 |
| 8 | 12975 | Q-NC0112082 | 3 | 92 | 89.1 | 93.9 |
| 8 | 12975 | Q-NC0056860 | 4 | 92.1 | 89.1 | 93.9 |
| 8 | 12975 | Q-NC0021895 | 5 | 92.2 | 89.1 | 93.9 |
| 8 | 12975 | Q-NC0032337 | 6 | 92.7 | 89.1 | 93.9 |
| 8 | 12975 | Q-NC0048562 | 7 | 92.7 | 89.1 | 93.9 |
| 8 | 12975 | Q-NC0082295 | 8 | 93.7 | 89.1 | 93.9 |
| 8 | 12975 | Q-NC0020514 | 9 | 93.9 | 89.1 | 93.9 |
| 8 | 12869 | Q-NC0004504 | 1 | 95.6 | 95.6 | 97.2 |
| 8 | 12869 | Q-NC0104858 | 2 | 96.2 | 95.6 | 97.2 |
| 8 | 12869 | Q-NC0155749 | 3 | 96.2 | 95.6 | 97.2 |
| 8 | 12869 | Q-NC0012023 | 4 | 96.4 | 95.6 | 97.2 |
| 8 | 12869 | Q-NC0104389 | 5 | 97.1 | 95.6 | 97.2 |
| 8 | 12869 | Q-NC0152566 | 6 | 97.2 | 95.6 | 97.2 |
| 8 | 13072 | Q-NC0105835 | 1 | 104 | 104 | 108.5 |
| 8 | 13072 | Q-NC0027300 | 2 | 108.5 | 104 | 108.5 |
| 8 | 13072 | Q-NC0031025 | 3 | 108.5 | 104 | 108.5 |
| 8 | 13072 | Q-NC0082386 | 4 | 108.5 | 104 | 108.5 |
| 8 | 13103 | Q-NC0110684 | 1 | 111.2 | 111.2 | 115.6 |
| 8 | 13103 | Q-NC0112497 | 2 | 111.7 | 111.2 | 115.6 |
| 8 | 13103 | Q-NC0010392 | 3 | 115.4 | 111.2 | 115.6 |
| 8 | 13103 | Q-NC0012656 | 4 | 115.6 | 111.2 | 115.6 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 8 | 13103 | Q-NC0020546 | 5 | 115.6 | 111.2 | 115.6 |
| 8 | 12928 | Q-NC0008831 | 1 | 116.3 | 116.3 | 118.6 |
| 8 | 12928 | Q-NC0153229 | 2 | 116.4 | 116.3 | 118.6 |
| 8 | 12928 | Q-NC0153243 | 3 | 116.4 | 116.3 | 118.6 |
| 8 | 12928 | Q-NC0143432 | 4 | 117.9 | 116.3 | 118.6 |
| 8 | 12928 | Q-NC0020537 | 5 | 118.6 | 116.3 | 118.6 |
| 8 | 12956 | Q-NC0004586 | 1 | 125.1 | 125.1 | 125.1 |
| 8 | 12956 | Q-NC0031630 | 2 | 125.1 | 125.1 | 125.1 |
| 8 | 13098 | Q-NC0003008 | 1 | 130.7 | 130.7 | 134.5 |
| 8 | 13098 | Q-NC0005592 | 2 | 134.5 | 130.7 | 134.5 |
| 8 | 12993 | Q-NC0013100 | 1 | 138.8 | 138.8 | 139.7 |
| 8 | 12993 | Q-NC0027810 | 2 | 139.4 | 138.8 | 139.7 |
| 8 | 12993 | Q-NC0107286 | 3 | 139.7 | 138.8 | 139.7 |
| 8 | 12993 | Q-NC0108962 | 4 | 139.7 | 138.8 | 139.7 |
| 8 | 13059 | Q-NC0145077 | 1 | 149.2 | 149.2 | 149.2 |
| 8 | 13059 | Q-NC0145298 | 2 | 149.2 | 149.2 | 149.2 |
| 8 | 13059 | Q-NC0154802 | 3 | 149.2 | 149.2 | 149.2 |
| 8 | 12872 | Q-NC0014566 | 1 | 155.1 | 155.1 | 156.3 |
| 8 | 12872 | Q-NC0008757 | 2 | 156.3 | 155.1 | 156.3 |
| 8 | 13057 | Q-NC0000561 | 1 | 168.3 | 168.3 | 169.9 |
| 8 | 13057 | Q-NC0060573 | 2 | 169.9 | 168.3 | 169.9 |
| 9 | 12906 | Q-NC0014476 | 1 | 0.8 | 0.8 | 0.8 |
| 9 | 12906 | Q-NC0014479 | 2 | 0.8 | 0.8 | 0.8 |
| 9 | 12943 | Q-NC0054684 | 1 | 8.3 | 8.3 | 8.3 |
| 9 | 13073 | Q-NC0020781 | 1 | 16 | 16 | 19.6 |
| 9 | 13073 | Q-NC0112118 | 2 | 16 | 16 | 19.6 |
| 9 | 13073 | Q-NC0002735 | 3 | 17.6 | 16 | 19.6 |
| 9 | 13073 | Q-NC0113434 | 4 | 19.6 | 16 | 19.6 |
| 9 | 13067 | Q-NC0049557 | 1 | 25.7 | 25.7 | 25.7 |
| 9 | 12986 | Q-NC0012830 | 1 | 33.1 | 33.1 | 36.6 |
| 9 | 12986 | Q-NC0148121 | 2 | 36.6 | 33.1 | 36.6 |
| 9 | 13009 | Q-NC0025198 | 1 | 45.7 | 45.7 | 46.5 |
| 9 | 13009 | Q-NC0029745 | 2 | 45.7 | 45.7 | 46.5 |
| 9 | 13009 | Q-NC0041796 | 3 | 46.5 | 45.7 | 46.5 |
| 9 | 12955 | Q-NC0029436 | 1 | 51.5 | 51.5 | 51.5 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 9 | 12868 | Q-NC0028095 | 1 | 59.4 | 59.4 | 63.4 |
| 9 | 12868 | Q-NC0010643 | 2 | 60.6 | 59.4 | 63.4 |
| 9 | 12868 | Q-NC0055759 | 3 | 62.1 | 59.4 | 63.4 |
| 9 | 12868 | Q-NC0004049 | 4 | 62.5 | 59.4 | 63.4 |
| 9 | 12868 | Q-NC0107905 | 5 | 63.4 | 59.4 | 63.4 |
| 9 | 12877 | Q-NC0080382 | 1 | 65 | 65 | 66.5 |
| 9 | 12877 | Q-NC0018302 | 2 | 65.1 | 65 | 66.5 |
| 9 | 12877 | Q-NC0145117 | 3 | 65.9 | 65 | 66.5 |
| 9 | 12877 | Q-NC0145814 | 4 | 65.9 | 65 | 66.5 |
| 9 | 12877 | Q-NC0031233 | 5 | 66.5 | 65 | 66.5 |
| 9 | 12877 | Q-NC0055370 | 6 | 66.5 | 65 | 66.5 |
| 9 | 12877 | Q-NC0107095 | 7 | 66.5 | 65 | 66.5 |
| 9 | 12877 | Q-NC0109526 | 8 | 66.5 | 65 | 66.5 |
| 9 | 12877 | Q-NC0144042 | 9 | 66.5 | 65 | 66.5 |
| 9 | 12877 | Q-NC0153885 | 10 | 66.5 | 65 | 66.5 |
| 9 | 12926 | Q-NC0029832 | 1 | 66.6 | 66.6 | 68.5 |
| 9 | 12926 | Q-NC0144850 | 2 | 67 | 66.6 | 68.5 |
| 9 | 12926 | Q-NC0004407 | 3 | 67.2 | 66.6 | 68.5 |
| 9 | 12926 | Q-NC0086681 | 4 | 67.5 | 66.6 | 68.5 |
| 9 | 12926 | Q-NC0113113 | 5 | 67.5 | 66.6 | 68.5 |
| 9 | 12926 | Q-NC0025961 | 6 | 68.5 | 66.6 | 68.5 |
| 9 | 12926 | Q-NC0104195 | 7 | 68.5 | 66.6 | 68.5 |
| 9 | 12926 | Q-NC0106345 | 8 | 68.5 | 66.6 | 68.5 |
| 9 | 12926 | Q-NC0106748 | 9 | 68.5 | 66.6 | 68.5 |
| 9 | 12926 | Q-NC0106791 | 10 | 68.5 | 66.6 | 68.5 |
| 9 | 12970 | Q-NC0031039 | 1 | 70.9 | 70.9 | 75.9 |
| 9 | 12970 | Q-NC0009397 | 2 | 72.6 | 70.9 | 75.9 |
| 9 | 12970 | Q-NC0029595 | 3 | 73.1 | 70.9 | 75.9 |
| 9 | 12970 | Q-NC0021430 | 4 | 74.2 | 70.9 | 75.9 |
| 9 | 12970 | Q-NC0028354 | 5 | 75.2 | 70.9 | 75.9 |
| 9 | 12970 | Q-NC0002611 | 6 | 75.9 | 70.9 | 75.9 |
| 9 | 12957 | Q-NC0112189 | 1 | 76.2 | 76.2 | 80.1 |
| 9 | 12957 | Q-NC0020851 | 2 | 76.3 | 76.2 | 80.1 |
| 9 | 12957 | Q-NC0020048 | 3 | 77.5 | 76.2 | 80.1 |
| 9 | 12957 | Q-NC0153427 | 4 | 77.5 | 76.2 | 80.1 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 9 | 12957 | Q-NC0153921 | 5 | 77.5 | 76.2 | 80.1 |
| 9 | 12957 | Q-NC0003231 | 6 | 78.7 | 76.2 | 80.1 |
| 9 | 12957 | Q-NC0111177 | 7 | 80.1 | 76.2 | 80.1 |
| 9 | 12874 | Q-NC0014826 | 1 | 81.8 | 81.8 | 84.5 |
| 9 | 12874 | Q-NC0008937 | 2 | 81.9 | 81.8 | 84.5 |
| 9 | 12874 | Q-NC0110272 | 3 | 82.9 | 81.8 | 84.5 |
| 9 | 12874 | Q-NC0002383 | 4 | 83.3 | 81.8 | 84.5 |
| 9 | 12874 | Q-NC0053284 | 5 | 83.3 | 81.8 | 84.5 |
| 9 | 12874 | Q-NC0061433 | 6 | 83.3 | 81.8 | 84.5 |
| 9 | 12874 | Q-NC0110125 | 7 | 83.4 | 81.8 | 84.5 |
| 9 | 12874 | Q-NC0003425 | 8 | 84.5 | 81.8 | 84.5 |
| 9 | 12874 | Q-NC0038548 | 9 | 84.5 | 81.8 | 84.5 |
| 9 | 12874 | Q-NC0105297 | 10 | 84.5 | 81.8 | 84.5 |
| 9 | 13093 | Q-NC0004123 | 1 | 84.6 | 84.6 | 87.3 |
| 9 | 13093 | Q-NC0031490 | 2 | 84.6 | 84.6 | 87.3 |
| 9 | 13093 | Q-NC0078438 | 3 | 84.6 | 84.6 | 87.3 |
| 9 | 13093 | Q-NC0013086 | 4 | 87.3 | 84.6 | 87.3 |
| 9 | 13026 | Q-NC0081074 | 1 | 90.4 | 90.4 | 91.7 |
| 9 | 13026 | Q-NC0145318 | 2 | 91 | 90.4 | 91.7 |
| 9 | 13026 | Q-NC0108275 | 3 | 91.6 | 90.4 | 91.7 |
| 9 | 13026 | Q-NC0110293 | 4 | 91.7 | 90.4 | 91.7 |
| 9 | 13075 | Q-NC0004890 | 1 | 98.4 | 98.4 | 102.1 |
| 9 | 13075 | Q-NC0106442 | 2 | 98.4 | 98.4 | 102.1 |
| 9 | 13075 | Q-NC0041196 | 3 | 101.5 | 98.4 | 102.1 |
| 9 | 13075 | Q-NC0042348 | 4 | 101.8 | 98.4 | 102.1 |
| 9 | 13075 | Q-NC0018417 | 5 | 102.1 | 98.4 | 102.1 |
| 9 | 13090 | Q-NC0066389 | 1 | 105.5 | 105.5 | 110.5 |
| 9 | 13090 | Q-NC0066390 | 2 | 105.5 | 105.5 | 110.5 |
| 9 | 13090 | Q-NC0036022 | 3 | 107.9 | 105.5 | 110.5 |
| 9 | 13090 | Q-NC0016689 | 4 | 110.4 | 105.5 | 110.5 |
| 9 | 13090 | Q-NC0018446 | 5 | 110.4 | 105.5 | 110.5 |
| 9 | 13090 | Q-NC0035380 | 6 | 110.4 | 105.5 | 110.5 |
| 9 | 13090 | Q-NC0110938 | 7 | 110.5 | 105.5 | 110.5 |
| 9 | 13099 | Q-NC0020368 | 1 | 114.4 | 114.4 | 117.7 |
| 9 | 13099 | Q-NC0151505 | 2 | 114.5 | 114.4 | 117.7 |

TABLE 1-continued

Characterization of haplotype windows in the corn genome based on 465
elite lines and 1231 SNP markers. Haplotype windows in each chromosome are identified
and the markers (disclosed in U.S. Pat. Applications 2005/0218305 and serial no.
11/504,538 which are incorporated herein by reference in their entirety) within each
window are described.

| CHROMOSOME | HAPLOTYPE WINDOW ID | MARKER NAME | MARKER ORDER | POSITION | START POSITION | END POSITION |
|---|---|---|---|---|---|---|
| 9 | 13099 | Q-NC0029176 | 3 | 116 | 114.4 | 117.7 |
| 9 | 13099 | Q-NC0110800 | 4 | 117.7 | 114.4 | 117.7 |
| 9 | 12899 | Q-NC0035729 | 1 | 120.3 | 120.3 | 122.7 |
| 9 | 12899 | Q-NC0039475 | 2 | 122.7 | 120.3 | 122.7 |
| 9 | 13021 | Q-NC0042929 | 1 | 130 | 130 | 133.5 |
| 9 | 13021 | Q-NC0111292 | 2 | 131.1 | 130 | 133.5 |
| 9 | 13021 | Q-NC0009407 | 3 | 133.5 | 130 | 133.5 |
| 9 | 13021 | Q-NC0026895 | 4 | 133.5 | 130 | 133.5 |
| 9 | 13049 | Q-NC0083647 | 1 | 136.7 | 136.7 | 136.7 |
| 9 | 13097 | Q-NC0077194 | 1 | 147.7 | 147.7 | 147.7 |
| 9 | 13094 | Q-NC0049286 | 1 | 153 | 153 | 153.2 |
| 9 | 13094 | Q-NC0147417 | 2 | 153.2 | 153 | 153.2 |
| 10 | 13086 | Q-NC0020088 | 1 | 8.6 | 8.6 | 8.6 |
| 10 | 13077 | Q-NC0153632 | 1 | 24.1 | 24.1 | 24.1 |
| 10 | 12984 | Q-NC0020502 | 1 | 30.3 | 30.3 | 32.2 |
| 10 | 12984 | Q-NC0009645 | 2 | 32.1 | 30.3 | 32.2 |
| 10 | 12984 | Q-NC0104672 | 3 | 32.2 | 30.3 | 32.2 |
| 10 | 13089 | Q-NC0111004 | 1 | 36.7 | 36.7 | 40.8 |
| 10 | 13089 | Q-NC0111682 | 2 | 36.7 | 36.7 | 40.8 |
| 10 | 13089 | Q-NC0154801 | 3 | 40 | 36.7 | 40.8 |
| 10 | 13089 | Q-NC0008956 | 4 | 40.8 | 36.7 | 40.8 |
| 10 | 13080 | Q-NC0016045 | 1 | 43.7 | 43.7 | 47.3 |
| 10 | 13080 | Q-NC0028604 | 2 | 43.7 | 43.7 | 47.3 |
| 10 | 13080 | Q-NC0005255 | 3 | 45 | 43.7 | 47.3 |
| 10 | 13080 | Q-NC0004887 | 4 | 45.2 | 43.7 | 47.3 |
| 10 | 13080 | Q-NC0155598 | 5 | 45.2 | 43.7 | 47.3 |
| 10 | 13080 | Q-NC0000531 | 6 | 45.3 | 43.7 | 47.3 |
| 10 | 13080 | Q-NC0029123 | 7 | 45.3 | 43.7 | 47.3 |
| 10 | 13080 | Q-NC0111212 | 8 | 45.9 | 43.7 | 47.3 |
| 10 | 13080 | Q-NC0143762 | 9 | 46.7 | 43.7 | 47.3 |
| 10 | 13080 | Q-NC0025218 | 10 | 47.3 | 43.7 | 47.3 |
| 10 | 13039 | Q-NC0051974 | 1 | 48.3 | 48.3 | 53 |
| 10 | 13039 | Q-NC0109648 | 2 | 49.1 | 48.3 | 53 |
| 10 | 13039 | Q-NC0109058 | 3 | 49.2 | 48.3 | 53 |
| 10 | 13039 | Q-NC0109866 | 4 | 49.2 | 48.3 | 53 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 10 | 13039 | Q-NC0112238 | 5 | 49.2 | 48.3 | 53 |
| 10 | 13039 | Q-NC0005140 | 6 | 51 | 48.3 | 53 |
| 10 | 13039 | Q-NC0012984 | 7 | 51.3 | 48.3 | 53 |
| 10 | 13039 | Q-NC0105175 | 8 | 51.6 | 48.3 | 53 |
| 10 | 13039 | Q-NC0143388 | 9 | 51.6 | 48.3 | 53 |
| 10 | 13039 | Q-NC0009350 | 10 | 53 | 48.3 | 53 |
| 10 | 13017 | Q-NC0009755 | 1 | 54.2 | 54.2 | 58.9 |
| 10 | 13017 | Q-NC0002285 | 2 | 55.4 | 54.2 | 58.9 |
| 10 | 13017 | Q-NC0039275 | 3 | 55.4 | 54.2 | 58.9 |
| 10 | 13017 | Q-NC0104512 | 4 | 57.3 | 54.2 | 58.9 |
| 10 | 13017 | Q-NC0022717 | 5 | 57.8 | 54.2 | 58.9 |
| 10 | 13017 | Q-NC0003206 | 6 | 58.6 | 54.2 | 58.9 |
| 10 | 13017 | Q-NC0003640 | 7 | 58.9 | 54.2 | 58.9 |
| 10 | 12953 | Q-NC0111360 | 1 | 61.2 | 61.2 | 64.8 |
| 10 | 12953 | Q-NC0009295 | 2 | 61.3 | 61.2 | 64.8 |
| 10 | 12953 | Q-NC0002940 | 3 | 61.4 | 61.2 | 64.8 |
| 10 | 12953 | Q-NC0109090 | 4 | 61.5 | 61.2 | 64.8 |
| 10 | 12953 | Q-NC0084196 | 5 | 63.6 | 61.2 | 64.8 |
| 10 | 12953 | Q-NC0016730 | 6 | 63.8 | 61.2 | 64.8 |
| 10 | 12953 | Q-NC0031358 | 7 | 64.2 | 61.2 | 64.8 |
| 10 | 12953 | Q-NC0107941 | 8 | 64.3 | 61.2 | 64.8 |
| 10 | 12953 | Q-NC0112090 | 9 | 64.8 | 61.2 | 64.8 |
| 10 | 13095 | Q-NC0018392 | 1 | 71.5 | 71.5 | 75.8 |
| 10 | 13095 | Q-NC0027447 | 2 | 75.6 | 71.5 | 75.8 |
| 10 | 13095 | Q-NC0081776 | 3 | 75.8 | 71.5 | 75.8 |
| 10 | 12983 | Q-NC0030134 | 1 | 79.4 | 79.4 | 79.4 |
| 10 | 12901 | Q-NC0011115 | 1 | 90 | 90 | 92.1 |
| 10 | 12901 | Q-NC0070905 | 2 | 92.1 | 90 | 92.1 |
| 10 | 12876 | Q-NC0067173 | 1 | 98 | 98 | 102.2 |
| 10 | 12876 | Q-NC0154948 | 2 | 102.2 | 98 | 102.2 |
| 10 | 13064 | Q-NC0143657 | 1 | 103.5 | 103.5 | 108.3 |
| 10 | 13064 | Q-NC0009486 | 2 | 105.5 | 103.5 | 108.3 |
| 10 | 13064 | Q-NC0109723 | 3 | 108.3 | 103.5 | 108.3 |
| 10 | 12916 | Q-NC0008954 | 1 | 112 | 112 | 114.6 |
| 10 | 12916 | Q-NC0107333 | 2 | 113.1 | 112 | 114.6 |

TABLE 1-continued

Characterization of haplotype windows in the corn genome based on 465 elite lines and 1231 SNP markers. Haplotype windows in each chromosome are identified and the markers (disclosed in U.S. Pat. Applications 2005/0218305 and serial no. 11/504,538 which are incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 10 | 12916 | Q-NC0109666 | 3 | 113.1 | 112 | 114.6 |
| 10 | 12916 | Q-NC0151488 | 4 | 114.6 | 112 | 114.6 |
| 10 | 12967 | Q-NC0008643 | 1 | 119.1 | 119.1 | 123.3 |
| 10 | 12967 | Q-NC0111488 | 2 | 123.3 | 119.1 | 123.3 |

TABLE 2

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 13610 | Q-NS0092678 | 1 | 0 | 0 | 3 |
| 1 | 13610 | Q-NS0092617 | 2 | 0.4 | 0 | 3 |
| 1 | 13610 | Q-NS0101549 | 3 | 1.4 | 0 | 3 |
| 1 | 13610 | Q-NS0127917 | 4 | 1.4 | 0 | 3 |
| 1 | 13610 | Q-NS0120003 | 5 | 1.8 | 0 | 3 |
| 1 | 13610 | Q-NS0118494 | 6 | 3 | 0 | 3 |
| 1 | 13610 | Q-NS0124158 | 7 | 3 | 0 | 3 |
| 1 | 13659 | Q-NS0101025 | 1 | 11.3 | 11.3 | 16.2 |
| 1 | 13659 | Q-NS0101038 | 2 | 11.3 | 11.3 | 16.2 |
| 1 | 13659 | Q-NS0127234 | 3 | 11.3 | 11.3 | 16.2 |
| 1 | 13659 | Q-NS0129173 | 4 | 11.3 | 11.3 | 16.2 |
| 1 | 13659 | Q-NS0097228 | 5 | 16.2 | 11.3 | 16.2 |
| 1 | 13828 | Q-NS0123726 | 1 | 17.9 | 17.9 | 22.1 |
| 1 | 13828 | Q-NS0096824 | 2 | 18.8 | 17.9 | 22.1 |
| 1 | 13828 | Q-NS0096307 | 3 | 22.1 | 17.9 | 22.1 |
| 1 | 13828 | Q-NS0120370 | 4 | 22.1 | 17.9 | 22.1 |
| 1 | 13688 | Q-NS0121738 | 1 | 23.1 | 23.1 | 26.2 |
| 1 | 13688 | Q-NS0118969 | 2 | 25.1 | 23.1 | 26.2 |
| 1 | 13688 | Q-NS0120079 | 3 | 25.1 | 23.1 | 26.2 |
| 1 | 13688 | Q-NS0124450 | 4 | 25.1 | 23.1 | 26.2 |
| 1 | 13688 | Q-NS0126493 | 5 | 25.1 | 23.1 | 26.2 |
| 1 | 13688 | Q-NS0094900 | 6 | 26.2 | 23.1 | 26.2 |
| 1 | 13748 | Q-NS0100189 | 1 | 28.6 | 28.6 | 32 |
| 1 | 13748 | Q-NS0115741 | 2 | 32 | 28.6 | 32 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 1 | 13865 | Q-NS0098951 | 1 | 35 | 35 | 38.3 |
| 1 | 13865 | Q-NS0125096 | 2 | 36.2 | 35 | 38.3 |
| 1 | 13865 | Q-NS0117863 | 3 | 38.3 | 35 | 38.3 |
| 1 | 13865 | Q-NS0122151 | 4 | 38.3 | 35 | 38.3 |
| 1 | 13673 | Q-NS0119049 | 1 | 47.5 | 47.5 | 51.5 |
| 1 | 13673 | Q-NS0115450 | 2 | 47.9 | 47.5 | 51.5 |
| 1 | 13673 | Q-NS0129555 | 3 | 47.9 | 47.5 | 51.5 |
| 1 | 13673 | Q-NS0135427 | 4 | 48.1 | 47.5 | 51.5 |
| 1 | 13673 | Q-NS0093252 | 5 | 51.1 | 47.5 | 51.5 |
| 1 | 13673 | Q-NS0120948 | 6 | 51.1 | 47.5 | 51.5 |
| 1 | 13673 | Q-NS0119584 | 7 | 51.5 | 47.5 | 51.5 |
| 1 | 13716 | Q-NS0119795 | 1 | 53.3 | 53.3 | 55.2 |
| 1 | 13716 | Q-NS0124652 | 2 | 55.2 | 53.3 | 55.2 |
| 1 | 13842 | Q-NS0093775 | 1 | 64.1 | 64.1 | 66.8 |
| 1 | 13842 | Q-NS0136063 | 2 | 66.8 | 64.1 | 66.8 |
| 1 | 13632 | Q-NS0116003 | 1 | 70 | 70 | 73.9 |
| 1 | 13632 | Q-NS0121329 | 2 | 70 | 70 | 73.9 |
| 1 | 13632 | Q-NS0097011 | 3 | 70.4 | 70 | 73.9 |
| 1 | 13632 | Q-NS0136255 | 4 | 73.9 | 70 | 73.9 |
| 1 | 13740 | Q-NS0125407 | 1 | 78.4 | 78.4 | 83.3 |
| 1 | 13740 | Q-NS0115925 | 2 | 79.9 | 78.4 | 83.3 |
| 1 | 13740 | Q-NS0117865 | 3 | 79.9 | 78.4 | 83.3 |
| 1 | 13740 | Q-NS0118789 | 4 | 83.3 | 78.4 | 83.3 |
| 1 | 13707 | Q-NS0115445 | 1 | 90 | 90 | 90 |
| 1 | 13707 | Q-NS0127094 | 2 | 90 | 90 | 90 |
| 1 | 13786 | Q-NS0099886 | 1 | 95.9 | 95.9 | 98.4 |
| 1 | 13786 | Q-NS0101558 | 2 | 97.4 | 95.9 | 98.4 |
| 1 | 13786 | Q-NS0121865 | 3 | 98.4 | 95.9 | 98.4 |
| 1 | 13833 | Q-NS0100425 | 1 | 110.8 | 110.8 | 112 |
| 1 | 13833 | Q-NS0098341 | 2 | 112 | 110.8 | 112 |
| 2 | 13718 | Q-NS0092792 | 1 | 0.4 | 0.4 | 3.7 |
| 2 | 13718 | Q-NS0135783 | 2 | 3.7 | 0.4 | 3.7 |
| 2 | 13758 | Q-NS0093345 | 1 | 22.5 | 22.5 | 23.2 |
| 2 | 13758 | Q-NS0098139 | 2 | 23.2 | 22.5 | 23.2 |
| 2 | 13572 | Q-NS0096933 | 1 | 34.8 | 34.8 | 38.8 |
| 2 | 13572 | Q-NS0094031 | 2 | 38.8 | 34.8 | 38.8 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 2 | 13624 | Q-NS0126797 | 1 | 39.9 | 39.9 | 44 |
| 2 | 13624 | Q-NS0096219 | 2 | 40.3 | 39.9 | 44 |
| 2 | 13624 | Q-NS0125781 | 3 | 42.4 | 39.9 | 44 |
| 2 | 13624 | Q-NS0102988 | 4 | 44 | 39.9 | 44 |
| 2 | 13624 | Q-NS0120970 | 5 | 44 | 39.9 | 44 |
| 2 | 13796 | Q-NS0097413 | 1 | 48.1 | 48.1 | 48.1 |
| 2 | 13818 | Q-NS0124916 | 1 | 56.5 | 56.5 | 57.7 |
| 2 | 13818 | Q-NS0128764 | 2 | 56.5 | 56.5 | 57.7 |
| 2 | 13818 | Q-NS0099649 | 3 | 57.7 | 56.5 | 57.7 |
| 2 | 13776 | Q-NS0128262 | 1 | 62.1 | 62.1 | 62.1 |
| 2 | 13776 | Q-NS0135057 | 2 | 62.1 | 62.1 | 62.1 |
| 2 | 13855 | Q-NS0094352 | 1 | 67.6 | 67.6 | 67.6 |
| 2 | 13861 | Q-NS0103318 | 1 | 73.5 | 73.5 | 76.6 |
| 2 | 13861 | Q-NS0119250 | 2 | 73.7 | 73.5 | 76.6 |
| 2 | 13861 | Q-NS0122142 | 3 | 73.7 | 73.5 | 76.6 |
| 2 | 13861 | Q-NS0119892 | 4 | 76.6 | 73.5 | 76.6 |
| 2 | 13689 | Q-NS0094025 | 1 | 82.3 | 82.3 | 86 |
| 2 | 13689 | Q-NS0136630 | 2 | 83 | 82.3 | 86 |
| 2 | 13689 | Q-NS0093040 | 3 | 85.3 | 82.3 | 86 |
| 2 | 13689 | Q-NS0098210 | 4 | 86 | 82.3 | 86 |
| 2 | 13689 | Q-NS0100393 | 5 | 86 | 82.3 | 86 |
| 2 | 13689 | Q-NS0102832 | 6 | 86 | 82.3 | 86 |
| 2 | 13689 | Q-NS0114305 | 7 | 86 | 82.3 | 86 |
| 2 | 13639 | Q-NS0119402 | 1 | 88.4 | 88.4 | 93.2 |
| 2 | 13639 | Q-NS0137326 | 2 | 93.2 | 88.4 | 93.2 |
| 2 | 13767 | Q-NS0115399 | 1 | 103.9 | 103.9 | 106.7 |
| 2 | 13767 | Q-NS0123688 | 2 | 103.9 | 103.9 | 106.7 |
| 2 | 13767 | Q-NS0124925 | 3 | 104.3 | 103.9 | 106.7 |
| 2 | 13767 | Q-NS0113961 | 4 | 105.8 | 103.9 | 106.7 |
| 2 | 13767 | Q-NS0117731 | 5 | 106.3 | 103.9 | 106.7 |
| 2 | 13767 | Q-NS0121937 | 6 | 106.3 | 103.9 | 106.7 |
| 2 | 13767 | Q-NS0121929 | 7 | 106.7 | 103.9 | 106.7 |
| 2 | 13589 | Q-NS0115045 | 1 | 115.4 | 115.4 | 115.4 |
| 2 | 13589 | Q-NS0130507 | 2 | 115.4 | 115.4 | 115.4 |
| 2 | 13862 | Q-NS0099483 | 1 | 120.6 | 120.6 | 120.6 |
| 3 | 13676 | Q-NS0095629 | 1 | 3.8 | 3.8 | 8.5 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 3 | 13676 | Q-NS0135494 | 2 | 8.5 | 3.8 | 8.5 |
| 3 | 13859 | Q-NS0103206 | 1 | 10.6 | 10.6 | 11 |
| 3 | 13859 | Q-NS0120038 | 2 | 10.6 | 10.6 | 11 |
| 3 | 13859 | Q-NS0124701 | 3 | 11 | 10.6 | 11 |
| 3 | 13761 | Q-NS0099457 | 1 | 16.1 | 16.1 | 16.1 |
| 3 | 13761 | Q-NS0099713 | 2 | 16.1 | 16.1 | 16.1 |
| 3 | 13761 | Q-NS0101568 | 3 | 16.1 | 16.1 | 16.1 |
| 3 | 13761 | Q-NS0118537 | 4 | 16.1 | 16.1 | 16.1 |
| 3 | 13761 | Q-NS0129433 | 5 | 16.1 | 16.1 | 16.1 |
| 3 | 13722 | Q-NS0116069 | 1 | 25 | 25 | 29.8 |
| 3 | 13722 | Q-NS0130106 | 2 | 29.4 | 25 | 29.8 |
| 3 | 13722 | Q-NS0128396 | 3 | 29.8 | 25 | 29.8 |
| 3 | 13715 | Q-NS0127872 | 1 | 31.8 | 31.8 | 31.8 |
| 3 | 13849 | Q-NS0137810 | 1 | 37.9 | 37.9 | 39.3 |
| 3 | 13849 | Q-NS0138025 | 2 | 39.3 | 37.9 | 39.3 |
| 3 | 13680 | Q-NS0115007 | 1 | 43.5 | 43.5 | 45.2 |
| 3 | 13680 | Q-NS0119972 | 2 | 43.5 | 43.5 | 45.2 |
| 3 | 13680 | Q-NS0120592 | 3 | 43.5 | 43.5 | 45.2 |
| 3 | 13680 | Q-NS0124149 | 4 | 43.5 | 43.5 | 45.2 |
| 3 | 13680 | Q-NS0135644 | 5 | 43.5 | 43.5 | 45.2 |
| 3 | 13680 | Q-NS0118628 | 6 | 45.2 | 43.5 | 45.2 |
| 3 | 13626 | Q-NS0098544 | 1 | 50.1 | 50.1 | 55 |
| 3 | 13626 | Q-NS0129502 | 2 | 50.1 | 50.1 | 55 |
| 3 | 13626 | Q-NS0100204 | 3 | 51.3 | 50.1 | 55 |
| 3 | 13626 | Q-NS0102351 | 4 | 51.3 | 50.1 | 55 |
| 3 | 13626 | Q-NS0126363 | 5 | 51.3 | 50.1 | 55 |
| 3 | 13626 | Q-NS0126717 | 6 | 51.3 | 50.1 | 55 |
| 3 | 13626 | Q-NS0098843 | 7 | 53.8 | 50.1 | 55 |
| 3 | 13626 | Q-NS0115031 | 8 | 55 | 50.1 | 55 |
| 3 | 13626 | Q-NS0129945 | 9 | 55 | 50.1 | 55 |
| 3 | 13629 | Q-NS0102924 | 1 | 55.4 | 55.4 | 55.4 |
| 3 | 13850 | Q-NS0123576 | 1 | 71.4 | 71.4 | 74.2 |
| 3 | 13850 | Q-NS0103052 | 2 | 74.2 | 71.4 | 74.2 |
| 3 | 13646 | Q-NS0097691 | 1 | 84.9 | 84.9 | 87.3 |
| 3 | 13646 | Q-NS0124550 | 2 | 87.3 | 84.9 | 87.3 |
| 3 | 13701 | Q-NS0093020 | 1 | 96.9 | 96.9 | 101.2 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 3 | 13701 | Q-NS0103626 | 2 | 99.1 | 96.9 | 101.2 |
| 3 | 13701 | Q-NS0103742 | 3 | 99.1 | 96.9 | 101.2 |
| 3 | 13701 | Q-NS0129472 | 4 | 99.1 | 96.9 | 101.2 |
| 3 | 13701 | Q-NS0125388 | 5 | 99.7 | 96.9 | 101.2 |
| 3 | 13701 | Q-NS0119893 | 6 | 100.3 | 96.9 | 101.2 |
| 3 | 13701 | Q-NS0119938 | 7 | 100.3 | 96.9 | 101.2 |
| 3 | 13701 | Q-NS0121650 | 8 | 100.3 | 96.9 | 101.2 |
| 3 | 13701 | Q-NS0122057 | 9 | 100.3 | 96.9 | 101.2 |
| 3 | 13701 | Q-NS0104071 | 10 | 101.2 | 96.9 | 101.2 |
| 3 | 13737 | Q-NS0096110 | 1 | 103.5 | 103.5 | 103.5 |
| 3 | 13725 | Q-NS0123951 | 1 | 110.6 | 110.6 | 115.6 |
| 3 | 13725 | Q-NS0100940 | 2 | 112.6 | 110.6 | 115.6 |
| 3 | 13725 | Q-NS0118018 | 3 | 113.6 | 110.6 | 115.6 |
| 3 | 13725 | Q-NS0095558 | 4 | 115.6 | 110.6 | 115.6 |
| 3 | 13655 | Q-NS0122225 | 1 | 117 | 117 | 117 |
| 3 | 13752 | Q-NS0103909 | 1 | 126.6 | 126.6 | 130.6 |
| 3 | 13752 | Q-NS0134693 | 2 | 130.6 | 126.6 | 130.6 |
| 3 | 13669 | Q-NS0136661 | 1 | 132.7 | 132.7 | 133.8 |
| 3 | 13669 | Q-NS0120054 | 2 | 133.4 | 132.7 | 133.8 |
| 3 | 13669 | Q-NS0093291 | 3 | 133.8 | 132.7 | 133.8 |
| 3 | 13669 | Q-NS0097611 | 4 | 133.8 | 132.7 | 133.8 |
| 3 | 13669 | Q-NS0103125 | 5 | 133.8 | 132.7 | 133.8 |
| 3 | 13669 | Q-NS0116590 | 6 | 133.8 | 132.7 | 133.8 |
| 3 | 13741 | Q-NS0094097 | 1 | 138.8 | 138.8 | 139.2 |
| 3 | 13741 | Q-NS0114874 | 2 | 138.8 | 138.8 | 139.2 |
| 3 | 13741 | Q-NS0115159 | 3 | 138.8 | 138.8 | 139.2 |
| 3 | 13741 | Q-NS0127432 | 4 | 138.8 | 138.8 | 139.2 |
| 3 | 13741 | Q-NS0097878 | 5 | 139.2 | 138.8 | 139.2 |
| 3 | 13717 | Q-NS0097078 | 1 | 150.2 | 150.2 | 151.3 |
| 3 | 13717 | Q-NS0115022 | 2 | 150.2 | 150.2 | 151.3 |
| 3 | 13717 | Q-NS0118268 | 3 | 150.2 | 150.2 | 151.3 |
| 3 | 13717 | Q-NS0102044 | 4 | 151.3 | 150.2 | 151.3 |
| 3 | 13717 | Q-NS0137989 | 5 | 151.3 | 150.2 | 151.3 |
| 4 | 13809 | Q-NS0097943 | 1 | 0 | 0 | 0 |
| 4 | 13864 | Q-NS0114876 | 1 | 5.1 | 5.1 | 10 |
| 4 | 13864 | Q-NS0115398 | 2 | 5.1 | 5.1 | 10 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 13864 | Q-NS0128006 | 3 | 5.1 | 5.1 | 10 |
| 4 | 13864 | Q-NS0128286 | 4 | 7.4 | 5.1 | 10 |
| 4 | 13864 | Q-NS0126057 | 5 | 8.3 | 5.1 | 10 |
| 4 | 13864 | Q-NS0097763 | 6 | 8.7 | 5.1 | 10 |
| 4 | 13864 | Q-NS0120344 | 7 | 8.7 | 5.1 | 10 |
| 4 | 13864 | Q-NS0094035 | 8 | 10 | 5.1 | 10 |
| 4 | 13757 | Q-NS0119793 | 1 | 11.8 | 11.8 | 11.8 |
| 4 | 13585 | Q-NS0092597 | 1 | 19 | 19 | 19.4 |
| 4 | 13585 | Q-NS0121753 | 2 | 19.4 | 19 | 19.4 |
| 4 | 13585 | Q-NS0135269 | 3 | 19.4 | 19 | 19.4 |
| 4 | 13751 | Q-NS0128418 | 1 | 24.1 | 24.1 | 24.1 |
| 4 | 13628 | Q-NS0100939 | 1 | 32.4 | 32.4 | 33.6 |
| 4 | 13628 | Q-NS0122451 | 2 | 32.4 | 32.4 | 33.6 |
| 4 | 13628 | Q-NS0103121 | 3 | 33.6 | 32.4 | 33.6 |
| 4 | 13687 | Q-NS0118936 | 1 | 41.5 | 41.5 | 45.6 |
| 4 | 13687 | Q-NS0122458 | 2 | 41.5 | 41.5 | 45.6 |
| 4 | 13687 | Q-NS0102629 | 3 | 44.8 | 41.5 | 45.6 |
| 4 | 13687 | Q-NS0103927 | 4 | 44.8 | 41.5 | 45.6 |
| 4 | 13687 | Q-NS0124687 | 5 | 44.8 | 41.5 | 45.6 |
| 4 | 13687 | Q-NS0126961 | 6 | 44.8 | 41.5 | 45.6 |
| 4 | 13687 | Q-NS0098239 | 7 | 45.2 | 41.5 | 45.6 |
| 4 | 13687 | Q-NS0093253 | 8 | 45.6 | 41.5 | 45.6 |
| 4 | 13747 | Q-NS0119674 | 1 | 47.7 | 47.7 | 51.6 |
| 4 | 13747 | Q-NS0128628 | 2 | 47.7 | 47.7 | 51.6 |
| 4 | 13747 | Q-NS0098444 | 3 | 48.1 | 47.7 | 51.6 |
| 4 | 13747 | Q-NS0128393 | 4 | 51.6 | 47.7 | 51.6 |
| 4 | 13784 | Q-NS0100200 | 1 | 53.6 | 53.6 | 53.6 |
| 4 | 13784 | Q-NS0113972 | 2 | 53.6 | 53.6 | 53.6 |
| 4 | 13739 | Q-NS0100304 | 1 | 69 | 69 | 73.1 |
| 4 | 13739 | Q-NS0123567 | 2 | 73.1 | 69 | 73.1 |
| 4 | 13712 | Q-NS0093333 | 1 | 76.6 | 76.6 | 80.8 |
| 4 | 13712 | Q-NS0134715 | 2 | 80.8 | 76.6 | 80.8 |
| 4 | 13853 | Q-NS0136358 | 1 | 91.2 | 91.2 | 92.4 |
| 4 | 13853 | Q-NS0116010 | 2 | 92.4 | 91.2 | 92.4 |
| 4 | 13804 | Q-NS0127436 | 1 | 110.6 | 110.6 | 114.7 |
| 4 | 13804 | Q-NS0102719 | 2 | 113.5 | 110.6 | 114.7 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 4 | 13804 | Q-NS0121437 | 3 | 113.5 | 110.6 | 114.7 |
| 4 | 13804 | Q-NS0120511 | 4 | 113.9 | 110.6 | 114.7 |
| 4 | 13804 | Q-NS0103916 | 5 | 114.7 | 110.6 | 114.7 |
| 4 | 13804 | Q-NS0122402 | 6 | 114.7 | 110.6 | 114.7 |
| 4 | 13807 | Q-NS0093229 | 1 | 125.6 | 125.6 | 125.6 |
| 4 | 13798 | Q-NS0124735 | 1 | 132.1 | 132.1 | 132.1 |
| 4 | 13831 | Q-NS0101355 | 1 | 138.6 | 138.6 | 139 |
| 4 | 13831 | Q-NS0119353 | 2 | 138.6 | 138.6 | 139 |
| 4 | 13831 | Q-NS0128057 | 3 | 138.6 | 138.6 | 139 |
| 4 | 13831 | Q-NS0116504 | 4 | 139 | 138.6 | 139 |
| 5 | 13825 | Q-NS0135209 | 1 | 0 | 0 | 0.2 |
| 5 | 13825 | Q-NS0135791 | 2 | 0 | 0 | 0.2 |
| 5 | 13825 | Q-NS0137720 | 3 | 0.2 | 0 | 0.2 |
| 5 | 13613 | Q-NS0094787 | 1 | 6 | 6 | 10.3 |
| 5 | 13613 | Q-NS0095037 | 2 | 9.1 | 6 | 10.3 |
| 5 | 13613 | Q-NS0096065 | 3 | 9.1 | 6 | 10.3 |
| 5 | 13613 | Q-NS0115071 | 4 | 9.1 | 6 | 10.3 |
| 5 | 13613 | Q-NS0116035 | 5 | 9.1 | 6 | 10.3 |
| 5 | 13613 | Q-NS0102722 | 6 | 9.9 | 6 | 10.3 |
| 5 | 13613 | Q-NS0123078 | 7 | 9.9 | 6 | 10.3 |
| 5 | 13613 | Q-NS0125565 | 8 | 9.9 | 6 | 10.3 |
| 5 | 13613 | Q-NS0130504 | 9 | 9.9 | 6 | 10.3 |
| 5 | 13613 | Q-NS0096316 | 10 | 10.3 | 6 | 10.3 |
| 5 | 13830 | Q-NS0103750 | 1 | 10.7 | 10.7 | 12.9 |
| 5 | 13830 | Q-NS0124929 | 2 | 12.4 | 10.7 | 12.9 |
| 5 | 13830 | Q-NS0100555 | 3 | 12.9 | 10.7 | 12.9 |
| 5 | 13830 | Q-NS0100959 | 4 | 12.9 | 10.7 | 12.9 |
| 5 | 13830 | Q-NS0119950 | 5 | 12.9 | 10.7 | 12.9 |
| 5 | 13830 | Q-NS0121934 | 6 | 12.9 | 10.7 | 12.9 |
| 5 | 13848 | Q-NS0143014 | 1 | 16.4 | 16.4 | 18.5 |
| 5 | 13848 | Q-NS0101671 | 2 | 18.5 | 16.4 | 18.5 |
| 5 | 13848 | Q-NS0101672 | 3 | 18.5 | 16.4 | 18.5 |
| 5 | 13848 | Q-NS0129284 | 4 | 18.5 | 16.4 | 18.5 |
| 5 | 13652 | Q-NS0096897 | 1 | 21.7 | 21.7 | 21.7 |
| 5 | 13652 | Q-NS0096931 | 2 | 21.7 | 21.7 | 21.7 |
| 5 | 13788 | Q-NS0113766 | 1 | 27.1 | 27.1 | 28.6 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 5 | 13788 | Q-NS0128011 | 2 | 27.1 | 27.1 | 28.6 |
| 5 | 13788 | Q-NS0128679 | 3 | 27.1 | 27.1 | 28.6 |
| 5 | 13788 | Q-NS0102713 | 4 | 28.6 | 27.1 | 28.6 |
| 5 | 13788 | Q-NS0102714 | 5 | 28.6 | 27.1 | 28.6 |
| 5 | 13714 | Q-NS0096121 | 1 | 43 | 43 | 43 |
| 5 | 13615 | Q-NS0098536 | 1 | 50.1 | 50.1 | 54.9 |
| 5 | 13615 | Q-NS0098306 | 2 | 50.5 | 50.1 | 54.9 |
| 5 | 13615 | Q-NS0094224 | 3 | 53.8 | 50.1 | 54.9 |
| 5 | 13615 | Q-NS0135800 | 4 | 53.8 | 50.1 | 54.9 |
| 5 | 13615 | Q-NS0094172 | 5 | 54.9 | 50.1 | 54.9 |
| 5 | 13615 | Q-NS0099900 | 6 | 54.9 | 50.1 | 54.9 |
| 5 | 13615 | Q-NS0103417 | 7 | 54.9 | 50.1 | 54.9 |
| 5 | 13615 | Q-NS0115642 | 8 | 54.9 | 50.1 | 54.9 |
| 5 | 13615 | Q-NS0123196 | 9 | 54.9 | 50.1 | 54.9 |
| 5 | 13615 | Q-NS0124052 | 10 | 54.9 | 50.1 | 54.9 |
| 5 | 13598 | Q-NS0094180 | 1 | 55.6 | 55.6 | 60.5 |
| 5 | 13598 | Q-NS0100930 | 2 | 57.8 | 55.6 | 60.5 |
| 5 | 13598 | Q-NS0136594 | 3 | 59.6 | 55.6 | 60.5 |
| 5 | 13598 | Q-NS0099350 | 4 | 59.8 | 55.6 | 60.5 |
| 5 | 13598 | Q-NS0128324 | 5 | 59.8 | 55.6 | 60.5 |
| 5 | 13598 | Q-NS0119989 | 6 | 60.5 | 55.6 | 60.5 |
| 5 | 13710 | Q-NS0095012 | 1 | 61.2 | 61.2 | 64.1 |
| 5 | 13710 | Q-NS0093594 | 2 | 64.1 | 61.2 | 64.1 |
| 5 | 13711 | Q-NS0115460 | 1 | 67.5 | 67.5 | 71.8 |
| 5 | 13711 | Q-NS0119496 | 2 | 67.9 | 67.5 | 71.8 |
| 5 | 13711 | Q-NS0119590 | 3 | 67.9 | 67.5 | 71.8 |
| 5 | 13711 | Q-NS0125448 | 4 | 68.3 | 67.5 | 71.8 |
| 5 | 13711 | Q-NS0126706 | 5 | 68.3 | 67.5 | 71.8 |
| 5 | 13711 | Q-NS0093190 | 6 | 71.8 | 67.5 | 71.8 |
| 5 | 13711 | Q-NS0097813 | 7 | 71.8 | 67.5 | 71.8 |
| 5 | 13711 | Q-NS0103150 | 8 | 71.8 | 67.5 | 71.8 |
| 5 | 13584 | Q-NS0099531 | 1 | 80.3 | 80.3 | 84 |
| 5 | 13584 | Q-NS0119675 | 2 | 82.5 | 80.3 | 84 |
| 5 | 13584 | Q-NS0094114 | 3 | 84 | 80.3 | 84 |
| 5 | 13584 | Q-NS0121655 | 4 | 84 | 80.3 | 84 |
| 5 | 13777 | Q-NS0118422 | 1 | 87.4 | 87.4 | 90.8 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 5 | 13777 | Q-NS0099417 | 2 | 87.7 | 87.4 | 90.8 |
| 5 | 13777 | Q-NS0103945 | 3 | 87.7 | 87.4 | 90.8 |
| 5 | 13777 | Q-NS0116582 | 4 | 87.7 | 87.4 | 90.8 |
| 5 | 13777 | Q-NS0125754 | 5 | 87.7 | 87.4 | 90.8 |
| 5 | 13777 | Q-NS0092676 | 6 | 88.1 | 87.4 | 90.8 |
| 5 | 13777 | Q-NS0124537 | 7 | 88.7 | 87.4 | 90.8 |
| 5 | 13777 | Q-NS0095211 | 8 | 90.8 | 87.4 | 90.8 |
| 5 | 13777 | Q-NS0097307 | 9 | 90.8 | 87.4 | 90.8 |
| 5 | 13574 | Q-NS0093250 | 1 | 95.7 | 95.7 | 98.9 |
| 5 | 13574 | Q-NS0119710 | 2 | 96.5 | 95.7 | 98.9 |
| 5 | 13574 | Q-NS0099454 | 3 | 97.6 | 95.7 | 98.9 |
| 5 | 13574 | Q-NS0102630 | 4 | 97.6 | 95.7 | 98.9 |
| 5 | 13574 | Q-NS0102913 | 5 | 98.9 | 95.7 | 98.9 |
| 5 | 13574 | Q-NS0102915 | 6 | 98.9 | 95.7 | 98.9 |
| 5 | 13579 | Q-NS0102168 | 1 | 106.7 | 106.7 | 107.8 |
| 5 | 13579 | Q-NS0123728 | 2 | 106.7 | 106.7 | 107.8 |
| 5 | 13579 | Q-NS0129943 | 3 | 106.7 | 106.7 | 107.8 |
| 5 | 13579 | Q-NS0092723 | 4 | 107.4 | 106.7 | 107.8 |
| 5 | 13579 | Q-NS0098177 | 5 | 107.8 | 106.7 | 107.8 |
| 5 | 13579 | Q-NS0101121 | 6 | 107.8 | 106.7 | 107.8 |
| 5 | 13579 | Q-NS0127343 | 7 | 107.8 | 106.7 | 107.8 |
| 6 | 13576 | Q-NS0102060 | 1 | 0.2 | 0.2 | 1 |
| 6 | 13576 | Q-NS0100402 | 2 | 0.6 | 0.2 | 1 |
| 6 | 13576 | Q-NS0115649 | 3 | 0.6 | 0.2 | 1 |
| 6 | 13576 | Q-NS0121429 | 4 | 0.6 | 0.2 | 1 |
| 6 | 13576 | Q-NS0129808 | 5 | 1 | 0.2 | 1 |
| 6 | 13726 | Q-NS0119618 | 1 | 5.7 | 5.7 | 7.2 |
| 6 | 13726 | Q-NS0094170 | 2 | 7.2 | 5.7 | 7.2 |
| 6 | 13679 | Q-NS0129030 | 1 | 25.1 | 25.1 | 27.2 |
| 6 | 13679 | Q-NS0115157 | 2 | 26.8 | 25.1 | 27.2 |
| 6 | 13679 | Q-NS0117895 | 3 | 26.8 | 25.1 | 27.2 |
| 6 | 13679 | Q-NS0129008 | 4 | 26.8 | 25.1 | 27.2 |
| 6 | 13679 | Q-NS0127084 | 5 | 27.2 | 25.1 | 27.2 |
| 6 | 13582 | Q-NS0125775 | 1 | 30.3 | 30.3 | 32.9 |
| 6 | 13582 | Q-NS0130788 | 2 | 30.3 | 30.3 | 32.9 |
| 6 | 13582 | Q-NS0093984 | 3 | 32.9 | 30.3 | 32.9 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
| --- | --- | --- | --- | --- | --- | --- |
| 6 | 13582 | Q-NS0096925 | 4 | 32.9 | 30.3 | 32.9 |
| 6 | 13832 | Q-NS0102865 | 1 | 36.6 | 36.6 | 36.6 |
| 6 | 13832 | Q-NS0115923 | 2 | 36.6 | 36.6 | 36.6 |
| 6 | 13832 | Q-NS0119410 | 3 | 36.6 | 36.6 | 36.6 |
| 6 | 13832 | Q-NS0121338 | 4 | 36.6 | 36.6 | 36.6 |
| 6 | 13832 | Q-NS0121413 | 5 | 36.6 | 36.6 | 36.6 |
| 6 | 13832 | Q-NS0125467 | 6 | 36.6 | 36.6 | 36.6 |
| 6 | 13780 | Q-NS0125773 | 1 | 47.3 | 47.3 | 47.3 |
| 6 | 13593 | Q-NS0136566 | 1 | 67.8 | 67.8 | 69.7 |
| 6 | 13593 | Q-NS0118671 | 2 | 69.3 | 67.8 | 69.7 |
| 6 | 13593 | Q-NS0130775 | 3 | 69.7 | 67.8 | 69.7 |
| 6 | 13778 | Q-NS0114019 | 1 | 77.7 | 77.7 | 80.2 |
| 6 | 13778 | Q-NS0126986 | 2 | 79.8 | 77.7 | 80.2 |
| 6 | 13778 | Q-NS0123339 | 3 | 80.2 | 77.7 | 80.2 |
| 6 | 13696 | Q-NS0129403 | 1 | 90.6 | 90.6 | 90.6 |
| 6 | 13815 | Q-NS0128383 | 1 | 95.7 | 95.7 | 96.5 |
| 6 | 13815 | Q-NS0122122 | 2 | 96.5 | 95.7 | 96.5 |
| 6 | 13815 | Q-NS0126047 | 3 | 96.5 | 95.7 | 96.5 |
| 6 | 13815 | Q-NS0126800 | 4 | 96.5 | 95.7 | 96.5 |
| 6 | 13665 | Q-NS0098575 | 1 | 107.4 | 107.4 | 111.6 |
| 6 | 13665 | Q-NS0125835 | 2 | 107.4 | 107.4 | 111.6 |
| 6 | 13665 | Q-NS0115145 | 3 | 110.8 | 107.4 | 111.6 |
| 6 | 13665 | Q-NS0100501 | 4 | 111.6 | 107.4 | 111.6 |
| 6 | 13665 | Q-NS0102058 | 5 | 111.6 | 107.4 | 111.6 |
| 6 | 13665 | Q-NS0102300 | 6 | 111.6 | 107.4 | 111.6 |
| 6 | 13665 | Q-NS0102838 | 7 | 111.6 | 107.4 | 111.6 |
| 6 | 13665 | Q-NS0113988 | 8 | 111.6 | 107.4 | 111.6 |
| 6 | 13665 | Q-NS0114720 | 9 | 111.6 | 107.4 | 111.6 |
| 6 | 13665 | Q-NS0116250 | 10 | 111.6 | 107.4 | 111.6 |
| 6 | 13820 | Q-NS0098582 | 1 | 115.5 | 115.5 | 115.5 |
| 7 | 13685 | Q-NS0103153 | 1 | 0 | 0 | 2 |
| 7 | 13685 | Q-NS0118498 | 2 | 0 | 0 | 2 |
| 7 | 13685 | Q-NS0127563 | 3 | 0 | 0 | 2 |
| 7 | 13685 | Q-NS0135911 | 4 | 0 | 0 | 2 |
| 7 | 13685 | Q-NS0121512 | 5 | 2 | 0 | 2 |
| 7 | 13685 | Q-NS0131156 | 6 | 2 | 0 | 2 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 7 | 13700 | Q-NS0129617 | 1 | 5.7 | 5.7 | 10.3 |
| 7 | 13700 | Q-NS0103494 | 2 | 9.4 | 5.7 | 10.3 |
| 7 | 13700 | Q-NS0103496 | 3 | 9.4 | 5.7 | 10.3 |
| 7 | 13700 | Q-NS0125563 | 4 | 10.3 | 5.7 | 10.3 |
| 7 | 13586 | Q-NS0118654 | 1 | 14.4 | 14.4 | 16.4 |
| 7 | 13586 | Q-NS0104106 | 2 | 14.8 | 14.4 | 16.4 |
| 7 | 13586 | Q-NS0119615 | 3 | 14.8 | 14.4 | 16.4 |
| 7 | 13586 | Q-NS0126820 | 4 | 14.8 | 14.4 | 16.4 |
| 7 | 13586 | Q-NS0138064 | 5 | 15.9 | 14.4 | 16.4 |
| 7 | 13586 | Q-NS0100721 | 6 | 16.4 | 14.4 | 16.4 |
| 7 | 13586 | Q-NS0125981 | 7 | 16.4 | 14.4 | 16.4 |
| 7 | 13656 | Q-NS0119113 | 1 | 23.8 | 23.8 | 27.6 |
| 7 | 13656 | Q-NS0137732 | 2 | 27.6 | 23.8 | 27.6 |
| 7 | 13745 | Q-NS0092931 | 1 | 40.3 | 40.3 | 43.6 |
| 7 | 13745 | Q-NS0121692 | 2 | 41.4 | 40.3 | 43.6 |
| 7 | 13745 | Q-NS0130304 | 3 | 43.4 | 40.3 | 43.6 |
| 7 | 13745 | Q-NS0093980 | 4 | 43.6 | 40.3 | 43.6 |
| 7 | 13729 | Q-NS0127022 | 1 | 55.1 | 55.1 | 58.8 |
| 7 | 13729 | Q-NS0128455 | 2 | 55.1 | 55.1 | 58.8 |
| 7 | 13729 | Q-NS0094867 | 3 | 56.9 | 55.1 | 58.8 |
| 7 | 13729 | Q-NS0114918 | 4 | 56.9 | 55.1 | 58.8 |
| 7 | 13729 | Q-NS0115235 | 5 | 56.9 | 55.1 | 58.8 |
| 7 | 13729 | Q-NS0116059 | 6 | 56.9 | 55.1 | 58.8 |
| 7 | 13729 | Q-NS0100518 | 7 | 58.4 | 55.1 | 58.8 |
| 7 | 13729 | Q-NS0118021 | 8 | 58.4 | 55.1 | 58.8 |
| 7 | 13729 | Q-NS0094165 | 9 | 58.8 | 55.1 | 58.8 |
| 7 | 13729 | Q-NS0101015 | 10 | 58.8 | 55.1 | 58.8 |
| 7 | 13753 | Q-NS0092749 | 1 | 60.4 | 60.4 | 62.2 |
| 7 | 13753 | Q-NS0102633 | 2 | 60.8 | 60.4 | 62.2 |
| 7 | 13753 | Q-NS0096535 | 3 | 62.2 | 60.4 | 62.2 |
| 7 | 13596 | Q-NS0119248 | 1 | 71.2 | 71.2 | 71.2 |
| 7 | 13596 | Q-NS0120307 | 2 | 71.2 | 71.2 | 71.2 |
| 7 | 13607 | Q-NS0124199 | 1 | 78.3 | 78.3 | 80.6 |
| 7 | 13607 | Q-NS0093201 | 2 | 79.9 | 78.3 | 80.6 |
| 7 | 13607 | Q-NS0137459 | 3 | 80.6 | 78.3 | 80.6 |
| 7 | 13730 | Q-NS0101545 | 1 | 84.9 | 84.9 | 88.5 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 7 | 13730 | Q-NS0119241 | 2 | 84.9 | 84.9 | 88.5 |
| 7 | 13730 | Q-NS0093125 | 3 | 87.8 | 84.9 | 88.5 |
| 7 | 13730 | Q-NS0097856 | 4 | 88.5 | 84.9 | 88.5 |
| 7 | 13590 | Q-NS0121458 | 1 | 90.4 | 90.4 | 95.1 |
| 7 | 13590 | Q-NS0101422 | 2 | 92.1 | 90.4 | 95.1 |
| 7 | 13590 | Q-NS0102042 | 3 | 93.3 | 90.4 | 95.1 |
| 7 | 13590 | Q-NS0096207 | 4 | 95.1 | 90.4 | 95.1 |
| 7 | 13590 | Q-NS0097326 | 5 | 95.1 | 90.4 | 95.1 |
| 7 | 13590 | Q-NS0099217 | 6 | 95.1 | 90.4 | 95.1 |
| 7 | 13774 | Q-NS0097320 | 1 | 95.5 | 95.5 | 98 |
| 7 | 13774 | Q-NS0093998 | 2 | 98 | 95.5 | 98 |
| 7 | 13774 | Q-NS0099778 | 3 | 98 | 95.5 | 98 |
| 7 | 13774 | Q-NS0119657 | 4 | 98 | 95.5 | 98 |
| 7 | 13774 | Q-NS0122140 | 5 | 98 | 95.5 | 98 |
| 7 | 13799 | Q-NS0102358 | 1 | 101.3 | 101.3 | 104.9 |
| 7 | 13799 | Q-NS0116413 | 2 | 101.3 | 101.3 | 104.9 |
| 7 | 13799 | Q-NS0119886 | 3 | 101.3 | 101.3 | 104.9 |
| 7 | 13799 | Q-NS0121993 | 4 | 101.3 | 101.3 | 104.9 |
| 7 | 13799 | Q-NS0130102 | 5 | 101.3 | 101.3 | 104.9 |
| 7 | 13799 | Q-NS0122580 | 6 | 102.5 | 101.3 | 104.9 |
| 7 | 13799 | Q-NS0124022 | 7 | 103.7 | 101.3 | 104.9 |
| 7 | 13799 | Q-NS0124976 | 8 | 104.1 | 101.3 | 104.9 |
| 7 | 13799 | Q-NS0125451 | 9 | 104.1 | 101.3 | 104.9 |
| 7 | 13799 | Q-NS0116555 | 10 | 104.9 | 101.3 | 104.9 |
| 7 | 13763 | Q-NS0129726 | 1 | 105.7 | 105.7 | 108.9 |
| 7 | 13763 | Q-NS0116550 | 2 | 106.9 | 105.7 | 108.9 |
| 7 | 13763 | Q-NS0118234 | 3 | 106.9 | 105.7 | 108.9 |
| 7 | 13763 | Q-NS0101563 | 4 | 108.9 | 105.7 | 108.9 |
| 7 | 13763 | Q-NS0129188 | 5 | 108.9 | 105.7 | 108.9 |
| 8 | 13591 | Q-NS0098300 | 1 | 12.4 | 12.4 | 15.2 |
| 8 | 13591 | Q-NS0127931 | 2 | 12.4 | 12.4 | 15.2 |
| 8 | 13591 | Q-NS0128616 | 3 | 12.4 | 12.4 | 15.2 |
| 8 | 13591 | Q-NS0117725 | 4 | 13.6 | 12.4 | 15.2 |
| 8 | 13591 | Q-NS0118420 | 5 | 13.6 | 12.4 | 15.2 |
| 8 | 13591 | Q-NS0122753 | 6 | 13.6 | 12.4 | 15.2 |
| 8 | 13591 | Q-NS0125948 | 7 | 13.6 | 12.4 | 15.2 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 8 | 13591 | Q-NS0127510 | 8 | 13.6 | 12.4 | 15.2 |
| 8 | 13591 | Q-NS0122067 | 9 | 14.8 | 12.4 | 15.2 |
| 8 | 13591 | Q-NS0118665 | 10 | 15.2 | 12.4 | 15.2 |
| 8 | 13571 | Q-NS0127348 | 1 | 15.6 | 15.6 | 15.6 |
| 8 | 13845 | Q-NS0095317 | 1 | 22 | 22 | 22 |
| 8 | 13856 | Q-NS0126526 | 1 | 30.3 | 30.3 | 30.3 |
| 8 | 13621 | Q-NS0103262 | 1 | 38.2 | 38.2 | 42.7 |
| 8 | 13621 | Q-NS0102805 | 2 | 42.7 | 38.2 | 42.7 |
| 8 | 13713 | Q-NS0097658 | 1 | 47.4 | 47.4 | 50.7 |
| 8 | 13713 | Q-NS0098274 | 2 | 50.3 | 47.4 | 50.7 |
| 8 | 13713 | Q-NS0122141 | 3 | 50.3 | 47.4 | 50.7 |
| 8 | 13713 | Q-NS0138091 | 4 | 50.7 | 47.4 | 50.7 |
| 8 | 13611 | Q-NS0092580 | 1 | 54.5 | 54.5 | 58.9 |
| 8 | 13611 | Q-NS0096186 | 2 | 58.9 | 54.5 | 58.9 |
| 8 | 13634 | Q-NS0103570 | 1 | 66.5 | 66.5 | 71.5 |
| 8 | 13634 | Q-NS0125446 | 2 | 66.9 | 66.5 | 71.5 |
| 8 | 13634 | Q-NS0118503 | 3 | 69.2 | 66.5 | 71.5 |
| 8 | 13634 | Q-NS0130503 | 4 | 69.2 | 66.5 | 71.5 |
| 8 | 13634 | Q-NS0094846 | 5 | 71.5 | 66.5 | 71.5 |
| 8 | 13843 | Q-NS0100709 | 1 | 71.9 | 71.9 | 73.8 |
| 8 | 13843 | Q-NS0102926 | 2 | 71.9 | 71.9 | 73.8 |
| 8 | 13843 | Q-NS0114715 | 3 | 71.9 | 71.9 | 73.8 |
| 8 | 13843 | Q-NS0118680 | 4 | 71.9 | 71.9 | 73.8 |
| 8 | 13843 | Q-NS0124014 | 5 | 71.9 | 71.9 | 73.8 |
| 8 | 13843 | Q-NS0126939 | 6 | 71.9 | 71.9 | 73.8 |
| 8 | 13843 | Q-NS0121360 | 7 | 73.8 | 71.9 | 73.8 |
| 8 | 13744 | Q-NS0118909 | 1 | 78 | 78 | 80.1 |
| 8 | 13744 | Q-NS0126697 | 2 | 80.1 | 78 | 80.1 |
| 8 | 13732 | Q-NS0123385 | 1 | 89 | 89 | 91.5 |
| 8 | 13732 | Q-NS0124275 | 2 | 91.5 | 89 | 91.5 |
| 8 | 13821 | Q-NS0115372 | 1 | 97.7 | 97.7 | 102.1 |
| 8 | 13821 | Q-NS0118272 | 2 | 97.7 | 97.7 | 102.1 |
| 8 | 13821 | Q-NS0125762 | 3 | 97.7 | 97.7 | 102.1 |
| 8 | 13821 | Q-NS0131146 | 4 | 102.1 | 97.7 | 102.1 |
| 8 | 13705 | Q-NS0119058 | 1 | 104.1 | 104.1 | 107.3 |
| 8 | 13705 | Q-NS0119069 | 2 | 107.3 | 104.1 | 107.3 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 8 | 13635 | Q-NS0097123 | 1 | 112.8 | 112.8 | 116.7 |
| 8 | 13635 | Q-NS0098200 | 2 | 112.8 | 112.8 | 116.7 |
| 8 | 13635 | Q-NS0125799 | 3 | 115.9 | 112.8 | 116.7 |
| 8 | 13635 | Q-NS0119717 | 4 | 116.7 | 112.8 | 116.7 |
| 8 | 13602 | Q-NS0092799 | 1 | 127.2 | 127.2 | 127.2 |
| 8 | 13734 | Q-NS0118682 | 1 | 139.1 | 139.1 | 144 |
| 8 | 13734 | Q-NS0122106 | 2 | 140.3 | 139.1 | 144 |
| 8 | 13734 | Q-NS0099487 | 3 | 141.1 | 139.1 | 144 |
| 8 | 13734 | Q-NS0128284 | 4 | 141.1 | 139.1 | 144 |
| 8 | 13734 | Q-NS0135210 | 5 | 144 | 139.1 | 144 |
| 9 | 13773 | Q-NS0094289 | 1 | 2.2 | 2.2 | 2.9 |
| 9 | 13773 | Q-NS0096286 | 2 | 2.2 | 2.2 | 2.9 |
| 9 | 13773 | Q-NS0097663 | 3 | 2.9 | 2.2 | 2.9 |
| 9 | 13797 | Q-NS0092853 | 1 | 13.5 | 13.5 | 13.5 |
| 9 | 13577 | Q-NS0093625 | 1 | 25.4 | 25.4 | 27 |
| 9 | 13577 | Q-NS0119357 | 2 | 27 | 25.4 | 27 |
| 9 | 13728 | Q-NS0118923 | 1 | 31.7 | 31.7 | 33.7 |
| 9 | 13728 | Q-NS0096018 | 2 | 33.7 | 31.7 | 33.7 |
| 9 | 13641 | Q-NS0102076 | 1 | 45.3 | 45.3 | 45.3 |
| 9 | 13653 | Q-NS0099037 | 1 | 52.7 | 52.7 | 54.8 |
| 9 | 13653 | Q-NS0125846 | 2 | 54.8 | 52.7 | 54.8 |
| 9 | 13772 | Q-NS0118297 | 1 | 63.1 | 63.1 | 63.5 |
| 9 | 13772 | Q-NS0115731 | 2 | 63.5 | 63.1 | 63.5 |
| 9 | 13772 | Q-NS0119916 | 3 | 63.5 | 63.1 | 63.5 |
| 9 | 13772 | Q-NS0126153 | 4 | 63.5 | 63.1 | 63.5 |
| 9 | 13698 | Q-NS0114310 | 1 | 69 | 69 | 71.4 |
| 9 | 13698 | Q-NS0119715 | 2 | 69 | 69 | 71.4 |
| 9 | 13698 | Q-NS0130220 | 3 | 69 | 69 | 71.4 |
| 9 | 13698 | Q-NS0103038 | 4 | 70.3 | 69 | 71.4 |
| 9 | 13698 | Q-NS0103043 | 5 | 70.3 | 69 | 71.4 |
| 9 | 13698 | Q-NS0103137 | 6 | 70.3 | 69 | 71.4 |
| 9 | 13698 | Q-NS0102480 | 7 | 70.7 | 69 | 71.4 |
| 9 | 13698 | Q-NS0118662 | 8 | 70.7 | 69 | 71.4 |
| 9 | 13698 | Q-NS0121771 | 9 | 70.7 | 69 | 71.4 |
| 9 | 13698 | Q-NS0099654 | 10 | 71.4 | 69 | 71.4 |
| 9 | 13592 | Q-NS0092560 | 1 | 72.8 | 72.8 | 77.2 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 9 | 13592 | Q-NS0100727 | 2 | 73.9 | 72.8 | 77.2 |
| 9 | 13592 | Q-NS0100733 | 3 | 73.9 | 72.8 | 77.2 |
| 9 | 13592 | Q-NS0119594 | 4 | 73.9 | 72.8 | 77.2 |
| 9 | 13592 | Q-NS0120227 | 5 | 73.9 | 72.8 | 77.2 |
| 9 | 13592 | Q-NS0103000 | 6 | 77.2 | 72.8 | 77.2 |
| 9 | 13592 | Q-NS0104136 | 7 | 77.2 | 72.8 | 77.2 |
| 9 | 13592 | Q-NS0123823 | 8 | 77.2 | 72.8 | 77.2 |
| 9 | 13822 | Q-NS0118897 | 1 | 80.6 | 80.6 | 83.2 |
| 9 | 13822 | Q-NS0122349 | 2 | 80.6 | 80.6 | 83.2 |
| 9 | 13822 | Q-NS0130920 | 3 | 80.6 | 80.6 | 83.2 |
| 9 | 13822 | Q-NS0124601 | 4 | 83.2 | 80.6 | 83.2 |
| 9 | 13764 | Q-NS0103749 | 1 | 88.3 | 88.3 | 91.3 |
| 9 | 13764 | Q-NS0096829 | 2 | 89 | 88.3 | 91.3 |
| 9 | 13764 | Q-NS0099746 | 3 | 89 | 88.3 | 91.3 |
| 9 | 13764 | Q-NS0123747 | 4 | 89 | 88.3 | 91.3 |
| 9 | 13764 | Q-NS0125408 | 5 | 89 | 88.3 | 91.3 |
| 9 | 13764 | Q-NS0126598 | 6 | 89 | 88.3 | 91.3 |
| 9 | 13764 | Q-NS0128378 | 7 | 89 | 88.3 | 91.3 |
| 9 | 13764 | Q-NS0098902 | 8 | 89.7 | 88.3 | 91.3 |
| 9 | 13764 | Q-NS0099529 | 9 | 89.7 | 88.3 | 91.3 |
| 9 | 13764 | Q-NS0097798 | 10 | 91.3 | 88.3 | 91.3 |
| 9 | 13817 | Q-NS0137477 | 1 | 93.7 | 93.7 | 93.9 |
| 9 | 13817 | Q-NS0095322 | 2 | 93.9 | 93.7 | 93.9 |
| 9 | 13817 | Q-NS0136101 | 3 | 93.9 | 93.7 | 93.9 |
| 9 | 13783 | Q-NS0093385 | 1 | 98.8 | 98.8 | 103.7 |
| 9 | 13783 | Q-NS0093976 | 2 | 98.8 | 98.8 | 103.7 |
| 9 | 13783 | Q-NS0098982 | 3 | 98.8 | 98.8 | 103.7 |
| 9 | 13783 | Q-NS0135390 | 4 | 98.8 | 98.8 | 103.7 |
| 9 | 13783 | Q-NS0128617 | 5 | 103.7 | 98.8 | 103.7 |
| 9 | 13731 | Q-NS0095345 | 1 | 106.4 | 106.4 | 106.4 |
| 9 | 13800 | Q-NS0125281 | 1 | 114.3 | 114.3 | 115.9 |
| 9 | 13800 | Q-NS0118716 | 2 | 115.9 | 114.3 | 115.9 |
| 9 | 13637 | Q-NS0128026 | 1 | 121.9 | 121.9 | 122.6 |
| 9 | 13637 | Q-NS0136087 | 2 | 122.6 | 121.9 | 122.6 |
| 9 | 13771 | Q-NS0134935 | 1 | 128.1 | 128.1 | 131.5 |
| 9 | 13771 | Q-NS0095549 | 2 | 128.5 | 128.1 | 131.5 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 9 | 13771 | Q-NS0098169 | 3 | 128.5 | 128.1 | 131.5 |
| 9 | 13771 | Q-NS0116281 | 4 | 128.7 | 128.1 | 131.5 |
| 9 | 13771 | Q-NS0123870 | 5 | 128.7 | 128.1 | 131.5 |
| 9 | 13771 | Q-NS0094475 | 6 | 129.2 | 128.1 | 131.5 |
| 9 | 13771 | Q-NS0127833 | 7 | 131.5 | 128.1 | 131.5 |
| 10 | 13723 | Q-NS0113936 | 1 | 3.6 | 3.6 | 5.8 |
| 10 | 13723 | Q-NS0114153 | 2 | 3.6 | 3.6 | 5.8 |
| 10 | 13723 | Q-NS0119880 | 3 | 3.6 | 3.6 | 5.8 |
| 10 | 13723 | Q-NS0120346 | 4 | 3.6 | 3.6 | 5.8 |
| 10 | 13723 | Q-NS0102833 | 5 | 4 | 3.6 | 5.8 |
| 10 | 13723 | Q-NS0122064 | 6 | 4 | 3.6 | 5.8 |
| 10 | 13723 | Q-NS0127907 | 7 | 4 | 3.6 | 5.8 |
| 10 | 13723 | Q-NS0120032 | 8 | 4.4 | 3.6 | 5.8 |
| 10 | 13723 | Q-NS0129380 | 9 | 4.4 | 3.6 | 5.8 |
| 10 | 13723 | Q-NS0094318 | 10 | 5.8 | 3.6 | 5.8 |
| 10 | 13619 | Q-NS0103508 | 1 | 10.6 | 10.6 | 14 |
| 10 | 13619 | Q-NS0115254 | 2 | 10.6 | 10.6 | 14 |
| 10 | 13619 | Q-NS0103020 | 3 | 12.6 | 10.6 | 14 |
| 10 | 13619 | Q-NS0101266 | 4 | 13.3 | 10.6 | 14 |
| 10 | 13619 | Q-NS0125414 | 5 | 13.3 | 10.6 | 14 |
| 10 | 13619 | Q-NS0101200 | 6 | 14 | 10.6 | 14 |
| 10 | 13619 | Q-NS0103639 | 7 | 14 | 10.6 | 14 |
| 10 | 13619 | Q-NS0125552 | 8 | 14 | 10.6 | 14 |
| 10 | 13619 | Q-NS0128596 | 9 | 14 | 10.6 | 14 |
| 10 | 13785 | Q-NS0103500 | 1 | 20 | 20 | 23 |
| 10 | 13785 | Q-NS0092681 | 2 | 23 | 20 | 23 |
| 10 | 13785 | Q-NS0103490 | 3 | 23 | 20 | 23 |
| 10 | 13622 | Q-NS0122178 | 1 | 30.6 | 30.6 | 32.6 |
| 10 | 13622 | Q-NS0124951 | 2 | 30.6 | 30.6 | 32.6 |
| 10 | 13622 | Q-NS0137560 | 3 | 32.6 | 30.6 | 32.6 |
| 10 | 13677 | Q-NS0122466 | 1 | 39.3 | 39.3 | 39.3 |
| 10 | 13609 | Q-NS0100002 | 1 | 47.5 | 47.5 | 47.5 |
| 10 | 13609 | Q-NS0120004 | 2 | 47.5 | 47.5 | 47.5 |
| 10 | 13857 | Q-NS0099994 | 1 | 55.9 | 55.9 | 59.5 |
| 10 | 13857 | Q-NS0093271 | 2 | 58.7 | 55.9 | 59.5 |
| 10 | 13857 | Q-NS0095620 | 3 | 59.5 | 55.9 | 59.5 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 10 | 13671 | Q-NS0097162 | 1 | 72.5 | 72.5 | 74.3 |
| 10 | 13671 | Q-NS0097165 | 2 | 72.5 | 72.5 | 74.3 |
| 10 | 13671 | Q-NS0124883 | 3 | 72.5 | 72.5 | 74.3 |
| 10 | 13671 | Q-NS0100243 | 4 | 74.3 | 72.5 | 74.3 |
| 10 | 13580 | Q-NS0093353 | 1 | 98.9 | 98.9 | 99.3 |
| 10 | 13580 | Q-NS0100433 | 2 | 99.3 | 98.9 | 99.3 |
| 10 | 13580 | Q-NS0120122 | 3 | 99.3 | 98.9 | 99.3 |
| 10 | 13746 | Q-NS0124477 | 1 | 110.4 | 110.4 | 110.4 |
| 10 | 13746 | Q-NS0130660 | 2 | 110.4 | 110.4 | 110.4 |
| 11 | 13738 | Q-NS0102362 | 1 | 33 | 33 | 38 |
| 11 | 13738 | Q-NS0102871 | 2 | 33 | 33 | 38 |
| 11 | 13738 | Q-NS0101258 | 3 | 33.4 | 33 | 38 |
| 11 | 13738 | Q-NS0102684 | 4 | 33.4 | 33 | 38 |
| 11 | 13738 | Q-NS0119532 | 5 | 33.4 | 33 | 38 |
| 11 | 13738 | Q-NS0117716 | 6 | 38 | 33 | 38 |
| 11 | 13583 | Q-NS0100652 | 1 | 38.4 | 38.4 | 42.2 |
| 11 | 13583 | Q-NS0103073 | 2 | 38.4 | 38.4 | 42.2 |
| 11 | 13583 | Q-NS0119574 | 3 | 38.4 | 38.4 | 42.2 |
| 11 | 13583 | Q-NS0127728 | 4 | 38.4 | 38.4 | 42.2 |
| 11 | 13583 | Q-NS0129721 | 5 | 38.4 | 38.4 | 42.2 |
| 11 | 13583 | Q-NS0093520 | 6 | 39.1 | 38.4 | 42.2 |
| 11 | 13583 | Q-NS0124702 | 7 | 42.2 | 38.4 | 42.2 |
| 11 | 13604 | Q-NS0099639 | 1 | 43.5 | 43.5 | 47.1 |
| 11 | 13604 | Q-NS0093290 | 2 | 45.3 | 43.5 | 47.1 |
| 11 | 13604 | Q-NS0102656 | 3 | 47.1 | 43.5 | 47.1 |
| 11 | 13750 | Q-NS0119842 | 1 | 49.8 | 49.8 | 53.9 |
| 11 | 13750 | Q-NS0124584 | 2 | 49.8 | 49.8 | 53.9 |
| 11 | 13750 | Q-NS0095258 | 3 | 53.9 | 49.8 | 53.9 |
| 11 | 13706 | Q-NS0120298 | 1 | 55.9 | 55.9 | 58.7 |
| 11 | 13706 | Q-NS0103255 | 2 | 56.4 | 55.9 | 58.7 |
| 11 | 13706 | Q-NS0119106 | 3 | 56.4 | 55.9 | 58.7 |
| 11 | 13706 | Q-NS0119663 | 4 | 56.4 | 55.9 | 58.7 |
| 11 | 13706 | Q-NS0124762 | 5 | 56.4 | 55.9 | 58.7 |
| 11 | 13706 | Q-NS0125528 | 6 | 56.4 | 55.9 | 58.7 |
| 11 | 13706 | Q-NS0101020 | 7 | 58.7 | 55.9 | 58.7 |
| 11 | 13706 | Q-NS0101779 | 8 | 58.7 | 55.9 | 58.7 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 11 | 13706 | Q-NS0115345 | 9 | 58.7 | 55.9 | 58.7 |
| 11 | 13706 | Q-NS0115490 | 10 | 58.7 | 55.9 | 58.7 |
| 11 | 13691 | Q-NS0098838 | 1 | 60 | 60 | 62.5 |
| 11 | 13691 | Q-NS0122116 | 2 | 62.5 | 60 | 62.5 |
| 11 | 13691 | Q-NS0127464 | 3 | 62.5 | 60 | 62.5 |
| 11 | 13826 | Q-NS0097342 | 1 | 67.6 | 67.6 | 67.6 |
| 11 | 13651 | Q-NS0095603 | 1 | 75.9 | 75.9 | 78.1 |
| 11 | 13651 | Q-NS0100443 | 2 | 75.9 | 75.9 | 78.1 |
| 11 | 13651 | Q-NS0125951 | 3 | 75.9 | 75.9 | 78.1 |
| 11 | 13651 | Q-NS0129473 | 4 | 78.1 | 75.9 | 78.1 |
| 11 | 13651 | Q-NS0130101 | 5 | 78.1 | 75.9 | 78.1 |
| 11 | 13686 | Q-NS0101264 | 1 | 92.7 | 92.7 | 95.4 |
| 11 | 13686 | Q-NS0097285 | 2 | 93.1 | 92.7 | 95.4 |
| 11 | 13686 | Q-NS0102282 | 3 | 93.1 | 92.7 | 95.4 |
| 11 | 13686 | Q-NS0114731 | 4 | 95.4 | 92.7 | 95.4 |
| 11 | 13630 | Q-NS0120342 | 1 | 98.7 | 98.7 | 98.7 |
| 11 | 13627 | Q-NS0127549 | 1 | 111.1 | 111.1 | 111.1 |
| 12 | 13801 | Q-NS0118525 | 1 | 0 | 0 | 1.4 |
| 12 | 13801 | Q-NS0094896 | 2 | 1.4 | 0 | 1.4 |
| 12 | 13709 | Q-NS0102036 | 1 | 7.9 | 7.9 | 8.3 |
| 12 | 13709 | Q-NS0126300 | 2 | 7.9 | 7.9 | 8.3 |
| 12 | 13709 | Q-NS0092748 | 3 | 8.3 | 7.9 | 8.3 |
| 12 | 13709 | Q-NS0096662 | 4 | 8.3 | 7.9 | 8.3 |
| 12 | 13709 | Q-NS0102486 | 5 | 8.3 | 7.9 | 8.3 |
| 12 | 13709 | Q-NS0113966 | 6 | 8.3 | 7.9 | 8.3 |
| 12 | 13709 | Q-NS0115910 | 7 | 8.3 | 7.9 | 8.3 |
| 12 | 13709 | Q-NS0119246 | 8 | 8.3 | 7.9 | 8.3 |
| 12 | 13709 | Q-NS0119576 | 9 | 8.3 | 7.9 | 8.3 |
| 12 | 13709 | Q-NS0125455 | 10 | 8.3 | 7.9 | 8.3 |
| 12 | 13647 | Q-NS0096983 | 1 | 8.7 | 8.7 | 12.2 |
| 12 | 13647 | Q-NS0118149 | 2 | 11.4 | 8.7 | 12.2 |
| 12 | 13647 | Q-NS0127482 | 3 | 12.2 | 8.7 | 12.2 |
| 12 | 13851 | Q-NS0096191 | 1 | 18.8 | 18.8 | 21.8 |
| 12 | 13851 | Q-NS0096518 | 2 | 21.8 | 18.8 | 21.8 |
| 12 | 13851 | Q-NS0115081 | 3 | 21.8 | 18.8 | 21.8 |
| 12 | 13781 | Q-NS0126302 | 1 | 24.8 | 24.8 | 28.6 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 12 | 13781 | Q-NS0104050 | 2 | 25.2 | 24.8 | 28.6 |
| 12 | 13781 | Q-NS0118536 | 3 | 28.6 | 24.8 | 28.6 |
| 12 | 13668 | Q-NS0124644 | 1 | 30.2 | 30.2 | 30.2 |
| 12 | 13573 | Q-NS0095592 | 1 | 44.4 | 44.4 | 48.8 |
| 12 | 13573 | Q-NS0102848 | 2 | 47 | 44.4 | 48.8 |
| 12 | 13573 | Q-NS0122160 | 3 | 48.8 | 44.4 | 48.8 |
| 12 | 13720 | Q-NS0126422 | 1 | 50.9 | 50.9 | 55.7 |
| 12 | 13720 | Q-NS0119895 | 2 | 53.3 | 50.9 | 55.7 |
| 12 | 13720 | Q-NS0116502 | 3 | 53.7 | 50.9 | 55.7 |
| 12 | 13720 | Q-NS0096504 | 4 | 54.2 | 50.9 | 55.7 |
| 12 | 13720 | Q-NS0093247 | 5 | 55.3 | 50.9 | 55.7 |
| 12 | 13720 | Q-NS0119245 | 6 | 55.7 | 50.9 | 55.7 |
| 12 | 13575 | Q-NS0135192 | 1 | 63.7 | 63.7 | 65.4 |
| 12 | 13575 | Q-NS0124278 | 2 | 65 | 63.7 | 65.4 |
| 12 | 13575 | Q-NS0125101 | 3 | 65.4 | 63.7 | 65.4 |
| 12 | 13625 | Q-NS0096273 | 1 | 80.1 | 80.1 | 80.1 |
| 12 | 13625 | Q-NS0115806 | 2 | 80.1 | 80.1 | 80.1 |
| 12 | 13625 | Q-NS0125805 | 3 | 80.1 | 80.1 | 80.1 |
| 12 | 13816 | Q-NS0102910 | 1 | 86 | 86 | 89.1 |
| 12 | 13816 | Q-NS0103457 | 2 | 86 | 86 | 89.1 |
| 12 | 13816 | Q-NS0114554 | 3 | 86 | 86 | 89.1 |
| 12 | 13816 | Q-NS0104178 | 4 | 89.1 | 86 | 89.1 |
| 12 | 13816 | Q-NS0124144 | 5 | 89.1 | 86 | 89.1 |
| 12 | 13816 | Q-NS0126713 | 6 | 89.1 | 86 | 89.1 |
| 12 | 13816 | Q-NS0127437 | 7 | 89.1 | 86 | 89.1 |
| 12 | 13816 | Q-NS0129406 | 8 | 89.1 | 86 | 89.1 |
| 12 | 13636 | Q-NS0121640 | 1 | 91.9 | 91.9 | 93.1 |
| 12 | 13636 | Q-NS0125159 | 2 | 91.9 | 91.9 | 93.1 |
| 12 | 13636 | Q-NS0129803 | 3 | 91.9 | 91.9 | 93.1 |
| 12 | 13636 | Q-NS0100477 | 4 | 92.3 | 91.9 | 93.1 |
| 12 | 13636 | Q-NS0118058 | 5 | 92.3 | 91.9 | 93.1 |
| 12 | 13636 | Q-NS0115491 | 6 | 92.7 | 91.9 | 93.1 |
| 12 | 13636 | Q-NS0115737 | 7 | 93.1 | 91.9 | 93.1 |
| 12 | 13636 | Q-NS0122471 | 8 | 93.1 | 91.9 | 93.1 |
| 12 | 13708 | Q-NS0101012 | 1 | 99.6 | 99.6 | 104.1 |
| 12 | 13708 | Q-NS0116075 | 2 | 99.6 | 99.6 | 104.1 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 12 | 13708 | Q-NS0128274 | 3 | 99.6 | 99.6 | 104.1 |
| 12 | 13708 | Q-NS0103451 | 4 | 104.1 | 99.6 | 104.1 |
| 12 | 13708 | Q-NS0118034 | 5 | 104.1 | 99.6 | 104.1 |
| 12 | 13708 | Q-NS0128459 | 6 | 104.1 | 99.6 | 104.1 |
| 12 | 13657 | Q-NS0101552 | 1 | 120.9 | 120.9 | 120.9 |
| 12 | 13678 | Q-NS0102573 | 1 | 127.7 | 127.7 | 128.4 |
| 12 | 13678 | Q-NS0103760 | 2 | 127.7 | 127.7 | 128.4 |
| 12 | 13678 | Q-NS0103506 | 3 | 128.4 | 127.7 | 128.4 |
| 12 | 13803 | Q-NS0101550 | 1 | 135.9 | 135.9 | 135.9 |
| 13 | 13672 | Q-NS0118927 | 1 | 1.1 | 1.1 | 4.5 |
| 13 | 13672 | Q-NS0104048 | 2 | 1.5 | 1.1 | 4.5 |
| 13 | 13672 | Q-NS0115455 | 3 | 1.5 | 1.1 | 4.5 |
| 13 | 13672 | Q-NS0121436 | 4 | 1.5 | 1.1 | 4.5 |
| 13 | 13672 | Q-NS0128623 | 5 | 1.5 | 1.1 | 4.5 |
| 13 | 13672 | Q-NS0129014 | 6 | 1.5 | 1.1 | 4.5 |
| 13 | 13672 | Q-NS0130036 | 7 | 4.5 | 1.1 | 4.5 |
| 13 | 13806 | Q-NS0099503 | 1 | 8.1 | 8.1 | 12.2 |
| 13 | 13806 | Q-NS0129821 | 2 | 8.1 | 8.1 | 12.2 |
| 13 | 13806 | Q-NS0092979 | 3 | 12.2 | 8.1 | 12.2 |
| 13 | 13735 | Q-NS0127932 | 1 | 21.4 | 21.4 | 24.5 |
| 13 | 13735 | Q-NS0092810 | 2 | 23.6 | 21.4 | 24.5 |
| 13 | 13735 | Q-NS0103030 | 3 | 24 | 21.4 | 24.5 |
| 13 | 13735 | Q-NS0103033 | 4 | 24 | 21.4 | 24.5 |
| 13 | 13735 | Q-NS0094174 | 5 | 24.5 | 21.4 | 24.5 |
| 13 | 13614 | Q-NS0119974 | 1 | 26.5 | 26.5 | 30.8 |
| 13 | 13614 | Q-NS0124313 | 2 | 26.5 | 26.5 | 30.8 |
| 13 | 13614 | Q-NS0095551 | 3 | 30.8 | 26.5 | 30.8 |
| 13 | 13614 | Q-NS0135554 | 4 | 30.8 | 26.5 | 30.8 |
| 13 | 13633 | Q-NS0127031 | 1 | 31.6 | 31.6 | 36.6 |
| 13 | 13633 | Q-NS0099781 | 2 | 33.6 | 31.6 | 36.6 |
| 13 | 13633 | Q-NS0119495 | 3 | 36.6 | 31.6 | 36.6 |
| 13 | 13829 | Q-NS0093552 | 1 | 40.3 | 40.3 | 41.9 |
| 13 | 13829 | Q-NS0103479 | 2 | 41.5 | 40.3 | 41.9 |
| 13 | 13829 | Q-NS0103075 | 3 | 41.9 | 40.3 | 41.9 |
| 13 | 13684 | Q-NS0124935 | 1 | 45.7 | 45.7 | 49.6 |
| 13 | 13684 | Q-NS0093837 | 2 | 48.1 | 45.7 | 49.6 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 13 | 13684 | Q-NS0119927 | 3 | 49.1 | 45.7 | 49.6 |
| 13 | 13684 | Q-NS0097173 | 4 | 49.6 | 45.7 | 49.6 |
| 13 | 13793 | Q-NS0116174 | 1 | 51.4 | 51.4 | 53.3 |
| 13 | 13793 | Q-NS0119285 | 2 | 51.4 | 51.4 | 53.3 |
| 13 | 13793 | Q-NS0122022 | 3 | 51.4 | 51.4 | 53.3 |
| 13 | 13793 | Q-NS0129930 | 4 | 51.4 | 51.4 | 53.3 |
| 13 | 13793 | Q-NS0097434 | 5 | 51.8 | 51.4 | 53.3 |
| 13 | 13793 | Q-NS0098681 | 6 | 52.6 | 51.4 | 53.3 |
| 13 | 13793 | Q-NS0098848 | 7 | 52.6 | 51.4 | 53.3 |
| 13 | 13793 | Q-NS0093819 | 8 | 53.3 | 51.4 | 53.3 |
| 13 | 13600 | Q-NS0101743 | 1 | 59.2 | 59.2 | 59.6 |
| 13 | 13600 | Q-NS0118028 | 2 | 59.2 | 59.2 | 59.6 |
| 13 | 13600 | Q-NS0119602 | 3 | 59.2 | 59.2 | 59.6 |
| 13 | 13600 | Q-NS0123186 | 4 | 59.6 | 59.2 | 59.6 |
| 13 | 13760 | Q-NS0119484 | 1 | 65 | 65 | 67.4 |
| 13 | 13760 | Q-NS0100545 | 2 | 66.2 | 65 | 67.4 |
| 13 | 13760 | Q-NS0118889 | 3 | 66.2 | 65 | 67.4 |
| 13 | 13760 | Q-NS0104052 | 4 | 67.4 | 65 | 67.4 |
| 13 | 13760 | Q-NS0104054 | 5 | 67.4 | 65 | 67.4 |
| 13 | 13760 | Q-NS0113986 | 6 | 67.4 | 65 | 67.4 |
| 13 | 13760 | Q-NS0115630 | 7 | 67.4 | 65 | 67.4 |
| 13 | 13760 | Q-NS0121909 | 8 | 67.4 | 65 | 67.4 |
| 13 | 13760 | Q-NS0125744 | 9 | 67.4 | 65 | 67.4 |
| 13 | 13760 | Q-NS0128732 | 10 | 67.4 | 65 | 67.4 |
| 13 | 13721 | Q-NS0101382 | 1 | 71.4 | 71.4 | 75.5 |
| 13 | 13721 | Q-NS0125229 | 2 | 71.4 | 71.4 | 75.5 |
| 13 | 13721 | Q-NS0123719 | 3 | 72.2 | 71.4 | 75.5 |
| 13 | 13721 | Q-NS0100551 | 4 | 75.5 | 71.4 | 75.5 |
| 13 | 13649 | Q-NS0097084 | 1 | 79 | 79 | 79 |
| 13 | 13794 | Q-NS0121334 | 1 | 85.1 | 85.1 | 90.1 |
| 13 | 13794 | Q-NS0126308 | 2 | 85.1 | 85.1 | 90.1 |
| 13 | 13794 | Q-NS0114875 | 3 | 88.6 | 85.1 | 90.1 |
| 13 | 13794 | Q-NS0120375 | 4 | 88.6 | 85.1 | 90.1 |
| 13 | 13794 | Q-NS0126996 | 5 | 88.6 | 85.1 | 90.1 |
| 13 | 13794 | Q-NS0125887 | 6 | 88.7 | 85.1 | 90.1 |
| 13 | 13794 | Q-NS0093157 | 7 | 89.6 | 85.1 | 90.1 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 13 | 13794 | Q-NS0100436 | 8 | 89.6 | 85.1 | 90.1 |
| 13 | 13794 | Q-NS0126793 | 9 | 89.6 | 85.1 | 90.1 |
| 13 | 13794 | Q-NS0120123 | 10 | 90.1 | 85.1 | 90.1 |
| 13 | 13810 | Q-NS0101783 | 1 | 90.3 | 90.3 | 92.6 |
| 13 | 13810 | Q-NS0119535 | 2 | 90.3 | 90.3 | 92.6 |
| 13 | 13810 | Q-NS0124571 | 3 | 90.3 | 90.3 | 92.6 |
| 13 | 13810 | Q-NS0135251 | 4 | 92.6 | 90.3 | 92.6 |
| 13 | 13599 | Q-NS0119254 | 1 | 102.1 | 102.1 | 106 |
| 13 | 13599 | Q-NS0137093 | 2 | 106 | 102.1 | 106 |
| 13 | 13650 | Q-NS0100069 | 1 | 114.2 | 114.2 | 114.6 |
| 13 | 13650 | Q-NS0115394 | 2 | 114.2 | 114.2 | 114.6 |
| 13 | 13650 | Q-NS0115503 | 3 | 114.2 | 114.2 | 114.6 |
| 13 | 13650 | Q-NS0100947 | 4 | 114.6 | 114.2 | 114.6 |
| 13 | 13638 | Q-NS0119669 | 1 | 119.3 | 119.3 | 119.3 |
| 13 | 13581 | Q-NS0130052 | 1 | 127.3 | 127.3 | 127.7 |
| 13 | 13581 | Q-NS0099186 | 2 | 127.7 | 127.3 | 127.7 |
| 13 | 13581 | Q-NS0099329 | 3 | 127.7 | 127.3 | 127.7 |
| 13 | 13581 | Q-NS0102272 | 4 | 127.7 | 127.3 | 127.7 |
| 13 | 13581 | Q-NS0103825 | 5 | 127.7 | 127.3 | 127.7 |
| 13 | 13595 | Q-NS0096970 | 1 | 133.2 | 133.2 | 134.1 |
| 13 | 13595 | Q-NS0100088 | 2 | 134.1 | 133.2 | 134.1 |
| 14 | 13692 | Q-NS0101742 | 1 | 2.4 | 2.4 | 4 |
| 14 | 13692 | Q-NS0129138 | 2 | 2.4 | 2.4 | 4 |
| 14 | 13692 | Q-NS0093116 | 3 | 4 | 2.4 | 4 |
| 14 | 13692 | Q-NS0129925 | 4 | 4 | 2.4 | 4 |
| 14 | 13648 | Q-NS0103486 | 1 | 19.8 | 19.8 | 19.8 |
| 14 | 13743 | Q-NS0119002 | 1 | 30.1 | 30.1 | 30.2 |
| 14 | 13743 | Q-NS0128406 | 2 | 30.1 | 30.1 | 30.2 |
| 14 | 13743 | Q-NS0101863 | 3 | 30.2 | 30.1 | 30.2 |
| 14 | 13743 | Q-NS0113878 | 4 | 30.2 | 30.1 | 30.2 |
| 14 | 13743 | Q-NS0115066 | 5 | 30.2 | 30.1 | 30.2 |
| 14 | 13743 | Q-NS0118060 | 6 | 30.2 | 30.1 | 30.2 |
| 14 | 13743 | Q-NS0120015 | 7 | 30.2 | 30.1 | 30.2 |
| 14 | 13743 | Q-NS0123168 | 8 | 30.2 | 30.1 | 30.2 |
| 14 | 13743 | Q-NS0125714 | 9 | 30.2 | 30.1 | 30.2 |
| 14 | 13743 | Q-NS0130283 | 10 | 30.2 | 30.1 | 30.2 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 14 | 13566 | Q-NS0119165 | 1 | 31 | 31 | 33.5 |
| 14 | 13566 | Q-NS0099024 | 2 | 32.4 | 31 | 33.5 |
| 14 | 13566 | Q-NS0103446 | 3 | 32.4 | 31 | 33.5 |
| 14 | 13566 | Q-NS0123724 | 4 | 32.4 | 31 | 33.5 |
| 14 | 13566 | Q-NS0136439 | 5 | 32.4 | 31 | 33.5 |
| 14 | 13566 | Q-NS0101901 | 6 | 33.5 | 31 | 33.5 |
| 14 | 13566 | Q-NS0115556 | 7 | 33.5 | 31 | 33.5 |
| 14 | 13566 | Q-NS0115795 | 8 | 33.5 | 31 | 33.5 |
| 14 | 13566 | Q-NS0116115 | 9 | 33.5 | 31 | 33.5 |
| 14 | 13566 | Q-NS0122146 | 10 | 33.5 | 31 | 33.5 |
| 14 | 13631 | Q-NS0103932 | 1 | 54.1 | 54.1 | 57.8 |
| 14 | 13631 | Q-NS0125270 | 2 | 55.3 | 54.1 | 57.8 |
| 14 | 13631 | Q-NS0092556 | 3 | 57.8 | 54.1 | 57.8 |
| 14 | 13631 | Q-NS0116551 | 4 | 57.8 | 54.1 | 57.8 |
| 14 | 13839 | Q-NS0096193 | 1 | 61.5 | 61.5 | 63.1 |
| 14 | 13839 | Q-NS0103482 | 2 | 62.3 | 61.5 | 63.1 |
| 14 | 13839 | Q-NS0124990 | 3 | 62.3 | 61.5 | 63.1 |
| 14 | 13839 | Q-NS0103213 | 4 | 62.7 | 61.5 | 63.1 |
| 14 | 13839 | Q-NS0123569 | 5 | 63.1 | 61.5 | 63.1 |
| 14 | 13775 | Q-NS0096079 | 1 | 68.5 | 68.5 | 68.5 |
| 14 | 13792 | Q-NS0137954 | 1 | 82.5 | 82.5 | 87 |
| 14 | 13792 | Q-NS0126475 | 2 | 82.9 | 82.5 | 87 |
| 14 | 13792 | Q-NS0093197 | 3 | 86.6 | 82.5 | 87 |
| 14 | 13792 | Q-NS0096225 | 4 | 86.6 | 82.5 | 87 |
| 14 | 13792 | Q-NS0098853 | 5 | 86.6 | 82.5 | 87 |
| 14 | 13792 | Q-NS0136699 | 6 | 86.6 | 82.5 | 87 |
| 14 | 13792 | Q-NS0094891 | 7 | 87 | 82.5 | 87 |
| 14 | 13814 | Q-NS0092561 | 1 | 90.3 | 90.3 | 90.3 |
| 14 | 13695 | Q-NS0113929 | 1 | 103 | 103 | 103 |
| 14 | 13695 | Q-NS0115535 | 2 | 103 | 103 | 103 |
| 14 | 13695 | Q-NS0121511 | 3 | 103 | 103 | 103 |
| 14 | 13827 | Q-NS0097006 | 1 | 110.6 | 110.6 | 112.9 |
| 14 | 13827 | Q-NS0136544 | 2 | 112.9 | 110.6 | 112.9 |
| 14 | 13791 | Q-NS0103853 | 1 | 116.6 | 116.6 | 121 |
| 14 | 13791 | Q-NS0131014 | 2 | 116.6 | 116.6 | 121 |
| 14 | 13791 | Q-NS0124319 | 3 | 118.2 | 116.6 | 121 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 14 | 13791 | Q-NS0123708 | 4 | 121 | 116.6 | 121 |
| 14 | 13612 | Q-NS0114317 | 1 | 124.3 | 124.3 | 124.3 |
| 15 | 13694 | Q-NS0100932 | 1 | 0.7 | 0.7 | 0.7 |
| 15 | 13694 | Q-NS0100968 | 2 | 0.7 | 0.7 | 0.7 |
| 15 | 13694 | Q-NS0101546 | 3 | 0.7 | 0.7 | 0.7 |
| 15 | 13694 | Q-NS0127102 | 4 | 0.7 | 0.7 | 0.7 |
| 15 | 13694 | Q-NS0129174 | 5 | 0.7 | 0.7 | 0.7 |
| 15 | 13670 | Q-NS0114321 | 1 | 17.7 | 17.7 | 20.5 |
| 15 | 13670 | Q-NS0129515 | 2 | 17.7 | 17.7 | 20.5 |
| 15 | 13670 | Q-NS0120337 | 3 | 20.1 | 17.7 | 20.5 |
| 15 | 13670 | Q-NS0103503 | 4 | 20.5 | 17.7 | 20.5 |
| 15 | 13670 | Q-NS0103505 | 5 | 20.5 | 17.7 | 20.5 |
| 15 | 13670 | Q-NS0130033 | 6 | 20.5 | 17.7 | 20.5 |
| 15 | 13675 | Q-NS0098051 | 1 | 23.4 | 23.4 | 23.8 |
| 15 | 13675 | Q-NS0118672 | 2 | 23.8 | 23.4 | 23.8 |
| 15 | 13847 | Q-NS0129598 | 1 | 28.9 | 28.9 | 30.8 |
| 15 | 13847 | Q-NS0093272 | 2 | 30.8 | 28.9 | 30.8 |
| 15 | 13704 | Q-NS0095530 | 1 | 36.3 | 36.3 | 36.7 |
| 15 | 13704 | Q-NS0129004 | 2 | 36.7 | 36.3 | 36.7 |
| 15 | 13802 | Q-NS0114039 | 1 | 45 | 45 | 49.4 |
| 15 | 13802 | Q-NS0095959 | 2 | 47.9 | 45 | 49.4 |
| 15 | 13802 | Q-NS0098993 | 3 | 48.7 | 45 | 49.4 |
| 15 | 13802 | Q-NS0116137 | 4 | 48.7 | 45 | 49.4 |
| 15 | 13802 | Q-NS0125102 | 5 | 48.7 | 45 | 49.4 |
| 15 | 13802 | Q-NS0136761 | 6 | 48.7 | 45 | 49.4 |
| 15 | 13802 | Q-NS0114689 | 7 | 49.1 | 45 | 49.4 |
| 15 | 13802 | Q-NS0137544 | 8 | 49.4 | 45 | 49.4 |
| 15 | 13852 | Q-NS0092743 | 1 | 53.1 | 53.1 | 55.9 |
| 15 | 13852 | Q-NS0098176 | 2 | 53.8 | 53.1 | 55.9 |
| 15 | 13852 | Q-NS0128125 | 3 | 53.8 | 53.1 | 55.9 |
| 15 | 13852 | Q-NS0096612 | 4 | 55.5 | 53.1 | 55.9 |
| 15 | 13852 | Q-NS0129790 | 5 | 55.5 | 53.1 | 55.9 |
| 15 | 13852 | Q-NS0135595 | 6 | 55.9 | 53.1 | 55.9 |
| 15 | 13852 | Q-NS0137415 | 7 | 55.9 | 53.1 | 55.9 |
| 15 | 13779 | Q-NS0100078 | 1 | 60.3 | 60.3 | 62.7 |
| 15 | 13779 | Q-NS0130730 | 2 | 60.3 | 60.3 | 62.7 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 15 | 13779 | Q-NS0101482 | 3 | 61.6 | 60.3 | 62.7 |
| 15 | 13779 | Q-NS0103971 | 4 | 62.7 | 60.3 | 62.7 |
| 15 | 13608 | Q-NS0124956 | 1 | 69.7 | 69.7 | 69.7 |
| 15 | 13844 | Q-NS0137136 | 1 | 75.2 | 75.2 | 75.2 |
| 15 | 13681 | Q-NS0095234 | 1 | 80.7 | 80.7 | 80.7 |
| 15 | 13858 | Q-NS0099762 | 1 | 91.7 | 91.7 | 96.4 |
| 15 | 13858 | Q-NS0118867 | 2 | 91.7 | 91.7 | 96.4 |
| 15 | 13858 | Q-NS0122348 | 3 | 95.6 | 91.7 | 96.4 |
| 15 | 13858 | Q-NS0125459 | 4 | 96.4 | 91.7 | 96.4 |
| 15 | 13808 | Q-NS0098451 | 1 | 96.8 | 96.8 | 100.4 |
| 15 | 13808 | Q-NS0103775 | 2 | 98.3 | 96.8 | 100.4 |
| 15 | 13808 | Q-NS0120097 | 3 | 98.4 | 96.8 | 100.4 |
| 15 | 13808 | Q-NS0121400 | 4 | 98.4 | 96.8 | 100.4 |
| 15 | 13808 | Q-NS0122765 | 5 | 98.4 | 96.8 | 100.4 |
| 15 | 13808 | Q-NS0126718 | 6 | 98.4 | 96.8 | 100.4 |
| 15 | 13808 | Q-NS0129938 | 7 | 98.4 | 96.8 | 100.4 |
| 15 | 13808 | Q-NS0092721 | 8 | 98.9 | 96.8 | 100.4 |
| 15 | 13808 | Q-NS0119398 | 9 | 100.4 | 96.8 | 100.4 |
| 15 | 13808 | Q-NS0124986 | 10 | 100.4 | 96.8 | 100.4 |
| 15 | 13759 | Q-NS0136946 | 1 | 104.6 | 104.6 | 109.5 |
| 15 | 13759 | Q-NS0095623 | 2 | 106 | 104.6 | 109.5 |
| 15 | 13759 | Q-NS0116018 | 3 | 109.5 | 104.6 | 109.5 |
| 15 | 13854 | Q-NS0136706 | 1 | 112.2 | 112.2 | 115.8 |
| 15 | 13854 | Q-NS0123722 | 2 | 115 | 112.2 | 115.8 |
| 15 | 13854 | Q-NS0123945 | 3 | 115 | 112.2 | 115.8 |
| 15 | 13854 | Q-NS0125745 | 4 | 115 | 112.2 | 115.8 |
| 15 | 13854 | Q-NS0118445 | 5 | 115.8 | 112.2 | 115.8 |
| 15 | 13568 | Q-NS0137568 | 1 | 122.7 | 122.7 | 122.7 |
| 16 | 13749 | Q-NS0093510 | 1 | 3 | 3 | 5.3 |
| 16 | 13749 | Q-NS0114259 | 2 | 3.3 | 3 | 5.3 |
| 16 | 13749 | Q-NS0103498 | 3 | 3.7 | 3 | 5.3 |
| 16 | 13749 | Q-NS0114021 | 4 | 3.7 | 3 | 5.3 |
| 16 | 13749 | Q-NS0124013 | 5 | 3.7 | 3 | 5.3 |
| 16 | 13749 | Q-NS0126790 | 6 | 5.3 | 3 | 5.3 |
| 16 | 13618 | Q-NS0118859 | 1 | 15.1 | 15.1 | 18.3 |
| 16 | 13618 | Q-NS0119102 | 2 | 15.5 | 15.1 | 18.3 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 16 | 13618 | Q-NS0120377 | 3 | 15.5 | 15.1 | 18.3 |
| 16 | 13618 | Q-NS0096500 | 4 | 17.6 | 15.1 | 18.3 |
| 16 | 13618 | Q-NS0103114 | 5 | 17.6 | 15.1 | 18.3 |
| 16 | 13618 | Q-NS0119813 | 6 | 17.6 | 15.1 | 18.3 |
| 16 | 13618 | Q-NS0095810 | 7 | 18.3 | 15.1 | 18.3 |
| 16 | 13618 | Q-NS0114582 | 8 | 18.3 | 15.1 | 18.3 |
| 16 | 13645 | Q-NS0093934 | 1 | 22.3 | 22.3 | 25.6 |
| 16 | 13645 | Q-NS0095368 | 2 | 22.3 | 22.3 | 25.6 |
| 16 | 13645 | Q-NS0101368 | 3 | 22.3 | 22.3 | 25.6 |
| 16 | 13645 | Q-NS0115192 | 4 | 22.3 | 22.3 | 25.6 |
| 16 | 13645 | Q-NS0115515 | 5 | 22.3 | 22.3 | 25.6 |
| 16 | 13645 | Q-NS0113745 | 6 | 22.7 | 22.3 | 25.6 |
| 16 | 13645 | Q-NS0124203 | 7 | 23.5 | 22.3 | 25.6 |
| 16 | 13645 | Q-NS0120012 | 8 | 25.6 | 22.3 | 25.6 |
| 16 | 13703 | Q-NS0136618 | 1 | 33.8 | 33.8 | 38.4 |
| 16 | 13703 | Q-NS0136363 | 2 | 38.4 | 33.8 | 38.4 |
| 16 | 13674 | Q-NS0118063 | 1 | 40.1 | 40.1 | 40.9 |
| 16 | 13674 | Q-NS0097029 | 2 | 40.7 | 40.1 | 40.9 |
| 16 | 13674 | Q-NS0121903 | 3 | 40.9 | 40.1 | 40.9 |
| 16 | 13813 | Q-NS0135069 | 1 | 45.4 | 45.4 | 45.4 |
| 16 | 13697 | Q-NS0135056 | 1 | 50.9 | 50.9 | 54 |
| 16 | 13697 | Q-NS0098172 | 2 | 54 | 50.9 | 54 |
| 16 | 13860 | Q-NS0123031 | 1 | 58 | 58 | 58 |
| 16 | 13588 | Q-NS0101018 | 1 | 66.7 | 66.7 | 67.1 |
| 16 | 13588 | Q-NS0103722 | 2 | 66.7 | 66.7 | 67.1 |
| 16 | 13588 | Q-NS0128699 | 3 | 67.1 | 66.7 | 67.1 |
| 16 | 13588 | Q-NS0137274 | 4 | 67.1 | 66.7 | 67.1 |
| 16 | 13819 | Q-NS0119586 | 1 | 81.4 | 81.4 | 82.8 |
| 16 | 13819 | Q-NS0092616 | 2 | 82.8 | 81.4 | 82.8 |
| 16 | 13736 | Q-NS0102238 | 1 | 87.3 | 87.3 | 87.3 |
| 16 | 13736 | Q-NS0113752 | 2 | 87.3 | 87.3 | 87.3 |
| 16 | 13736 | Q-NS0114439 | 3 | 87.3 | 87.3 | 87.3 |
| 16 | 13736 | Q-NS0119225 | 4 | 87.3 | 87.3 | 87.3 |
| 16 | 13736 | Q-NS0119881 | 5 | 87.3 | 87.3 | 87.3 |
| 16 | 13736 | Q-NS0126813 | 6 | 87.3 | 87.3 | 87.3 |
| 16 | 13736 | Q-NS0128829 | 7 | 87.3 | 87.3 | 87.3 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 16 | 13762 | Q-NS0129591 | 1 | 95.9 | 95.9 | 96.6 |
| 16 | 13762 | Q-NS0095308 | 2 | 96.6 | 95.9 | 96.6 |
| 16 | 13617 | Q-NS0114263 | 1 | 101.2 | 101.2 | 103.2 |
| 16 | 13617 | Q-NS0113979 | 2 | 101.6 | 101.2 | 103.2 |
| 16 | 13617 | Q-NS0115738 | 3 | 103.2 | 101.2 | 103.2 |
| 16 | 13617 | Q-NS0124958 | 4 | 103.2 | 101.2 | 103.2 |
| 16 | 13836 | Q-NS0099221 | 1 | 108.2 | 108.2 | 110.7 |
| 16 | 13836 | Q-NS0102880 | 2 | 110.7 | 108.2 | 110.7 |
| 16 | 13836 | Q-NS0119281 | 3 | 110.7 | 108.2 | 110.7 |
| 16 | 13724 | Q-NS0101394 | 1 | 117.8 | 117.8 | 120 |
| 16 | 13724 | Q-NS0097666 | 2 | 120 | 117.8 | 120 |
| 16 | 13724 | Q-NS0103710 | 3 | 120 | 117.8 | 120 |
| 16 | 13644 | Q-NS0124590 | 1 | 130.2 | 130.2 | 134.1 |
| 16 | 13644 | Q-NS0098438 | 2 | 134.1 | 130.2 | 134.1 |
| 16 | 13654 | Q-NS0116125 | 1 | 139.1 | 139.1 | 141.5 |
| 16 | 13654 | Q-NS0125770 | 2 | 140.7 | 139.1 | 141.5 |
| 16 | 13654 | Q-NS0103497 | 3 | 141.5 | 139.1 | 141.5 |
| 16 | 13654 | Q-NS0103755 | 4 | 141.5 | 139.1 | 141.5 |
| 16 | 13654 | Q-NS0119653 | 5 | 141.5 | 139.1 | 141.5 |
| 16 | 13658 | Q-NS0125713 | 1 | 145.3 | 145.3 | 148.3 |
| 16 | 13658 | Q-NS0121770 | 2 | 148.3 | 145.3 | 148.3 |
| 16 | 13834 | Q-NS0102717 | 1 | 150.9 | 150.9 | 150.9 |
| 17 | 13690 | Q-NS0100100 | 1 | 19.6 | 19.6 | 20.7 |
| 17 | 13690 | Q-NS0117852 | 2 | 20.4 | 19.6 | 20.7 |
| 17 | 13690 | Q-NS0092907 | 3 | 20.7 | 19.6 | 20.7 |
| 17 | 13570 | Q-NS0094904 | 1 | 26.2 | 26.2 | 26.2 |
| 17 | 13570 | Q-NS0127879 | 2 | 26.2 | 26.2 | 26.2 |
| 17 | 13719 | Q-NS0134725 | 1 | 34.4 | 34.4 | 39 |
| 17 | 13719 | Q-NS0092843 | 2 | 34.8 | 34.4 | 39 |
| 17 | 13719 | Q-NS0115362 | 3 | 35.2 | 34.4 | 39 |
| 17 | 13719 | Q-NS0114274 | 4 | 36.9 | 34.4 | 39 |
| 17 | 13719 | Q-NS0097373 | 5 | 39 | 34.4 | 39 |
| 17 | 13683 | Q-NS0125264 | 1 | 48.7 | 48.7 | 50.7 |
| 17 | 13683 | Q-NS0125160 | 2 | 50.7 | 48.7 | 50.7 |
| 17 | 13623 | Q-NS0100428 | 1 | 54.5 | 54.5 | 59.4 |
| 17 | 13623 | Q-NS0137719 | 2 | 54.5 | 54.5 | 59.4 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 17 | 13623 | Q-NS0126724 | 3 | 55.9 | 54.5 | 59.4 |
| 17 | 13623 | Q-NS0119237 | 4 | 58.2 | 54.5 | 59.4 |
| 17 | 13623 | Q-NS0119597 | 5 | 58.2 | 54.5 | 59.4 |
| 17 | 13623 | Q-NS0123284 | 6 | 58.6 | 54.5 | 59.4 |
| 17 | 13623 | Q-NS0100080 | 7 | 59.4 | 54.5 | 59.4 |
| 17 | 13663 | Q-NS0124919 | 1 | 60.2 | 60.2 | 60.2 |
| 17 | 13840 | Q-NS0100914 | 1 | 71.8 | 71.8 | 71.8 |
| 17 | 13835 | Q-NS0115497 | 1 | 79.8 | 79.8 | 81 |
| 17 | 13835 | Q-NS0101797 | 2 | 81 | 79.8 | 81 |
| 17 | 13835 | Q-NS0122094 | 3 | 81 | 79.8 | 81 |
| 17 | 13835 | Q-NS0127404 | 4 | 81 | 79.8 | 81 |
| 17 | 13835 | Q-NS0129282 | 5 | 81 | 79.8 | 81 |
| 17 | 13768 | Q-NS0122335 | 1 | 88 | 88 | 92.5 |
| 17 | 13768 | Q-NS0098167 | 2 | 90 | 88 | 92.5 |
| 17 | 13768 | Q-NS0116559 | 3 | 91 | 88 | 92.5 |
| 17 | 13768 | Q-NS0094805 | 4 | 92.5 | 88 | 92.5 |
| 17 | 13594 | Q-NS0125185 | 1 | 94 | 94 | 94 |
| 17 | 13727 | Q-NS0100921 | 1 | 102.3 | 102.3 | 105.3 |
| 17 | 13727 | Q-NS0123506 | 2 | 102.3 | 102.3 | 105.3 |
| 17 | 13727 | Q-NS0097952 | 3 | 105.3 | 102.3 | 105.3 |
| 17 | 13597 | Q-NS0118907 | 1 | 109.7 | 109.7 | 109.7 |
| 17 | 13603 | Q-NS0101484 | 1 | 123.9 | 123.9 | 128.3 |
| 17 | 13603 | Q-NS0122182 | 2 | 123.9 | 123.9 | 128.3 |
| 17 | 13603 | Q-NS0126989 | 3 | 123.9 | 123.9 | 128.3 |
| 17 | 13603 | Q-NS0093160 | 4 | 124.6 | 123.9 | 128.3 |
| 17 | 13603 | Q-NS0097367 | 5 | 126.4 | 123.9 | 128.3 |
| 17 | 13603 | Q-NS0095677 | 6 | 127.8 | 123.9 | 128.3 |
| 17 | 13603 | Q-NS0101343 | 7 | 128.3 | 123.9 | 128.3 |
| 17 | 13756 | Q-NS0124051 | 1 | 129.5 | 129.5 | 129.5 |
| 17 | 13770 | Q-NS0135189 | 1 | 141 | 141 | 143.3 |
| 17 | 13770 | Q-NS0093254 | 2 | 143.3 | 141 | 143.3 |
| 17 | 13770 | Q-NS0096077 | 3 | 143.3 | 141 | 143.3 |
| 18 | 13606 | Q-NS0095567 | 1 | 0 | 0 | 0 |
| 18 | 13606 | Q-NS0125535 | 2 | 0 | 0 | 0 |
| 18 | 13606 | Q-NS0129407 | 3 | 0 | 0 | 0 |
| 18 | 13667 | Q-NS0124300 | 1 | 5.4 | 5.4 | 9.5 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 18 | 13667 | Q-NS0096741 | 2 | 9.5 | 5.4 | 9.5 |
| 18 | 13616 | Q-NS0117743 | 1 | 10.8 | 10.8 | 14.9 |
| 18 | 13616 | Q-NS0119006 | 2 | 10.8 | 10.8 | 14.9 |
| 18 | 13616 | Q-NS0119814 | 3 | 10.8 | 10.8 | 14.9 |
| 18 | 13616 | Q-NS0092838 | 4 | 14.9 | 10.8 | 14.9 |
| 18 | 13661 | Q-NS0121992 | 1 | 23.1 | 23.1 | 26.8 |
| 18 | 13661 | Q-NS0103247 | 2 | 23.5 | 23.1 | 26.8 |
| 18 | 13661 | Q-NS0103250 | 3 | 23.5 | 23.1 | 26.8 |
| 18 | 13661 | Q-NS0115306 | 4 | 23.9 | 23.1 | 26.8 |
| 18 | 13661 | Q-NS0095507 | 5 | 25.6 | 23.1 | 26.8 |
| 18 | 13661 | Q-NS0101434 | 6 | 25.6 | 23.1 | 26.8 |
| 18 | 13661 | Q-NS0095508 | 7 | 26 | 23.1 | 26.8 |
| 18 | 13661 | Q-NS0126290 | 8 | 26.8 | 23.1 | 26.8 |
| 18 | 13846 | Q-NS0093331 | 1 | 37.5 | 37.5 | 37.5 |
| 18 | 13766 | Q-NS0115464 | 1 | 44.5 | 44.5 | 47.9 |
| 18 | 13766 | Q-NS0104043 | 2 | 44.9 | 44.5 | 47.9 |
| 18 | 13766 | Q-NS0114001 | 3 | 44.9 | 44.5 | 47.9 |
| 18 | 13766 | Q-NS0127459 | 4 | 44.9 | 44.5 | 47.9 |
| 18 | 13766 | Q-NS0095584 | 5 | 45.7 | 44.5 | 47.9 |
| 18 | 13766 | Q-NS0096189 | 6 | 47.9 | 44.5 | 47.9 |
| 18 | 13766 | Q-NS0126809 | 7 | 47.9 | 44.5 | 47.9 |
| 18 | 13823 | Q-NS0120593 | 1 | 51.2 | 51.2 | 51.6 |
| 18 | 13823 | Q-NS0121444 | 2 | 51.6 | 51.2 | 51.6 |
| 18 | 13782 | Q-NS0124055 | 1 | 61.1 | 61.1 | 63.5 |
| 18 | 13782 | Q-NS0102047 | 2 | 61.5 | 61.1 | 63.5 |
| 18 | 13782 | Q-NS0114007 | 3 | 61.5 | 61.1 | 63.5 |
| 18 | 13782 | Q-NS0116014 | 4 | 61.5 | 61.1 | 63.5 |
| 18 | 13782 | Q-NS0120132 | 5 | 61.5 | 61.1 | 63.5 |
| 18 | 13782 | Q-NS0123650 | 6 | 61.5 | 61.1 | 63.5 |
| 18 | 13782 | Q-NS0122352 | 7 | 63.5 | 61.1 | 63.5 |
| 18 | 13824 | Q-NS0129428 | 1 | 70.8 | 70.8 | 73.4 |
| 18 | 13824 | Q-NS0100480 | 2 | 71.8 | 70.8 | 73.4 |
| 18 | 13824 | Q-NS0102647 | 3 | 71.8 | 70.8 | 73.4 |
| 18 | 13824 | Q-NS0114029 | 4 | 71.8 | 70.8 | 73.4 |
| 18 | 13824 | Q-NS0118026 | 5 | 71.8 | 70.8 | 73.4 |
| 18 | 13824 | Q-NS0122115 | 6 | 71.8 | 70.8 | 73.4 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 18 | 13824 | Q-NS0126826 | 7 | 71.8 | 70.8 | 73.4 |
| 18 | 13824 | Q-NS0129940 | 8 | 71.8 | 70.8 | 73.4 |
| 18 | 13824 | Q-NS0130969 | 9 | 71.8 | 70.8 | 73.4 |
| 18 | 13824 | Q-NS0095650 | 10 | 73.4 | 70.8 | 73.4 |
| 18 | 13837 | Q-NS0136158 | 1 | 74.1 | 74.1 | 76.8 |
| 18 | 13837 | Q-NS0119638 | 2 | 74.6 | 74.1 | 76.8 |
| 18 | 13837 | Q-NS0123806 | 3 | 74.6 | 74.1 | 76.8 |
| 18 | 13837 | Q-NS0128093 | 4 | 74.6 | 74.1 | 76.8 |
| 18 | 13837 | Q-NS0099376 | 5 | 76.8 | 74.1 | 76.8 |
| 18 | 13863 | Q-NS0136956 | 1 | 82.2 | 82.2 | 82.2 |
| 18 | 13769 | Q-NS0131055 | 1 | 88.9 | 88.9 | 89.7 |
| 18 | 13769 | Q-NS0129118 | 2 | 89.7 | 88.9 | 89.7 |
| 18 | 13567 | Q-NS0127007 | 1 | 99.9 | 99.9 | 99.9 |
| 18 | 13742 | Q-NS0125975 | 1 | 105.5 | 105.5 | 107.1 |
| 18 | 13742 | Q-NS0100454 | 2 | 107.1 | 105.5 | 107.1 |
| 18 | 13643 | Q-NS0097194 | 1 | 116.3 | 116.3 | 116.3 |
| 18 | 13754 | Q-NS0097882 | 1 | 123.1 | 123.1 | 126.8 |
| 18 | 13754 | Q-NS0130724 | 2 | 125.8 | 123.1 | 126.8 |
| 18 | 13754 | Q-NS0092851 | 3 | 126.8 | 123.1 | 126.8 |
| 19 | 13790 | Q-NS0101360 | 1 | 1.9 | 1.9 | 6.3 |
| 19 | 13790 | Q-NS0102889 | 2 | 4.9 | 1.9 | 6.3 |
| 19 | 13790 | Q-NS0116066 | 3 | 6.3 | 1.9 | 6.3 |
| 19 | 13805 | Q-NS0115656 | 1 | 7.9 | 7.9 | 12.5 |
| 19 | 13805 | Q-NS0121932 | 2 | 7.9 | 7.9 | 12.5 |
| 19 | 13805 | Q-NS0127429 | 3 | 7.9 | 7.9 | 12.5 |
| 19 | 13805 | Q-NS0098803 | 4 | 9.9 | 7.9 | 12.5 |
| 19 | 13805 | Q-NS0122058 | 5 | 12.1 | 7.9 | 12.5 |
| 19 | 13805 | Q-NS0115437 | 6 | 12.5 | 7.9 | 12.5 |
| 19 | 13795 | Q-NS0093343 | 1 | 16.4 | 16.4 | 16.4 |
| 19 | 13578 | Q-NS0122808 | 1 | 22.2 | 22.2 | 26.4 |
| 19 | 13578 | Q-NS0118342 | 2 | 25.6 | 22.2 | 26.4 |
| 19 | 13578 | Q-NS0119097 | 3 | 26.4 | 22.2 | 26.4 |
| 19 | 13578 | Q-NS0119605 | 4 | 26.4 | 22.2 | 26.4 |
| 19 | 13578 | Q-NS0122173 | 5 | 26.4 | 22.2 | 26.4 |
| 19 | 13664 | Q-NS0094222 | 1 | 29.4 | 29.4 | 31.6 |
| 19 | 13664 | Q-NS0115155 | 2 | 29.7 | 29.4 | 31.6 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 19 | 13664 | Q-NS0121598 | 3 | 29.7 | 29.4 | 31.6 |
| 19 | 13664 | Q-NS0096602 | 4 | 30.1 | 29.4 | 31.6 |
| 19 | 13664 | Q-NS0129719 | 5 | 30.1 | 29.4 | 31.6 |
| 19 | 13664 | Q-NS0103240 | 6 | 31.6 | 29.4 | 31.6 |
| 19 | 13664 | Q-NS0125285 | 7 | 31.6 | 29.4 | 31.6 |
| 19 | 13765 | Q-NS0103459 | 1 | 39.7 | 39.7 | 40.5 |
| 19 | 13765 | Q-NS0102576 | 2 | 40.5 | 39.7 | 40.5 |
| 19 | 13765 | Q-NS0121601 | 3 | 40.5 | 39.7 | 40.5 |
| 19 | 13660 | Q-NS0093513 | 1 | 44.9 | 44.9 | 48.1 |
| 19 | 13660 | Q-NS0103113 | 2 | 45.1 | 44.9 | 48.1 |
| 19 | 13660 | Q-NS0126786 | 3 | 45.1 | 44.9 | 48.1 |
| 19 | 13660 | Q-NS0102170 | 4 | 48.1 | 44.9 | 48.1 |
| 19 | 13662 | Q-NS0123570 | 1 | 53.3 | 53.3 | 53.3 |
| 19 | 13601 | Q-NS0097418 | 1 | 58.9 | 58.9 | 62.9 |
| 19 | 13601 | Q-NS0124192 | 2 | 58.9 | 58.9 | 62.9 |
| 19 | 13601 | Q-NS0129426 | 3 | 58.9 | 58.9 | 62.9 |
| 19 | 13601 | Q-NS0114884 | 4 | 61.9 | 58.9 | 62.9 |
| 19 | 13601 | Q-NS0092615 | 5 | 62.9 | 58.9 | 62.9 |
| 19 | 13601 | Q-NS0094157 | 6 | 62.9 | 58.9 | 62.9 |
| 19 | 13702 | Q-NS0097927 | 1 | 65.8 | 65.8 | 70.8 |
| 19 | 13702 | Q-NS0102506 | 2 | 65.8 | 65.8 | 70.8 |
| 19 | 13702 | Q-NS0104025 | 3 | 65.8 | 65.8 | 70.8 |
| 19 | 13702 | Q-NS0116157 | 4 | 70.8 | 65.8 | 70.8 |
| 19 | 13565 | Q-NS0103321 | 1 | 71.6 | 71.6 | 76 |
| 19 | 13565 | Q-NS0121433 | 2 | 71.6 | 71.6 | 76 |
| 19 | 13565 | Q-NS0101555 | 3 | 75.6 | 71.6 | 76 |
| 19 | 13565 | Q-NS0119135 | 4 | 75.6 | 71.6 | 76 |
| 19 | 13565 | Q-NS0100967 | 5 | 76 | 71.6 | 76 |
| 19 | 13565 | Q-NS0103141 | 6 | 76 | 71.6 | 76 |
| 19 | 13811 | Q-NS0121684 | 1 | 79.6 | 79.6 | 83.4 |
| 19 | 13811 | Q-NS0121806 | 2 | 80.2 | 79.6 | 83.4 |
| 19 | 13811 | Q-NS0104111 | 3 | 80.3 | 79.6 | 83.4 |
| 19 | 13811 | Q-NS0103773 | 4 | 80.4 | 79.6 | 83.4 |
| 19 | 13811 | Q-NS0124595 | 5 | 83 | 79.6 | 83.4 |
| 19 | 13811 | Q-NS0121755 | 6 | 83.4 | 79.6 | 83.4 |
| 19 | 13789 | Q-NS0094370 | 1 | 89.9 | 89.9 | 91.7 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 19 | 13789 | Q-NS0119073 | 2 | 90.9 | 89.9 | 91.7 |
| 19 | 13789 | Q-NS0123372 | 3 | 90.9 | 89.9 | 91.7 |
| 19 | 13789 | Q-NS0115621 | 4 | 91.3 | 89.9 | 91.7 |
| 19 | 13789 | Q-NS0129904 | 5 | 91.3 | 89.9 | 91.7 |
| 19 | 13789 | Q-NS0125418 | 6 | 91.7 | 89.9 | 91.7 |
| 19 | 13642 | Q-NS0100661 | 1 | 96.7 | 96.7 | 99.8 |
| 19 | 13642 | Q-NS0124579 | 2 | 97.5 | 96.7 | 99.8 |
| 19 | 13642 | Q-NS0102003 | 3 | 99.8 | 96.7 | 99.8 |
| 19 | 13642 | Q-NS0125760 | 4 | 99.8 | 96.7 | 99.8 |
| 19 | 13640 | Q-NS0100925 | 1 | 104.2 | 104.2 | 107.8 |
| 19 | 13640 | Q-NS0115516 | 2 | 104.2 | 104.2 | 107.8 |
| 19 | 13640 | Q-NS0123200 | 3 | 104.2 | 104.2 | 107.8 |
| 19 | 13640 | Q-NS0125532 | 4 | 104.2 | 104.2 | 107.8 |
| 19 | 13640 | Q-NS0094373 | 5 | 107.8 | 104.2 | 107.8 |
| 19 | 13640 | Q-NS0099203 | 6 | 107.8 | 104.2 | 107.8 |
| 19 | 13569 | Q-NS0092963 | 1 | 111.1 | 111.1 | 111.1 |
| 19 | 13841 | Q-NS0094048 | 1 | 116.2 | 116.2 | 120.7 |
| 19 | 13841 | Q-NS0135805 | 2 | 116.9 | 116.2 | 120.7 |
| 19 | 13841 | Q-NS0136435 | 3 | 117.7 | 116.2 | 120.7 |
| 19 | 13841 | Q-NS0094057 | 4 | 120.3 | 116.2 | 120.7 |
| 19 | 13841 | Q-NS0126722 | 5 | 120.3 | 116.2 | 120.7 |
| 19 | 13841 | Q-NS0093509 | 6 | 120.7 | 116.2 | 120.7 |
| 19 | 13733 | Q-NS0097606 | 1 | 121.8 | 121.8 | 125.1 |
| 19 | 13733 | Q-NS0098213 | 2 | 125.1 | 121.8 | 125.1 |
| 19 | 13733 | Q-NS0099578 | 3 | 125.1 | 121.8 | 125.1 |
| 20 | 13693 | Q-NS0103077 | 1 | 0.7 | 0.7 | 4.2 |
| 20 | 13693 | Q-NS0119065 | 2 | 0.7 | 0.7 | 4.2 |
| 20 | 13693 | Q-NS0125098 | 3 | 0.7 | 0.7 | 4.2 |
| 20 | 13693 | Q-NS0127757 | 4 | 0.7 | 0.7 | 4.2 |
| 20 | 13693 | Q-NS0127888 | 5 | 0.7 | 0.7 | 4.2 |
| 20 | 13693 | Q-NS0124715 | 6 | 2.7 | 0.7 | 4.2 |
| 20 | 13693 | Q-NS0099970 | 7 | 4.2 | 0.7 | 4.2 |
| 20 | 13682 | Q-NS0096558 | 1 | 6.5 | 6.5 | 11.1 |
| 20 | 13682 | Q-NS0100944 | 2 | 6.5 | 6.5 | 11.1 |
| 20 | 13682 | Q-NS0120072 | 3 | 6.5 | 6.5 | 11.1 |
| 20 | 13682 | Q-NS0103764 | 4 | 7.3 | 6.5 | 11.1 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 20 | 13682 | Q-NS0100097 | 5 | 7.7 | 6.5 | 11.1 |
| 20 | 13682 | Q-NS0095320 | 6 | 8.1 | 6.5 | 11.1 |
| 20 | 13682 | Q-NS0100457 | 7 | 9.1 | 6.5 | 11.1 |
| 20 | 13682 | Q-NS0121926 | 8 | 10.1 | 6.5 | 11.1 |
| 20 | 13682 | Q-NS0103646 | 9 | 11.1 | 6.5 | 11.1 |
| 20 | 13666 | Q-NS0115418 | 1 | 12.3 | 12.3 | 17.2 |
| 20 | 13666 | Q-NS0126785 | 2 | 12.7 | 12.3 | 17.2 |
| 20 | 13666 | Q-NS0093126 | 3 | 13.2 | 12.3 | 17.2 |
| 20 | 13666 | Q-NS0103045 | 4 | 14.6 | 12.3 | 17.2 |
| 20 | 13666 | Q-NS0116259 | 5 | 14.6 | 12.3 | 17.2 |
| 20 | 13666 | Q-NS0129134 | 6 | 14.6 | 12.3 | 17.2 |
| 20 | 13666 | Q-NS0093925 | 7 | 15 | 12.3 | 17.2 |
| 20 | 13666 | Q-NS0128634 | 8 | 15.4 | 12.3 | 17.2 |
| 20 | 13666 | Q-NS0092589 | 9 | 17.2 | 12.3 | 17.2 |
| 20 | 13699 | Q-NS0118785 | 1 | 19.9 | 19.9 | 24.2 |
| 20 | 13699 | Q-NS0102039 | 2 | 20.7 | 19.9 | 24.2 |
| 20 | 13699 | Q-NS0102090 | 3 | 20.7 | 19.9 | 24.2 |
| 20 | 13699 | Q-NS0103167 | 4 | 24.2 | 19.9 | 24.2 |
| 20 | 13699 | Q-NS0103180 | 5 | 24.2 | 19.9 | 24.2 |
| 20 | 13755 | Q-NS0103818 | 1 | 29.7 | 29.7 | 29.7 |
| 20 | 13620 | Q-NS0136539 | 1 | 39.9 | 39.9 | 44.7 |
| 20 | 13620 | Q-NS0092605 | 2 | 44.4 | 39.9 | 44.7 |
| 20 | 13620 | Q-NS0121801 | 3 | 44.7 | 39.9 | 44.7 |
| 20 | 13812 | Q-NS0092790 | 1 | 50.6 | 50.6 | 54.5 |
| 20 | 13812 | Q-NS0093326 | 2 | 53 | 50.6 | 54.5 |
| 20 | 13812 | Q-NS0114538 | 3 | 53.3 | 50.6 | 54.5 |
| 20 | 13812 | Q-NS0118690 | 4 | 53.3 | 50.6 | 54.5 |
| 20 | 13812 | Q-NS0125400 | 5 | 53.3 | 50.6 | 54.5 |
| 20 | 13812 | Q-NS0126994 | 6 | 53.3 | 50.6 | 54.5 |
| 20 | 13812 | Q-NS0124654 | 7 | 54.5 | 50.6 | 54.5 |
| 20 | 13787 | Q-NS0122456 | 1 | 56.9 | 56.9 | 59.1 |
| 20 | 13787 | Q-NS0120011 | 2 | 59.1 | 56.9 | 59.1 |
| 20 | 13838 | Q-NS0135986 | 1 | 62.3 | 62.3 | 66.8 |
| 20 | 13838 | Q-NS0127310 | 2 | 66.8 | 62.3 | 66.8 |
| 20 | 13605 | Q-NS0099767 | 1 | 75.4 | 75.4 | 75.4 |
| 20 | 13587 | Q-NS0096899 | 1 | 89.5 | 89.5 | 89.9 |

TABLE 2-continued

Characterization of haplotype windows in the soybean genome based on 149 elite lines and 1168 SNP markers. Haplotype windows in each chromosome are identified and the markers (disclosed in U.S. Pat. Applications 2005/0204780 and 2005/0216545, incorporated herein by reference in their entirety) within each window are described.

| CHROMOSOME | HAPLOTYPE WINDOW ID | MARKER NAME | MARKER ORDER | POSITION | START POSITION | END POSITION |
|---|---|---|---|---|---|---|
| 20 | 13587 | Q-NS0129792 | 2 | 89.5 | 89.5 | 89.9 |
| 20 | 13587 | Q-NS0125389 | 3 | 89.9 | 89.5 | 89.9 |

In one embodiment, a haplotype region is defined as a chromosome segment that persists over multiple generations of breeding and that is carried by one or more breeding lines. In one aspect, depending on the extent of LD, one example of a haplotype window is about 20 centiMorgans. In another aspect, depending on marker density, an exemplary haplotype window is about 1 to 5 centiMorgans or, in another example, even less than 1 centiMorgan. This segment is identified based on the one or more linked marker loci it contains, and the common haplotype identity at these loci in two lines gives a high degree of confidence of the identity by descent of the entire subjacent chromosome segment carried by these lines.

In another aspect of the present invention, it is useful to specify what the preferred haplotypes are and what their frequency is in the germplasm for a given crop. Thus, one would obtain or generate a molecular marker survey of the germplasm under consideration for breeding and/or propagation of a transformation event. This marker survey provides a fingerprint of each line. These markers are assumed to have their approximate genomic map position known. Tables 3 and 4 list haplotype effect estimates, haplotype frequencies, and haplotype fingerprint for the reference germplasm of soybean and corn, respectively. Haplotype frequency values are not fixed and will change over time as the breeding populations undergo selection. To simplify downstream analyses, quality assurance and missing data estimations steps may need to be implemented at this stage to produce a complete and accurate data matrix (marker genotype by line). Error detections and missing data estimations may require the use of parent-offspring tests, LD between marker loci, interval mapping, re-genotyping, etc.

Lengthy table referenced here

US10455783-20191029-T00001

Please refer to the end of the specification for access instructions.

Lengthy table referenced here

US10455783-20191029-T00002

Please refer to the end of the specification for access instructions.

Markers are then grouped based on their proximity. This grouping may be arbitrary (e.g. "start from one end of the chromosome and include all markers that are within 10 cM of the first marker included in the segment, before starting the next segment") or based on some statistical analysis (e.g. "define segment breakpoints based on LD patterns between adjacent loci").

When considering a large set of lines, wherein multiple lines have the same allele at a marker locus, it is necessary to ascertain whether identity by state (IBS) at the marker locus is a good predictor of identity by descent (IBD) at the chromosomal region surrounding the marker locus. "Identity by descent" (IBD) characterizes two loci/segment of DNA that are carried by two or more individuals and were all derived from the same ancestor. "Identity by state" (IBS) characterizes two loci/segments of DNA that are carried by two or more individuals and have the same observable alleles at those loci. A good indication that a number of marker loci in a segment are enough to characterize IBD for the segment is that they can predict the allele present at other marker loci within the segment.

To estimate the frequency of a haplotype, the base reference germplasm has to be defined (collection of elite inbred lines, population of random mating individuals, etc.) and a representative sample (or the entire population) has to be genotyped. For example, in one aspect, haplotype frequency is determined by simple counting if considering a set of inbred individuals. In another aspect, estimation methods that employ computing techniques like the Expectation/Maximization (EM) algorithm are required if individuals genotyped are heterozygous at more than one locus in the segment and linkage phase is unknown (Excoffier et al. 1995 Mol. Biol. Evol. 12: 921-927; Li et al. 2002 Biostatistics). Preferably, a method based on the EM algorithm (Dempster et al. 1977 J. R. Stat. Soc. Ser. B 39:1-38) leading to maximum-likelihood estimates of haplotype frequencies under the assumption of Hardy-Weinberg proportions (random mating) is used (Excoffier et al. 1995 Mol. Biol. Evol. 12: 921-927). Alternative approaches are known in the art that for association studies: genome-wide association studies, candidate region association studies and candidate gene association studies (Li et al. 2006 BMC Bioinformatics 7:258). The polymorphic markers of the present invention may be incorporated in any map of genetic markers of a plant genome in order to perform genome-wide association studies.

The present invention comprises methods to detect an association between at least one haplotype in a crop plant and a preferred trait, including a transgene, or a multiple trait index and calculate a haplotype effect estimate based on this association. In one aspect, the calculated haplotype effect estimates are used to make decisions in a breeding program. In another aspect, the calculated haplotype effect estimates are used in conjunction with the frequency of the at least one haplotype to calculate a haplotype breeding value that will be used to make decisions in a breeding program. A multiple trait index (MTI) is a numerical entity that is calculated through the combination of single trait values in a formula. Most often calculated as a linear combination of traits or normalized derivations of traits, it can also be the result of more sophisticated calculations (for example, use of ratios between traits). This MTI is used in genetic analysis as if it were a trait.

In one embodiment, historical data are used to determine associations between haplotypes and traits and haplotype effect estimates are computed. For the reference soybean and corn germplasm sets, the haplotype effect estimates for a set of relevant traits are listed in Tables 3 and 4, respectively. These haplotype effect estimates form the basis of ranking haplotypes for the purpose of decision-making in a breeding program. In one aspect, haplotypes are ranked using a haplotype breeding value calculation, based on the difference between the haplotype effect and the population mean, wherein the population mean is the summation of the products of each haplotype's frequency and effect estimate where haplotype frequencies are corrected based on the set of haplotypes included in the analysis. In another aspect, the haplotype breeding value calculation is employed to determine the effect of fixing a new haplotype, as would be the case in germplasm introgression or a transgenic event.

In the present invention, any given chromosome segment can be represented in a given population by a number of haplotypes that can vary from 1 (region is fixed), to the size of the population times the ploidy level of that species (2 in a diploid species), in a population in which every chromosome has a different haplotype. Identity-by-descent among haplotype carried by multiple individuals in a non-fixed population will result in an intermediate number of haplotype and possibly a differing frequency among the different haplotypes. New haplotypes may arise through recombination at meiosis between existing haplotypes in heterozygous progenitors. The frequency of each haplotype may be estimated by several means known to one versed in the art (e.g. by direct counting, or by using an EM algorithm). Let us assume that "k" different haplotypes, identified as "$h_i$" (i=1, . . . , k), are known, that their frequency in the population is "$f_i$" (i=1, . . . , k), and for each of these haplotypes we have an effect estimate "$Est_i$" (i=1, . . . , k). If we call the "haplotype breeding value" ($BV_i$) the effect on that population of fixing that haplotype, then this breeding value corresponds to the change in mean for the trait(s) of interest of that population between its original state of haplotype distribution at the window and a final state at which haplotype "$h_i$" encounters itself at a frequency of 100%.

The haplotype breeding value of $h_i$ in this population is calculated as:

$$BV_i = Est_i - \sum_{i=1}^{k} Est_i f_i$$

One skilled in the art will recognize that haplotypes that are rare in the population in which effects are estimated tend to be less precisely estimated, this difference of confidence may lead to adjustment in the calculation. For example one can ignore the effects of rare haplotypes, by calculating breeding value of better known haplotype after adjusting the frequency of these (by dividing it by the sum of frequency of the better known haplotypes). One could also provide confidence intervals for the breeding value of each haplotypes.

The present invention anticipates that any particular haplotype breeding value will change according to the population for which it is calculated, as a function of difference of haplotype frequencies. The term "population" will thus assume different meanings, below are two examples of special cases. In one aspect, a population is a single inbred in which one intends to replace its current haplotype $h_j$ by a new haplotype $h_i$, in this case $BV_i=Est_i-Est_j$. In another aspect, a "population" is a F2 population in which the two parental haplotype $h_i$ and $h_j$ are originally present in equal frequency (50%), in which case $BV_i=\frac{1}{2}(Est_i-Est_j)$.

These statistical approaches enable haplotype effect estimates to inform breeding decisions in multiple contexts. Other statistical approaches to calculate breeding values are known to those skilled in the art and can be used in substitution without departing from the spirit and scope of this invention.

Further, the present invention provides methods and compositions to determine the distribution of superior, or preferred, haplotypes in a germplasm collection in order to inform decisions pertaining to breeding and germplasm improvement activities. The following 230 Monsanto commercially released corn inbreds were fingerprinted: 01CWI6, 01DHD10, 01DHD16, 01DKD2, 01HFI3, 01HGI2, 01HGI4, 01IBH2, 01INL1, 01IUL6, 08DKS5, 08HAI5, 08SED1, 09DKD39A, 09DSQ1, 09DSS1, 09IDR9, 16IBL1, 16IDH1, 16IUL13, 16IUL2, 16IUL6, 16SEQ1, 17DHD16, 17DUD5, 17IFI2, 17IFI6, 17INI19, 17INI20, 17INI30, 17IVI7, 17QFB1, 18DHZ5, 19DAA1, 19DKS4, 19HGZ1, 1SF20790, 21GDM1_O, 22DHD11, 2MSBA7, 20F32B52, 3112, 3323, 3327, 34M837, 35CXZ3, 35ZXZ1, 3AZA1, 3IBZ2, 3IIH6, 49DKD4, 49DKQ1, 49IBI1, 4FCF1, 4GCG1, 4IDH1, 4SCQ3, 53DWD7A, 53DWQ1, 54DZD3, 54IUH1, 54MDC1, 5727, 5750, 5DJD2, 5GCG3, 5IDB3, 63CZC3W, 6950, 6DHD01, 6F545, 6F905, 6LDZ81, 7051, 7145, 7180, 7403, 7520W, 7571W, 7638, 7640, 7647, 7680, 7739Y, 7740, 7749, 7797, 7804, 7823, 7832, 7DCD2C, 7DCD5D, 80DJD5, 80DKD4, 80DKD5, 80IDM2, 83DIQ8, 83DNQ2, 83DOD5, 83DUD7, 83HGI6, 83IDI1, 83IDI3, 83INI14, 83INL2, 83SDD2, 86INI2, 86ISI26, 86ISI27, 86ISI5, 87ATD2, 87DFQ3, 87DIA4, 87DUA3, 87DUA5, 87DUA6, 87DUD3, 87IDI1, 87IDI2, 87IDI5, 8711119, 87ITI5, 87IZI8, 87LCC5, 89AHA1, 89AHD12, 89DRD5, 8F286, 8M116, 90DJD28, 90DKD11, 90IDR1, 90LBV1, 90LDC2, 90LDI1, 91AHB1, 91DHA1, 91DUA1, 91DUD5, 91DUQ1, 91DUQ2, 91DZB3, 9111118, 91INH2, 91INZ2, 91ISI5, 91QZA1, 93DKS3, 93QBS5, 94AHA8, 94DUD2, 94IGI6A, 94INK1A, 94INK1B, 94IYI3B, 94IZIll, 94IZI14, 94XCI5, C3DKS03, C3IDI02, C3IFI118, C31WI114, E2UBW1, EP67B26, F351, FBF79R2, GF6150, GM9215, HTV3A2, LH127, LH163, LH168, LH169, LH172, LH176, LH185, LH195, LH200, LH218, LH227, LH229, LH235, LH236, LH239, LH244, LH245, LH246, LH247, LH249, LH254, LH256, LH257, LH258, LH261, LH262, LH268, LH273, LH277, LH279, LH283, LH284, LH287, LH287BT1-1, LH290, LH295, LH302, LH303, LH304, LH305, LH310, LH311, LH320, LH321, LH322, LH324, LH331, LH332, LH350, LH360, LH370, MDF-13A, RDBQ2, SYNBA2, WDHQ11, WDHQ2, WKDL5, WKDL7, WQCD10, WQDS2, WQDS7. The preferred haplotypes were determined on the basis of haplotype effect estimates for the following key phenotypic traits: yield, moisture, plant height, and test weight. For each trait, a list of preferred haplotypes was generated according to ascending criteria; for example, the best 50, the best 40, and so on to the best 5 haplotypes. This germplasm collection was then surveyed to determine the distribution of those haplotypes in elite inbreds.

The results for female and male corn inbreds evaluated for these four key phenotypic traits are summarized in Table 5.

TABLE 5

Distribution of preferred haplotypes in a set of elite corn germplasm, composed of 230 Monsanto commercially released inbreds, divided by heterotic group. Listed are maximum number of haplotypes in a single inbred for each criterion (e.g., of top 5 haplotypes, of top 10, and so on) present in this germplasm for each trait.

|    | Yield |      | Moisture |      | Plant height |      | Test weight |      |
|----|-------|------|----------|------|--------------|------|-------------|------|
|    | female | male | female | male | female | male | female | male |
| 5  | 2  | 2  | 0  | 0  | 3  | 4  | 3  | 3  |
| 10 | 4  | 3  | 0  | 4  | 5  | 4  | 6  | 4  |
| 20 | 7  | 6  | 8  | 5  | 5  | 6  | 6  | 4  |
| 30 | 10 | 8  | 11 | 7  | 5  | 6  | 10 | 4  |
| 40 | 15 | 11 | 15 | 7  | 11 | 9  | 15 | 4  |
| 50 | 16 | 13 | 18 | 12 | 14 | 11 | 18 | 12 |

Further, it is of interest to determine the distribution of these preferred haplotypes in a set of germplasm for the implementation of both pre-selection and marker-assisted selection in order to drive the fixation of preferred haplotype compositions in breeding programs and other activities related to germplasm improvement. The commercially released corn female inbreds containing the greatest number of preferred haplotypes known to this date to exist in nature are described in Table 6. The commercially released corn male inbreds containing the greatest number of preferred haplotypes known to this date to exist in nature are described in Table 7.

TABLE 6

List of the commercially released female inbreds that contain the maximum number of preferred haplotypes for each superiority "class" for four different phenotypic traits (yield, moisture, plant height, and test weight).

| Name | Preferred haplotypes present | Total preferred haplotypes |
|------|------------------------------|----------------------------|
| YIELD 2:5 | | |
| LH236 | 1241745, 1245282 | 1241745, 1245282, 1243877, 1243070, 1245725 |
| LH310 | 1241745, 1245282 | |
| LH311 | 1241745, 1245282 | |
| YIELD 4:10 | | |
| 7DCD2C | 1242692, 1243137, 1243531, 1245725 | 1241745, 1245282, 1243877, 1243070, 1245725, 1243531, 1243137, 1244818, 1242935, 1242692 |
| YIELD 7:20 | | |
| LH311 | 1241745, 1242555, 1242764, 1243209, 1243921, 1245051, 1245282 | 1241745, 1245282, 1243877, 1243070, 1245725, 1243531, 1243137, 1244818, 1242935, 1242692, 1243209, 1239247, 1242639, 1245002, 1242764, 1245051, 1242555, 1241471, 1243921, 1245245 |
| YIELD 10:30 | | |
| 80DJD5 | 1238977, 1240194, 1241428, 1241471, 1241584, 1242555, 1243209, 1243531, 1243724, 1245725 | 1241745, 1245282, 1243877, 1243070, 1245725, 1243531, 1243137, 1244818, 1242935, 1242692, 1243209, 1239247, 1242639, 1245002, 1242764, 1245051, 1242555, 1241471, 1243921, 1245245, 1239097, 1244707, 1240716, 1243724, 1240194, 1238977, 1239277, 1241428, 1241344, 1241584 |
| YIELD 15:40 | | |
| 80DJD5 | 1238977, 1239269, 1240194, 1240798, 1241428, 1241471, 1241584, 1242169, 1242555, 1242655, 1243209, 1243531, 1243724, 1244582, 1245725 | 1241745, 1245282, 1243877, 1243070, 1245725, 1243531, 1243137, 1244818, 1242935, 1242692, 1243209, 1239247, 1242639, 1245002, 1242764, 1245051, 1242555, 1241471, 1243921, 1245245, 1239097, 1244707, 1240716, 1243724, 1240194, 1238977, 1239277, 1241428, 1241344, 1241584, 1243419, 1240798, 1239269, 1241694, 1244582, 1244051, 1242655, 1244350, 1240495, 1242169 |
| YIELD 16:50 | | |
| 80DJD5 | 1238977, 1239269, 1239572, 1240194, 1240798, 1241428, 1241471, 1241584, 1242169, 1242555, 1242655, 1243209, 1243531, 1243724, 1244582, 1245725 | 1241745, 1245282, 1243877, 1243070, 1245725, 1243531, 1243137, 1244818, 1242935, 1242692, 1243209, 1239247, 1242639, 1245002, 1242764, 1245051, 1242555, 1241471, 1243921, 1245245, 1239097, 1244707, 1240716, 1243724, 1240194, 1238977, 1239277, 1241428, 1241344, 1241584, 1243419, 1240798, 1239269, 1241694, 1244582, 1244051, 1242655, 1244350, 1240495, 1242169, 1241828, 1243958, 1241430, 1239542, |

TABLE 6-continued

List of the commercially released female inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| | | 1240734, 1244381, 1239572, 1243540, 1239335, 1240910 |
| MOISTURE 8:20 | | |
| 89AHD12 | 1239271, 1239569, 1239759, 1240800, 1241485, 1243051, 1243218, 1245744 | 1242746, 1241485, 1245310, 1240420, 1240492, 1239759, 1239569, 1243417, 1244049, 1240800, 1245000, 1240365, 1241593, 1245744, 1243051, 1243218, 1239271, 1243882, 1243381, 1243320 |
| 89DRD5 | 1239271, 1239569, 1240420, 1240800, 1241485, 1243218, 1245000, 1245744 | |
| 94DUD2 | 1239271, 1239569, 1240420, 1240800, 1241485, 1243218, 1245000, 1245744 | |
| MOISTURE 11:30 | | |
| 83DNQ2 | 1239271, 1239569, 1240420, 1240800, 1242655, 1243146, 1243218, 1243920, 1245179, 1245720, 1245744 | 1242746, 1241485, 1245310, 1240420, 1240492, 1239759, 1239569, 1243417, 1244049, 1240800, 1245000, 1240365, 1241593, 1245744, 1243051, 1243218, 1239271, 1243882, 1243381, 1243320, 1242721, 1245179, 1245720, 1243989, 1242655, 1243920, 1242720, 1243146, 1243420, 1245823 |
| 89AHD12 | 1239271, 1239569, 1239759, 1240800, 1241485, 1242720, 1243051, 1243218, 1243420, 1243920, 1245744 | |
| MOISTURE 15:40 | | |
| 91DUQ2 | 1239271, 1239569, 1240598, 1240800, 1241485, 1241721, 1242688, 1243051, 1243218, 1243858, 1243920, 1244067, 1245179, 1245720, 1245744 | 1242746, 1241485, 1245310, 1240420, 1240492, 1239759, 1239569, 1243417, 1244049, 1240800, 1245000, 1240365, 1241593, 1245744, 1243051, 1243218, 1239271, 1243882, 1243381, 1243320, 1242721, 1245179, 1245720, 1243989, 1242655, 1243920, 1242720, 1243146, 1243420, 1245823, 1240901, 1241721, 1240014, 1241038, 1242688, 1244169, 1244067, 1243858, 1244914, 1240598 |
| MOISTURE 18:50 | | |
| 89AHD12 | 1239271, 1239321, 1239569, 1239759, 1240282, 1240598, 1240800, 1241485, 1242720, 1243051, 1243218, 1243362, 1243420, 1243920, 1244272, 1244583, 1245072, 1245744 | 1242746, 1241485, 1245310, 1240420, 1240492, 1239759, 1239569, 1243417, 1244049, 1240800, 1245000, 1240365, 1241593, 1245744, 1243051, 1243218, 1239271, 1243882, 1243381, 1243320, 1242721, 1245179, 1245720, 1243989, 1242655, 1243920, 1242720, 1243146, 1243420, 1245823, 1240901, 1241721, 1240014, 1241038, 1242688, 1244169, 1244067, 1243858, 1244914, 1240598, 1244272, 1244583, 1243362, 1240747, 1241848, 1239321, 1240272, 1245072, 1240282, 1240573 |
| 91DUQ2 | 1239271, 1239569, 1240282, 1240598, 1240800, 1241485, 1241721, 1242688, 1243051, 1243218, 1243858, 1243920, 1244067, 1244272, 1244583, 1245179, 1245720, 1245744 | |
| PLANT HEIGHT 3:5 | | |
| 93DKS3 | 1239494, 1242654, 1245298 | 1240622, 1242654, 1241736, 1239494, 1245298 |
| LH245 | 1240622, 1242654, 1245298 | |
| PLANT HEIGHT 5:10 | | |
| 01DHD10 | 1242272, 1242654, 1242686, 1244689, 1245298 | 1240622, 1242654, 1241736, 1239494, 1245298, 1239848, 1240909, 1244689, 1242686, 1242272 |
| 49DKD4 | 1242272, 1242654, 1242686, 1244689, 1245298 | |
| 83SDD2 | 1242272, 1242654, 1242686, 1244689, 1245298 | |
| 93DKS3 | 1239494, 1242654, 1242686, 1244689, 1245298 | |
| PLANT HEIGHT 5:20 | | |
| 01DHD10 | 1242272, 1242654, 1242686, 1244689, 1245298 | 1240622, 1242654, 1241736, 1239494, 1245298, 1239848, 1240909, 1244689, 1242686, 1242272, 1240417, 1240747, 1244365, 1243882, 1243938, 1243725, 1243920, 1239423, 1244699, 1241274 |
| 49DKD4 | 1242272, 1242654, 1242686, 1244689, 1245298 | |
| 83SDD2 | 1242272, 1242654, 1242686, 1244689, 1245298 | |

TABLE 6-continued

List of the commercially released female inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| 93DKS3 | 1239494, 1242654, 1242686, 1244689, 1245298 | |

PLANT HEIGHT 5:30

| Name | Preferred haplotypes present | Total preferred haplotypes |
|---|---|---|
| 01DHD10 | 1242272, 1242654, 1242686, 1244689, 1245298 | 1240622, 1242654, 1241736, 1239494, 1245298, 1239848, 1240909, 1244689, |
| 49DKD4 | 1242272, 1242654, 1242686, 1244689, 1245298 | 1242686, 1242272, 1240417, 1240747, 1244365, 1243882, 1243938, 1243725, |
| 83SDD2 | 1242272, 1242654, 1242686, 1244689 1245298 | 1243920, 1239423, 1244699, 1241274, 1239868, 1241848, 1241565, 1243566, |
| 93DKS3 | 1239494, 1242654, 1242686, 1244689, 1245298 | 1240481, 1244846, 1242341, 1245643, 1241796, 1244356 |

PLANT HEIGHT 11:40

| Name | Preferred haplotypes present | Total preferred haplotypes |
|---|---|---|
| 49DKD4 | 1239868, 1240481, 1241274, 1242272, 1242654, 1242686, 1243920, 1244050, 1244113, 1244689, 1245298 | 1240622, 1242654, 1241736, 1239494, 1245298, 1239848, 1240909, 1244689, 1242686, 1242272, 1240417, 1240747, 1244365, 1243882, 1243938, 1243725, 1243920, 1239423, 1244699, 1241274, |
| 83SDD2 | 1239868, 1240481, 1240747, 1241274, 1242272, 1242654, 1242686, 1243920, 1244050, 1244689, 1245298 | 1239868, 1241848, 1241565, 1243566, 1240481, 1244846, 1242341, 1245643, 1241796, 1244356, 1241746, 1244050, 1241531, 1242570, 1244113, 1245075, 1245676, 1240726, 1242368, 1241784 |
| 87DUA5 | 1240481, 1240726, 1240909, 1241274, 1241746, 1242570, 1242654, 1242686, 1244365, 1244699, 1245075 | |
| 87DUA6 | 1240481, 1240726, 1241274, 1241746, 1242368, 1242570, 1242654, 1242686, 1244365, 1244699, 1245298 | |

PLANT HEIGHT 14:50

| Name | Preferred haplotypes present | Total preferred haplotypes |
|---|---|---|
| 87DUA5 | 1240038, 1240481, 1240598, 1240726, 1240909, 1241274, 1241746, 1242570, 1242654, 1242686, 1244272, 1244365, 1244699, 1245075 | 1240622, 1242654, 1241736, 1239494, 1245298, 1239848, 1240909, 1244689, 1242686, 1242272, 1240417, 1240747, 1244365, 1243882, 1243938, 1243725, 1243920, 1239423, 1244699, 1241274, |
| 87DUA6 | 1240038, 1240481, 1240598, 1240726, 1241274, 1241746, 1242368, 1242570, 1242654, 1242686, 1244272, 1244365, 1244699, 1245298 | 1239868, 1241848, 1241565, 1243566, 1240481, 1244846, 1242341, 1245643, 1241796, 1244356, 1241746, 1244050, 1241531, 1242570, 1244113, 1245075, 1245676, 1240726, 1242368, 1241784, |
| 94AHA8 | 1239327, 1240038, 1240481, 1240598, 1240726, 1241848, 1242341, 1242570, 1242654, 1242686, 1243725, 1243938, 1244272, 1244699 | 1244272, 1240038, 1239330, 1245014, 1239327, 1243554, 1240248, 1240598, 1241718, 1240348 |

TEST WEIGHT 3:5

| Name | Preferred haplotypes present | Total preferred haplotypes |
|---|---|---|
| 87DUA3 | 1239172, 1240420, 1244276 | 1239172, 1240420, 1244276, 1240365, 1240353 |

TEST WEIGHT 6:10

| Name | Preferred haplotypes present | Total preferred haplotypes |
|---|---|---|
| 87DUA6 | 1239172, 1239490, 1240420, 1241219, 1242131, 1244365 | 1239172, 1240420, 1244276, 1240365, 1240353, 1241219, 1239490, 1243351, 1242131, 1244365 |

TEST WEIGHT 6:20

| Name | Preferred haplotypes present | Total preferred haplotypes |
|---|---|---|
| 87DUA6 | 1239172, 1239490, 1240420, 1241219, 1242131, 1244365 | 1239172, 1240420, 1244276, 1240365, 1240353, 1241219, 1239490, 1243351, 1242131, 1244365, 1242728, 1242929, 1242400, 1240422, 1239330, 1240240, 1244998, 1242746, 1242338, 1243554 |

TEST WEIGHT 10:30

| Name | Preferred haplotypes present | Total preferred haplotypes |
|---|---|---|
| 19DKS4 | 1239330, 1239344, 1239490, 1239569, 1240240, 1242929, 1243554, 1244168, 1244998, 1245720 | 1239172, 1240420, 1244276, 1240365, 1240353, 1241219, 1239490, 1243351, 1242131, 1244365, 1242728, 1242929, 1242400, 1240422, 1239330, 1240240, 1244998, 1242746, 1242338, 1243554, 1240016, 1245720, 1244635, 1239344, |

TABLE 6-continued

List of the commercially released female inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| | | 1242367, 1242512, 1239253, 1239569, 1244168, 1244171 |
| TEST WEIGHT 15:40 | | |
| 87DUA6 | 1239172, 1239325, 1239416, 1239490, 1239569, 1240420, 1240681, 1240726, 1241219, 1242131, 1242338, 1242424, 1243873, 1244171, 1244365 | 1239172, 1240420, 1244276, 1240365, 1240353, 1241219, 1239490, 1243351, 1242131, 1244365, 1242728, 1242929, 1242400, 1240422, 1239330, 1240240, 1244998, 1242746, 1242338, 1243554, 1240016, 1245720, 1244635, 1239344, 1242367, 1242512, 1239253, 1239569, 1244168, 1244171, 1239416, 1240681, 1243596, 1239325, 1242424, 1243873, 1240726, 1240718, 1241487, 1238959 |
| TEST WEIGHT 18:50 | | |
| 3AZA1 | 1239172, 1239325, 1239416, 1239490, 1239569, 1240420, 1240726, 1241219, 1241706, 1242131, 1242338, 1242367, 1242424, 1242686, 1243873, 1244059, 1244171, 1245919 | 1239172, 1240420, 1244276, 1240365, 1240353, 1241219, 1239490, 1243351, 1242131, 1244365, 1242728, 1242929, 1242400, 1240422, 1239330, 1240240, 1244998, 1242746, 1242338, 1243554, 1240016, 1245720, 1244635, 1239344, 1242367, 1242512, 1239253, 1239569, 1244168, 1244171, 1239416, 1240681, 1243596, 1239325, 1242424, 1243873, 1240726, 1240718, 1241487, 1238959, 1241736, 1244113, 1240906, 1243854, 1241706, 1242662, 1242686, 1244059, 1241442, 1245919 |
| 87DUA6 | 1239172, 1239325, 1239416, 1239490, 1239569, 1240420, 1240681, 1240726, 1241219, 1241706, 1242131, 1242338, 1242424, 1242686, 1243873, 1244171, 1244365, 1245919 | |

TABLE 7

List of the commercially released male inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| YIELD 2:5 | | |
| LH262 | 1239500, 1243877 | 1240437, 1244921, 1239500, 1242504, 1243877 |
| 3140 | 1242504, 1243877 | |
| 34CDK2 | 1239500, 1243877 | |
| LH185 | 1239500, 1243877 | |
| LH254 | 1239500, 1243877 | |
| LH256 | 1239500, 1243877 | |
| LH258 | 1239500, 1243877 | |
| LH279 | 1239500, 1242504 | |
| LH287 | 1239500, 1243877 | |
| LH287BT1-1 | 1239500, 1243877 | |
| LH350 | 1239500, 1243877 | |
| MDF-13A | 1239500, 1243877 | |
| PA2121 | 1240437, 1244921 | |
| PA3003 | 1240437, 1244921 | |
| PZ7012 | 1240437, 1244921 | |
| PZ7149 | 1240437, 1244921 | |
| SH7202 | 1240437, 1244921 | |
| YIELD 3:10 | | |
| 34CDK2 | 1239500, 1240805, 1243877 | 1240437, 1244921, 1239500, 1242504, 1243877, 1240280, 1243378, 1240805, 1245695, 1239419 |
| 4GCG1 | 1239419, 1240280, 1240805 | |
| LH254 | 1239500, 1243378, 1243877 | |
| LH350 | 1239500, 1240805, 1243877 | |
| MDF-13A | 1239500, 1243378, 1243877 | |
| YIELD 6:20 | | |
| MDF-13A | 1238927, 1239500, 1241957, 1242383, 1243378, 1243877 | 1240437, 1244921, 1239500, 1242504, 1243877, 1240280, 1243378, 1240805, 1245695, 1239419, 1238927, 1240824, 1244751, 1242383, 1244958, 1245723, 1241440, 1245503, 1241364, 1241957 |

TABLE 7-continued

List of the commercially released male inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| YIELD 8:30 | | |
| 19HGZ1 | 1238927, 1239043, 1239273, 1239419, 1240424, 1240824, 1242383, 1245503 | 1240437, 1244921, 1239500, 1242504, 1243877, 1240280, 1243378, 1240805, 1245695, 1239419, 1238927, 1240824, 1244751, 1242383, 1244958, 1245723, 1241440, 1245503, 1241364, 1241957, 123 273, 1241211, 1242153, 1240424, 1243448, 1238980, 1242540, 1239043, 1241410, 1244018 |
| YIELD 11:40 | | |
| 19HGZ1 | 1238927, 1239043, 1239273, 1239419, 1240041, 1240266, 1240424, 1240824, 1242383, 1243787, 1245503 | 1240437, 1244921, 1239500, 1242504, 1243877, 1240280, 1243378, 1240805, 1245695, 1239419, 1238927, 1240824, 1244751, 1242383, 1244958, 1245723, 1241440, 1245503, 1241364, 1241957, 123 273, 1241211, 1242153, 1240424, 1243448, 1238980, 1242540, 1239043, 1241410, 1244018, 1240701, 1244097, 1239740, 1243704, 1240041, 1242667, 1245003, 1242567, 1240266, 1243787 |
| YIELD 13:50 | | |
| 19HGZ1 | 1238927, 1239043, 1239172, 1239273, 1239419, 1240041, 1240266, 1240424, 1240824, 1242383, 1243787, 1245503 | 1240437, 1244921, 1239500, 1242504, 1243877, 1240280, 1243378, 1240805, 1245695, 1239419, 1238927, 1240824, 1244751, 1242383, 1244958, 1245723, 1241440, 1245503, 1241364, 1241957, 123 273, 1241211, 1242153, 1240424, 1243448, 1238980, 1242540, 1239043, 1241410, 1244018, 1240701, 1244097, 1239740, 1243704, 1240041, 1242667, 1245003, 1242567, 1240266, 1243787, 1242636, 1245927, 1241224, 1242665, 1241195, 1240251, 1239172, 1244508, 1240253, 1241110 |
| MOISTURE 4:10 | | |
| 86ISI5 | 1242556, 1244950, 1243377, 1244778 | 1242879, 1241721, 1244978, 1245717, 1242556, 1244950, 1241235, 1240902, 1243377, 1244778 |
| MOISTURE 5:20 | | |
| 2MSBA7 | 1239982, 1241235, 1241586, 1241721, 1244878 | 1242879, 1241721, 1244978, 1245717, 1242556, 1244950, 1241235, 1240902, 1243377, 1244778, 1241213, 1241586, 1242344, 1240804, 1244529, 1244878, 1239982, 1242571, 1244976, 1241714 |
| 86ISI5 | 1242556, 1243377, 1244529, 1244778, 1244950 | |
| 87LCC5 | 1239982, 1240902, 1241586, 1242556, 1244976 | |
| SYNBA2 | 1239982, 1241235, 1241586, 1241721, 1244878 | |
| MOISTURE 7:30 | | |
| LH176 | 1239982, 1240902, 1241095, 1241606, 1243377, 1244507, 1244529 | 1242879, 1241721, 1244978, 1245717, 1242556, 1244950, 1241235, 1240902, 1243377, 1244778, 1241213, 1241586, 1242344, 1240804, 1244529, 1244878, 1239982, 1242571, 1244976, 1241714, 1242285, 1241606, 1245670, 1241241, 1243263, 1245889, 1241095, 1241577, 1243398, 1244507 |
| LH295 | 1239982, 1240804, 1240902, 1241095, 1241606, 1243377, 1244507 | |
| MOISTURE 7:40 | | |
| LH176 | 1239982, 1240902, 1241095, 1241606, 1243377, 1244507, 1244529 | 1242879, 1241721, 1244978, 1245717, 1242556, 1244950, 1241235, 1240902, 1243377, 1244778, 1241213, 1241586, 1242344, 1240804, 1244529, 1244878, 1239982, 1242571, 1244976, 1241714, 1242285, 1241606, 1245670, 1241241, 1243263, 1245889, 1241095, 1241577, 1243398, 1244507, 1240882, 1243118, 1239897, 1242971, 1245130, 1243499, 1241490, 1244486, 1245883, 1241958 |
| LH295 | 1239982, 1240804, 1240902, 1241095, 1241606, 1243377, 1244507 | |

TABLE 7-continued

List of the commercially released male inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| MOISTURE 12:50 | | |
| 86ISI5 | 1240036, 1240968, 1241606, 1241958, 1242556, 1242713, 1243118, 1243377, 1243865, 1244529, 1244778, 1244950 | 1242879, 1241721, 1244978, 1245717, 1242556, 1244950, 1241235, 1240902, 1243377, 1244778, 1241213, 1241586, 1242344, 1240804, 1244529, 1244878, 1239982, 1242571, 1244976, 1241714, 1242285, 1241606, 1245670, 1241241, 1243263, 1245889, 1241095, 1241577, 1243398, 1244507, 1240882, 1243118, 1239897, 1242971, 1245130, 1243499, 1241490, 1244486, 1245883, 1241958, 1239361, 1245894, 1240968, 1242713, 1240036, 1242040, 1239883, 1240487, 1243865, 1243242 |
| PLANT HEIGHT 4:5 | | |
| 3140 | 1239420, 1240760, 1242162, 1242662 | 1239420, 1242162, 1242662, 1242335, 1240760 |
| LH168 | 1239420, 1240760, 1242162, 1242662 | |
| LH295 | 1239420, 1240760, 1242162, 1242662 | |
| PLANT HEIGHT 4:10 | | |
| 3140 | 1239420, 1240760, 1242162, 1242662 | 1239420, 1242162, 1242662, 1242335, 1240760, 1242879, 1241832, 1242358, 1242687, 1244302 |
| LH168 | 1239420, 1240760, 1242162, 1242662 | |
| LH172 | 1239420, 1240760, 1242358, 1242662 | |
| LH277 | 1239420, 1240760, 1242358, 1242662 | |
| LH295 | 1239420, 1240760, 1242162, 1242662 | |
| LH322 | 1239420, 1240760, 1242358, 1242662 | |
| PLANT HEIGHT 6:20 | | |
| LH295 | 1239361, 1239420, 1240760, 1241349, 1242162, 1242662 | 1239420, 1242162, 1242662, 1242335, 1240760, 1242879, 1241832, 1242358, 1242687, 1244302, 1239494, 1240264, 1239361, 1242369, 1243789, 1245719, 1241349, 1242714, 1240439, 1239164 |
| PLANT HEIGHT 6:30 | | |
| LH254 | 1240264, 1241412, 1242687, 1243210, 1243789, 1245719 | 1239420, 1242162, 1242662, 1242335, 1240760, 1242879, 1241832, 1242358, 1242687, 1244302, 1239494, 1240264, 1239361, 1242369, 1243789, 1245719, 1241349, 1242714, 1240439, 1239164, 1239990, 1239061, 1243210, 1241610, 1245642, 1238912, 1240040, 1241412, 1242371, 1245006 |
| LH295 | 1239361, 1239420, 1240760, 1241349, 1242162, 1242662 | |
| PLANT HEIGHT 9:40 | | |
| LH295 | 1239361, 1239420, 1239501, 1240031, 1240760, 1241349, 1242162, 1242662, 1245929 | 1239420, 1242162, 1242662, 1242335, 1240760, 1242879, 1241832, 1242358, 1242687, 1244302, 1239494, 1240264, 1239361, 1242369, 1243789, 1245719, 1241349, 1242714, 1240439, 1239164, 1239990, 1239061, 1243210, 1241610, 1245642, 1238912, 1240040, 1241412, 1242371, 1245006, 1242344, 1239501, 1239370, 1239843, 1244784, 1240031, 1241099, 1243727, 1245929, 1240687 |
| PLANT HEIGHT 11:50 | | |
| LH172 | 1239370, 1239420, 1239501, 1239578, 1239843, 1240760, 1242358, 1242658, 1242662, 1242692, 1245929 | 1239420, 1242162, 1242662, 1242335, 1240760, 1242879, 1241832, 1242358, 1242687, 1244302, 1239494, 1240264, 1239361, 1242369, 1243789, 1245719, 1241349, 1242714, 1240439, 1239164, 1239990, 1239061, 1243210, 1241610, |
| LH277 | 1239370, 1239420, 1239578, 1239843, 1240249, 1240760, | |

TABLE 7-continued

List of the commercially released male inbreds that contain the maximum number of preferred haplotypes for each superiority "class" for four different phenotypic traits (yield, moisture, plant height, and test weight).

| Name | Preferred haplotypes present | Total preferred haplotypes |
|---|---|---|
| LH295 | 1242358, 1242658, 1242662, 1242692, 1245929 1239361, 1239420, 1239501, 1240031, 1240760, 1241349, 1242162, 1242662, 1242692, 1243377, 1245929 | 1245642, 1238912, 1240040, 1241412, 1242371, 1245006, 1242344, 1239501, 1239370, 1239843, 1244784, 1240031, 1241099, 1243727, 1245929, 1240687, 1240249, 1243213, 1240271, 1238993, 1239578, 1245372, 1243377, 1242692, 1245121, 1242658 |

TEST WEIGHT 3:5

| LH185 | 1243269, 1239739, 1241036 | 1244555, 1243269, 1239739, 1243708, 1241036 |
| LH321 | 1244555, 1243269, 1239739 | |

TEST WEIGHT 4:10

| 4GCG1 | 1241036, 1241468, 1242162, 1243269 | 1244555, 1243269, 1239739, 1243708, 1241036, 1244878, 1244529, 1240820, 1242162, 1241468 |
| LH321 | 1239739, 1242162, 1243269, 1244555 | |

TEST WEIGHT 4:20

| 4GCG1 | 1241036, 1241468, 1242162, 1243269 | 1244555, 1243269, 1239739, 1243708, 1241036, 1244878, 1244529, 1240820, 1242162, 1241468, 1239003, 1240431, 1240018, 1241714, 1241721, 1243058, 1245769, 1244918, 1239002, 1240331 |
| LH321 | 1239739, 1242162, 1243269, 1244555 | |

TEST WEIGHT 4:30

| 4GCG1 | 1241036, 1241468, 1242162, 1243269 | 1244555, 1243269, 1239739, 1243708, 1241036, 1244878, 1244529, 1240820, 1242162, 1241468, 1239003, 1240431, 1240018, 1241714, 1241721, 1243058, 1245769, 1244918, 1239002, 1240331, 1239048, 1244778, 1240013, 1244637, 1245257, 1244973, 1244379, 1242662, 1240042, 1244302 |
| LH321 | 1239739, 1242162, 1243269, 1244555 | |

TEST WEIGHT 4:40

| 4GCG1 | 1241036, 1241468, 1242162, 1243269 | 1244555, 1243269, 1239739, 1243708, 1241036, 1244878, 1244529, 1240820, 1242162, 1241468, 1239003, 1240431, 1240018, 1241714, 1241721, 1243058, 1245769, 1244918, 1239002, 1240331, 1239048, 1244778, 1240013, 1244637, 1245257, 1244973, 1244379, 1242662, 1240042, 1244302, 1240031, 1242713, 1241610, 1245072, 1241430, 1242369, 1239987, 1241966, 1245118, 1244207 |
| LH321 | 1239739, 1242162, 1243269, 1244555 | |

TEST WEIGHT 12:50

| LH295 | 1239161, 1240018, 1240031, 1241430, 1241588, 1242162, 1242662, 1242713, 1244207, 1244555, 1245710, 1245773 | 1244555, 1243269, 1239739, 1243708, 1241036, 1244878, 1244529, 1240820, 1242162, 1241468, 1239003, 1240431, 1240018, 1241714, 1241721, 1243058, 1245769, 1244918, 1239002, 1240331, 1239048, 1244778, 1240013, 1244637, 1245257, 1244973, 1244379, 1242662, 1240042, 1244302, 1240031, 1242713, 1241610, 1245072, 1241430, 1242369, 1239987, 1241966, 1245118, 1244207, 1244279, 1245648, 1244352, 1240910, 1239161, 1244226, 1245710, 1241588, 1245773, 1245198 |

In another embodiment, preferred haplotypes are determined by evaluating trait ratios, given that certain phenotypic traits are negatively correlated with yield and, in corn, it is advantageous to select for positive yield and negative plant height or negative moisture. Exemplary trait ratios include greater than 2 or less than zero, greater than 3 or less than zero, and so on, wherein yield is positive and either plant height or moisture is negative. In one aspect, a preferred haplotype is one with a trait ratio of greater than 5 or less than zero (bu/acre:inches or bu/acre:% moisture, respectively), wherein yield is positive and either plant height or moisture is negative. For a preferred yield-plant height trait ratio, the following 485 preferred haplotypes were identified in female corn inbreds: 1240330, 1240341, 1240365, 1240373, 1240335, 1244963, 1244954, 1244998, 1245002, 1242131, 1242134, 1242136, 1245111, 1240904, 1240906, 1244818, 1244826, 1242719, 1242728, 1242731, 1242738, 1242720, 1242721, 1241220, 1241234, 1244641, 1244644, 1244657, 1244635, 1238977, 1238987, 1239022, 1239028, 1245360, 1245372, 1245362, 1245368, 1242928, 1242929, 1243964, 1240029, 1241366, 1241347, 1241350, 1243703, 1243714, 1243717, 1243724, 1243705, 1243710, 1239181, 1239198, 1239210, 1242381, 1242367, 1242368, 1244274, 1244285, 1244276, 1244525, 1244526, 1244527, 1244531, 1243862, 1243873, 1239490, 1239496, 1244516, 1240415, 1240416, 1241563, 1241564, 1241567, 1243917, 1243918, 1241406, 1239845, 1239846, 1239848, 1240428, 1240454, 1240420, 1240422, 1240679, 1240681, 1240687, 1244774, 1240798, 1240811, 1240800, 1240964, 1240977, 1240971, 1243373, 1243382, 1243375, 1245130, 1245120, 1239147, 1239148, 1240261, 1240263, 1240264, 1240265, 1240266, 1242866, 1242878, 1242881, 1242869, 1240252, 1239338, 1239340, 1239341, 1243999, 1244000, 1244001, 1243110, 1243120, 1243112, 1243116, 1243118, 1239652, 1239653, 1243796, 1243790, 1239532, 1239542, 1239533, 1239539, 1242230, 1242220, 1242221, 1242225, 1242227, 1244500, 1244501, 1239981, 1244168, 1244169, 1240495, 1240484, 1242688, 1242692, 1245718, 1245720, 1244300, 1244316, 1244305, 1241580, 1241603, 1241428, 1241447, 1241450, 1241430, 1241436, 1242932, 1242942, 1242934, 1242935, 1242938, 1243209, 1243218, 1240932, 1240935, 1245511, 1240241, 1240242, 1240246, 1239406, 1238934, 1244187, 1244189, 1244190, 1240670, 1243051, 1243070, 1243080, 1243059, 1243540, 1243596, 1243538, 1242065, 1242095, 1242067, 1242115, 1242072, 1240119, 1241885, 1241906, 1241924, 1245917, 1245918, 1245923, 1242628, 1243967, 1243970, 1243972, 1243974, 1239572, 1239583, 1239574, 1239623, 1245562, 1245575, 1245564, 1245595, 1245565, 1241099, 1241108, 1241112, 1241124, 1241638, 1241632, 1241633, 1241634, 1243417, 1243429, 1243436, 1243444, 1243419, 1243420, 1240194, 1240181, 1240184, 1240922, 1240924, 1240926, 1245090, 1245089, 1242986, 1242995, 1243001, 1242988, 1243018, 1243036, 1243042, 1242994, 1244006, 1244007, 1244008, 1244009, 1244095, 1244097, 1239866, 1239867, 1242537, 1242546, 1242550, 1242539, 1242540, 1242543, 1242545, 1245411, 1245422, 1245413, 1245447, 1242785, 1242797, 1242787, 1242792, 1241025, 1241035, 1241038, 1241045, 1241071, 1241030, 1241969, 1241960, 1242952, 1242954, 1244874, 1244875, 1240270, 1240281, 1240282, 1244220, 1244202, 1244235, 1240714, 1244914, 1245916, 1243855, 1243858, 1245929, 1245930, 1242663, 1243607, 1243608, 1243609, 1242149, 1242150, 1242151, 1242156, 1245199, 1244602, 1244596, 1239058, 1241872, 1242632, 1242644, 1242633, 1242639, 1242507, 1242510, 1243273, 1243274, 1243261, 1244106, 1244115, 1244118, 1241706, 1245881, 1245882, 1243346, 1243347, 1243348, 1243351, 1243352, 1243355, 1242982, 1245072, 1245073, 1245074, 1240007, 1240016, 1240014, 1243847, 1243623, 1243632, 1241461, 1241471, 1241474, 1241487, 1243315, 1243320, 1243322, 1242169, 1242179, 1245828, 1245846, 1245822, 1245824, 1239328, 1243135, 1243137, 1243174, 1243979, 1241284, 1241307, 1241278, 1239904, 1239915, 1245245, 1244077, 1244079, 1244081, 1244082, 1241088, 1240589, 1240602, 1240590, 1240596, 1244196, 1244198, 1242055, 1242062, 1242034, 1242037, 1240174, 1240175, 1244692, 1245772, 1239065, 1239074, 1239066, 1239068, 1242252, 1242289, 1242253, 1239655, 1239671, 1239674, 1239687, 1239662, 1239663, 1244023, 1244013, 1239269, 1239271, 1239273, 1239277, 1240881, 1240884, 1245794, 1242970, 1240709, 1240710, 1240712, 1239972, 1239978, 1241786, 1241790, 1240572, 1240573, 1240576, 1240580, 1239759, 1239761, 1239809, 1245274, 1245277, 1245281, 1245282, 1241165, 1244700, 1242555, 1242557, 1242560, 1240718, 1242338, 1241826, 1241838, 1239344, 1239353, 1239376, 1239348, 1245744, 1245745, 1244048, 1244049, 1244050, 1244053, 1245207, 1245208, 1245210, 1245659, 1245676, 1245662, 1245663, 1240112, 1240113, 1240114, 1240257, 1240259, 1243987, 1243989, 1245760, 1245761, 1241458, 1241459, 1245189, 1245192, 1241818, 1241819, 1239244, 1239253, 1239245, 1239425, 1239411, 1239413, 1240616, 1240621, 1242214, 1242216, 1245554, 1245555, 1242713, 1245637, 1245643, 1245298, 1245308, 1245326, 1244360, 1244381, 1244410, 1243933, 1243938, 1243926, 1241746, 1245763, 1245764, 1245765, 1245766, 1245768, and 1245769. To date, the greatest number of said preferred yield-plant height trait ratio haplotypes occurring in a commercially released female inbred is 117, wherein the inbred is 83DIQ8 and the 117 preferred haplotypes are: 1239058, 1239068, 1239148, 1239210, 1239245, 1239271, 1239340, 1239353, 1239411, 1239490, 1239653, 1239846, 1239866, 1240029, 1240114, 1240175, 1240181, 1240263, 1240281, 1240415, 1240454, 1240484, 1240572, 1240596, 1240670, 1240679, 1240709, 1240800, 1240881, 1240906, 1240924, 1240935, 1241088, 1241099, 1241220, 1241447, 1241458, 1241471, 1241564, 1241580, 1241786, 1241818, 1241838, 1241872, 1241885, 1242115, 1242136, 1242149, 1242169, 1242214, 1242253, 1242338, 1242367, 1242510, 1242550, 1242639, 1242663, 1242692, 1242785, 1242869, 1242928, 1242934, 1242954, 1242970, 1242982, 1242988, 1243051, 1243112, 1243135, 1243218, 1243261, 1243315, 1243346, 1243375, 1243420, 1243607, 1243623, 1243790, 1243862, 1243917, 1243967, 1243979, 1243987, 1243999, 1244009, 1244013, 1244048, 1244077, 1244095, 1244106, 1244190, 1244274, 1244316, 1244501, 1244525, 1244644, 1244954, 1244998, 1245074, 1245120, 1245189, 1245208, 1245274, 1245298, 1245360, 1245411, 1245554, 1245564, 1245637, 1245662, 1245744, 1245760, 1245763, 1245772, 1245794, 1245881, and 1245929.

For a preferred yield-moisture trait ratio, the following 676 preferred haplotypes were identified in female corn inbreds: 1240341, 1240348, 1240353, 1240365, 1240373, 1240386, 1240335, 1244946, 1244963, 1244948, 1244998, 1245007, 1245011, 1245014, 1245051, 1242130, 1242131, 1242132, 1242134, 1245110, 1245111, 1245112, 1245114, 1240910, 1240904, 1240909, 1244805, 1244815, 1244818, 1244826, 1244846, 1242719, 1242728, 1242731, 1242734, 1242738, 1242721, 1242764, 1241207, 1241219, 1241220, 1241234, 1244631, 1244641, 1244643, 1244644, 1244657, 1244633, 1244635, 1238977, 1238987, 1238988, 1239022, 1239028, 1245362, 1242931, 1243958, 1243959, 1245709, 1240029, 1241344, 1241346, 1241347, 1243714, 1243717, 1243724, 1243705, 1243710, 1239155, 1239172, 1239156, 1239181, 1239158, 1239198, 1239210, 1242365, 1242367, 1242400, 1242368, 1244274, 1244285, 1244276, 1244526, 1244527, 1243862, 1243871, 1243873, 1243877, 1243863, 1243882, 1243904, 1239494, 1239496, 1240415, 1240416, 1241563, 1241565, 1241567, 1241568, 1243917, 1243918, 1241406, 1241407, 1239842, 1239845, 1239846, 1239848, 1244582, 1240428, 1240419, 1240451, 1240454, 1240679, 1240681, 1240687, 1244774, 1244776, 1244780, 1240811, 1240813, 1240800, 1240964, 1240977, 1240966, 1241001, 1240971, 1243373, 1243382, 1243375, 1245118, 1245120, 1245125, 1239147, 1239148, 1241605, 1241621, 1241607, 1241608, 1240261, 1240262, 1240263, 1240264, 1240265, 1240266, 1242881, 1242869, 1245557, 1245558, 1240248, 1240250, 1240252, 1240254, 1239340, 1239341, 1243999, 1244000, 1244001, 1244502, 1244504, 1239968, 1239969, 1244063, 1244064, 1244065, 1241571, 1241573, 1244900, 1244901, 1244902, 1244907, 1243110, 1243120, 1243112, 1243116, 1239652, 1239653, 1243786, 1243796, 1243797, 1239542, 1239533, 1239539, 1239540, 1242219, 1242220, 1242221, 1242225, 1242226, 1242227, 1239981, 1239985, 1244168, 1244171, 1240481, 1240492, 1240493, 1240495, 1240484, 1242686, 1242690, 1242691, 1242692, 1245718, 1245720, 1245721, 1245725, 1244300, 1244316, 1244305, 1241580, 1241593, 1241584, 1241585, 1241428, 1241438, 1241442, 1241447, 1241430, 1241436, 1242932, 1242942, 1242934, 1242935, 1243209, 1243215, 1243216, 1240932, 1240935, 1245511, 1245513, 1240241, 1240242, 1240246, 1241694, 1241696, 1241697, 1239403, 1239405, 1238906, 1238916, 1238934, 1238959, 1244187, 1244189, 1239312, 1239321, 1239320, 1240668, 1240670, 1240671, 1240106, 1240107, 1243051, 1243070, 1243080, 1243056, 1243057, 1243059, 1243531, 1243540, 1243554, 1243566, 1243596, 1243538, 1242065, 1242115, 1240118, 1241885, 1241906, 1241887, 1241924, 1244892, 1244894, 1245404, 1239034, 1243489, 1244887, 1244888, 1245918, 1245919, 1245923, 1242628, 1242629, 1243968, 1243970, 1243972, 1243974, 1239572, 1239582, 1239583, 1239585, 1239574, 1239623, 1239577, 1245562, 1245575, 1245584, 1245564, 1245595, 1245565, 1242424, 1242432, 1241112, 1241124, 1241626, 1241634, 1243428, 1243436, 1243444, 1243419, 1240179, 1240192, 1240194, 1240184, 1240923, 1240924, 1240925, 1240926, 1245081, 1245090, 1245085, 1245087, 1245089, 1242986, 1242995, 1243001, 1242988, 1243018, 1243036, 1243042, 1242994, 1244438, 1244439, 1244440, 1244441, 1244006, 1244007, 1244009, 1244095, 1244096, 1244097, 1242537, 1242546, 1242550, 1242540, 1242543, 1242545, 1245411, 1245422, 1245413, 1245447, 1242797, 1242787, 1242790, 1241035, 1241045, 1241027, 1241071, 1241030, 1240036, 1241956, 1241958, 1241960, 1242952, 1242954, 1244872, 1244875, 1244200, 1244220, 1244202, 1244235, 1240713, 1240714, 1244918, 1245914, 1245916, 1239856, 1243854, 1245927, 1245929, 1245930, 1242662, 1242675, 1243608, 1243609, 1243610, 1242161, 1242150, 1242151, 1242155, 1242156, 1245197, 1245199, 1245200, 1245203, 1244588, 1244602, 1244596, 1239058, 1239059, 1239062, 1239868, 1239870, 1239876, 1241870, 1241871, 1241874, 1240676, 1240677, 1242632, 1242642, 1242633, 1242639, 1242640, 1242497, 1242512, 1243259, 1243273, 1243274, 1243261, 1243292, 1244118, 1244119, 1244131, 1244108, 1244113, 1241699, 1241702, 1241706, 1245881, 1245882, 1245883, 1245885, 1243362, 1243351, 1243352, 1243355, 1242982, 1242983, 1245073, 1245075, 1245076, 1245077, 1240016, 1240664, 1240665, 1240666, 1243846, 1243847, 1243632, 1243652, 1241461, 1241471, 1241473, 1241485, 1241487, 1241531, 1242654, 1242655, 1243318, 1243322, 1242169, 1242171, 1242172, 1245819, 1245828, 1245846, 1245822, 1245823, 1245824, 1239325, 1239327, 1239328, 1239330, 1243135, 1243146, 1243149, 1243137, 1243977, 1243979, 1243981, 1241271, 1241284, 1241273, 1241307, 1241274, 1241278, 1239893, 1239915, 1239895, 1245237, 1245251, 1245238, 1245245, 1244077, 1244079, 1244080, 1244082, 1244083, 1240108, 1240109, 1240699, 1241093, 1241094, 1241090, 1240598, 1240601, 1240590, 1244196, 1244197, 1244198, 1242055, 1242033, 1242062, 1242034, 1242037, 1242039, 1244690, 1244691, 1244692, 1245773, 1239065, 1239074, 1239066, 1239067, 1239097, 1239068, 1242250, 1242261, 1242272, 1242289, 1242253, 1239666, 1239671, 1239674, 1239675, 1239657, 1239662, 1239663, 1244023, 1244013, 1244017, 1239269, 1239280, 1239271, 1239277, 1245180, 1245889, 1245891, 1240881, 1240884, 1244881, 1239335, 1240709, 1240710, 1239972, 1239974, 1239976, 1239979, 1241784, 1241798, 1241787, 1240582, 1240573, 1240576, 1240580, 1239748, 1239761, 1239778, 1239809, 1245274, 1245277, 1245279, 1245282, 1241155, 1241165, 1241177, 1244697, 1244707, 1244699, 1244700, 1244705, 1242555, 1242568, 1242570, 1242557, 1240716, 1240726, 1240734, 1240747, 1240718, 1242330, 1242341, 1242338, 1241848, 1241828, 1239344, 1239353, 1239365, 1239376, 1239348, 1245742, 1245747, 1244051, 1244053, 1245207, 1245209, 1245210, 1245659, 1245676, 1245661, 1245662, 1245663, 1245799, 1245802, 1240112, 1240113, 1240257, 1240259, 1243987, 1243988, 1243989, 1245759, 1245760, 1245761, 1241458, 1241459, 1245189, 1245190, 1245192, 1243614, 1241818, 1241819, 1239244, 1239262, 1239245, 1239247, 1239416, 1239423, 1240615, 1240616, 1240619, 1240621, 1240622, 1242214, 1242216, 1245554, 1245555, 1245272, 1245273, 1242711, 1242712, 1242713, 1245637, 1245308, 1245299, 1244349, 1244360, 1244365, 1244350, 1244381, 1244410, 1244356, 1243920, 1243938, 1243921, 1243951, 1241736, 1241745, 1241746, 1241718, 1245763, 1245764, 1245765, 1245768, and 1245769. To date, the greatest number of said yield-moisture trait ratio preferred haplotypes occurring in commercially released female inbreds is 168, wherein the 168 preferred haplotypes in 87DUA5 are: 1238906, 1239022, 1239034, 1239062, 1239074, 1239147, 1239156, 1239247, 1239271, 1239320, 1239325, 1239335, 1239341, 1239365, 1239416, 1239542, 1239572, 1239653, 1239657, 1239748, 1239842, 1239870, 1239969, 1239976, 1239981, 1240029, 1240106, 1240109, 1240113, 1240246, 1240250, 1240259, 1240265, 1240335, 1240415, 1240419, 1240481, 1240598, 1240615, 1240666, 1240670, 1240676, 1240687, 1240699, 1240713, 1240726, 1240800, 1240881, 1240909, 1240924, 1240935, 1240966, 1241030, 1241090, 1241094, 1241155, 1241220, 1241274, 1241347, 1241406, 1241436, 1241459, 1241485, 1241567, 1241573, 1241580, 1241607, 1241626, 1241694, 1241699, 1241746, 1241819, 1241874, 1241924, 1241958, 1242033, 1242065, 1242132, 1242156, 1242172, 1242214, 1242226, 1242253, 1242338, 1242367, 1242424, 1242537, 1242570, 1242629, 1242640, 1242654, 1242686, 1242712, 1242734, 1242934, 1242954, 1242982, 1242988, 1243059, 1243110, 1243135, 1243274, 1243322, 1243375, 1243489, 1243540, 1243608, 1243846, 1243862, 1243917, 1243959, 1243968, 1243979, 1243987, 1244001, 1244006, 1244013, 1244083, 1244097, 1244119, 1244171, 1244187, 1244196, 1244220, 1244274, 1244300, 1244365, 1244438, 1244504, 1244527, 1244588, 1244644, 1244692, 1244699, 1244815, 1244875, 1244887, 1244900, 1244948, 1245051, 1245075, 1245110, 1245120, 1245192, 1245199, 1245210, 1245251, 1245272, 1245274, 1245299, 1245404, 1245411, 1245554, 1245557, 1245562, 1245662, 1245709, 1245742, 1245759, 1245763, 1245773, 1245799, 1245822, 1245881, 1245889, 1245916, 1245919, and 1245929; and the 168 preferred haplotypes in LH244 and are: 1238916, 1238988, 1239034, 1239058, 1239097, 1239147, 1239198, 1239245, 1239269, 1239312, 1239325, 1239335, 1239341, 1239344, 1239403, 1239623, 1239652, 1239663, 1239748, 1239842, 1239856, 1239868, 1239895, 1239968, 1239974, 1239985, 1240016, 1240029, 1240036, 1240106, 1240109, 1240112, 1240118, 1240194, 1240254, 1240257, 1240266, 1240386, 1240415, 1240451, 1240493, 1240615, 1240666, 1240668, 1240677, 1240679, 1240699, 1240709, 1240714, 1240734, 1240800, 1240881, 1240925, 1240932, 1240966, 1241071, 1241093, 1241112, 1241155, 1241207, 1241284, 1241436, 1241458, 1241531, 1241571, 1241585, 1241621, 1241696, 1241699, 1241818, 1241870, 1241887, 1241956, 1242132, 1242151, 1242216, 1242219, 1242261, 1242330, 1242497, 1242568, 1242629, 1242642, 1242654, 1242662, 1242691, 1242711, 1242764, 1242787, 1242932, 1242952, 1242983, 1243018, 1243057, 1243120, 1243146, 1243209, 1243292, 1243352, 1243375, 1243428, 1243489, 1243538, 1243614, 1243652, 1243786, 1243846, 1243854, 1243882, 1243917, 1243951, 1243959, 1243972, 1243981, 1243987, 1244001, 1244017, 1244065, 1244080, 1244095, 1244108, 1244187, 1244196, 1244202, 1244274, 1244305, 1244410, 1244439, 1244502, 1244588, 1244631, 1244690, 1244707, 1244776, 1244872, 1244887, 1244892, 1244946, 1245051, 1245073, 1245090, 1245112, 1245120, 1245192, 1245207, 1245238, 1245272, 1245274, 1245362, 1245404, 1245413, 1245511, 1245554, 1245557, 1245584, 1245637, 1245659, 1245709, 1245720, 1245742, 1245759, 1245763, 1245799, 1245828, 1245885, 1245889, 1245914, and 1245927.

For a preferred yield-plant height trait ratio, the following 707 preferred haplotypes were identified in male corn inbreds: 1240342, 1240346, 1240331, 1240352, 1240354, 1240334, 1244957, 1244947, 1244971, 1244973, 1244988, 1244950, 1244951, 1245009, 1245034, 1245038, 1245003, 1245006, 1242130, 1242134, 1242135, 1242136, 1245111, 1245112, 1240910, 1240911, 1240902, 1240903, 1244815, 1244810, 1242730, 1242720, 1242722, 1242724, 1241217, 1241208, 1241209, 1241241, 1241211, 1241215, 1244640, 1244632, 1238986, 1239002, 1239003, 1238980, 1238983, 1238985, 1245370, 1245361, 1245362, 1245367, 1245368, 1242928, 1243959, 1243961, 1245709, 1245710, 1245711, 1245714, 1245717, 1240033, 1241350, 1243712, 1243715, 1243721, 1243755, 1243708, 1243710, 1239164, 1239167, 1239172, 1239159, 1242375, 1242366, 1242387, 1242372, 1242373, 1244274, 1244285, 1244277, 1244278, 1244279, 1243133, 1243134, 1244540, 1244529, 1243863, 1243865, 1243866, 1239505, 1239491, 1239494, 1239495, 1239497, 1239569, 1239570, 1242968, 1242969, 1240707, 1244517, 1244519, 1241563, 1241566, 1244159, 1244160, 1244161, 1241409, 1241411, 1241412, 1239842, 1239844, 1239845, 1244582, 1244583, 1244586, 1240431, 1240418, 1240437, 1240421, 1240424, 1240679, 1240682, 1240684, 1244774, 1244778, 1244780, 1244781, 1240824, 1240835, 1240802, 1240803, 1240804, 1240972, 1243373, 1243386, 1243392, 1243401, 1243378, 1243381, 1245133, 1245154, 1245122, 1245124, 1239147, 1241610, 1240265, 1242880, 1242881, 1242874, 1240248, 1240250, 1239339, 1239343, 1244001, 1244502, 1244504, 1244505, 1244064, 1244065, 1241571, 1241572, 1241573, 1241574, 1241577, 1244900, 1244901, 1244905, 1244907, 1243110, 1243112, 1243113, 1243116, 1243118, 1239654, 1243795, 1243788, 1243825, 1243789, 1243790, 1243792, 1239532, 1239534, 1239536, 1239540, 1242237, 1242221, 1242222, 1242224, 1239739, 1239740, 1239981, 1239990, 1239982, 1239985, 1239987, 1244170, 1244175, 1240481, 1240490, 1240513, 1240518, 1240484, 1240485, 1240488, 1242696, 1242700, 1242689, 1245728, 1245736, 1245725, 1244300, 1244301, 1244304, 1241581, 1241437, 1241440, 1241452, 1241430, 1241431, 1241433, 1241434, 1242943, 1242934, 1242935, 1242938, 1243224, 1243232, 1243214, 1240935, 1240937, 1245521, 1245530, 1245513, 1245514, 1245516, 1240241, 1240243, 1240245, 1239405, 1239406, 1238917, 1238922, 1238926, 1238927, 1238933, 1238938, 1238910, 1244507, 1244508, 1244509, 1244187, 1244188, 1244189, 1244190, 1244191, 1244192, 1244194, 1239312, 1239313, 1239315, 1239316, 1240669, 1240671, 1245499, 1245500, 1245502, 1245503, 1244272, 1244273, 1243070, 1243052, 1243057, 1243058, 1243546, 1243553, 1243592, 1243539, 1242074, 1242066, 1242069, 1242073, 1240117, 1240152, 1240124, 1241899, 1244891, 1244895, 1245405, 1245406, 1245408, 1239043, 1239048, 1239035, 1239037, 1243505, 1243490, 1243510, 1243511, 1243493, 1243495, 1244889, 1244890, 1245917, 1245923, 1243968, 1243969, 1243970, 1243974, 1239573, 1239603, 1239576, 1239577, 1245572, 1245574, 1245598, 1245565, 1245568, 1245569, 1242424, 1242433, 1242444, 1242451, 1242455, 1242426, 1242428, 1242431, 1241112, 1241121, 1241106, 1241627, 1241651, 1241634, 1243417, 1243430, 1243431, 1243447, 1243448, 1243421, 1240196, 1240197, 1240199, 1240182, 1240923, 1240924, 1240926, 1242989, 1243033, 1242994, 1245296, 1245297, 1244007, 1244008, 1244095, 1244097, 1244098, 1244099, 1244101, 1242538, 1245420, 1245437, 1245416, 1245417, 1242795, 1242800, 1242786, 1241036, 1241037, 1241046, 1241048, 1241062, 1241029, 1241030, 1240036, 1240046, 1240037, 1240072, 1240082, 1240041, 1240042, 1241967, 1241970, 1241971, 1241974, 1241958, 1241961, 1242954, 1242956, 1242960, 1244872, 1240280, 1240289, 1240293, 1240275, 1240276, 1244216, 1244218, 1244204, 1244207, 1240713, 1240714, 1244923, 1244913, 1244914, 1244915, 1244917, 1245915, 1239856, 1243857, 1245928, 1245930, 1242664, 1242666, 1242667, 1243609, 1243612, 1243613, 1242163, 1242151, 1242153, 1242157, 1245197, 1245200, 1244588, 1244607, 1244589, 1244592, 1244593, 1239059, 1239877, 1239883, 1239869, 1239889, 1239871, 1239873, 1239874, 1239876, 1241880, 1241874, 1241875, 1241876, 1242649, 1242635, 1242638, 1242639, 1242640, 1242508, 1242513, 1242498, 1242502, 1242503, 1242504, 1243269, 1243282, 1243285, 1243262, 1243263, 1243264, 1244110, 1244112, 1244113, 1241700, 1241702, 1245882, 1245883, 1245884, 1245885, 1245886, 1243346, 1243356, 1243349, 1243350, 1243351, 1245072, 1245074, 1245076, 1245814, 1245815, 1240008, 1240011, 1240012, 1240013, 1240666, 1243846, 1243847, 1243848, 1243850, 1240638, 1240640, 1240647, 1240630, 1240652, 1240633, 1243623, 1243646, 1243629, 1241475, 1241462, 1241490, 1241468, 1242655, 1242656, 1243326, 1243321, 1243322, 1242170, 1242197, 1242208, 1242175, 1245838, 1245862, 1245827, 1239326, 1243157, 1243138, 1243142, 1241282, 1239893, 1239903, 1239895, 1239934, 1239897, 1245250, 1245257, 1245245, 1244080, 1240108, 1240109, 1240699, 1240700, 1240599, 1240601, 1240603, 1240590, 1240593, 1240596, 1241949, 1241950, 1242040, 1242034, 1242036, 1239234, 1239226, 1239228, 1240175, 1240176, 1245782, 1245775, 1239065, 1239082, 1239066, 1239096, 1239102, 1239068, 1239123, 1242262, 1242251, 1242271, 1242278, 1242285, 1242293, 1242309, 1242311, 1242256, 1242257, 1244444, 1244456, 1244461, 1244445, 1244486, 1244449, 1239676, 1239686, 1239659, 1239713, 1244020, 1244014, 1244015, 1244017, 1244018, 1239278, 1239281, 1239273, 1245180, 1245181, 1245899, 1245891, 1245893, 1245894, 1240882, 1240887, 1240889, 1241820, 1241821, 1241822, 1245795, 1245796, 1245797, 1242970, 1242973, 1242974, 1242975, 1240709, 1240711, 1241794, 1241802, 1241787, 1241788, 1241790, 1240581, 1240573, 1240574, 1240575, 1240580, 1239758, 1239749, 1239810, 1245275, 1245276, 1245277, 1241195, 1241159, 1244712, 1244713, 1244715, 1244698, 1244729, 1244751, 1244702, 1242567, 1242556, 1242561, 1240727, 1240742, 1240775, 1240723, 1242344, 1242331, 1242332, 1241838, 1241828, 1241829, 1239353, 1239370, 1239347, 1239389, 1245743, 1245744, 1245745, 1245747, 1245750, 1244049, 1245208, 1245211, 1245214, 1245216, 1245665, 1245666, 1245810, 1245801, 1245802, 1245805, 1240258, 1240259, 1243992, 1245190, 1242780, 1242781, 1243615, 1239244, 1239251, 1239434, 1244934, 1244935, 1244936, 1244937, 1244940, 1244941, 1240618, 1245554, 1245555, 1245272, 1245273, 1242711, 1242712, 1245648, 1245649, 1245640, 1245641, 1245642, 1245644, 1245645, 1245310, 1245299, 1245301, 1245303, 1245305, 1244350, 1244370, 1244379, 1241721, 1241730, 1241712, 1241713, 1241714, 1245764, and 1245765. To date, the greatest number of said preferred yield-plant height trait ratio haplotypes occurring in a commercially released male inbred is 127, wherein the inbred is 5750 and the 127 preferred haplotypes are: 1238926, 1238983, 1239037, 1239059, 1239096, 1239147, 1239159, 1239244, 1239278, 1239313, 1239339, 1239405, 1239497, 1239536, 1239569, 1239573, 1239713, 1239740, 1239874, 1239987, 1240109, 1240176, 1240199, 1240241, 1240259, 1240280, 1240331, 1240421, 1240490, 1240575, 1240671, 1240707, 1240713, 1240723, 1240882, 1240902, 1240972, 1241036, 1241112, 1241159, 1241215, 1241430, 1241475, 1241572, 1241581, 1241634, 1241712, 1241788, 1241821, 1241970, 1242069, 1242135, 1242153, 1242175, 1242222, 1242309, 1242387, 1242433, 1242502, 1242561, 1242649, 1242712, 1242780, 1242874, 1242928, 1242935, 1242954, 1242969, 1243113, 1243134, 1243214, 1243269, 1243447, 1243493, 1243615, 1243623, 1243710, 1243792, 1243847, 1243863, 1243969, 1244001, 1244007, 1244015, 1244049, 1244064, 1244080, 1244095, 1244159, 1244188, 1244272, 1244279, 1244301, 1244350, 1244445, 1244509, 1244593, 1244702, 1244774, 1244905, 1244913, 1244935, 1245006, 1245074, 1245180, 1245190, 1245208, 1245273, 1245277, 1245297, 1245303, 1245367, 1245406, 1245416, 1245500, 1245554, 1245598, 1245644, 1245710, 1245743, 1245764, 1245795, 1245815, 1245884, 1245915, 1245917, and 1245928.

For a preferred yield-moisture trait ratio, the following 973 preferred haplotypes were identified in male corn inbreds: 1244629, 1240342, 1240346, 1240331, 1240349, 1240354, 1240334, 1240336, 1240337, 1244955, 1244957, 1244958, 1244964, 1244971, 1244973, 1244948, 1244976, 1244951, 1245015, 1245034, 1245038, 1245002, 1245003, 1245006, 1242130, 1242131, 1242133, 1242134, 1242135, 1245111, 1245112, 1240910, 1240911, 1240904, 1240909, 1244815, 1244806, 1244808, 1244811, 1242730, 1242720, 1242724, 1241217, 1241224, 1241226, 1241208, 1241241, 1241211, 1241212, 1241215, 1244632, 1244658, 1244634, 1244635, 1244637, 1244639, 1238986, 1238993, 1238978, 1239002, 1239003, 1238980, 1238982, 1238983, 1238985, 1245370, 1245361, 1245362, 1245363, 1245367, 1245368, 1242928, 1242929, 1242931, 1243958, 1243959, 1243962, 1245709, 1245710, 1245711, 1245714, 1240031, 1240033, 1241356, 1241345, 1241349, 1241350, 1243712, 1243715, 1243721, 1243704, 1243727, 1243755, 1243710, 1243711, 1239167, 1239171, 1239172, 1239156, 1239159, 1239209, 1242375, 1242379, 1242383, 1242366, 1242385, 1242387, 1242410, 1242371, 1242372, 1242373, 1244285, 1244275, 1244276, 1244279, 1243133, 1243134, 1244534, 1244555, 1244529, 1244530, 1244531, 1243877, 1243864, 1243901, 1243865, 1243866, 1243867, 1239500, 1239501, 1239506, 1239508, 1239491, 1239493, 1239494, 1239497, 1239569, 1239570, 1242968, 1242969, 1240707, 1244515, 1244516, 1244519, 1241565, 1241567, 1243917, 1243918, 1244159, 1244160, 1244161, 1244164, 1244166, 1241406, 1241415, 1241417, 1241407, 1241408, 1241409, 1241410, 1241411, 1239842, 1239843, 1239845, 1239846, 1244582, 1244584, 1244587, 1240431, 1240437, 1240439, 1240421, 1240424, 1240679, 1240680, 1240682, 1240684, 1240685, 1240687, 1244783, 1244784, 1244779, 1244781, 1240812, 1240820, 1240824, 1240835, 1240802, 1240803, 1240964, 1240998, 1240967, 1241015, 1243373, 1243383, 1243386, 1243392, 1243399, 1243376, 1243381, 1245131, 1245133, 1245119, 1245122, 1245124, 1245126, 1239147, 1239149, 1239150, 1241605, 1241609, 1241610, 1240262, 1240263, 1240264, 1240265, 1240266, 1242881, 1242870, 1242871, 1242874, 1245557, 1240248, 1240249, 1240250, 1240251, 1240252, 1240253, 1239342, 1244000, 1244001, 1244502, 1244503, 1244504, 1244505, 1241571, 1241572, 1241573, 1241574, 1244900, 1244902, 1244903, 1244906, 1244907, 1243110, 1243122, 1243112, 1243115, 1243116, 1243117, 1243795, 1243787, 1243788, 1243825, 1243789, 1243790, 1243792, 1239532, 1239533, 1239559, 1239534, 1239536, 1239537, 1242237, 1242220, 1242221, 1242222, 1242224, 1242226, 1239737, 1239738, 1239739, 1239740, 1239745, 1239981, 1239990, 1239983, 1239985, 1239987, 1244168, 1244180, 1244169, 1244170, 1244175, 1240481, 1240490, 1240521, 1240484, 1240485, 1240487, 1240488, 1242696, 1242687, 1242688, 1242689, 1242690, 1242691, 1245719, 1245724, 1245725, 1244300, 1244311, 1244301, 1244302, 1244304, 1241591, 1241583, 1241584, 1241588, 1241437, 1241440, 1241441, 1241432, 1241433, 1241434, 1242943, 1242933, 1242935, 1242938, 1243218, 1243210, 1243234, 1243211, 1243242, 1243213, 1243214, 1243217, 1240948, 1240933, 1240934, 1240937, 1245530, 1245513, 1245516, 1240241, 1240243, 1239403, 1239404, 1239406, 1238917, 1238922, 1238926, 1238907, 1238927, 1238933, 1238938, 1238908, 1238909, 1238912, 1244508, 1244509, 1244187, 1244188, 1244189, 1244190, 1244192, 1244801, 1244802, 1244803, 1239313, 1239314, 1239315, 1239316, 1240668, 1240669, 1240670, 1240671, 1245499, 1245500, 1245502, 1245503, 1245505, 1244272, 1244273, 1243068, 1243070, 1243052, 1243081, 1243054, 1243546, 1243553, 1243534, 1243535, 1243592, 1243539, 1242074, 1242077, 1242066, 1242069, 1242071, 1242073, 1240127, 1240117, 1240142, 1240152, 1240120, 1240123, 1240124, 1241899, 1244891, 1244894, 1244895, 1245405, 1245406, 1245407, 1245408, 1239034, 1239043, 1239048, 1239035, 1239037, 1243502, 1243505, 1243510, 1243493, 1243495, 1244888, 1244889, 1244890, 1245917, 1245920, 1245923, 1243967, 1243968, 1243969, 1243970, 1243974, 1239581, 1239590, 1239573, 1239603, 1239624, 1239577, 1239578, 1245572, 1245574, 1245589, 1245598, 1245565, 1245566, 1245567, 1245569, 1242424, 1242433, 1242444, 1242451, 1242426, 1242464, 1242427, 1242428, 1242431, 1241099, 1241110, 1241112, 1241121, 1241124, 1241101, 1241102, 1241106, 1241107, 1241635, 1241637, 1241627, 1241647, 1241651, 1241629, 1243417, 1243441, 1243447, 1243448, 1243463, 1243424, 1240189, 1240196, 1240197, 1240180, 1240184, 1240185, 1240922, 1240923, 1240924, 1245091, 1245083, 1245087, 1242987, 1242989, 1243033, 1242992, 1242994, 1245296, 1245297, 1244438, 1244439, 1244440, 1244441, 1244007, 1244095, 1244097, 1244098, 1244101, 1242537, 1242548, 1242538, 1242540, 1242541, 1242542, 1245420, 1245412, 1242795, 1242800, 1242786, 1242793, 1241037, 1241046, 1241048, 1241062, 1241029, 1241030, 1241031, 1240036, 1240037, 1240072, 1240082, 1240041, 1240042, 1240043, 1241971, 1241974, 1241957, 1241983, 1241958, 1241961, 1242953, 1242954, 1242955, 1242956, 1242960, 1244872, 1240279, 1240280, 1240289, 1240293, 1240272, 1240274, 1240275, 1244211, 1244216, 1244218, 1244201, 1244226, 1244202, 1244238, 1244203, 1240713, 1240714, 1244921, 1244913, 1244915, 1244917, 1244918, 1244919, 1239856, 1239857, 1239859, 1243855, 1243857, 1243859, 1245927, 1245928, 1245929, 1245930, 1245931, 1242662, 1242663, 1242664, 1242665, 1242666, 1242667, 1243607, 1243608, 1243609, 1243612, 1243613, 1242159, 1242162, 1242163, 1242151, 1242152, 1242153, 1242154, 1242157, 1245197, 1245198, 1245199, 1245200, 1245203, 1244588, 1244606, 1244607, 1244589, 1244590, 1244591, 1244592, 1244593, 1239058, 1239059, 1239060, 1239061, 1239885, 1239871, 1239873, 1239874, 1239876, 1241880, 1241871, 1241873, 1241874, 1241876, 1240676, 1240677, 1240678, 1242649, 1242633, 1242635, 1242636, 1242637, 1242638, 1242639, 1242640, 1242506, 1242508, 1242513, 1242498, 1242502, 1242503, 1242504, 1243277, 1243282, 1243285, 1243262, 1243264, 1243265, 1244115, 1244116, 1244107, 1244130, 1244110, 1244112, 1244113, 1241699, 1241700, 1241702, 1245882, 1245883, 1245885, 1243356, 1243347, 1243348, 1243349, 1243350, 1243351, 1243352, 1242982, 1242984, 1244003, 1244004, 1245073, 1245074, 1245075, 1245076, 1245814, 1245816, 1240018, 1240009, 1240011, 1240012, 1240665, 1240666, 1243846, 1243847, 1243848, 1243850, 1242681, 1242682, 1240638, 1240640, 1240641, 1240655, 1243623, 1243633, 1243624, 1243662, 1243628, 1243629, 1241472, 1241475, 1241462, 1241482, 1241520, 1241468, 1242654, 1242656, 1242658, 1242659, 1243328, 1243340, 1243317, 1243320, 1243321, 1243322, 1242170, 1242197, 1245838, 1245862, 1245824, 1245827, 1239326, 1239327, 1243157, 1243170, 1243172, 1243138, 1243185, 1243139, 1241282, 1241288, 1241289, 1241300, 1241306, 1241274, 1239902, 1239904, 1239914, 1239895, 1239934, 1239897, 1245250, 1245251, 1245253, 1245255, 1245238, 1245257, 1245239, 1245245, 1244077, 1244078, 1244080, 1244081, 1244082, 1240108, 1240109, 1240701, 1241093, 1241094, 1241088, 1241089, 1241090, 1240589, 1240599, 1240601, 1240603, 1240593, 1240596, 1240597, 1241950, 1241951, 1241952, 1242037, 1242039, 1239237, 1239240, 1239224, 1239226, 1239228, 1240174, 1240175, 1240176, 1245782, 1245773, 1245775, 1239066, 1239098, 1239068, 1239069, 1239123, 1242262, 1242271, 1242278, 1242293, 1242311, 1242256, 1242257, 1244444, 1244456, 1244461, 1244467, 1244449, 1239666, 1239656, 1239676, 1239686, 1239659, 1239713, 1244020, 1244012, 1244015, 1244017, 1244018, 1244019, 1239278, 1239281, 1239270, 1239272, 1239273, 1245179, 1245180, 1245181, 1245899, 1245892, 1240881, 1240884, 1240886, 1241821, 1241822, 1245794, 1245795, 1245796, 1242981, 1242971, 1242972, 1242974, 1242976, 1239334, 1239336, 1241794, 1241802, 1241787, 1241788, 1241790, 1240581, 1240573, 1240574, 1240575, 1240576, 1240580, 1239758, 1239749, 1239750, 1239751, 1239810, 1245275, 1245276, 1245277, 1245278, 1241157, 1241195, 1241159, 1244712, 1244713, 1244698, 1244729, 1244700, 1244751, 1244702, 1242567, 1242561, 1240742, 1240752, 1240760, 1240719, 1240720, 1240775, 1240723, 1242340, 1242344, 1242331, 1242358, 1242332, 1242335, 1242337, 1241828, 1241830, 1241832, 1239353, 1239357, 1239370, 1239347, 1239389, 1245743, 1245744, 1245745, 1245749, 1245750, 1244048, 1244053, 1244055, 1245208, 1245211, 1245212, 1245214, 1245216, 1245660, 1245661, 1245695, 1245665, 1245801, 1245804, 1245805, 1240112, 1240113, 1240114, 1240115, 1243992, 1243993, 1245190, 1245192, 1242779, 1242781, 1243616, 1243617, 1239244, 1239245, 1239246, 1239248, 1239416, 1239430, 1239434, 1239419, 1239420, 1239424, 1242708, 1242709, 1240169, 1240171, 1244935, 1244936, 1244937, 1244940, 1244941, 1240617, 1240618, 1242214, 1242215, 1242216, 1245554, 1245555, 1245272, 1245273, 1242714, 1242715, 1242717, 1245648, 1245649, 1245638, 1245640, 1245642, 1245645, 1245310, 1245299, 1245301, 1245303, 1245305, 1244350, 1244370, 1244379, 1244354, 1243921, 1243922, 1243924, 1241713, 1241714, 1245764, and 1245769. To date, the greatest number of said preferred yield-moisture trait ratio haplotypes occurring in a commercially released male inbred is 176, wherein the inbred is 19HGZ1 and the 176 preferred haplotypes are: 1238927, 1238986, 1239043, 1239059, 1239147, 1239172, 1239226, 1239246, 1239273, 1239315, 1239336, 1239357, 1239419, 1239532, 1239569, 1239666, 1239737, 1239750, 1239846, 1239856, 1239871, 1239981, 1240009, 1240031, 1240041, 1240109, 1240113, 1240117, 1240171, 1240174, 1240241, 1240252, 1240266, 1240289, 1240354, 1240424, 1240485, 1240574, 1240601, 1240617, 1240665, 1240669, 1240676, 1240680, 1240707, 1240713, 1240720, 1240824, 1240881, 1240911, 1240933, 1241046, 1241088, 1241102, 1241157, 1241226, 1241289, 1241345, 1241408, 1241572, 1241583, 1241629, 1241700, 1241787, 1241821, 1241828, 1241871, 1241951, 1241974, 1242066, 1242130, 1242154, 1242215, 1242221, 1242271, 1242332, 1242383, 1242427, 1242503, 1242537, 1242633, 1242654, 1242663, 1242682, 1242690, 1242708, 1242714, 1242720, 1242786, 1242928, 1242935, 1242954, 1242969, 1242974, 1242982, 1242989, 1243068, 1243115, 1243134, 1243138, 1243211, 1243317, 1243349, 1243386, 1243502, 1243534, 1243608, 1243727, 1243787, 1243847, 1243855, 1243864, 1243917, 1243921, 1243958, 1243967, 1244000, 1244004, 1244007, 1244080, 1244110, 1244159, 1244175, 1244188, 1244218, 1244273, 1244300, 1244350, 1244438, 1244456, 1244505, 1244509, 1244515, 1244582, 1244590, 1244629, 1244634, 1244700, 1244784, 1244802, 1244808, 1244889, 1244891, 1244903, 1244913, 1244936, 1244964, 1245002, 1245073, 1245111, 1245119, 1245180, 1245190, 1245203, 1245211, 1245238, 1245273, 1245276, 1245296, 1245299, 1245361, 1245407, 1245412, 1245503, 1245555, 1245557, 1245565, 1245648, 1245724, 1245764, 1245773, 1245796, 1245814, 1245824, 1245885 and 1245931.

In addition, the following 81 Monsanto commercially released soybean varieties were fingerprinted: A5547, A3244, A3904, A2553, A5959, AG2101, A0868, AG4702, A4459, A3469, AG2903, AG3302, AG3502, AP1275, AGA22802, DKB26-52, AG3003, H6255RR, AG0901, AG4902, AG0801, CX284C, AG2703, A2824, AG3201, AG5501, DKB03-51, AG1602, CSR3322, DKB32-51, AG2905, CSRX922, DKB23-51, DKB28-51, AG3902, A4324, CSR3403, DKB31-51, AG4403, DKB37-51, AG1401, AG1701, AG2403, DKB25-51, AG4201, AG3903, AG4603, DKB46-51, AG5301, CSRS3433, DKB38-52, DKB20-52, DKB28-52, DKB36-52, AG1102, AG2106, AG2107, AG3101, AG3602, AG3802, AG3905, AG5605, AG5905, AG3202, AG1501, AG2405, AG2801, AG2203, DKB34-51, DKB58-51, DKB07-52, 26-02R, A3525, EX927A, EXP125A, EXP2702REN, WP25920, CSR2104, CX075, DKB16-51, A19788. The preferred haplotypes were determined on the basis of haplotype effect estimates for the following key phenotypic traits: yield, maturity, lodging, and plant height. For each trait, a list of preferred haplotypes was generated according to ascending criteria; for example, the best 50, the best 40, and so on to the best 5 haplotypes. This germplasm collection was then surveyed to determine the distribution of those haplotypes in elite varieties. The results for the commercially released soybean varieties evaluated for these four key phenotypic traits are summarized in Table 8. The commercially released soybean varieties containing the greatest number of preferred haplotypes known to this date to exist in nature are described in Table 9.

TABLE 8

Distribution of preferred haplotypes in a set of elite soybean germplasm, composed of 81 commercially released soybean varieties. Listed are maximum number of haplotypes in a single variety for each criterion (e.g., of top 5 haplotypes, of top 10, and so on) present in this germplasm for each trait.

|  | Yield | Maturity | Lodging | Plant height |
|---|---|---|---|---|
| 5 | 2 | 4 | 2 | 3 |
| 10 | 2 | 4 | 4 | 4 |
| 20 | 6 | 4 | 6 | 6 |
| 30 | 6 | 7 | 8 | 8 |
| 40 | 6 | 10 | 10 | 10 |
| 50 | 6 | 10 | 13 | 11 |

TABLE 9

List of the commercially released soybean varieties that contain the maximum number of preferred haplotypes for each superiority "class" for four different phenotypic traits (yield, moisture, lodging, and plant height).

| Name | Preferred haplotypes present | Total preferred haplotypes |
|---|---|---|
| YIELD 2:5 | | |
| A3244 | 1263534, 1262082 | 1262140, 1263534, 1262082, 1262411, 1263994 |
| AG3502 | 1263534, 1262082 | |
| CX284C | 1262140, 1262082 | |
| DKB36-52 | 1263534, 1262082 | |
| WP25920 | 1263534, 1262082 | |
| YIELD 2:10 | | |
| A3244 | 1263534, 1262082 | 1262140, 1263534, 1262082, 1262411, 1263994, 1264220, 1264704, 1262403, 1263084, 1264607 |
| AG3502 | 1263534, 1262082 | |
| CX284C | 1262140, 1262082 | |
| DKB36-52 | 1263534, 1262082 | |
| WP25920 | 1263534, 1262082 | |
| YIELD 6:20 | | |
| A4324 | 1263544, 1262066, 1264076, 1263534, 1264607, 1264257 | 1262140, 1263534, 1262082, 1262411, 1263994, 1264220, 1264704, 1262403, 1263084, 1264607, 1264076, 1262066, 1262410, 1264390, 1263544, 1263999, 1264257, 1261823, 1264702, 1264603 |
| AG2903 | 1263544, 1262066, 1262082, 1264607, 1264220, 1264702 | |
| AG3101 | 1263544, 1262066, 1262082, 1264076, 1264607, 1264220 | |
| AG4403 | 1262066, 1262082, 1261823, 1264607, 1264220, 1264257 | |
| YIELD 6:30 | | |
| A4324 | 1263544, 1262066, 1264076, 1263534, 1264607, 1264257 | 1262140, 1263534, 1262082, 1262411, 1263994, 1264220, 1264704, 1262403, 1263084, 1264607, 1264076, 1262066, 1262410, 1264390, 1263544, 1263999, 1264257, 1261823, 1264702, 1264603, 1263717, 1264740, 1263391, 1262138, 1262086, 1264237, 1264188, 1264473, 1262143, 1261808 |
| AG2903 | 1263544, 1262066, 1262082, 1264607, 1264220, 1264702 | |
| AG3101 | 1263544, 1262066, 1262082, 1264076, 1264607, 1264220 | |
| AG4403 | 1262066, 1262082, 1261823, 1264607, 1264220, 1264257 | |
| YIELD 6:40 | | |
| A4324 | 1263544, 1262066, 1264076, 1263534, 1264607, 1264257 | 1262140, 1263534, 1262082, 1262411, 1263994, 1264220, 1264704, 1262403, 1263084, 1264607, 1264076, 1262066, 1262410, 1264390, 1263544, 1263999, 1264257, 1261823, 1264702, 1264603, 1263717, 1264740, 1263391, 1262138, 1262086, 1264237, 1264188, 1264473, 1262143, 1261808, 1262894, 1264610, 1262441, 1264701, 1263533, 1262106, 1264638, 1264078, 1263993, 1262139 |
| AG2903 | 1263544, 1262066, 1262082, 1264607, 1264220, 1264702 | |
| AG3101 | 1263544, 1262066, 1262082, 1264076, 1264607, 1264220 | |
| AG4403 | 1262066, 1262082, 1261823, 1264607, 1264220, 1264257 | |
| YIELD 6:50 | | |
| A4324 | 1263544, 1262066, 1264076, 1263534, 1264607, 1264257 | 1262140, 1263534, 1262082, 1262411, 1263994, 1264220, 1264704, 1262403, 1263084, 1264607, 1264076, 1262066, 1262410, 1264390, 1263544, 1263999, 1264257, 1261823, 1264702, 1264603, 1263717, 1264740, 1263391, 1262138, 1262086, 1264237, 1264188, 1264473, 1262143, 1261808, 1262894, 1264610, 1262441, 1264701, 1263533, 1262106, 1264638, 1264078, 1263993, 1262139, 1262984, 1263155, 1262487, 1263696, 1262884, 1264703, 1264551, 1264379, 1262220, 1263150 |
| AG2903 | 1263544, 1262066, 1262082, 1264607, 1264220, 1264702 | |
| AG3101 | 1263544, 1262066, 1262082, 1264076, 1264607, 1264220 | |
| AG4403 | 1262066, 1262082, 1261823, 1264607, 1264220, 1264257 | |
| MATURITY 4:5 | | |
| AG0901 | 1262081, 1263532, 1264608, 1262142, | 1264608, 1264243, 1263532, 1262142, 1262081 |
| AG1401 | 1262081, 1263532, 1264608, 1262142 | |
| MATURITY 4:10 | | |
| AG0901 | 1262081, 1263532, 1264608, 1262142, | 1264608, 1264243, 1263532, 1262142, 1262081, 1261912, 1264707, 1262065, 1261923, 1262490 |
| AG1401 | 1262081, 1263532, 1264608, 1262142 | |
| AP1275 | 1262081, 1263532, 1264608, 1264707 | |
| DKB03-51 | 1262081, 1263532, 1264608, 1262065 | |
| MATURITY 4:20 | | |
| AG0901 | 1262081, 1263532, 1264608, 1262142, | 1264608, 1264243, 1263532, 1262142, 1262081, 1261912, 1264707, 1262065, 1261923, 1262490, 1264754, 1263996, 1262494, 1263165, 1263627, 1261816, 1263168, 1263703, 1262321, 1262761, 1263984, 1262316, 1264739 |
| AG1401 | 1262081, 1263532, 1264608, 1262142 | |
| AP1275 | 1262081, 1263532, 1264608, 1264707 | |
| DKB03-51 | 1262081, 1263532, 1264608, 1262065 | |
| MATURITY 7:30 | | |
| A0868 | 1262081, 1263532, 1261816, 1262761, 1264608, 1262321, 1263296 | 1264608, 1264243, 1263532, 1262142, 1262081, 1261912, 1264707, 1262065, 1261923, 1262490, 1264754, 1263996, 1262494, 1263165, 1263627, 1261816, 1263168, 1263703, 1262321, 1262761, 1263984, 1262316, 1264739, 1264239, 1263708, 1263709, 1264232, 1263296, 1262407, 1264226 |
| AG0901 | 1262081, 1263532, 1262316, 1262761, 1264608, 1262142, 1263296 | |
| AG1401 | 1262081, 1263532, 1262761, 1264608, 1262142, 1263165, 1263296 | |
| MATURITY 10:40 | | |
| AG0901 | 1262081, 1264726, 1263532, 1262316, 1262761, 1264608, 1264737, 1262142, 1262704, 1263296 | 1264608, 1264243, 1263532, 1262142, 1262081, 1261912, 1264707, 1262065, 1261923, 1262490, 1264754, 1263996, 1262494, 1263165, 1263627, 1261816, 1263168, 1263703, 1262321, 1262761, 1263984, 1262316, 1264739, 1264239, 1263708, 1263709, 1264232, 1263296, 1262407, 1264226, 1264755, 1263710, 1262883, 1264587, 1264737, 1262704, 1262428, 1264081, 1264726, 1264748 |
| MATURITY 10:50 | | |
| AG0901 | 1262081, 1264726, 1263532, 1262316, 1262761, 1264608, 1264737, 1262142, 1262704, 1263296 | 1264608, 1264243, 1263532, 1262142, 1262081, 1261912, 1264707, 1262065, 1261923, 1262490, 1264754, 1263996, 1262494, 1263165, 1263627, 1261816, 1263168, 1263703, 1262321, 1262761, 1263984, 1262316, 1264739, 1264239, 1263708, 1263709, 1264232, 1263296, 1262407, 1264226, 1264755, 1263710, 1262883, 1264587, 1264737, 1262704, 1262428, 1264081, 1264726, 1264748, 1263161, 1262324, 1263299, 1263535, 1261807, 1262329, 1263317, 1262962, 1263779, 1263645 |

TABLE 9-continued

List of the commercially released soybean varieties that contain the maximum number of preferred haplotypes for each superiority "class" for four different phenotypic traits (yield, moisture, lodging, and plant height).

| Name | Preferred haplotypes present | Total preferred haplotypes |
|---|---|---|
| LODGING 2:5 | | |
| A4459 | 1261887, 1264287 | 1262671, 1264471, 1261887, 1262675, 1264287 |
| A5959 | 1262675, 1264287 | |
| AG0901 | 1262671, 1264471 | |
| AG4403 | 1262671, 1264471 | |
| AG4902 | 1264471, 1262675 | |
| DKB23-51 | 1262671, 1264471 | |
| DKB58-51 | 1264471, 1262675 | |
| LODGING 4:10 | | |
| 26-02R | 1264236, 1264608, 1264471, 1263477 | 1262671, 1264471, 1261887, 1262675, 1264287, 1262108, 1264282, 1264608, 1263477, 1264236 |
| AG0901 | 1264236, 1264608, 1264471, 1262671 | |
| DKB25-51 | 1264236, 1264608, 1264471, 1264282 | |
| LODGING 6:20 | | |
| AG0901 | 1263695, 1264236, 1264608, 1264471, 1262671, 1261807 | 1262671, 1264471, 1261887, 1262675, 1264287, 1262108, 1264282, 1264608, 1263477, 1264236, 1263866, 1263843, 1262099, 1263848, 1263833, 1263695, 1262837, 1263710, 1264309, 1261807 |
| DKB25-51 | 1263695, 1262099, 1264236, 1264608, 1264471, 1264282 | |
| LODGING 8:30 | | |
| AG0901 | 1263604, 1263695, 1264236, 1264608, 1264471, 1262671, 1262239, 1261807 | 1262671, 1264471, 1261887, 1262675, 1264287, 1262108, 1264282, 1264608, 1263477, 1264236, 1263866, 1263843, 1262099, 1263848, 1263833, 1263695, 1262837, 1263710, 1264309, 1261807, 1264240, 1264189, 1263604, 1261923, 1264298, 1262239, 1262132, 1263161, 1264265, 1264564 |
| AG1701 | 1263604, 1263695, 1262099, 1264608, 1264471, 1262132, 1262239, 1261807 | |
| LODGING 10:40 | | |
| AG0901 | 1262081, 1263604, 1263695, 1264785, 1264236, 1264608, 1264471, 1262671, 1262239, 1261807 | 1262671, 1264471, 1261887, 1262675, 1264287, 1262108, 1264282, 1264608, 1263477, 1264236, 1263866, 1263843, 1262099, 1263848, 1263833, 1263695, 1262837, 1263710, 1264309, 1261807, 1264240, 1264189, 1263604, 1261923, 1264298, 1262239, 1262132, 1263161, 1264265, 1264564, 1263138, 1263173, 1264232, 1262678, 1264785, 1264250, 1262081, 1262989, 1264527, 1263535 |
| AG1701 | 1262081, 1263604, 1263695, 1264785, 1262099, 1264608, 1264471, 1262132, 1262239, 1261807 | |
| LODGING 13:50 | | |
| AG1701 | 1262081, 1262581, 1263604, 1263695, 1264785, 1262099, 1264075, 1264608, 1262551, 1264471, 1262132, 1262239, 1261807 | 1262671, 1264471, 1261887, 1262675, 1264287, 1262108, 1264282, 1264608, 1263477, 1264236, 1263866, 1263843, 1262099, 1263848, 1263833, 1263695, 1262837, 1263710, 1264309, 1261807, 1264240, 1264189, 1263604, 1261923, 1264298, 1262239, 1262132, 1263161, 1264265, 1264564, 1263138, 1263173, 1264232, 1262678, 1264785, 1264250, 1262081, 1262989, 1264527, 1263535, 1264825, 1264075, 1262581, 1262491, 1263921, 1262823, 1263455, 1262551, 1262787, 1264754 |
| PLANT HEIGHT 3:5 | | |
| AG4902 | 1264471, 1262675, 1263161 | 1264471, 1262675, 1263161, 1264608, 1264287 |
| DKB26-52 | 1264471, 1263161, 1264608 | |
| DKB28-52 | 1264471, 1263161, 1264608 | |
| PLANT HEIGHT 4:10 | | |
| 26-02R | 1262081, 1263532, 1264608, 1264471 | 1264471, 1262675, 1263161, 1264608, 1264287, 1263710, 1264226, 1262136, 1262081, 1263532 |
| A0868 | 1262081, 1263532, 1264608, 1264471 | |
| A5959 | 1262081, 1263532, 1264287, 1262675 | |
| AG0801 | 1262081, 1263532, 1264608, 1264471 | |
| AG0901 | 1262081, 1263532, 1264608, 1264471 | |
| AG1102 | 1262081, 1263532, 1264608, 1264471 | |
| AG1401 | 1262081, 1263532, 1264608, 1264471 | |
| AG1701 | 1262081, 1263532, 1264608, 1264471 | |
| AP1275 | 1262081, 1263532, 1264608, 1264471 | |
| DKB03-51 | 1262081, 1263532, 1264608, 1264471 | |
| DKB07-52 | 1262081, 1263532, 1264226, 1264608 | |
| DKB58-51 | 1262081, 1263532, 1264471, 1262675 | |
| PLANT HEIGHT 6:20 | | |
| A0868 | 1262081, 1263532, 1264280, 1262099, 1264608, 1264471 | 1264471, 1262675, 1263161, 1264608, 1264287, 1263710, 1264226, 1262136, 1262081, 1263532, 1262678, 1264281, 1264250, 1264296, 1262099, 1263031, 1263697, 1264280, 1263996, 1264292 |
| AG1401 | 1262081, 1263532, 1264280, 1262099, 1264608, 1264471 | |
| AG1701 | 1262081, 1263532, 1264280, 1262099, 1264608, 1264471 | |
| PLANT HEIGHT 8:30 | | |
| AG1401 | 1262081, 1264585, 1263532, 1264280, 1262099, 1264608, 1264471, 1262240 | 1264471, 1262675, 1263161, 1264608, 1264287, 1263710, 1264226, 1262136, 1262081, 1263532, 1262678, 1264281, 1264250, 1264296, 1262099, 1263031, 1263697, 1264280, 1263996, 1264292, 1262494, 1264223, 1264243, 1262146, 1262108, 1262240, 1264585, 1264251, 1261887, 1262246 |
| PLANT HEIGHT 10:40 | | |
| AG1401 | 1262081, 1264585, 1263532, 1264280, 1262099, 1264608, 1264471, 1262240, 1264843, 1261807 | 1264471, 1262675, 1263161, 1264608, 1264287, 1263710, 1264226, 1262136, 1262081, 1263532, 1262678, 1264281, 1264250, 1264296, 1262099, 1263031, 1263697, 1264280, 1263996, 1264292, 1262494, 1264223, 1264243, 1262146, 1262108, 1262240, 1264585, 1264251, 1261887, 1262246, 1262490, 1261807, 1263352, 1263866, 1262426, 1263478, 1262568, 1262912, 1264843, 1262523 |

TABLE 9-continued

List of the commercially released soybean varieties that contain the maximum number of preferred haplotypes for each superiority "class" for four different phenotypic traits (yield, moisture, lodging, and plant height).

| Name | Preferred haplotypes present | Total preferred haplotypes |
|---|---|---|
| PLANT HEIGHT 11:50 | | |
| AG0901 | 1262081, 1262523, 1263532, 1264280, 1264223, 1263364, 1264608, 1264471, 1262671, 1264843, 1261807 | 1264471, 1262675, 1263161, 1264608, 1264287, 1263710, 1264226, 1262136, 1262081, 1263532, 1262678, 1264281, 1264250, 1264296, 1262099, 1263031, 1263697, 1264280, 1263996, 1264292, 1262494, 1264223, 1264243, 1262146, 1262108, 1262240, 1264585, 1264251, 1261887, 1262246, 1262490, 1261807, 1263352, 1263866, 1262426, 1263478, 1262568, 1262912, 1264843, 1262523, 1264282, 1261923, 1262065, 1262671, 1261917, 1263477, 1263318, 1264167, 1264316, 1263364 |

In another embodiment, preferred haplotypes are determined by evaluating trait ratios, given that certain phenotypic traits are negatively correlated with yield and, in soybean, it is advantageous to select for positive yield and negative plant height or negative maturity. Exemplary trait ratios include greater than 2 or less than zero, greater than 3 or less than zero, and so on, wherein yield is positive and either plant height or maturity is negative. In one aspect, a preferred haplotype is one with a trait ratio of greater than 5 or less than zero (bu/acre:inches or bu/acre:days, respectively), wherein yield is positive and either plant height or maturity is negative. For a preferred yield-plant height trait ratio, the following 666 preferred haplotypes were identified in soybean varieties: 1261747, 1261748, 1261750, 1261751, 1261757, 1261765, 1261769, 1261778, 1261782, 1261783, 1261791, 1261800, 1261801, 1261802, 1261803, 1261808, 1261810, 1261814, 1261818, 1261819, 1261822, 1261823, 1261836, 1261837, 1261840, 1261849, 1261857, 1261858, 1261863, 1261867, 1261872, 1261877, 1261881, 1261883, 1261910, 1261915, 1261916, 1261918, 1261919, 1261920, 1261926, 1261931, 1261944, 1261948, 1261949, 1261952, 1261963, 1261987, 1261988, 1261992, 1261993, 1261997, 1262002, 1262004, 1262007, 1262010, 1262017, 1262021, 1262022, 1262026, 1262032, 1262039, 1262040, 1262047, 1262068, 1262070, 1262086, 1262088, 1262097, 1262098, 1262106, 1262109, 1262110, 1262132, 1262134, 1262135, 1262142, 1262152, 1262217, 1262218, 1262222, 1262223, 1262239, 1262255, 1262256, 1262258, 1262260, 1262262, 1262268, 1262270, 1262271, 1262276, 1262279, 1262286, 1262312, 1262313, 1262314, 1262315, 1262316, 1262320, 1262323, 1262324, 1262325, 1262326, 1262342, 1262351, 1262352, 1262355, 1262356, 1262357, 1262365, 1262366, 1262371, 1262376, 1262380, 1262383, 1262384, 1262390, 1262391, 1262394, 1262397, 1262404, 1262406, 1262407, 1262410, 1262411, 1262420, 1262426, 1262428, 1262430, 1262447, 1262451, 1262452, 1262465, 1262477, 1262478, 1262479, 1262480, 1262490, 1262495, 1262506, 1262508, 1262510, 1262511, 1262512, 1262520, 1262522, 1262524, 1262527, 1262528, 1262529, 1262530, 1262531, 1262533, 1262534, 1262536, 1262540, 1262543, 1262549, 1262550, 1262551, 1262563, 1262569, 1262575, 1262587, 1262623, 1262626, 1262627, 1262629, 1262633, 1262641, 1262642, 1262646, 1262675, 1262681, 1262685, 1262695, 1262696, 1262698, 1262725, 1262726, 1262727, 1262728, 1262737, 1262743, 1262745, 1262746, 1262749, 1262751, 1262753, 1262763, 1262766, 1262767, 1262773, 1262774, 1262778, 1262781, 1262787, 1262790, 1262791, 1262793, 1262794, 1262803, 1262806, 1262810, 1262811, 1262814, 1262822, 1262824, 1262825, 1262828, 1262829, 1262830, 1262839, 1262840, 1262845, 1262849, 1262865, 1262868, 1262869, 1262877, 1262881, 1262882, 1262883, 1262884, 1262887, 1262888, 1262892, 1262893, 1262894, 1262899, 1262901, 1262909, 1262910, 1262912, 1262915, 1262952, 1262954, 1262961, 1262962, 1262981, 1262985, 1262987, 1262988, 1262989, 1262991, 1262993, 1263004, 1263005, 1263008, 1263014, 1263015, 1263016, 1263017, 1263021, 1263022, 1263029, 1263030, 1263031, 1263041, 1263043, 1263044, 1263045, 1263048, 1263053, 1263054, 1263061, 1263063, 1263064, 1263067, 1263071, 1263072, 1263078, 1263079, 1263084, 1263087, 1263088, 1263091, 1263100, 1263102, 1263103, 1263104, 1263107, 1263108, 1263110, 1263111, 1263115, 1263120, 1263124, 1263128, 1263129, 1263131, 1263132, 1263133, 1263134, 1263135, 1263137, 1263139, 1263140, 1263142, 1263143, 1263170, 1263172, 1263173, 1263178, 1263182, 1263183, 1263184, 1263185, 1263209, 1263210, 1263225, 1263228, 1263233, 1263234, 1263236, 1263240, 1263242, 1263243, 1263244, 1263247, 1263248, 1263265, 1263271, 1263273, 1263274, 1263281, 1263283, 1263285, 1263286, 1263287, 1263288, 1263291, 1263296, 1263299, 1263304, 1263306, 1263309, 1263310, 1263314, 1263315, 1263319, 1263320, 1263323, 1263325, 1263370, 1263371, 1263377, 1263381, 1263386, 1263392, 1263397, 1263402, 1263405, 1263406, 1263418, 1263419, 1263421, 1263423, 1263425, 1263428, 1263434, 1263454, 1263455, 1263464, 1263472, 1263475, 1263477, 1263499, 1263500, 1263504, 1263505, 1263509, 1263510, 1263511, 1263515, 1263543, 1263544, 1263545, 1263546, 1263550, 1263553, 1263560, 1263589, 1263593, 1263603, 1263604, 1263606, 1263608, 1263620, 1263632, 1263633, 1263642, 1263645, 1263647, 1263649, 1263650, 1263652, 1263657, 1263660, 1263661, 1263662, 1263665, 1263667, 1263669, 1263674, 1263675, 1263678, 1263680, 1263681, 1263682, 1263701, 1263709, 1263711, 1263712, 1263715, 1263716, 1263718, 1263720, 1263721, 1263725, 1263727, 1263728, 1263731, 1263732, 1263738, 1263742, 1263744, 1263745, 1263746, 1263774, 1263775, 1263776, 1263781, 1263782, 1263786, 1263804, 1263805, 1263806, 1263810, 1263811, 1263812, 1263813, 1263814, 1263815, 1263820, 1263823, 1263825, 1263831, 1263832, 1263834, 1263842, 1263843, 1263849, 1263866, 1263871, 1263874, 1263894, 1263895, 1263898, 1263899, 1263906, 1263908, 1263911, 1263913, 1263915, 1263966, 1263967, 1263968, 1263969, 1263970, 1263974, 1263976, 1263984, 1263992, 1263994, 1264016, 1264018, 1264020, 1264022, 1264028, 1264050, 1264055, 1264058, 1264060, 1264064, 1264067, 1264068, 1264069, 1264070, 1264071, 1264072, 1264075, 1264077, 1264078, 1264079, 1264080, 1264084, 1264091, 1264097, 1264111, 1264115, 1264123, 1264124, 1264149, 1264150, 1264161, 1264163, 1264164, 1264183, 1264184, 1264185, 1264188, 1264189, 1264190, 1264191, 1264194, 1264195, 1264197, 1264202, 1264204, 1264209, 1264215, 1264217, 1264223, 1264236, 1264237, 1264247, 1264249, 1264261, 1264265, 1264268, 1264272, 1264278, 1264281, 1264282, 1264285, 1264287, 1264290, 1264293, 1264298, 1264300, 1264301, 1264302, 1264308, 1264314, 1264316, 1264331, 1264332, 1264336, 1264339, 1264350, 1264351, 1264362, 1264364, 1264366, 1264370, 1264371, 1264374, 1264376, 1264377, 1264379, 1264382, 1264383, 1264390, 1264391, 1264392, 1264398, 1264401, 1264403, 1264404, 1264407, 1264408, 1264413, 1264415, 1264439, 1264441, 1264446, 1264447, 1264448, 1264451, 1264452, 1264458, 1264459, 1264460, 1264463, 1264464, 1264466, 1264468, 1264478, 1264483, 1264484, 1264485, 1264493, 1264494, 1264529, 1264531, 1264537, 1264540, 1264543, 1264548, 1264550, 1264551, 1264552, 1264554, 1264556, 1264557, 1264558, 1264589, 1264592, 1264597, 1264599, 1264601, 1264624, 1264634, 1264635, 1264643, 1264646, 1264648, 1264659, 1264699, 1264700, 1264701, 1264704, 1264716, 1264737, 1264738, 1264740, 1264743, 1264744, 1264748, 1264754, 1264757, 1264766, 1264768, 1264775, 1264776, 1264777, 1264786, 1264788, 1264789, 1264792, 1264793, 1264795, 1264799, 1264801, 1264802, 1264844, 1264913, 1264919, 1264920, 1264921, 1264922, 1264924, 1264930, 1264932, 1264935, 1264937, 1264938, 1264939, 1264942, 1264943, 1264950, 1264953, 1264954, and 1264955. To date, the greatest number of said preferred haplotypes occurring in a commercially released soybean variety is 97, wherein the line is AG3802 and the 97 preferred haplotypes are: 1263544, 1263589, 1263620, 1263660, 1263665, 1263680, 1263701, 1263725, 1263775, 1263781, 1263805, 1263806, 1263825, 1263895, 1263968, 1263992, 1264050, 1264060, 1264068, 1264070, 1264150, 1264184, 1264189, 1264281, 1264332, 1264371, 1264391, 1264439, 1264446, 1264483, 1264531, 1264540, 1264557, 1264597, 1264624, 1264634, 1264700, 1264738, 1264766, 1264920, 1264942, and 1264953.

For a preferred yield-maturity trait ratio, the following 490 preferred haplotypes were identified in soybean varieties: 1261748, 1261751, 1261753, 1261765, 1261766, 1261769, 1261791, 1261793, 1261794, 1261805, 1261810, 1261818, 1261819, 1261823, 1261837, 1261839, 1261857, 1261858, 1261863, 1261864, 1261867, 1261872, 1261877, 1261890, 1261892, 1261895, 1261896, 1261910, 1261911, 1261916, 1261920, 1261926, 1261929, 1261931, 1261933, 1261942, 1261943, 1261947, 1261948, 1261949, 1261955, 1261961, 1261968, 1261991, 1261993, 1261997, 1262040, 1262084, 1262087, 1262094, 1262099, 1262105, 1262107, 1262109, 1262110, 1262132, 1262133, 1262134, 1262140, 1262151, 1262181, 1262183, 1262189, 1262190, 1262202, 1262208, 1262222, 1262223, 1262239, 1262241, 1262255, 1262257, 1262259, 1262261, 1262262, 1262263, 1262268, 1262276, 1262279, 1262286, 1262312, 1262315, 1262317, 1262320, 1262325, 1262326, 1262331, 1262333, 1262335, 1262342, 1262383, 1262384, 1262385, 1262388, 1262389, 1262390, 1262391, 1262393, 1262397, 1262401, 1262404, 1262405, 1262409, 1262410, 1262411, 1262412, 1262415, 1262420, 1262426, 1262440, 1262447, 1262450, 1262451, 1262452, 1262453, 1262457, 1262465, 1262480, 1262490, 1262495, 1262505, 1262506, 1262509, 1262510, 1262517, 1262520, 1262522, 1262524, 1262549, 1262550, 1262553, 1262573, 1262575, 1262587, 1262617, 1262618, 1262619, 1262620, 1262622, 1262623, 1262626, 1262628, 1262632, 1262633, 1262634, 1262636, 1262642, 1262646, 1262656, 1262726, 1262728, 1262747, 1262751, 1262753, 1262763, 1262766, 1262767, 1262773, 1262783, 1262787, 1262789, 1262794, 1262796, 1262798, 1262799, 1262807, 1262810, 1262814, 1262822, 1262824, 1262825, 1262829, 1262830, 1262840, 1262845, 1262864, 1262868, 1262876, 1262877, 1262881, 1262882, 1262888, 1262893, 1262899, 1262907, 1262911, 1262914, 1262916, 1262917, 1262953, 1262959, 1262960, 1263014, 1263015, 1263016, 1263017, 1263027, 1263028, 1263029, 1263040, 1263041, 1263043, 1263046, 1263048, 1263067, 1263068, 1263069, 1263079, 1263084, 1263093, 1263102, 1263103, 1263108, 1263111, 1263113, 1263115, 1263120, 1263121, 1263129, 1263131, 1263133, 1263134, 1263139, 1263140, 1263152, 1263157, 1263165, 1263168, 1263169, 1263170, 1263172, 1263173, 1263174, 1263182, 1263183, 1263191, 1263206, 1263207, 1263234, 1263240, 1263242, 1263245, 1263246, 1263273, 1263274, 1263283, 1263285, 1263287, 1263289, 1263297, 1263304, 1263310, 1263315, 1263323, 1263329, 1263371, 1263377, 1263386, 1263396, 1263397, 1263403, 1263419, 1263421, 1263428, 1263434, 1263454, 1263455, 1263472, 1263474, 1263477, 1263499, 1263504, 1263509, 1263510, 1263511, 1263515, 1263537, 1263539, 1263543, 1263545, 1263552, 1263555, 1263560, 1263589, 1263594, 1263597, 1263603, 1263604, 1263606, 1263608, 1263611, 1263624, 1263630, 1263631, 1263636, 1263640, 1263641, 1263644, 1263647, 1263649, 1263652, 1263662, 1263665, 1263672, 1263696, 1263711, 1263715, 1263716, 1263719, 1263721, 1263722, 1263723, 1263727, 1263744, 1263746, 1263810, 1263811, 1263812, 1263814, 1263815, 1263832, 1263834, 1263836, 1263843, 1263848, 1263849, 1263854, 1263866, 1263907, 1263910, 1263912, 1263913, 1263918, 1263921, 1263924, 1263966, 1263973, 1263983, 1263984, 1263993, 1264033, 1264034, 1264049, 1264055, 1264060, 1264064, 1264072, 1264077, 1264078, 1264084, 1264089, 1264090, 1264094, 1264111, 1264123, 1264148, 1264150, 1264152, 1264153, 1264155, 1264160, 1264161, 1264164, 1264176, 1264177, 1264178, 1264182, 1264183, 1264188, 1264189, 1264190, 1264191, 1264193, 1264194, 1264195, 1264199, 1264201, 1264202, 1264206, 1264222, 1264223, 1264225, 1264239, 1264240, 1264244, 1264247, 1264254, 1264257, 1264261, 1264265, 1264268, 1264272, 1264278, 1264282, 1264286, 1264289, 1264290, 1264295, 1264296, 1264298, 1264300, 1264303, 1264308, 1264311, 1264331, 1264332, 1264333, 1264338, 1264339, 1264377, 1264383, 1264392, 1264400, 1264405, 1264415, 1264441, 1264445, 1264446, 1264447, 1264448, 1264460, 1264464, 1264468, 1264478, 1264480, 1264481, 1264482, 1264484, 1264490, 1264532, 1264533, 1264538, 1264539, 1264543, 1264550, 1264552, 1264588, 1264597, 1264599, 1264601, 1264636, 1264642, 1264643, 1264646, 1264658, 1264693, 1264707, 1264710, 1264729, 1264738, 1264743, 1264746, 1264748, 1264754, 1264755, 1264757, 1264766, 1264768, 1264771, 1264777, 1264782, 1264787, 1264788, 1264789, 1264802, 1264848, 1264849, 1264851, 1264853, 1264856, 1264857, 1264858, 1264860, 1264869, 1264874, 1264877, 1264883, 1264904, 1264910, 1264913, 1264919, 1264924, 1264930, 1264934, 1264937, 1264939, 1264947, 1264953, 1264955, and 1264956. To date, the greatest number of said preferred haplotypes occurring in commercially released soybean varieties is 63, wherein the 63 preferred haplotypes for A5547 are: 1261751, 1261810, 1261839, 1261857, 1261929, 1261948, 1262110, 1262151, 1262223, 1262241, 1262259, 1262384, 1262391, 1262410, 1262440, 1262505, 1262522, 1262620, 1262628, 1262773, 1262783, 1262829, 1263015, 1263027, 1263028, 1263041, 1263103, 1263157, 1263170, 1263191, 1263206, 1263273, 1263289, 1263297, 1263329, 1263377, 1263396, 1263403, 1263455, 1263543, 1263606, 1263630, 1263641, 1264049, 1264148, 1264161, 1264176, 1264183, 1264189, 1264199, 1264225, 1264240, 1264300, 1264446, 1264490, 1264550, 1264636, 1264693, 1264766, 1264789, 1264848, 1264919, and 1264955; and the 63 preferred haplotypes for AP1275 are: 1261791, 1261857, 1261890, 1261910, 1261926, 1262105, 1262132, 1262239, 1262312, 1262388, 1262401, 1262506, 1262553, 1262619, 1262773, 1262783, 1262824, 1262881, 1262953, 1262959, 1263015, 1263028, 1263040, 1263067, 1263157, 1263206, 1263273, 1263472, 1263499, 1263539, 1263543, 1263589, 1263591, 1263604, 1263640, 1263652, 1263662, 1263723, 1263810, 1263832, 1263910, 1263966, 1263983, 1264033, 1264049, 1264111, 1264148, 1264160, 1264183, 1264188, 1264201, 1264225, 1264247, 1264295, 1264331, 1264448, 1264597, 1264693, 1264707, 1264766, 1264848, 1264904, and 1264930.

In a preferred embodiment of the present invention, a haplotype comprises at least one polymorphic marker. Changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in our definition of what constitutes a haplotype so long as the functional integrity of that genomic region is unchanged or improved. The functional integrity of a haplotype is considered to be unchanged if its haplotype effect estimate is not negative with respect to yield, or is not positive with respect to maturity, or is null with respect to maturity, or amongst the best 50 percent with respect to a phenotypic trait, transgene, and/or a multiple trait index when compared to any other haplotype at the same chromosome segment in a set of germplasm (breeding germplasm, breeding population, collection of elite inbred lines, population of random mating individuals, biparental cross), or amongst the best 50 percent with respect to a phenotypic trait, transgene, and/or a multiple trait index when compared to any other haplotype across the entire genome in a set of germplasm, or the haplotype being present with a frequency of 75 percent or more in a breeding population or a set of germplasm provides evidence of its high value, or any combination of these. Further, for the purpose of this invention a haplotype is defined as preferred if it is amongst the best 25 percent with respect to a phenotypic trait, transgene, and/or a multiple trait index when compared to any other haplotype across the entire genome in a set of germplasm, or the haplotype being present with a frequency of 75 percent or more in a breeding population or a set of germplasm provides evidence of its high value, or any combination of these.

A unique aspect of this invention is the combination of high-density fingerprinting to identify large segments of DNA, wherever they occur in a set of germplasm, as being indicative of the conservation of genetic identity of all intervening genes from a common progenitor. In cases where conserved genetic segments, or haplotype windows, are coincident with segments in which QTL have been identified it is possible to deduce with high probability that QTL inferences can be extrapolated to other germplasm having an identical haplotype in that haplotype window. This a priori information provides the basis to select for favorable QTLs prior to QTL mapping within a given population.

For example, plant breeding decisions could comprise:
a) Selection among breeding populations to determine which populations have the highest frequency of favorable haplotypes, wherein haplotypes are designated as favorable based on coincidence with previous QTL mapping; or
b) Selection of progeny containing the favorable haplotypes in breeding populations prior to, or in substitution for, QTL mapping within that population, wherein selection could be done at any stage of breeding and at any generation of a selection; or
c) Prediction of progeny performance for specific breeding crosses; or
d) Selection of lines for germplasm improvement activities based on the favorable haplotypes, including line development, hybrid development, selection among transgenic events based on the breeding value of the haplotype that the transgene was inserted into, making breeding crosses, testing and advancing a plant through self fertilization, using plant or parts thereof for transformation, using plants or parts thereof for candidates for expression constructs, and using plant or parts thereof for mutagenesis.

An additional unique aspect of this invention and the combination of high-density fingerprinting and the designation of haplotype windows is the ability to select for specific genes or gene alleles. For example, in cases where haplotype windows are coincident with segments in which genes have been identified it is possible to deduce with high probability that gene inferences can be extrapolated to other germplasm having an identical genotype, or haplotype, in that haplotype window. This a priori information provides the basis to select for favorable genes or gene alleles on the basis of haplotype identification within a given population. For example, plant breeding decisions could comprise:
a) Selection among breeding populations to determine which populations have the highest frequency of favorable haplotypes, wherein haplotypes are designated as favorable based on coincidence with previous gene mapping; or
b) Selection of progeny containing the favorable haplotypes in breeding populations, wherein selection is effectively enabled at the gene level, wherein selection could be done at any stage of breeding and at any generation of a selection; or
c) Prediction of progeny performance for specific breeding crosses; or
d) Selection of lines for germplasm improvement activities based on the favorable haplotypes, including line development, hybrid development, selection among transgenic events based on the breeding value of the haplotype that the transgene was inserted into, making breeding crosses, testing and advancing a plant through self fertilization, using plant or parts thereof for transformation, using plants or parts thereof for candidates for expression constructs, and using plant or parts thereof for mutagenesis.

Further, in another preferred embodiment of this invention, the a priori information on the frequency of favorable haplotypes in breeding populations enables pre-selection. That is, the present invention provides methods for pre-selection, consisting of the selection of parental lines, based on historical haplotype-phenotype association information, for the purpose of driving favorable allele frequency for multiple traits simultaneously. In pre-selection, breeders predict the phenotypic contribution for multiple traits of any line based on that line's fingerprint information, which corresponds to a composition of pre-defined haplotypes. This multi-trait haplotype selection approach economizes a breeding program by initiating selection at the initial stage of choosing parental crosses and it also reduces the need for costly, time-consuming phenotyping of progeny.

A preferred haplotype provides a preferred property to a parent plant and to the progeny of the parent when selected by a marker means or phenotypic means. The method of the present invention provides for selection of preferred haplotypes, or haplotypes of interest, and the accumulation of these haplotypes in a breeding population.

In the present invention, haplotypes and associations of haplotypes to one or more phenotypic traits provide the basis for making breeding decisions and germplasm improvement activities. Non-limiting examples of breeding decisions include progeny selection, parent selection, and recurrent selection for at least one haplotype. In another aspect, breeding decisions relating to development of plants for commercial release comprise advancing plants for testing, advancing plants for purity, purification of sublines during development, inbred development, variety development, and hybrid development.

In yet other aspects, breeding decisions and germplasm improvement activities comprise transgenic event selection, making breeding crosses, testing and advancing a plant through self-fertilization, using plants or parts thereof for transformation, using plants or parts thereof for candidates for expression constructs, and using plants or parts thereof for mutagenesis.

In another embodiment, this invention enables indirect selection through selection decisions for at least one phenotype based on at least one numerical value that is correlated, either positively or negatively, with one or more other phenotypic traits. For example, a selection decision for any given haplotype effectively results in selection for multiple phenotypic traits that are associated with the haplotype.

In still another embodiment, the present invention acknowledges that preferred haplotypes identified by the methods presented herein may be advanced as candidate genes for inclusion in expression constructs, i.e., transgenes. Nucleic acids underlying haplotypes of interest may be expressed in plant cells by operably linking them to a promoter functional in plants. In another aspect, nucleic acids underlying haplotypes of interest may have their expression modified by double-stranded RNA-mediated gene suppression, also known as RNA interference ("RNAi"), which includes suppression mediated by small interfering RNAs ("siRNA"), trans-acting small interfering RNAs ("ta-siRNA"), or microRNAs ("miRNA"). Examples of RNAi methodology suitable for use in plants are described in detail in U.S. patent application publications 2006/0200878 and 2007/0011775.

Methods are known in the art for assembling and introducing constructs into a cell in such a manner that the nucleic acid molecule for a trait is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell, and N. Irwin, Cold Spring Harbor Laboratory Press. Methods for making transformation constructs particularly suited to plant transformation include, without limitation, those described in U.S. Pat. Nos. 4,971,908, 4,940,835, 4,769,061 and 4,757,011, all of which are herein incorporated by reference in their entirety. Transformation methods for the introduction of expression units into plants are known in the art and include electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; protoplast transformation as illustrated in U.S. Pat. No. 5,508,184; and *Agrobacterium*-mediated transformation as illustrated in U.S. Pat. Nos. 5,635,055; 5,824,877; 5,591,616; 5,981,840; and 6,384,301.

Another preferred embodiment of the present invention is to build additional value by selecting a composition of haplotypes wherein each haplotype has a haplotype effect estimate that is not negative with respect to yield, or is not positive with respect to maturity, or is null with respect to maturity, or amongst the best 50 percent with respect to a phenotypic trait, transgene, and/or a multiple trait index when compared to any other haplotype at the same chromosome segment in a set of germplasm, or amongst the best 50 percent with respect to a phenotypic trait, transgene, and/or a multiple trait index when compared to any other haplotype across the entire genome in a set of germplasm, or the haplotype being present with a frequency of 75 percent or more in a breeding population or a set of germplasm provides evidence of its high value, or any combination of these.

This invention anticipates a stacking of haplotypes from multiple windows into plants or lines by crossing parent plants or lines containing different haplotype regions. The value of the plant or line comprising in its genome stacked haplotype regions is estimated by a composite breeding value, which depends on a combination of the value of the traits and the value of the haplotype(s) to which the traits are linked. The present invention further anticipates that the composite breeding value of a plant or line is improved by modifying the components of one or each of the haplotypes. Additionally, the present invention anticipates that additional value can be built into the composite breeding value of a plant or line by selection of at least one recipient haplotype with a preferred haplotype effect estimate or, in conjunction with the haplotype frequency, breeding value to which one or any of the other haplotypes are linked, or by selection of plants or lines for stacking haplotypes by breeding.

Another embodiment of this invention is a method for enhancing breeding populations by accumulation of one or more preferred haplotypes in a set of germplasm. Genomic regions defined as haplotype windows include genetic information that contribute to one or more phenotypic traits of the plant. Variations in the genetic information at one or more loci can result in variation of one or more phenotypic traits, wherein the value of the phenotype can be measured. The genetic mapping of the haplotype windows allows for a determination of linkage across haplotypes. A haplotype of interest has a DNA sequence that is novel in the genome of the progeny plant and can in itself serve as a genetic marker for the haplotype of interest. Notably, this marker can also be used as an identifier for a gene or QTL. For example, in the event of multiple traits or trait effects associated with the haplotype, only one marker would be necessary for selection purposes. Additionally, the haplotype of interest may provide a means to select for plants that have the linked haplotype region. Selection can be performed by screening for tolerance to an applied phytotoxic chemical, such as an herbicide or antibiotic, or to pathogen resistance. Selection may be performed using phenotypic selection means, such as, a morphological phenotype that is easy to observe such as seed color, seed germination characteristic, seedling growth characteristic, leaf appearance, plant architecture, plant height, and flower and fruit morphology.

The present invention also provides for the screening of progeny plants haplotypes of interest and using haplotype effect estimates as the basis for selection for use in a breeding program to enhance the accumulation of preferred haplotypes. The method includes: a) providing a breeding population comprising at least two plants wherein the genome of the breeding population comprises a plurality of haplotype windows and each of the plurality of haplotype windows comprises at least one haplotype; and b) associating a haplotype effect estimate for one or more traits for two or more haplotypes from one or more of the plurality of haplotype windows, wherein the haplotype effect estimate can then be used to calculate a breeding value that is a function of the estimated effect for any given phenotypic trait and the frequency of each of the at least two haplotypes; and c) ranking one or more of the haplotypes on the basis of a value, wherein the value is a haplotype effect estimate, a haplotype frequency, or a breeding value and wherein the value is the basis for determining whether a haplotype is a preferred haplotype, or haplotype of interest; and d) utilizing the ranking as the basis for decision-making in a breeding program; and e) at least one progeny plant is selected on the basis of the presence of the respective markers associated with the haplotypes of interest, wherein the progeny plant comprises in its genome at least a portion of the haplotype or haplotypes of interest of the first plant and at least one preferred haplotype of the second plant; and f) using the progeny plant in activities related to germplasm improvement wherein the activities are selected from the group consisting of line and variety development, hybrid development, transgenic event selection, making breeding crosses, testing and advancing a plant through self fertilization, using plant or parts thereof for transformation, using plants or parts thereof for candidates for expression constructs, and using plant or parts thereof for mutagenesis.

Using this method, the present invention contemplates that haplotypes of interest are selected from a large population of plants, and the selected haplotypes can have a synergistic breeding value in the germplasm of a crop plant. Additionally, this invention provides for using the selected haplotypes in the described breeding methods to accumulate other beneficial and preferred haplotype regions and to be maintained in a breeding population to enhance the overall germplasm of the crop plant.

Crop plants considered for use in the method include but are not limited to maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including indica and *japonica* varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*), members of the genus *Brassica*, broccoli, cabbage, carrot, cauliflower, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut.

Plants of the present invention can be part of or generated from a breeding program. The choice of breeding method depends on the mode of plant reproduction, the heritability of the trait(s) being improved, and the type of cultivar used commercially (e.g., $F_i$ hybrid cultivar, pureline cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program.

Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

For hybrid crops, the development of new elite hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

The doubled haploid (DH) approach achieves isogenic plants in a shorter time frame. DH plants provide an invaluable tool to plant breeders, particularly for generating inbred lines and quantitative genetics studies. For breeders, DH populations have been particularly useful in QTL mapping, cytoplasmic conversions, and trait introgression. Moreover, there is value in testing and evaluating homozygous lines for plant breeding programs. All of the genetic variance is among progeny in a breeding cross, which improves selection gain.

Most research and breeding applications rely on artificial methods of DH production. The initial step involves the haploidization of the plant which results in the production of a population comprising haploid seed. Non-homozygous lines are crossed with an inducer parent, resulting in the production of haploid seed. Seed that has a haploid embryo, but normal triploid endosperm, advances to the second stage. That is, haploid seed and plants are any plant with a haploid embryo, independent of the ploidy level of the endosperm.

After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number These chimeric plants are self-pollinated to produce diploid (doubled haploid) seed. This DH seed is cultivated and subsequently evaluated and used in hybrid testcross production.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, *In: Soybeans: Improvement, Production and Uses,* 2nd Edition, *Monograph.,* 16:249, 1987; Fehr, "Principles of variety development," *Theory and Technique,* (Vol. 1) and *Crop Species Soybean* (Vol. 2), Iowa State Univ., Macmillan Pub. Co., NY, 360-376, 1987).

In another aspect, the methods of the present invention can be used for breeding any non-human organism. Specifically, the methods of the present invention can be used in breeding mammals, such as mice, swine, and cattle, and birds, such as poultry livestock. The methods of the present invention apply to any organism with a recombinant genome.

EXAMPLES

The following examples are included to demonstrate aspects of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific aspects which are disclosed and still obtain a like or similar result without departing from the spirit and scope of the invention.

Example 1. An Example of Haplotype-Trait Association Analysis: Grain Yield QTL on Chromosome 4 in Corn A key benefit of associating traits at the haplotype, rather than marker, level is the degree of resolution achieved. An initial QTL analysis from two different breeding crosses projects (herein denoted 1 and 2) were yield tested at 8 locations. A QTL was identified for grain yield on Chromosome 4 located approximately between 48 and 78 cM. The estimated QTL effect was similar in magnitude (4.2 Bu/Acre) for both projects. In the project 1, the genomic region from the inbred 5750 increased grain yield relative to the genomic region from the inbred 3140 when tested on the inbred 7051. In the project 2, the genomic region from the inbred 3323 increased grain yield relative to the genomic region from the inbred 90LDC2 when tested on the inbred WQDS7. The current breeding methodology uses this type of information (marker-QTL associations) to do recurrent selection within each population (project) independently.

Figure 2:
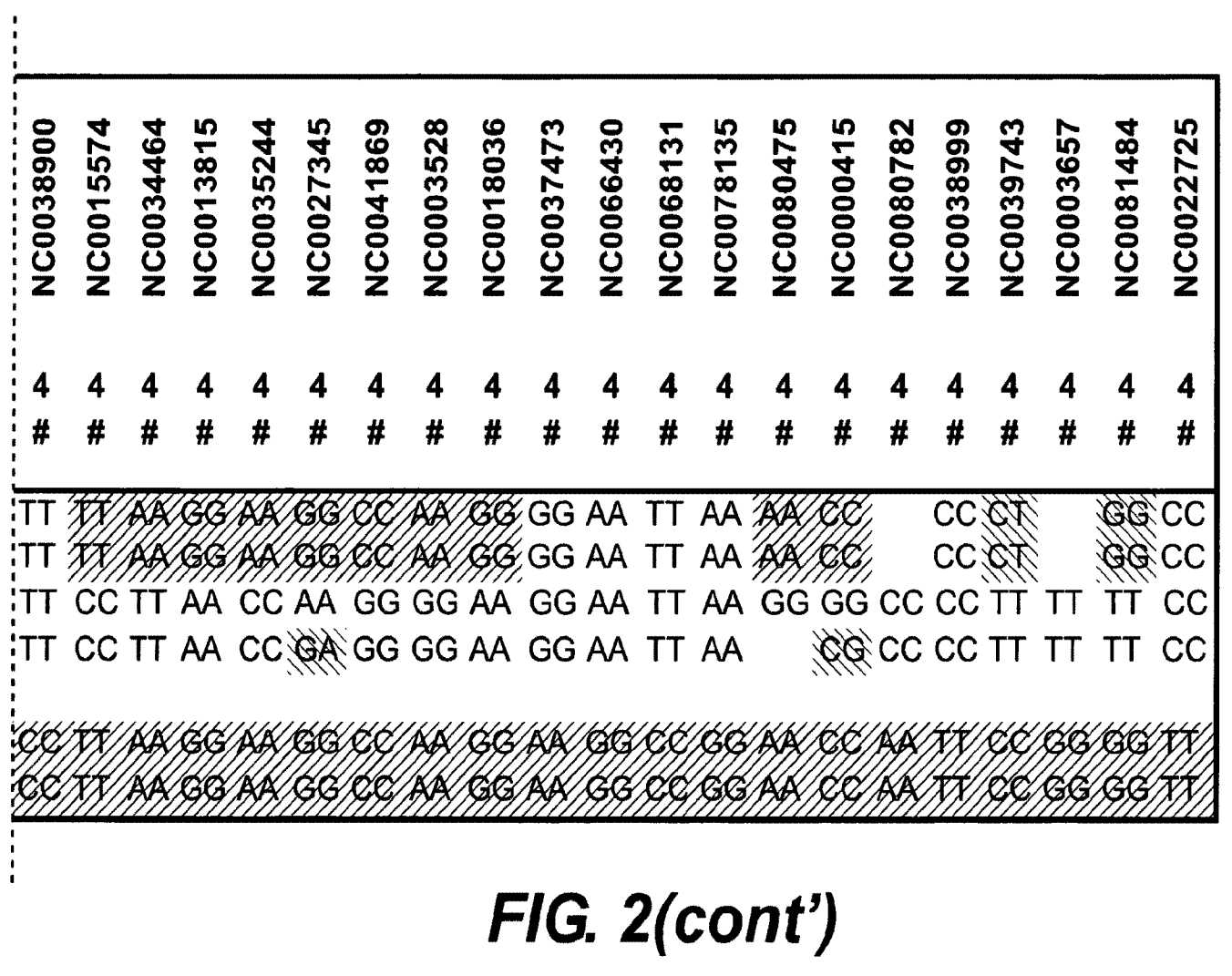

Application of a haplotype, rather than marker, based approach further resolved the QTL. Examination of the high density fingerprint information, reveals that the favorable inbreds (5750 and 3323) have the same haplotype for the entire 30 cM region based on 40 SNP markers in this region (FIGS. 1, 2). In addition, the unfavorable inbreds (3140 and 90LDC2) have the same haplotype, but a different haplotype relative to the favorable inbreds. The two testers (WQDS7 and 7051) also have the same haplotype, but it is a different variant from the favorable and unfavorable inbred haplotypes. Therefore, at the genetic level, the same genetic comparison was tested in both populations and resulted in the same relative value of the 2 different haplotypes being compared.

Utilizing these haplotypes as the search target, the hypothesized inference space can be expanded to include other lines that have the same haplotype. Searching the current database of lines in the reference germplasm that have high density SNP fingerprints (FIG. 2), 4 other lines (2 have 1 SNP locus with a different genotype) are considered to have the same unfavorable haplotype, while 22 other potential testers have the same haplotypes (with one line have 1 SNP locus with a different genotype). This new inference space defines the selection rules that could be applied to the breeding program within this set of germplasm.

Example 2. Use of Breeding Values for Informing Decisions in a Breeding Program

A primary innovation of the present invention is the ability to simultaneously select for multiple traits and target regions throughout the genome. Furthermore, this invention leverages historical marker-phenotype information, enabling pre-selection.

A key aspect of predictive haplotype-assisted selection is the ability to rank haplotypes. This example includes a subset of 10 preferred haplotypes, across 10 haplotype windows, for yield from elite temperate female corn inbreds that have been ranked using haplotype breeding value calculations. The haplotype effect estimates for each of the haplotypes for six different phenotypic traits is shown in Table 10. This example illustrates the application of breeding values in decisions relating to germplasm improvement.

TABLE 10

Haplotype effect estimates for six traits in 10 haplotypes from 10 different haplotype windows based on historical haplotype-phenotype associations.

| Haplotype window | Haplotype | YLD | MST | PHT | TWT | STLP | RTLP |
|---|---|---|---|---|---|---|---|
| 12953 | 1241745 | 1.352 | 0.2151 | 1.459 | −0.2599 | 0.2232 | 0.416 |
| 12982 | 1242692 | 0.9621 | 0.07775 | 0.03957 | −0.03569 | −0.06116 | −0.1129 |
| 12990 | 1242935 | 0.9671 | 0.04194 | 0.05432 | −0.02923 | −0.1668 | 0.1005 |
| 12996 | 1243070 | 1.155 | 0.0853 | 0.1127 | −0.03878 | −0.07303 | −0.06234 |
| 12999 | 1243137 | 1.07 | 0.06604 | 0.04864 | −0.1115 | −0.021 | −0.00063 |
| 13007 | 1243531 | 1.072 | 0.1053 | 0.2309 | −0.04918 | 0 | −0.09158 |
| 13015 | 1243877 | 1.264 | 0.07502 | 0.7479 | −0.02212 | 0.05377 | 0.4506 |
| 13056 | 1244818 | 1.049 | −0.04826 | 0.1025 | −0.03896 | 0.0773 | 0.2719 |
| 13078 | 1245282 | 1.758 | 0.02896 | 0.1952 | −0.1369 | −0.04367 | 0.1156 |
| 13092 | 1245725 | 1.09 | 0.197 | 0.4063 | −0.06211 | −0.1563 | 0.02841 |

YLD = yield (bushels/acre),
MST = moisture (%),
PHT = plant height (inches),
TWT = test weight (lbs/bushel),
STLP = stalk lodging (% of row; counts of total plants in row that are lodged),
RTLP = root lodging (% of row; counts of total plants in row that are lodged).

Inferring the breeding value of a haplotype corresponds to answering the question: by how much will the mean of the germplasm change by changing the frequency of this haplotype from its current value to fixation? This depends on the effects and frequency of other haplotypes in the same window. When analyzing a subset of haplotypes, a correction factor needs to be used, which corresponds to the sum of frequencies of the haplotypes retained, and haplotype frequencies are adjusted by dividing them with this correction factor (Table 11).

TABLE 11

Calculation of adjusted haplotype frequency.

| Haplotype | Haplotype frequency in germplasm | Correction Factor | Corrected haplotype frequency |
|---|---|---|---|
| 1241745 | 0.017391 | 0.384783 | 0.045198 |
| 1242692 | 0.096774 | 0.75914 | 0.127479 |
| 1242935 | 0.262366 | 0.722581 | 0.363095 |
| 1243070 | 0.037118 | 0.473799 | 0.078341 |
| 1243137 | 0.078603 | 0.362445 | 0.216867 |
| 1243531 | 0.097614 | 0.295011 | 0.330882 |
| 1243877 | 0.0671 | 0.448052 | 0.149758 |
| 1244818 | 0.021786 | 0.400871 | 0.054348 |
| 1245282 | 0.04086 | 0.548387 | 0.07451 |
| 1245725 | 0.083691 | 0.461373 | 0.181395 |

The next step in ranking haplotypes is to calculate the haplotype breeding value by calculating the difference of the population mean and the haplotype effect estimate, wherein the population mean is the sum of the products of each haplotype's corrected frequency and estimated effect (Table 12). The result listed in Table 13 represents the average effect of fixing that haplotype and the breeding value for each trait. In order to find the multiple trait score of any given haplotype, a weighted sum of breeding values for the multiple traits is obtained for each haplotype. For this example, the following trait weights were used: YLD: 60% (+); MST: 15% (−); STLP: 9% (−); PHT: 8% (−); TWT: 4% (+); RTLP: 4% (−); the sign of each trait's correlation with yield is indicated in parentheses. The resulting index is shown in Table 13. Haplotype 1245282, of window 13078, clearly is the most desirable. Interestingly, for all of the other haplotypes in this analysis, the ranking based on breeding values for all 6 traits is different from a simple ranking of the yield effect estimates. That is, a selection strategy based on yield alone may not produce the best overall plant. This finding reiterates the importance of considering multiple traits in selection models, particularly in light of the negative correlation between yield and many phenotypic traits.

TABLE 12

Calculation of population mean for each trait, wherein the population mean is the sum of the products of each haplotype's frequency and effect estimate.

| Haplotype | YLD mean | MST mean | PHT mean | TWT mean | STLP mean | RTLP mean |
|---|---|---|---|---|---|---|
| 1241745 | −0.090837853 | −0.043306192 | −0.0827 | 0.007891638 | −0.062215853 | −0.070758814 |
| 1242692 | 0.014551841 | −0.015110453 | 0.014922295 | −0.000895269 | 0.017879405 | −0.004469858 |
| 1242935 | 0.121041369 | 0.002742946 | 0.03235881 | 0.000743887 | −0.017505446 | 0.036984851 |
| 1243070 | 0.107389862 | −0.010304101 | 0.0093003 | 0.01050318 | 0.04445318 | 0.058784931 |
| 1243137 | −0.008991506 | −0.01716759 | 0.038747651 | −0.012664398 | 0.009967952 | 0.011827682 |
| 1243531 | 0.476469265 | 0.026092059 | 0.055694853 | −0.041073309 | 0 | −0.009946765 |
| 1243877 | 0.137087923 | 0.009745411 | 0.020751981 | 0.016647971 | −0.016325256 | 0.031501304 |

TABLE 12-continued

Calculation of population mean for each trait, wherein the population mean is the sum of the products of each haplotype's frequency and effect estimate.

| Haplotype | YLD mean | MST mean | PHT mean | TWT mean | STLP mean | RTLP mean |
|---|---|---|---|---|---|---|
| 1244818 | 0.084271739 | 0.019438859 | 0.030198261 | 0.022125924 | −0.045735109 | −0.100301848 |
| 1245282 | −0.049701765 | 0.030483529 | 0.027517227 | −0.004194745 | 0.021528059 | 0.049876863 |
| 1245725 | −0.286935116 | −0.029174977 | −0.046871888 | 0.023150336 | 0.00831414 | −0.009225116 |

YLD = yield (bushels/acre),
MST = moisture (%),
PHT = plant height (inches),
TWT = test weight (lbs/bushel),
STLP = stalk lodging (% of row; counts of total plants in row that are lodged),
RTLP = root lodging (% of row; counts of total plants in row that are lodged).

TABLE 13

Calculation of breeding value (BV) for each trait and calculation of breeding index.

| Haplotype | YLD BV | MST BV | PHT BV | TWT BV | STLP BV | RTLP BV | Index |
|---|---|---|---|---|---|---|---|
| 1241745 | 1.442837853 | 0.258406192 | 1.5417 | −0.267791638 | 0.285415853 | 0.486758814 | 0.647736338 |
| 1242692 | 0.947548159 | 0.092860453 | 0.024647705 | −0.034794731 | −0.079039405 | −0.108430142 | 0.562686974 |
| 1242935 | 0.846058631 | 0.039197054 | 0.02196119 | −0.029973887 | −0.149294554 | 0.063515149 | 0.509695674 |
| 1243070 | 1.047610138 | 0.095604101 | 0.1033997 | −0.04928318 | −0.11748318 | −0.121124931 | 0.619400648 |
| 1243137 | 1.078991506 | 0.08320759 | 0.009892349 | −0.098835602 | −0.030967952 | −0.012459482 | 0.633454448 |
| 1243531 | 0.595530735 | 0.079207941 | 0.175205147 | −0.008106691 | 0 | −0.081633235 | 0.3343619 |
| 1243877 | 1.126912077 | 0.065274589 | 0.727148019 | −0.038767971 | 0.070095256 | 0.419098696 | 0.583560977 |
| 1244818 | 0.964728261 | −0.067698859 | 0.072301739 | −0.061085924 | 0.123035109 | 0.372201848 | 0.554802976 |
| 1245282 | 1.807701765 | −0.001523529 | 0.167682773 | −0.132705255 | −0.065198059 | 0.065723137 | 1.069365656 |
| 1245725 | 1.376935116 | 0.226174977 | 0.453171888 | −0.085260336 | −0.16461414 | 0.037635116 | 0.765880527 |

YLD = yield (bushels/acre),
MST = moisture (%),
PHT = plant height (inches),
TWT = test weight (lbs/bushel),
STLP = stalk lodging (% of row; counts of total plants in row that are lodged),
RTLP = root lodging (% of row; counts of total plants in row that are lodged).

One skilled in the art can recognize the tremendous advantage of having these indices available for a set of germplasm in a breeding program. In particular, these values enable pre-selection, the next generation of marker-assisted selection. Pre-selection further economizes breeding by not only removing the need for phenotyping but by enabling screening inbred lines for multiple traits prior to actually making breeding crosses. Further, knowing a priori which chromosomal regions in which lines are favorable not only allows more informed breeding decisions but capitalizes on historical marker-phenotype data in an entirely new and highly beneficial manner.

Figure 3:
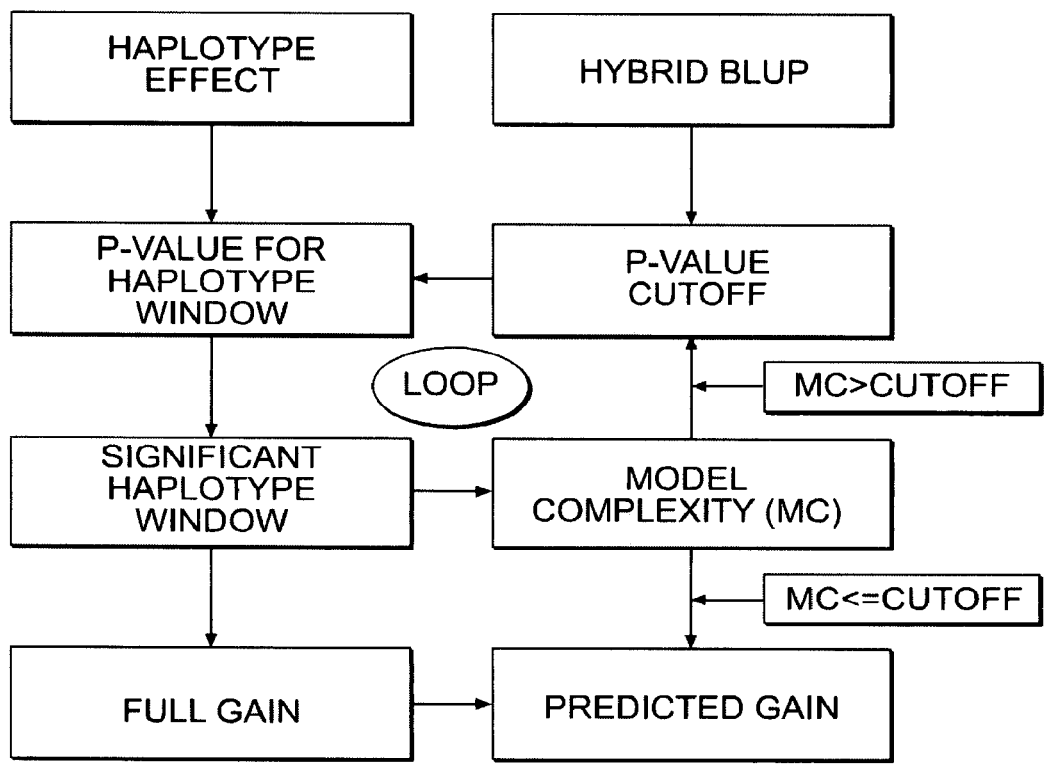
FIG. 3 is a flow chart illustrating the sequence of Automatic Model Picking (AMP), an algorithm that assists breeders with haplotype-based selection and, more specifically, enable pre-selection.

Example 3. Implementation of Pre-Selection in a Breeding Program Via Automatic Model Picking With haplotype estimation, pre-selection can be applied to a breeding program. This enables breeders, through marker-assisted selection on pre-determined significant haplotypes, to make genetic gain before new lines and breeding crosses are tested in the field. Breeders start pre-selection projects by selecting a list of crosses and building models based on the haplotypes carried by each parental line in the cross. One approach is to manually select haplotypes, but this hampers the breeders' ability to sort through a large number of possible crosses. There may also be inconsistencies in the way haplotypes are selected from cross to cross and there may be a need to restrain the choice of too many genomic regions in the model. For instance, if the model is too complex, predictive ability, and potential genetic gain, will likely be compromised. To control for model complexity and also meet high-throughput requirement, an Automatic Model Picking (AMP) algorithm has been developed for two-way and three-way crosses. This process involves (1) establishing the cutoff for picking up significant haplotypes; (2) selection of significant haplotypes from different traits into the model; (3) handling negative correlations between certain traits; and (4) optimization of the model using model complexity (FIG. 3).

The first step is to establish the cutoff for significance for haplotypes for different traits. The p-value for significance of the difference between the haplotypes from each parent at a window is calculated using an unpaired t test. The next step is to establish the p-value cutoff as a pre-requisite for inclusion into the model. The yield p-value cutoff is set as the lowest among all of the traits across all of the breeding populations (e.g., 0.15). For all other traits, the p-value cutoff is determined based on the perceived weaknesses of any given breeding cross (e.g., when both parents of a breeding cross are know to have stalk problems, it is probably wise to include more haplotypes that are expected to increase stalk strength). An approach to predict strengths or weaknesses of a breeding cross is to use Best Linear Unbiased Predictions (BLUP's) calculated on the parental lines using phenotypic data (see Bernardo, Breeding for Quantitative Traits in Plants, Stemma Press, Woodbury, M N, 2002). How the average of the parental BLUPs for any trait in a cross compares to the same metric in other crosses will provide an indication of the relative advantage of that cross. The breeding cross BLUP is the weighted average of the parental BLUPs (weighted according to the relative contribution of the parents to the cross: e.g., 50% for both parents of an F2, 25% and 75% for the donor and recurrent parents of a BC1, respectively). Each breeding cross is subsequently be compared to a population of breeding crosses based on the means and standard deviations of BLUP values for each trait in that population and, from this benchmarking, p-value cutoffs may be chosen (Tables 14 and 15).

TABLE 14

Hybrid BLUP p value cutoff for Moisture.

| Hybrid BLUP Distribution | p-value cutoff |
|---|---|
| mean + 2 * std < hybrid BLUP | 0.15 |
| mean + std < hybrid BLUP < mean + 2 * std | 0.12 |
| mean < hybrid BLUP < mean + std | 0.1 |
| mean − std < hybrid BLUP < mean | 0.09 |
| mean − 2 * std < hybrid BLUP < mean − std | 0.07 |
| hybrid BLUP < mean − 2 * std | 0.04 |

BLUP = best linear unbiased prediction,
std = standard deviation.

TABLE 15

Hybrid BLUP p value cutoff for test weight.

| Hybrid BLUP Distribution | p-value cutoff |
|---|---|
| mean + 2 * std < hybrid BLUP | 0.001 |
| mean + std < hybrid BLUP < mean + 2 * std | 0.01 |
| mean < hybrid BLUP < mean + std | 0.03 |
| mean − std < hybrid BLUP < mean | 0.04 |
| mean − 2 * std < hybrid BLUP < mean − std | 0.06 |
| hybrid BLUP < mean − 2 * std | 0.09 |

BLUP = best linear unbiased prediction,
std = standard deviation.

A major concern for breeders using selection models is the negative correlation between yield and other phenotypic traits, such as moisture and plant height. This AMP strategy directly addresses this issue by using trait ratios that allow a breeder to simultaneously select for high yield and low moisture (or plant height). The trait ratio is chosen to either exceed a certain level (e.g., 5 Bushels/acre for each additional percent of moisture) or be less than zero, which ensures higher yield and lower moisture (or plant height).

The breeder is then able to initiate model building. Significant haplotype windows for each trait are sequentially selected in the following order: yield, moisture, plant height, stalk lodging, test weight, and root lodging. Also, negative correlations are considered for yield and moisture and for yield and plant height. Polymorphic markers are selected for each set of parents for each of the significant haplotype windows. Based on the resulting model, model complexity is estimated. If the model exceeds the complexity cutoff, the p-value cutoff is then decreased and the model is re-built; this cycle will be repeated until the model complexity is appropriate (FIG. 3).

In order to understand the number of haplotype windows that will be assumed using this algorithm, assume a model complexity cutoff of 7.5. Model complexity is represented as −log 10 (probability of a perfect F1 gamete). In the case of one 12 cM region, assuming 15% recombination for the sake of simplicity, the probability of a perfect gamete is: 0.5*0.85=0.425. The model complexity is represented by: −log 10 (0.425)=0.37. Thus, the number of possible independent regions is: n=7.5/0.372=20.2. Therefore, in this case, selection will be performed on between 10 and 25 regions. As prediction capabilities improve and computational capabilities are enhanced, one skilled in the art can anticipate a greater number of haplotypes to be included in pre-selection models.

Once the final model is obtained, the full gain (at fixation for all favorable haplotypes) for each trait is calculated by adding half of the difference of haplotype effects across all of the selected haplotype windows. The frequency-adjusted predicted gain is obtained based on the expected allele frequency once the pre-selection process is complete; as model complexity increases, the average frequency across selected haplotypes will decrease for a given pre-selection protocol. Based on frequency-adjusted predicted gain, an additional optimization step can be included to either increase or decrease the importance of secondary traits in the model.

This algorithm represents a powerful tool for breeders. Those skilled in the art can appreciate the benefits of a model selection tool that "self-corrects" for complexity, thus maintaining predictive ability. This type of tool is easily implemented in an existing computer-based breeding package that contains genotype, phenotype, and pedigree information for a set of germplasm.

Example 4. Use of Haplotype Effect Estimates in Making Breeding Decisions

The present invention provides haplotype information that enables a breeder to make informed breeding decisions. The methods and compositions of the present invention enable the determination of the genotype of one or more plants, using markers underlying at least one haplotype window, and the resulting fingerprint is used to identify the haplotypic composition of the haplotype window which is subsequently associated with one or more haplotype effect estimates for one or more phenotypic traits as disclosed herein. This information is valuable in decision-making for a breeder because it enables a selection decision to be based on estimated phenotype without having to phenotype the plant per se. Further, it is preferred to make decisions based on genotype rather than phenotype due the fact phenotype is influenced by multiple biotic and abiotic factors that can confound evaluation of any given trait and performance prediction.

In one aspect, one or more haplotypes are determined by genotyping one or more plants using markers for one or more haplotype windows. The breeder is able to correspond the haplotypes with their respective haplotype effect estimates for one or more phenotypes of interest and make a decision based on the preferred haplotype. Plants comprising one or more preferred haplotypes are then advanced in the breeding program.

In one aspect, advancement decisions in line development breeding are traditionally made based on phenotype, wherein decisions are made between two or more plants showing segregation for one or more phenotypic traits. An advantage of the present invention is the ability to make decisions based on haplotypes wherein a priori information is leveraged, enabling "predictive breeding." In this aspect, during line development breeding for a crop plant, sublines are evaluated for segregation at one or more marker loci. Individuals segregating at one or more haplotype windows can be identified unambiguously using genotyping and, for any given haplotype window, individuals comprising the preferred haplotype are selected. In preferred aspects, the selection decision is based on a haplotype effect estimate, a haplotype frequency, or a breeding value.

All publications and published patent documents cited in this specification are incorporated herein by reference to the same extent as if each individual publication or patent application was specifically and individually indicated to be incorporated by reference.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

LENGTHY TABLES

The patent contains a lengthy table section. A copy of the table is available in electronic form from the USPTO web site (http://seqdata.uspto.gov/?pageRequest=docDetail&DocID=US10455783B2). An electronic copy of the table will also be available from the USPTO upon request and payment of the fee set forth in 37 CFR 1.19(b)(3).

What is claimed is:

1. A method for preparing a transgenic soybean plant, the method comprising the steps of:
    transforming a parent plant comprising a chromosomal region at map position 114.30 cM to 115.90 cM on chromosome 6 identifiable by SEQ ID NOs:518 and 519, with a recombinant DNA and producing at least two transgenic progeny soybean plants; and
    selecting a transgenic progeny soybean plant for breeding from said at least two transgenic progeny soybean plants, wherein said selected transgenic progeny soybean plant comprises said transgene comprising said recombinant DNA linked within 10 cM of said chromosomal region at map position 114.30 to 115.90 on chromosome 6 identifiable by SEQ ID NOs:518 and 519.

2. The method of claim 1, wherein said transgene confers a phenotypic trait selected from the group consisting of herbicide tolerance, disease resistance, insect resistance, pest resistance, altered fatty acid, protein or carbohydrate metabolism, increased grain yield, increased oil, enhanced nutritional content, increased growth rates, enhanced stress tolerance, preferred maturity, enhanced organoleptic properties, altered morphological characteristics, and sterility.

3. The method of claim 1, wherein said transgene comprises a recombinant DNA that is transcribed into a functional mRNA molecule that is translated and expressed as a protein product.

4. The method of claim 1, wherein said transgene comprises a recombinant DNA that is transcribed into a double-stranded RNA for RNA interference (RNAi).

5. The method of claim 4, wherein said double-stranded RNA is a small interfering RNA (siRNA).

6. The method of claim 4, wherein said double-stranded RNA is a trans-acting small interfering RNA (ta-siRNA).

7. The method of claim 4, wherein said double-stranded RNA is a microRNA (miRNA).

8. The method of claim 1, further comprising crossing said selected transgenic soybean plant with a second soybean plant to produce a progeny plant having said transgene linked to said chromosomal region at map position 114.30 to 115.90 on chromosome 6 identifiable by SEQ ID NOs:518 and 519.

9. The method of claim 1, wherein said transgene and said chromosomal region at map position 114.30 to 115.90 on chromosome 6 identifiable by SEQ ID NOs:518 and 519 are within 5 cM of each other.

10. The method of claim 9, wherein said transgene and said chromosomal region at map position 114.30 to 115.90 on chromosome 6 identifiable by SEQ ID NOs:518 and 519 are within 1 cM of each other.

11. The method of claim 10, wherein said transgene is within said chromosomal region at map position 114.30 to 115.90 on chromosome 6 identifiable by SEQ ID NOs:518 and 519.

12. The method of claim 2, wherein said transgene confers herbicide tolerance.

* * * * *

```
                              SEQUENCE LISTING

<160> NUMBER OF SEQ ID NOS: 519

<210> SEQ ID NO 1
    <211> LENGTH: 10
    <212> TYPE: DNA
    <213> ORGANISM: Zea mays

<400> SEQUENCE: 1
gagggcatcc                                                              10

<210> SEQ ID NO 2
    <211> LENGTH: 10
    <212> TYPE: DNA
    <213> ORGANISM: Zea mays

<400> SEQUENCE: 2
gaaatcacac                                                              10

<210> SEQ ID NO 3
    <211> LENGTH: 10
    <212> TYPE: DNA
    <213> ORGANISM: Zea mays

<400> SEQUENCE: 3
gcgatcacat                                                              10

<210> SEQ ID NO 4
    <211> LENGTH: 10
    <212> TYPE: DNA
    <213> ORGANISM: Zea mays

<400> SEQUENCE: 4
gagatcacac                                                              10

<210> SEQ ID NO 5
    <211> LENGTH: 10
    <212> TYPE: DNA
    <213> ORGANISM: Zea mays

<400> SEQUENCE: 5
gcgggcatcc                                                              10

<210> SEQ ID NO 6
    <211> LENGTH: 10
```

```
<212> TYPE: DNA
<213> ORGANISM: Zea mays

<400> SEQUENCE: 6
gagatcatat                                                          10

<210> SEQ ID NO 7
<211> LENGTH: 10
<212> TYPE: DNA
<213> ORGANISM: Zea mays

<400> SEQUENCE: 7
gcgggcgtac                                                          10

<210> SEQ ID NO 8
<211> LENGTH: 10
<212> TYPE: DNA
<213> ORGANISM: Zea mays

<400> SEQUENCE: 8
acgggcgtac                                                          10

<210> SEQ ID NO 9
<211> LENGTH: 10
<212> TYPE: DNA
<213> ORGANISM: Zea mays

<400> SEQUENCE: 9
gcgatcatat                                                          10

<210> SEQ ID NO 10
<211> LENGTH: 10
<212> TYPE: DNA
<213> ORGANISM: Zea mays

<400> SEQUENCE: 10
acgggtgtac                                                          10

<210> SEQ ID NO 11
<211> LENGTH: 10
<212> TYPE: DNA
<213> ORGANISM: Zea mays

<400> SEQUENCE: 11
gcgagtgcac                                                          10

<210> SEQ ID NO 12
<211> LENGTH: 10
<212> TYPE: DNA
<213> ORGANISM: Zea mays

<400> SEQUENCE: 12
gagggtgtac                                                          10

<210> SEQ ID NO 13
<211> LENGTH: 10
<212> TYPE: DNA
<213> ORGANISM: Zea mays

<400> SEQUENCE: 13
gcaggtgtac                                                          10

<210> SEQ ID NO 14
```

```
<211> LENGTH: 10
<212> TYPE: DNA
<213> ORGANISM: Zea mays

<400> SEQUENCE: 14
gagggcatac                                                          10

<210> SEQ ID NO 15
<211> LENGTH: 10
<212> TYPE: DNA
<213> ORGANISM: Zea mays

<400> SEQUENCE: 15
ctcacgggtg                                                          10

<210> SEQ ID NO 16
<211> LENGTH: 10
<212> TYPE: DNA
<213> ORGANISM: Zea mays

<400> SEQUENCE: 16
tacgtaacgg                                                          10

<210> SEQ ID NO 17
<211> LENGTH: 10
<212> TYPE: DNA
<213> ORGANISM: Zea mays

<400> SEQUENCE: 17
cacacggcgg                                                          10

<210> SEQ ID NO 18
<211> LENGTH: 10
<212> TYPE: DNA
<213> ORGANISM: Zea mays

<400> SEQUENCE: 18
ctcacggcgg                                                          10

<210> SEQ ID NO 19
<211> LENGTH: 10
<212> TYPE: DNA
<213> ORGANISM: Zea mays

<400> SEQUENCE: 19
cacacgacgg                                                          10

<210> SEQ ID NO 20
<211> LENGTH: 10
<212> TYPE: DNA
<213> ORGANISM: Zea mays

<400> SEQUENCE: 20
tacacgggtg                                                          10

<210> SEQ ID NO 21
<211> LENGTH: 10
<212> TYPE: DNA
<213> ORGANISM: Zea mays

<400> SEQUENCE: 21
taaacggcgg                                                          10
```

-continued

```
<210> SEQ ID NO 22
<211> LENGTH: 10
<212> TYPE: DNA
<213> ORGANISM: Zea mays

<400> SEQUENCE: 22
cacgtgacgg                                                            10

<210> SEQ ID NO 23
<211> LENGTH: 10
<212> TYPE: DNA
<213> ORGANISM: Zea mays

<400> SEQUENCE: 23
ttcacgggtg                                                            10

<210> SEQ ID NO 24
<211> LENGTH: 10
<212> TYPE: DNA
<213> ORGANISM: Zea mays

<400> SEQUENCE: 24
taaacgggtc                                                            10

<210> SEQ ID NO 25
<211> LENGTH: 10
<212> TYPE: DNA
<213> ORGANISM: Zea mays

<400> SEQUENCE: 25
tacgtgacgg                                                            10

<210> SEQ ID NO 26
<211> LENGTH: 10
<212> TYPE: DNA
<213> ORGANISM: Zea mays

<400> SEQUENCE: 26
caaacggcgc                                                            10

<210> SEQ ID NO 27
<211> LENGTH: 10
<212> TYPE: DNA
<213> ORGANISM: Zea mays

<400> SEQUENCE: 27
cacacaacgg                                                            10

<210> SEQ ID NO 28
<211> LENGTH: 10
<212> TYPE: DNA
<213> ORGANISM: Zea mays

<400> SEQUENCE: 28
ctcacgggtc                                                            10

<210> SEQ ID NO 29
<211> LENGTH: 10
<212> TYPE: DNA
<213> ORGANISM: Zea mays

<400> SEQUENCE: 29
tacacgactg                                                            10
```

```
<210> SEQ ID NO 30
<211> LENGTH: 10
<212> TYPE: DNA
<213> ORGANISM: Zea mays

<400> SEQUENCE: 30
ctcacggctg                                                              10

<210> SEQ ID NO 31
<211> LENGTH: 10
<212> TYPE: DNA
<213> ORGANISM: Zea mays

<400> SEQUENCE: 31
agtgccacct                                                              10

<210> SEQ ID NO 32
<211> LENGTH: 10
<212> TYPE: DNA
<213> ORGANISM: Zea mays

<400> SEQUENCE: 32
agcgccacat                                                              10

<210> SEQ ID NO 33
<211> LENGTH: 10
<212> TYPE: DNA
<213> ORGANISM: Zea mays

<400> SEQUENCE: 33
catgccagat                                                              10

<210> SEQ ID NO 34
<211> LENGTH: 10
<212> TYPE: DNA
<213> ORGANISM: Zea mays

<400> SEQUENCE: 34
agtgatacac                                                              10

<210> SEQ ID NO 35
<211> LENGTH: 10
<212> TYPE: DNA
<213> ORGANISM: Zea mays

<400> SEQUENCE: 35
cacaccacat                                                              10

<210> SEQ ID NO 36
<211> LENGTH: 10
<212> TYPE: DNA
<213> ORGANISM: Zea mays

<400> SEQUENCE: 36
agtgccagct                                                              10

<210> SEQ ID NO 37
<211> LENGTH: 10
<212> TYPE: DNA
<213> ORGANISM: Zea mays

<400> SEQUENCE: 37
cgtgccagat                                                              10
```

<210> SEQ ID NO 38
<211> LENGTH: 10
<212> TYPE: DNA
<213> ORGANISM: Zea mays

<400> SEQUENCE: 38
cacaatacat                                                            10

<210> SEQ ID NO 39
<211> LENGTH: 10
<212> TYPE: DNA
<213> ORGANISM: Zea mays

<400> SEQUENCE: 39
cgtgacacct                                                            10

<210> SEQ ID NO 40
<211> LENGTH: 10
<212> TYPE: DNA
<213> ORGANISM: Zea mays

<400> SEQUENCE: 40
cacaacacct                                                            10

<210> SEQ ID NO 41
<211> LENGTH: 10
<212> TYPE: DNA
<213> ORGANISM: Zea mays

<400> SEQUENCE: 41
agcaatacat                                                            10

<210> SEQ ID NO 42
<211> LENGTH: 10
<212> TYPE: DNA
<213> ORGANISM: Zea mays

<400> SEQUENCE: 42
cgcaatacat                                                            10

<210> SEQ ID NO 43
<211> LENGTH: 10
<212> TYPE: DNA
<213> ORGANISM: Zea mays

<400> SEQUENCE: 43
cataccacct                                                            10

<210> SEQ ID NO 44
<211> LENGTH: 10
<212> TYPE: DNA
<213> ORGANISM: Zea mays

<400> SEQUENCE: 44
cgcaccacct                                                            10

<210> SEQ ID NO 45
<211> LENGTH: 10
<212> TYPE: DNA
<213> ORGANISM: Zea mays

<400> SEQUENCE: 45
tccagtccgg                                                                  10

<210> SEQ ID NO 46
<211> LENGTH: 10
<212> TYPE: DNA
<213> ORGANISM: Zea mays

<400> SEQUENCE: 46
cgggacataa                                                                  10

<210> SEQ ID NO 47
<211> LENGTH: 10
<212> TYPE: DNA
<213> ORGANISM: Zea mays

<400> SEQUENCE: 47
tccggcctga                                                                  10

<210> SEQ ID NO 48
<211> LENGTH: 10
<212> TYPE: DNA
<213> ORGANISM: Zea mays

<400> SEQUENCE: 48
cgcggcctga                                                                  10

<210> SEQ ID NO 49
<211> LENGTH: 10
<212> TYPE: DNA
<213> ORGANISM: Zea mays

<400> SEQUENCE: 49
cgcgatctaa                                                                  10

<210> SEQ ID NO 50
<211> LENGTH: 10
<212> TYPE: DNA
<213> ORGANISM: Zea mays

<400> SEQUENCE: 50
cggagtctga                                                                  10

<210> SEQ ID NO 51
<211> LENGTH: 10
<212> TYPE: DNA
<213> ORGANISM: Zea mays

<400> SEQUENCE: 51
cggagcccga                                                                  10

<210> SEQ ID NO 52
<211> LENGTH: 10
<212> TYPE: DNA
<213> ORGANISM: Zea mays

<400> SEQUENCE: 52
cccggcctga                                                                  10

<210> SEQ ID NO 53
<211> LENGTH: 10
<212> TYPE: DNA
<213> ORGANISM: Zea mays

<400> SEQUENCE: 53 cggaacctga	10

<210> SEQ ID NO 54
<211> LENGTH: 10
<212> TYPE: DNA
<213> ORGANISM: Zea mays

<400> SEQUENCE: 54 cgcagtctag	10

<210> SEQ ID NO 55
<211> LENGTH: 10
<212> TYPE: DNA
<213> ORGANISM: Zea mays

<400> SEQUENCE: 55 tccagtctga	10

<210> SEQ ID NO 56
<211> LENGTH: 10
<212> TYPE: DNA
<213> ORGANISM: Zea mays

<400> SEQUENCE: 56 cggggtctga	10

<210> SEQ ID NO 57
<211> LENGTH: 10
<212> TYPE: DNA
<213> ORGANISM: Zea mays

<400> SEQUENCE: 57 cgcgacctaa	10

<210> SEQ ID NO 58
<211> LENGTH: 10
<212> TYPE: DNA
<213> ORGANISM: Zea mays

<400> SEQUENCE: 58 cggagcctga	10

<210> SEQ ID NO 59
<211> LENGTH: 10
<212> TYPE: DNA
<213> ORGANISM: Zea mays

<400> SEQUENCE: 59 cgcgacctga	10

<210> SEQ ID NO 60
<211> LENGTH: 10
<212> TYPE: DNA
<213> ORGANISM: Zea mays

<400> SEQUENCE: 60 cggaatccgg	10

<210> SEQ ID NO 61
<211> LENGTH: 10
<212> TYPE: DNA
<213> ORGANISM: Zea mays

```
<400> SEQUENCE: 61
cgcagcctgg                                                          10

<210> SEQ ID NO 62
<211> LENGTH: 10
<212> TYPE: DNA
<213> ORGANISM: Zea mays

<400> SEQUENCE: 62
tccggtccgg                                                          10

<210> SEQ ID NO 63
<211> LENGTH: 10
<212> TYPE: DNA
<213> ORGANISM: Zea mays

<400> SEQUENCE: 63
cgcggcccgg                                                          10

<210> SEQ ID NO 64
<211> LENGTH: 10
<212> TYPE: DNA
<213> ORGANISM: Zea mays

<400> SEQUENCE: 64
cggagtccgg                                                          10

<210> SEQ ID NO 65
<211> LENGTH: 10
<212> TYPE: DNA
<213> ORGANISM: Zea mays

<400> SEQUENCE: 65
cggagtccga                                                          10

<210> SEQ ID NO 66
<211> LENGTH: 10
<212> TYPE: DNA
<213> ORGANISM: Zea mays

<400> SEQUENCE: 66
cgcgatctga                                                          10

<210> SEQ ID NO 67
<211> LENGTH: 10
<212> TYPE: DNA
<213> ORGANISM: Zea mays

<400> SEQUENCE: 67
cgcggcctgg                                                          10

<210> SEQ ID NO 68
<211> LENGTH: 10
<212> TYPE: DNA
<213> ORGANISM: Zea mays

<400> SEQUENCE: 68
cccgatctga                                                          10

<210> SEQ ID NO 69
<211> LENGTH: 10
<212> TYPE: DNA
<213> ORGANISM: Zea mays
```

```
<400> SEQUENCE: 69
cgcgatccgg                                                          10

<210> SEQ ID NO 70
<211> LENGTH: 10
<212> TYPE: DNA
<213> ORGANISM: Zea mays

<400> SEQUENCE: 70
ccgagcccgg                                                          10

<210> SEQ ID NO 71
<211> LENGTH: 10
<212> TYPE: DNA
<213> ORGANISM: Zea mays

<400> SEQUENCE: 71
cgggatctga                                                          10

<210> SEQ ID NO 72
<211> LENGTH: 10
<212> TYPE: DNA
<213> ORGANISM: Zea mays

<400> SEQUENCE: 72
cggggcatga                                                          10

<210> SEQ ID NO 73
<211> LENGTH: 10
<212> TYPE: DNA
<213> ORGANISM: Zea mays

<400> SEQUENCE: 73
tataatccta                                                          10

<210> SEQ ID NO 74
<211> LENGTH: 10
<212> TYPE: DNA
<213> ORGANISM: Zea mays

<400> SEQUENCE: 74
tgtaatccta                                                          10

<210> SEQ ID NO 75
<211> LENGTH: 10
<212> TYPE: DNA
<213> ORGANISM: Zea mays

<400> SEQUENCE: 75
tgtaatcgaa                                                          10

<210> SEQ ID NO 76
<211> LENGTH: 10
<212> TYPE: DNA
<213> ORGANISM: Zea mays

<400> SEQUENCE: 76
cataattgtg                                                          10

<210> SEQ ID NO 77
<211> LENGTH: 10
<212> TYPE: DNA
```

```
<213> ORGANISM: Zea mays

<400> SEQUENCE: 77
tgtaattgag                                                            10

<210> SEQ ID NO 78
<211> LENGTH: 10
<212> TYPE: DNA
<213> ORGANISM: Zea mays

<400> SEQUENCE: 78
cataattgta                                                            10

<210> SEQ ID NO 79
<211> LENGTH: 10
<212> TYPE: DNA
<213> ORGANISM: Zea mays

<400> SEQUENCE: 79
tgtaaccgtg                                                            10

<210> SEQ ID NO 80
<211> LENGTH: 10
<212> TYPE: DNA
<213> ORGANISM: Zea mays

<400> SEQUENCE: 80
cataattgaa                                                            10

<210> SEQ ID NO 81
<211> LENGTH: 10
<212> TYPE: DNA
<213> ORGANISM: Zea mays

<400> SEQUENCE: 81
cacaattgtg                                                            10

<210> SEQ ID NO 82
<211> LENGTH: 10
<212> TYPE: DNA
<213> ORGANISM: Zea mays

<400> SEQUENCE: 82
tgtaattgtg                                                            10

<210> SEQ ID NO 83
<211> LENGTH: 10
<212> TYPE: DNA
<213> ORGANISM: Zea mays

<400> SEQUENCE: 83
tgtaatcctg                                                            10

<210> SEQ ID NO 84
<211> LENGTH: 10
<212> TYPE: DNA
<213> ORGANISM: Zea mays

<400> SEQUENCE: 84
cataattcaa                                                            10

<210> SEQ ID NO 85
<211> LENGTH: 10
```

```
<212> TYPE: DNA
<213> ORGANISM: Zea mays

<400> SEQUENCE: 85
tgctgaaggt                                                          10

<210> SEQ ID NO 86
<211> LENGTH: 10
<212> TYPE: DNA
<213> ORGANISM: Zea mays

<400> SEQUENCE: 86
tggtgaaggc                                                          10

<210> SEQ ID NO 87
<211> LENGTH: 10
<212> TYPE: DNA
<213> ORGANISM: Zea mays

<400> SEQUENCE: 87
tagtggacat                                                          10

<210> SEQ ID NO 88
<211> LENGTH: 10
<212> TYPE: DNA
<213> ORGANISM: Zea mays

<400> SEQUENCE: 88
tagaggacat                                                          10

<210> SEQ ID NO 89
<211> LENGTH: 10
<212> TYPE: DNA
<213> ORGANISM: Zea mays

<400> SEQUENCE: 89
tagtggacgt                                                          10

<210> SEQ ID NO 90
<211> LENGTH: 10
<212> TYPE: DNA
<213> ORGANISM: Zea mays

<400> SEQUENCE: 90
tggtggagac                                                          10

<210> SEQ ID NO 91
<211> LENGTH: 10
<212> TYPE: DNA
<213> ORGANISM: Zea mays

<400> SEQUENCE: 91
tacaaaacat                                                          10

<210> SEQ ID NO 92
<211> LENGTH: 10
<212> TYPE: DNA
<213> ORGANISM: Zea mays

<400> SEQUENCE: 92
cgctgggcat                                                          10

<210> SEQ ID NO 93
```

```
<211> LENGTH: 10
<212> TYPE: DNA
<213> ORGANISM: Zea mays

<400> SEQUENCE: 93
tagtagaggt                                                            10

<210> SEQ ID NO 94
<211> LENGTH: 10
<212> TYPE: DNA
<213> ORGANISM: Zea mays

<400> SEQUENCE: 94
tggtgaaggt                                                            10

<210> SEQ ID NO 95
<211> LENGTH: 10
<212> TYPE: DNA
<213> ORGANISM: Zea mays

<400> SEQUENCE: 95
tgctggacgt                                                            10

<210> SEQ ID NO 96
<211> LENGTH: 10
<212> TYPE: DNA
<213> ORGANISM: Zea mays

<400> SEQUENCE: 96
cgctgaacgt                                                            10

<210> SEQ ID NO 97
<211> LENGTH: 10
<212> TYPE: DNA
<213> ORGANISM: Zea mays

<400> SEQUENCE: 97
cggaagacat                                                            10

<210> SEQ ID NO 98
<211> LENGTH: 10
<212> TYPE: DNA
<213> ORGANISM: Zea mays

<400> SEQUENCE: 98
tactggaggt                                                            10

<210> SEQ ID NO 99
<211> LENGTH: 10
<212> TYPE: DNA
<213> ORGANISM: Zea mays

<400> SEQUENCE: 99
tgctggggat                                                            10

<210> SEQ ID NO 100
<211> LENGTH: 10
<212> TYPE: DNA
<213> ORGANISM: Zea mays

<400> SEQUENCE: 100
tggtggagat                                                            10
```

```
<210> SEQ ID NO 101
<211> LENGTH: 10
<212> TYPE: DNA
<213> ORGANISM: Zea mays

<400> SEQUENCE: 101
tggtggggat                                                            10

<210> SEQ ID NO 102
<211> LENGTH: 10
<212> TYPE: DNA
<213> ORGANISM: Zea mays

<400> SEQUENCE: 102
cagaaggcat                                                            10

<210> SEQ ID NO 103
<211> LENGTH: 10
<212> TYPE: DNA
<213> ORGANISM: Zea mays

<400> SEQUENCE: 103
cgctggacat                                                            10

<210> SEQ ID NO 104
<211> LENGTH: 10
<212> TYPE: DNA
<213> ORGANISM: Zea mays

<400> SEQUENCE: 104
tagtggagac                                                            10

<210> SEQ ID NO 105
<211> LENGTH: 10
<212> TYPE: DNA
<213> ORGANISM: Zea mays

<400> SEQUENCE: 105
tgcaagaggt                                                            10

<210> SEQ ID NO 106
<211> LENGTH: 10
<212> TYPE: DNA
<213> ORGANISM: Zea mays

<400> SEQUENCE: 106
gtgcgtgcta                                                            10

<210> SEQ ID NO 107
<211> LENGTH: 10
<212> TYPE: DNA
<213> ORGANISM: Zea mays

<400> SEQUENCE: 107
gtgcatctcg                                                            10

<210> SEQ ID NO 108
<211> LENGTH: 10
<212> TYPE: DNA
<213> ORGANISM: Zea mays

<400> SEQUENCE: 108
gtgcatgcta                                                            10
```

```
<210> SEQ ID NO 109
<211> LENGTH: 10
<212> TYPE: DNA
<213> ORGANISM: Zea mays

<400> SEQUENCE: 109
gcgcatctcg                                                            10

<210> SEQ ID NO 110
<211> LENGTH: 10
<212> TYPE: DNA
<213> ORGANISM: Zea mays

<400> SEQUENCE: 110
gtgcatgtca                                                            10

<210> SEQ ID NO 111
<211> LENGTH: 10
<212> TYPE: DNA
<213> ORGANISM: Zea mays

<400> SEQUENCE: 111
gtgcatgctg                                                            10

<210> SEQ ID NO 112
<211> LENGTH: 10
<212> TYPE: DNA
<213> ORGANISM: Zea mays

<400> SEQUENCE: 112
gcgcatctca                                                            10

<210> SEQ ID NO 113
<211> LENGTH: 10
<212> TYPE: DNA
<213> ORGANISM: Zea mays

<400> SEQUENCE: 113
ccgtatgcta                                                            10

<210> SEQ ID NO 114
<211> LENGTH: 10
<212> TYPE: DNA
<213> ORGANISM: Zea mays

<400> SEQUENCE: 114
gcgcatcctg                                                            10

<210> SEQ ID NO 115
<211> LENGTH: 10
<212> TYPE: DNA
<213> ORGANISM: Zea mays

<400> SEQUENCE: 115
gcgtatctcg                                                            10

<210> SEQ ID NO 116
<211> LENGTH: 10
<212> TYPE: DNA
<213> ORGANISM: Zea mays

<400> SEQUENCE: 116
gcgcatgcta                                                            10
```

```
<210> SEQ ID NO 117
<211> LENGTH: 10
<212> TYPE: DNA
<213> ORGANISM: Zea mays

<400> SEQUENCE: 117
gtgtgcgcta                                                          10

<210> SEQ ID NO 118
<211> LENGTH: 10
<212> TYPE: DNA
<213> ORGANISM: Zea mays

<400> SEQUENCE: 118
gcgcatgtta                                                          10

<210> SEQ ID NO 119
<211> LENGTH: 10
<212> TYPE: DNA
<213> ORGANISM: Zea mays

<400> SEQUENCE: 119
gtgtatgtca                                                          10

<210> SEQ ID NO 120
<211> LENGTH: 10
<212> TYPE: DNA
<213> ORGANISM: Zea mays

<400> SEQUENCE: 120
gtgcatgcca                                                          10

<210> SEQ ID NO 121
<211> LENGTH: 10
<212> TYPE: DNA
<213> ORGANISM: Zea mays

<400> SEQUENCE: 121
ccgtatctcg                                                          10

<210> SEQ ID NO 122
<211> LENGTH: 10
<212> TYPE: DNA
<213> ORGANISM: Zea mays

<400> SEQUENCE: 122
gcgcatgccg                                                          10

<210> SEQ ID NO 123
<211> LENGTH: 10
<212> TYPE: DNA
<213> ORGANISM: Zea mays

<400> SEQUENCE: 123
gcgcatgcca                                                          10

<210> SEQ ID NO 124
<211> LENGTH: 10
<212> TYPE: DNA
<213> ORGANISM: Zea mays

<400> SEQUENCE: 124
```
ccgcatgtcg                                                                10

<210> SEQ ID NO 125
<211> LENGTH: 10
<212> TYPE: DNA
<213> ORGANISM: Zea mays

<400> SEQUENCE: 125
ccgtatctca                                                                10

<210> SEQ ID NO 126
<211> LENGTH: 10
<212> TYPE: DNA
<213> ORGANISM: Zea mays

<400> SEQUENCE: 126
ctgcatgtca                                                                10

<210> SEQ ID NO 127
<211> LENGTH: 10
<212> TYPE: DNA
<213> ORGANISM: Zea mays

<400> SEQUENCE: 127
gtgcgcgcca                                                                10

<210> SEQ ID NO 128
<211> LENGTH: 10
<212> TYPE: DNA
<213> ORGANISM: Zea mays

<400> SEQUENCE: 128
ctgtgcctcg                                                                10

<210> SEQ ID NO 129
<211> LENGTH: 10
<212> TYPE: DNA
<213> ORGANISM: Zea mays

<400> SEQUENCE: 129
gcacgaggtc                                                                10

<210> SEQ ID NO 130
<211> LENGTH: 10
<212> TYPE: DNA
<213> ORGANISM: Zea mays

<400> SEQUENCE: 130
gcgcgagatc                                                                10

<210> SEQ ID NO 131
<211> LENGTH: 10
<212> TYPE: DNA
<213> ORGANISM: Zea mays

<400> SEQUENCE: 131
acacgaggtc                                                                10

<210> SEQ ID NO 132
<211> LENGTH: 10
<212> TYPE: DNA
<213> ORGANISM: Zea mays

<400> SEQUENCE: 132
acacggaatc 10

<210> SEQ ID NO 133
<211> LENGTH: 10
<212> TYPE: DNA
<213> ORGANISM: Zea mays

<400> SEQUENCE: 133
gcatgaggtc 10

<210> SEQ ID NO 134
<211> LENGTH: 10
<212> TYPE: DNA
<213> ORGANISM: Zea mays

<400> SEQUENCE: 134
acgcgaggtc 10

<210> SEQ ID NO 135
<211> LENGTH: 10
<212> TYPE: DNA
<213> ORGANISM: Zea mays

<400> SEQUENCE: 135
gcgcaaaact 10

<210> SEQ ID NO 136
<211> LENGTH: 10
<212> TYPE: DNA
<213> ORGANISM: Zea mays

<400> SEQUENCE: 136
acgcggggtc 10

<210> SEQ ID NO 137
<211> LENGTH: 10
<212> TYPE: DNA
<213> ORGANISM: Zea mays

<400> SEQUENCE: 137
gcgcggggtc 10

<210> SEQ ID NO 138
<211> LENGTH: 10
<212> TYPE: DNA
<213> ORGANISM: Zea mays

<400> SEQUENCE: 138
gcgcggaatc 10

<210> SEQ ID NO 139
<211> LENGTH: 10
<212> TYPE: DNA
<213> ORGANISM: Zea mays

<400> SEQUENCE: 139
acacggggtc 10

<210> SEQ ID NO 140
<211> LENGTH: 10
<212> TYPE: DNA
<213> ORGANISM: Zea mays

```
<400> SEQUENCE: 140
gcacggaatc                                                          10

<210> SEQ ID NO 141
<211> LENGTH: 10
<212> TYPE: DNA
<213> ORGANISM: Zea mays

<400> SEQUENCE: 141
gcgtgaggtc                                                          10

<210> SEQ ID NO 142
<211> LENGTH: 10
<212> TYPE: DNA
<213> ORGANISM: Zea mays

<400> SEQUENCE: 142
gcgcgaggtc                                                          10

<210> SEQ ID NO 143
<211> LENGTH: 10
<212> TYPE: DNA
<213> ORGANISM: Zea mays

<400> SEQUENCE: 143
gcgcaaagct                                                          10

<210> SEQ ID NO 144
<211> LENGTH: 10
<212> TYPE: DNA
<213> ORGANISM: Zea mays

<400> SEQUENCE: 144
acatggaatc                                                          10

<210> SEQ ID NO 145
<211> LENGTH: 10
<212> TYPE: DNA
<213> ORGANISM: Zea mays

<400> SEQUENCE: 145
tgaaaccgcg                                                          10

<210> SEQ ID NO 146
<211> LENGTH: 10
<212> TYPE: DNA
<213> ORGANISM: Zea mays

<400> SEQUENCE: 146
ggcggttatg                                                          10

<210> SEQ ID NO 147
<211> LENGTH: 10
<212> TYPE: DNA
<213> ORGANISM: Zea mays

<400> SEQUENCE: 147
ggaaaccgca                                                          10

<210> SEQ ID NO 148
<211> LENGTH: 10
<212> TYPE: DNA
<213> ORGANISM: Zea mays
```

```
<400> SEQUENCE: 148
ggcagttatg                                                            10

<210> SEQ ID NO 149
<211> LENGTH: 10
<212> TYPE: DNA
<213> ORGANISM: Zea mays

<400> SEQUENCE: 149
tgaagttatg                                                            10

<210> SEQ ID NO 150
<211> LENGTH: 10
<212> TYPE: DNA
<213> ORGANISM: Zea mays

<400> SEQUENCE: 150
tgcagtcgca                                                            10

<210> SEQ ID NO 151
<211> LENGTH: 10
<212> TYPE: DNA
<213> ORGANISM: Zea mays

<400> SEQUENCE: 151
tgaaactata                                                            10

<210> SEQ ID NO 152
<211> LENGTH: 10
<212> TYPE: DNA
<213> ORGANISM: Zea mays

<400> SEQUENCE: 152
ggcagtcgtg                                                            10

<210> SEQ ID NO 153
<211> LENGTH: 10
<212> TYPE: DNA
<213> ORGANISM: Zea mays

<400> SEQUENCE: 153
taaggccgcg                                                            10

<210> SEQ ID NO 154
<211> LENGTH: 10
<212> TYPE: DNA
<213> ORGANISM: Zea mays

<400> SEQUENCE: 154
tgaagccgtg                                                            10

<210> SEQ ID NO 155
<211> LENGTH: 10
<212> TYPE: DNA
<213> ORGANISM: Zea mays

<400> SEQUENCE: 155
taaggccgtg                                                            10

<210> SEQ ID NO 156
<211> LENGTH: 10
<212> TYPE: DNA
```

<213> ORGANISM: Zea mays

<400> SEQUENCE: 156
ggcaaccgtg                                                           10

<210> SEQ ID NO 157
<211> LENGTH: 10
<212> TYPE: DNA
<213> ORGANISM: Zea mays

<400> SEQUENCE: 157
ggcagtcgcg                                                           10

<210> SEQ ID NO 158
<211> LENGTH: 10
<212> TYPE: DNA
<213> ORGANISM: Zea mays

<400> SEQUENCE: 158
taaggccgta                                                           10

<210> SEQ ID NO 159
<211> LENGTH: 10
<212> TYPE: DNA
<213> ORGANISM: Zea mays

<400> SEQUENCE: 159
tgcagccgtg                                                           10

<210> SEQ ID NO 160
<211> LENGTH: 10
<212> TYPE: DNA
<213> ORGANISM: Zea mays

<400> SEQUENCE: 160
ggaagtcgtg                                                           10

<210> SEQ ID NO 161
<211> LENGTH: 10
<212> TYPE: DNA
<213> ORGANISM: Zea mays

<400> SEQUENCE: 161
taaggccgca                                                           10

<210> SEQ ID NO 162
<211> LENGTH: 10
<212> TYPE: DNA
<213> ORGANISM: Zea mays

<400> SEQUENCE: 162
tgcagccgta                                                           10

<210> SEQ ID NO 163
<211> LENGTH: 10
<212> TYPE: DNA
<213> ORGANISM: Zea mays

<400> SEQUENCE: 163
gacagtcgca                                                           10

<210> SEQ ID NO 164
<211> LENGTH: 10

```
<212> TYPE: DNA
<213> ORGANISM: Zea mays

<400> SEQUENCE: 164
tgaagttata                                                          10

<210> SEQ ID NO 165
<211> LENGTH: 10
<212> TYPE: DNA
<213> ORGANISM: Zea mays

<400> SEQUENCE: 165
tgcagccgcg                                                          10

<210> SEQ ID NO 166
<211> LENGTH: 10
<212> TYPE: DNA
<213> ORGANISM: Zea mays

<400> SEQUENCE: 166
taaggctata                                                          10

<210> SEQ ID NO 167
<211> LENGTH: 10
<212> TYPE: DNA
<213> ORGANISM: Zea mays

<400> SEQUENCE: 167
caattgcgct                                                          10

<210> SEQ ID NO 168
<211> LENGTH: 10
<212> TYPE: DNA
<213> ORGANISM: Zea mays

<400> SEQUENCE: 168
tcgacataac                                                          10

<210> SEQ ID NO 169
<211> LENGTH: 10
<212> TYPE: DNA
<213> ORGANISM: Zea mays

<400> SEQUENCE: 169
tcaacgcact                                                          10

<210> SEQ ID NO 170
<211> LENGTH: 10
<212> TYPE: DNA
<213> ORGANISM: Zea mays

<400> SEQUENCE: 170
tcattgcgct                                                          10

<210> SEQ ID NO 171
<211> LENGTH: 10
<212> TYPE: DNA
<213> ORGANISM: Zea mays

<400> SEQUENCE: 171
cagacgcgcc                                                          10

<210> SEQ ID NO 172
```

```
<211> LENGTH: 10
<212> TYPE: DNA
<213> ORGANISM: Zea mays

<400> SEQUENCE: 172
tcaacgcacc                                                          10

<210> SEQ ID NO 173
<211> LENGTH: 10
<212> TYPE: DNA
<213> ORGANISM: Zea mays

<400> SEQUENCE: 173
tcgacgtgcc                                                          10

<210> SEQ ID NO 174
<211> LENGTH: 10
<212> TYPE: DNA
<213> ORGANISM: Zea mays

<400> SEQUENCE: 174
tcaacgcgcc                                                          10

<210> SEQ ID NO 175
<211> LENGTH: 10
<212> TYPE: DNA
<213> ORGANISM: Zea mays

<400> SEQUENCE: 175
tcaacgcgct                                                          10

<210> SEQ ID NO 176
<211> LENGTH: 10
<212> TYPE: DNA
<213> ORGANISM: Zea mays

<400> SEQUENCE: 176
tcgacataat                                                          10

<210> SEQ ID NO 177
<211> LENGTH: 10
<212> TYPE: DNA
<213> ORGANISM: Zea mays

<400> SEQUENCE: 177
tcgacgcgct                                                          10

<210> SEQ ID NO 178
<211> LENGTH: 10
<212> TYPE: DNA
<213> ORGANISM: Zea mays

<400> SEQUENCE: 178
tcgacgcgcc                                                          10

<210> SEQ ID NO 179
<211> LENGTH: 10
<212> TYPE: DNA
<213> ORGANISM: Zea mays

<400> SEQUENCE: 179
tcaacgcgac                                                          10
```

```
<210> SEQ ID NO 180
<211> LENGTH: 10
<212> TYPE: DNA
<213> ORGANISM: Zea mays

<400> SEQUENCE: 180
tcgacatgcc                                                            10

<210> SEQ ID NO 181
<211> LENGTH: 10
<212> TYPE: DNA
<213> ORGANISM: Zea mays

<400> SEQUENCE: 181
tcaacacact                                                            10

<210> SEQ ID NO 182
<211> LENGTH: 10
<212> TYPE: DNA
<213> ORGANISM: Zea mays

<400> SEQUENCE: 182
tcgacgcgac                                                            10

<210> SEQ ID NO 183
<211> LENGTH: 10
<212> TYPE: DNA
<213> ORGANISM: Zea mays

<400> SEQUENCE: 183
caattgcgcc                                                            10

<210> SEQ ID NO 184
<211> LENGTH: 10
<212> TYPE: DNA
<213> ORGANISM: Zea mays

<400> SEQUENCE: 184
tcaacgcaat                                                            10

<210> SEQ ID NO 185
<211> LENGTH: 10
<212> TYPE: DNA
<213> ORGANISM: Zea mays

<400> SEQUENCE: 185
ttccgatgtg                                                            10

<210> SEQ ID NO 186
<211> LENGTH: 10
<212> TYPE: DNA
<213> ORGANISM: Zea mays

<400> SEQUENCE: 186
ttttgatgta                                                            10

<210> SEQ ID NO 187
<211> LENGTH: 10
<212> TYPE: DNA
<213> ORGANISM: Zea mays

<400> SEQUENCE: 187
tcttgatgtg                                                            10
```

```
<210> SEQ ID NO 188
<211> LENGTH: 10
<212> TYPE: DNA
<213> ORGANISM: Zea mays

<400> SEQUENCE: 188
tcttgctgcg                                                          10

<210> SEQ ID NO 189
<211> LENGTH: 10
<212> TYPE: DNA
<213> ORGANISM: Zea mays

<400> SEQUENCE: 189
tcctacagta                                                          10

<210> SEQ ID NO 190
<211> LENGTH: 10
<212> TYPE: DNA
<213> ORGANISM: Zea mays

<400> SEQUENCE: 190
tcctacagtg                                                          10

<210> SEQ ID NO 191
<211> LENGTH: 10
<212> TYPE: DNA
<213> ORGANISM: Zea mays

<400> SEQUENCE: 191
ttccaatgtg                                                          10

<210> SEQ ID NO 192
<211> LENGTH: 10
<212> TYPE: DNA
<213> ORGANISM: Zea mays

<400> SEQUENCE: 192
ttccactgtg                                                          10

<210> SEQ ID NO 193
<211> LENGTH: 10
<212> TYPE: DNA
<213> ORGANISM: Zea mays

<400> SEQUENCE: 193
ttccgctgcg                                                          10

<210> SEQ ID NO 194
<211> LENGTH: 10
<212> TYPE: DNA
<213> ORGANISM: Zea mays

<400> SEQUENCE: 194
tcttaatgtg                                                          10

<210> SEQ ID NO 195
<211> LENGTH: 10
<212> TYPE: DNA
<213> ORGANISM: Zea mays

<400> SEQUENCE: 195
ccttgcaatg                                                          10
```

```
<210> SEQ ID NO 196
<211> LENGTH: 10
<212> TYPE: DNA
<213> ORGANISM: Zea mays

<400> SEQUENCE: 196
ttttgatgtg                                                          10

<210> SEQ ID NO 197
<211> LENGTH: 10
<212> TYPE: DNA
<213> ORGANISM: Zea mays

<400> SEQUENCE: 197
tttcgatgtg                                                          10

<210> SEQ ID NO 198
<211> LENGTH: 10
<212> TYPE: DNA
<213> ORGANISM: Zea mays

<400> SEQUENCE: 198
tcctactgtg                                                          10

<210> SEQ ID NO 199
<211> LENGTH: 10
<212> TYPE: DNA
<213> ORGANISM: Zea mays

<400> SEQUENCE: 199
tcctgatgtg                                                          10

<210> SEQ ID NO 200
<211> LENGTH: 10
<212> TYPE: DNA
<213> ORGANISM: Zea mays

<400> SEQUENCE: 200
tcctgctgcg                                                          10

<210> SEQ ID NO 201
<211> LENGTH: 10
<212> TYPE: DNA
<213> ORGANISM: Zea mays

<400> SEQUENCE: 201
tcttgcaaca                                                          10

<210> SEQ ID NO 202
<211> LENGTH: 10
<212> TYPE: DNA
<213> ORGANISM: Zea mays

<400> SEQUENCE: 202
tcttacaatg                                                          10

<210> SEQ ID NO 203
<211> LENGTH: 10
<212> TYPE: DNA
<213> ORGANISM: Zea mays

<400> SEQUENCE: 203
```
tcctaatgtg                                                                  10

<210> SEQ ID NO 204
<211> LENGTH: 10
<212> TYPE: DNA
<213> ORGANISM: Zea mays

<400> SEQUENCE: 204
tcttgcagtg                                                                  10

<210> SEQ ID NO 205
<211> LENGTH: 10
<212> TYPE: DNA
<213> ORGANISM: Zea mays

<400> SEQUENCE: 205
ttctgatgtg                                                                  10

<210> SEQ ID NO 206
<211> LENGTH: 10
<212> TYPE: DNA
<213> ORGANISM: Zea mays

<400> SEQUENCE: 206
ccttgcaaca                                                                  10

<210> SEQ ID NO 207
<211> LENGTH: 10
<212> TYPE: DNA
<213> ORGANISM: Zea mays

<400> SEQUENCE: 207
tcctgcagtg                                                                  10

<210> SEQ ID NO 208
<211> LENGTH: 10
<212> TYPE: DNA
<213> ORGANISM: Zea mays

<400> SEQUENCE: 208
tcctaatgta                                                                  10

<210> SEQ ID NO 209
<211> LENGTH: 10
<212> TYPE: DNA
<213> ORGANISM: Zea mays

<400> SEQUENCE: 209
ttctgatgta                                                                  10

<210> SEQ ID NO 210
<211> LENGTH: 10
<212> TYPE: DNA
<213> ORGANISM: Zea mays

<400> SEQUENCE: 210
ccccatctca                                                                  10

<210> SEQ ID NO 211
<211> LENGTH: 10
<212> TYPE: DNA
<213> ORGANISM: Zea mays

<400> SEQUENCE: 211

| | |
|---|---|
| ccccagcgtg | 10 |

<210> SEQ ID NO 212
<211> LENGTH: 10
<212> TYPE: DNA
<213> ORGANISM: Zea mays

<400> SEQUENCE: 212

| | |
|---|---|
| ctcggtctca | 10 |

<210> SEQ ID NO 213
<211> LENGTH: 10
<212> TYPE: DNA
<213> ORGANISM: Zea mays

<400> SEQUENCE: 213

| | |
|---|---|
| ccccatcgta | 10 |

<210> SEQ ID NO 214
<211> LENGTH: 10
<212> TYPE: DNA
<213> ORGANISM: Zea mays

<400> SEQUENCE: 214

| | |
|---|---|
| ccccgtcgtg | 10 |

<210> SEQ ID NO 215
<211> LENGTH: 10
<212> TYPE: DNA
<213> ORGANISM: Zea mays

<400> SEQUENCE: 215

| | |
|---|---|
| tctcatcgta | 10 |

<210> SEQ ID NO 216
<211> LENGTH: 10
<212> TYPE: DNA
<213> ORGANISM: Zea mays

<400> SEQUENCE: 216

| | |
|---|---|
| tcccagcgtg | 10 |

<210> SEQ ID NO 217
<211> LENGTH: 10
<212> TYPE: DNA
<213> ORGANISM: Zea mays

<400> SEQUENCE: 217

| | |
|---|---|
| cctcatctcg | 10 |

<210> SEQ ID NO 218
<211> LENGTH: 10
<212> TYPE: DNA
<213> ORGANISM: Zea mays

<400> SEQUENCE: 218

| | |
|---|---|
| ctcgggcgtg | 10 |

<210> SEQ ID NO 219
<211> LENGTH: 10
<212> TYPE: DNA
<213> ORGANISM: Zea mays

```
<400> SEQUENCE: 219
cctcatcgta                                                          10

<210> SEQ ID NO 220
<211> LENGTH: 10
<212> TYPE: DNA
<213> ORGANISM: Zea mays

<400> SEQUENCE: 220
tcccatctca                                                          10

<210> SEQ ID NO 221
<211> LENGTH: 10
<212> TYPE: DNA
<213> ORGANISM: Zea mays

<400> SEQUENCE: 221
cctcatctca                                                          10

<210> SEQ ID NO 222
<211> LENGTH: 10
<212> TYPE: DNA
<213> ORGANISM: Zea mays

<400> SEQUENCE: 222
ctagagtgct                                                          10

<210> SEQ ID NO 223
<211> LENGTH: 10
<212> TYPE: DNA
<213> ORGANISM: Zea mays

<400> SEQUENCE: 223
taacaccgct                                                          10

<210> SEQ ID NO 224
<211> LENGTH: 10
<212> TYPE: DNA
<213> ORGANISM: Zea mays

<400> SEQUENCE: 224
ctcggccgcc                                                          10

<210> SEQ ID NO 225
<211> LENGTH: 10
<212> TYPE: DNA
<213> ORGANISM: Zea mays

<400> SEQUENCE: 225
taacgcctcc                                                          10

<210> SEQ ID NO 226
<211> LENGTH: 10
<212> TYPE: DNA
<213> ORGANISM: Zea mays

<400> SEQUENCE: 226
taccgcctgc                                                          10

<210> SEQ ID NO 227
<211> LENGTH: 10
<212> TYPE: DNA
<213> ORGANISM: Zea mays
```

```
<400> SEQUENCE: 227
ctacgccgct                                                              10

<210> SEQ ID NO 228
<211> LENGTH: 10
<212> TYPE: DNA
<213> ORGANISM: Zea mays

<400> SEQUENCE: 228
taacacctcc                                                              10

<210> SEQ ID NO 229
<211> LENGTH: 10
<212> TYPE: DNA
<213> ORGANISM: Zea mays

<400> SEQUENCE: 229
taaggcctct                                                              10

<210> SEQ ID NO 230
<211> LENGTH: 10
<212> TYPE: DNA
<213> ORGANISM: Zea mays

<400> SEQUENCE: 230
taacgccgct                                                              10

<210> SEQ ID NO 231
<211> LENGTH: 10
<212> TYPE: DNA
<213> ORGANISM: Zea mays

<400> SEQUENCE: 231
taacgctgct                                                              10

<210> SEQ ID NO 232
<211> LENGTH: 10
<212> TYPE: DNA
<213> ORGANISM: Zea mays

<400> SEQUENCE: 232
taacgctgcc                                                              10

<210> SEQ ID NO 233
<211> LENGTH: 10
<212> TYPE: DNA
<213> ORGANISM: Zea mays

<400> SEQUENCE: 233
ctagagttct                                                              10

<210> SEQ ID NO 234
<211> LENGTH: 10
<212> TYPE: DNA
<213> ORGANISM: Zea mays

<400> SEQUENCE: 234
taacgctggc                                                              10

<210> SEQ ID NO 235
<211> LENGTH: 10
<212> TYPE: DNA
```

<213> ORGANISM: Zea mays

<400> SEQUENCE: 235
taacactgct                                                          10

<210> SEQ ID NO 236
<211> LENGTH: 10
<212> TYPE: DNA
<213> ORGANISM: Zea mays

<400> SEQUENCE: 236
taacaccgcc                                                          10

<210> SEQ ID NO 237
<211> LENGTH: 10
<212> TYPE: DNA
<213> ORGANISM: Zea mays

<400> SEQUENCE: 237
taacaccgcc                                                          10

<210> SEQ ID NO 238
<211> LENGTH: 10
<212> TYPE: DNA
<213> ORGANISM: Zea mays

<400> SEQUENCE: 238
caccgcctgc                                                          10

<210> SEQ ID NO 239
<211> LENGTH: 10
<212> TYPE: DNA
<213> ORGANISM: Zea mays

<400> SEQUENCE: 239
caacgctgcc                                                          10

<210> SEQ ID NO 240
<211> LENGTH: 10
<212> TYPE: DNA
<213> ORGANISM: Zea mays

<400> SEQUENCE: 240
ccactagtgc                                                          10

<210> SEQ ID NO 241
<211> LENGTH: 10
<212> TYPE: DNA
<213> ORGANISM: Zea mays

<400> SEQUENCE: 241
ccactaacat                                                          10

<210> SEQ ID NO 242
<211> LENGTH: 10
<212> TYPE: DNA
<213> ORGANISM: Zea mays

<400> SEQUENCE: 242
ccactgatgc                                                          10

<210> SEQ ID NO 243
<211> LENGTH: 10

```
<212> TYPE: DNA
<213> ORGANISM: Zea mays

<400> SEQUENCE: 243
ccactggtgc                                                              10

<210> SEQ ID NO 244
<211> LENGTH: 10
<212> TYPE: DNA
<213> ORGANISM: Zea mays

<400> SEQUENCE: 244
ccactagcgc                                                              10

<210> SEQ ID NO 245
<211> LENGTH: 10
<212> TYPE: DNA
<213> ORGANISM: Zea mays

<400> SEQUENCE: 245
tcactggtgc                                                              10

<210> SEQ ID NO 246
<211> LENGTH: 10
<212> TYPE: DNA
<213> ORGANISM: Zea mays

<400> SEQUENCE: 246
ccactaatgc                                                              10

<210> SEQ ID NO 247
<211> LENGTH: 10
<212> TYPE: DNA
<213> ORGANISM: Zea mays

<400> SEQUENCE: 247
tcactaatgc                                                              10

<210> SEQ ID NO 248
<211> LENGTH: 10
<212> TYPE: DNA
<213> ORGANISM: Zea mays

<400> SEQUENCE: 248
tcactgacgc                                                              10

<210> SEQ ID NO 249
<211> LENGTH: 10
<212> TYPE: DNA
<213> ORGANISM: Zea mays

<400> SEQUENCE: 249
gcagtgcagt                                                              10

<210> SEQ ID NO 250
<211> LENGTH: 10
<212> TYPE: DNA
<213> ORGANISM: Zea mays

<400> SEQUENCE: 250
gccgtgcgat                                                              10

<210> SEQ ID NO 251
```

-continued

<211> LENGTH: 10
<212> TYPE: DNA
<213> ORGANISM: Zea mays

<400> SEQUENCE: 251
atcgtgcaat                                                                10

<210> SEQ ID NO 252
<211> LENGTH: 10
<212> TYPE: DNA
<213> ORGANISM: Zea mays

<400> SEQUENCE: 252
gcaatgcggt                                                                10

<210> SEQ ID NO 253
<211> LENGTH: 10
<212> TYPE: DNA
<213> ORGANISM: Zea mays

<400> SEQUENCE: 253
gccacatgac                                                                10

<210> SEQ ID NO 254
<211> LENGTH: 10
<212> TYPE: DNA
<213> ORGANISM: Zea mays

<400> SEQUENCE: 254
gcagtgcaat                                                                10

<210> SEQ ID NO 255
<211> LENGTH: 10
<212> TYPE: DNA
<213> ORGANISM: Zea mays

<400> SEQUENCE: 255
atcacatgac                                                                10

<210> SEQ ID NO 256
<211> LENGTH: 10
<212> TYPE: DNA
<213> ORGANISM: Zea mays

<400> SEQUENCE: 256
gtcgtgcgat                                                                10

<210> SEQ ID NO 257
<211> LENGTH: 10
<212> TYPE: DNA
<213> ORGANISM: Zea mays

<400> SEQUENCE: 257
atcgcgtgac                                                                10

<210> SEQ ID NO 258
<211> LENGTH: 10
<212> TYPE: DNA
<213> ORGANISM: Zea mays

<400> SEQUENCE: 258
gcagtgtagt                                                                10

```
<210> SEQ ID NO 259
<211> LENGTH: 10
<212> TYPE: DNA
<213> ORGANISM: Zea mays

<400> SEQUENCE: 259
gccgtgcaat                                                            10

<210> SEQ ID NO 260
<211> LENGTH: 10
<212> TYPE: DNA
<213> ORGANISM: Zea mays

<400> SEQUENCE: 260
atagtgcagt                                                            10

<210> SEQ ID NO 261
<211> LENGTH: 10
<212> TYPE: DNA
<213> ORGANISM: Zea mays

<400> SEQUENCE: 261
agccgccctc                                                            10

<210> SEQ ID NO 262
<211> LENGTH: 10
<212> TYPE: DNA
<213> ORGANISM: Zea mays

<400> SEQUENCE: 262
agccgccctt                                                            10

<210> SEQ ID NO 263
<211> LENGTH: 10
<212> TYPE: DNA
<213> ORGANISM: Zea mays

<400> SEQUENCE: 263
agctccagtc                                                            10

<210> SEQ ID NO 264
<211> LENGTH: 10
<212> TYPE: DNA
<213> ORGANISM: Zea mays

<400> SEQUENCE: 264
agccgcagtc                                                            10

<210> SEQ ID NO 265
<211> LENGTH: 10
<212> TYPE: DNA
<213> ORGANISM: Zea mays

<400> SEQUENCE: 265
agctgcactc                                                            10

<210> SEQ ID NO 266
<211> LENGTH: 10
<212> TYPE: DNA
<213> ORGANISM: Zea mays

<400> SEQUENCE: 266
agctccacac                                                            10
```

```
<210> SEQ ID NO 267
<211> LENGTH: 10
<212> TYPE: DNA
<213> ORGANISM: Zea mays

<400> SEQUENCE: 267
agctccagat                                                          10

<210> SEQ ID NO 268
<211> LENGTH: 10
<212> TYPE: DNA
<213> ORGANISM: Zea mays

<400> SEQUENCE: 268
agctccactc                                                          10

<210> SEQ ID NO 269
<211> LENGTH: 10
<212> TYPE: DNA
<213> ORGANISM: Zea mays

<400> SEQUENCE: 269
agcccccgac                                                          10

<210> SEQ ID NO 270
<211> LENGTH: 10
<212> TYPE: DNA
<213> ORGANISM: Zea mays

<400> SEQUENCE: 270
agccgcccac                                                          10

<210> SEQ ID NO 271
<211> LENGTH: 10
<212> TYPE: DNA
<213> ORGANISM: Zea mays

<400> SEQUENCE: 271
ggctccacac                                                          10

<210> SEQ ID NO 272
<211> LENGTH: 10
<212> TYPE: DNA
<213> ORGANISM: Zea mays

<400> SEQUENCE: 272
gtacgtccat                                                          10

<210> SEQ ID NO 273
<211> LENGTH: 10
<212> TYPE: DNA
<213> ORGANISM: Zea mays

<400> SEQUENCE: 273
agcccccgtc                                                          10

<210> SEQ ID NO 274
<211> LENGTH: 10
<212> TYPE: DNA
<213> ORGANISM: Zea mays

<400> SEQUENCE: 274
agctccagtt                                                          10
```

```
<210> SEQ ID NO 275
<211> LENGTH: 10
<212> TYPE: DNA
<213> ORGANISM: Zea mays

<400> SEQUENCE: 275
agccgccgtt                                                          10

<210> SEQ ID NO 276
<211> LENGTH: 10
<212> TYPE: DNA
<213> ORGANISM: Zea mays

<400> SEQUENCE: 276
agccgccgtc                                                          10

<210> SEQ ID NO 277
<211> LENGTH: 10
<212> TYPE: DNA
<213> ORGANISM: Zea mays

<400> SEQUENCE: 277
gtccgtcgac                                                          10

<210> SEQ ID NO 278
<211> LENGTH: 10
<212> TYPE: DNA
<213> ORGANISM: Zea mays

<400> SEQUENCE: 278
aggatctaaa                                                          10

<210> SEQ ID NO 279
<211> LENGTH: 10
<212> TYPE: DNA
<213> ORGANISM: Zea mays

<400> SEQUENCE: 279
catacctaaa                                                          10

<210> SEQ ID NO 280
<211> LENGTH: 10
<212> TYPE: DNA
<213> ORGANISM: Zea mays

<400> SEQUENCE: 280
cagatctaaa                                                          10

<210> SEQ ID NO 281
<211> LENGTH: 10
<212> TYPE: DNA
<213> ORGANISM: Zea mays

<400> SEQUENCE: 281
cggatctaaa                                                          10

<210> SEQ ID NO 282
<211> LENGTH: 10
<212> TYPE: DNA
<213> ORGANISM: Zea mays

<400> SEQUENCE: 282
```
aagatagcgg                                                          10

<210> SEQ ID NO 283
<211> LENGTH: 10
<212> TYPE: DNA
<213> ORGANISM: Zea mays

<400> SEQUENCE: 283
aagatctaaa                                                          10

<210> SEQ ID NO 284
<211> LENGTH: 10
<212> TYPE: DNA
<213> ORGANISM: Zea mays

<400> SEQUENCE: 284
cagatagcgg                                                          10

<210> SEQ ID NO 285
<211> LENGTH: 10
<212> TYPE: DNA
<213> ORGANISM: Zea mays

<400> SEQUENCE: 285
aagttctaaa                                                          10

<210> SEQ ID NO 286
<211> LENGTH: 10
<212> TYPE: DNA
<213> ORGANISM: Zea mays

<400> SEQUENCE: 286
aggttctaaa                                                          10

<210> SEQ ID NO 287
<211> LENGTH: 10
<212> TYPE: DNA
<213> ORGANISM: Zea mays

<400> SEQUENCE: 287
catatctaaa                                                          10

<210> SEQ ID NO 288
<211> LENGTH: 10
<212> TYPE: DNA
<213> ORGANISM: Zea mays

<400> SEQUENCE: 288
aggttagcgg                                                          10

<210> SEQ ID NO 289
<211> LENGTH: 10
<212> TYPE: DNA
<213> ORGANISM: Zea mays

<400> SEQUENCE: 289
aatatctaaa                                                          10

<210> SEQ ID NO 290
<211> LENGTH: 10
<212> TYPE: DNA
<213> ORGANISM: Zea mays

<400> SEQUENCE: 290
cggttagcgg                                                          10

<210> SEQ ID NO 291
<211> LENGTH: 10
<212> TYPE: DNA
<213> ORGANISM: Zea mays

<400> SEQUENCE: 291
catacagcgg                                                          10

<210> SEQ ID NO 292
<211> LENGTH: 10
<212> TYPE: DNA
<213> ORGANISM: Zea mays

<400> SEQUENCE: 292
aatacctaaa                                                          10

<210> SEQ ID NO 293
<211> LENGTH: 10
<212> TYPE: DNA
<213> ORGANISM: Glycine max

<400> SEQUENCE: 293
aggaaaattt                                                          10

<210> SEQ ID NO 294
<211> LENGTH: 10
<212> TYPE: DNA
<213> ORGANISM: Glycine max

<400> SEQUENCE: 294
gaaggttacg                                                          10

<210> SEQ ID NO 295
<211> LENGTH: 10
<212> TYPE: DNA
<213> ORGANISM: Glycine max

<400> SEQUENCE: 295
gggaaaattg                                                          10

<210> SEQ ID NO 296
<211> LENGTH: 10
<212> TYPE: DNA
<213> ORGANISM: Glycine max

<400> SEQUENCE: 296
aaaggttacg                                                          10

<210> SEQ ID NO 297
<211> LENGTH: 10
<212> TYPE: DNA
<213> ORGANISM: Glycine max

<400> SEQUENCE: 297
gaaagtattg                                                          10

<210> SEQ ID NO 298
<211> LENGTH: 10
<212> TYPE: DNA
<213> ORGANISM: Glycine max

```
<400> SEQUENCE: 298
gaaagttact                                                            10

<210> SEQ ID NO 299
<211> LENGTH: 10
<212> TYPE: DNA
<213> ORGANISM: Glycine max

<400> SEQUENCE: 299
agaggactaa                                                            10

<210> SEQ ID NO 300
<211> LENGTH: 10
<212> TYPE: DNA
<213> ORGANISM: Glycine max

<400> SEQUENCE: 300
agaggactga                                                            10

<210> SEQ ID NO 301
<211> LENGTH: 10
<212> TYPE: DNA
<213> ORGANISM: Glycine max

<400> SEQUENCE: 301
gataagccag                                                            10

<210> SEQ ID NO 302
<211> LENGTH: 10
<212> TYPE: DNA
<213> ORGANISM: Glycine max

<400> SEQUENCE: 302
agaggaccga                                                            10

<210> SEQ ID NO 303
<211> LENGTH: 10
<212> TYPE: DNA
<213> ORGANISM: Glycine max

<400> SEQUENCE: 303
agaaggccgg                                                            10

<210> SEQ ID NO 304
<211> LENGTH: 10
<212> TYPE: DNA
<213> ORGANISM: Glycine max

<400> SEQUENCE: 304
agaggactgg                                                            10

<210> SEQ ID NO 305
<211> LENGTH: 10
<212> TYPE: DNA
<213> ORGANISM: Glycine max

<400> SEQUENCE: 305
agtaggccga                                                            10

<210> SEQ ID NO 306
<211> LENGTH: 10
<212> TYPE: DNA
<213> ORGANISM: Glycine max
```

```
<400> SEQUENCE: 306
agaaggccga                                                            10

<210> SEQ ID NO 307
<211> LENGTH: 10
<212> TYPE: DNA
<213> ORGANISM: Glycine max

<400> SEQUENCE: 307
gataaggcag                                                            10

<210> SEQ ID NO 308
<211> LENGTH: 10
<212> TYPE: DNA
<213> ORGANISM: Glycine max

<400> SEQUENCE: 308
aatgggctga                                                            10

<210> SEQ ID NO 309
<211> LENGTH: 10
<212> TYPE: DNA
<213> ORGANISM: Glycine max

<400> SEQUENCE: 309
agagggccga                                                            10

<210> SEQ ID NO 310
<211> LENGTH: 10
<212> TYPE: DNA
<213> ORGANISM: Glycine max

<400> SEQUENCE: 310
ggaaagccgg                                                            10

<210> SEQ ID NO 311
<211> LENGTH: 10
<212> TYPE: DNA
<213> ORGANISM: Glycine max

<400> SEQUENCE: 311
agagggccgg                                                            10

<210> SEQ ID NO 312
<211> LENGTH: 10
<212> TYPE: DNA
<213> ORGANISM: Glycine max

<400> SEQUENCE: 312
gaaaaggtag                                                            10

<210> SEQ ID NO 313
<211> LENGTH: 10
<212> TYPE: DNA
<213> ORGANISM: Glycine max

<400> SEQUENCE: 313
gaaaggccga                                                            10

<210> SEQ ID NO 314
<211> LENGTH: 10
<212> TYPE: DNA
```

<213> ORGANISM: Glycine max

<400> SEQUENCE: 314
agaaagccag                                                          10

<210> SEQ ID NO 315
<211> LENGTH: 10
<212> TYPE: DNA
<213> ORGANISM: Glycine max

<400> SEQUENCE: 315
agagggctga                                                          10

<210> SEQ ID NO 316
<211> LENGTH: 10
<212> TYPE: DNA
<213> ORGANISM: Glycine max

<400> SEQUENCE: 316
aataaggcag                                                          10

<210> SEQ ID NO 317
<211> LENGTH: 10
<212> TYPE: DNA
<213> ORGANISM: Glycine max

<400> SEQUENCE: 317
gatagggcga                                                          10

<210> SEQ ID NO 318
<211> LENGTH: 10
<212> TYPE: DNA
<213> ORGANISM: Glycine max

<400> SEQUENCE: 318
gataggccga                                                          10

<210> SEQ ID NO 319
<211> LENGTH: 10
<212> TYPE: DNA
<213> ORGANISM: Glycine max

<400> SEQUENCE: 319
agtggactga                                                          10

<210> SEQ ID NO 320
<211> LENGTH: 10
<212> TYPE: DNA
<213> ORGANISM: Glycine max

<400> SEQUENCE: 320
ggaaggccgg                                                          10

<210> SEQ ID NO 321
<211> LENGTH: 10
<212> TYPE: DNA
<213> ORGANISM: Glycine max

<400> SEQUENCE: 321
agaaggctgg                                                          10

<210> SEQ ID NO 322
<211> LENGTH: 10

-continued

<212> TYPE: DNA
<213> ORGANISM: Glycine max

<400> SEQUENCE: 322
ggaggggcag                                                              10

<210> SEQ ID NO 323
<211> LENGTH: 10
<212> TYPE: DNA
<213> ORGANISM: Glycine max

<400> SEQUENCE: 323
agaagaccga                                                              10

<210> SEQ ID NO 324
<211> LENGTH: 10
<212> TYPE: DNA
<213> ORGANISM: Glycine max

<400> SEQUENCE: 324
ttatactata                                                              10

<210> SEQ ID NO 325
<211> LENGTH: 10
<212> TYPE: DNA
<213> ORGANISM: Glycine max

<400> SEQUENCE: 325
gcgcgacata                                                              10

<210> SEQ ID NO 326
<211> LENGTH: 10
<212> TYPE: DNA
<213> ORGANISM: Glycine max

<400> SEQUENCE: 326
ttacaccata                                                              10

<210> SEQ ID NO 327
<211> LENGTH: 10
<212> TYPE: DNA
<213> ORGANISM: Glycine max

<400> SEQUENCE: 327
gcgtactctg                                                              10

<210> SEQ ID NO 328
<211> LENGTH: 10
<212> TYPE: DNA
<213> ORGANISM: Glycine max

<400> SEQUENCE: 328
ttacaaccta                                                              10

<210> SEQ ID NO 329
<211> LENGTH: 10
<212> TYPE: DNA
<213> ORGANISM: Glycine max

<400> SEQUENCE: 329
ttacaacata                                                              10

<210> SEQ ID NO 330

```
<211> LENGTH: 10
<212> TYPE: DNA
<213> ORGANISM: Glycine max

<400> SEQUENCE: 330
ttacactata                                                          10

<210> SEQ ID NO 331
<211> LENGTH: 10
<212> TYPE: DNA
<213> ORGANISM: Glycine max

<400> SEQUENCE: 331
gtgcgacata                                                          10

<210> SEQ ID NO 332
<211> LENGTH: 10
<212> TYPE: DNA
<213> ORGANISM: Glycine max

<400> SEQUENCE: 332
ttataacata                                                          10

<210> SEQ ID NO 333
<211> LENGTH: 10
<212> TYPE: DNA
<213> ORGANISM: Glycine max

<400> SEQUENCE: 333
ttacgaccca                                                          10

<210> SEQ ID NO 334
<211> LENGTH: 10
<212> TYPE: DNA
<213> ORGANISM: Glycine max

<400> SEQUENCE: 334
ttataatata                                                          10

<210> SEQ ID NO 335
<211> LENGTH: 10
<212> TYPE: DNA
<213> ORGANISM: Glycine max

<400> SEQUENCE: 335
gtatactata                                                          10

<210> SEQ ID NO 336
<211> LENGTH: 10
<212> TYPE: DNA
<213> ORGANISM: Glycine max

<400> SEQUENCE: 336
ttacaccta                                                           10

<210> SEQ ID NO 337
<211> LENGTH: 10
<212> TYPE: DNA
<213> ORGANISM: Glycine max

<400> SEQUENCE: 337
ttataccata                                                          10
```

```
<210> SEQ ID NO 338
<211> LENGTH: 10
<212> TYPE: DNA
<213> ORGANISM: Glycine max

<400> SEQUENCE: 338
ccggagatct                                                          10

<210> SEQ ID NO 339
<211> LENGTH: 10
<212> TYPE: DNA
<213> ORGANISM: Glycine max

<400> SEQUENCE: 339
tcacaaagct                                                          10

<210> SEQ ID NO 340
<211> LENGTH: 10
<212> TYPE: DNA
<213> ORGANISM: Glycine max

<400> SEQUENCE: 340
tcacgaggta                                                          10

<210> SEQ ID NO 341
<211> LENGTH: 10
<212> TYPE: DNA
<213> ORGANISM: Glycine max

<400> SEQUENCE: 341
tcgggggca                                                           10

<210> SEQ ID NO 342
<211> LENGTH: 10
<212> TYPE: DNA
<213> ORGANISM: Glycine max

<400> SEQUENCE: 342
taacgaggta                                                          10

<210> SEQ ID NO 343
<211> LENGTH: 10
<212> TYPE: DNA
<213> ORGANISM: Glycine max

<400> SEQUENCE: 343
caggagatct                                                          10

<210> SEQ ID NO 344
<211> LENGTH: 10
<212> TYPE: DNA
<213> ORGANISM: Glycine max

<400> SEQUENCE: 344
caacgaggta                                                          10

<210> SEQ ID NO 345
<211> LENGTH: 10
<212> TYPE: DNA
<213> ORGANISM: Glycine max

<400> SEQUENCE: 345
tcacaaagta                                                          10
```

```
<210> SEQ ID NO 346
<211> LENGTH: 10
<212> TYPE: DNA
<213> ORGANISM: Glycine max

<400> SEQUENCE: 346
ccacgaggta                                                          10

<210> SEQ ID NO 347
<211> LENGTH: 10
<212> TYPE: DNA
<213> ORGANISM: Glycine max

<400> SEQUENCE: 347
tcgcagggta                                                          10

<210> SEQ ID NO 348
<211> LENGTH: 10
<212> TYPE: DNA
<213> ORGANISM: Glycine max

<400> SEQUENCE: 348
taggagatct                                                          10

<210> SEQ ID NO 349
<211> LENGTH: 10
<212> TYPE: DNA
<213> ORGANISM: Glycine max

<400> SEQUENCE: 349
taagagatct                                                          10

<210> SEQ ID NO 350
<211> LENGTH: 10
<212> TYPE: DNA
<213> ORGANISM: Glycine max

<400> SEQUENCE: 350
tcacaaagtt                                                          10

<210> SEQ ID NO 351
<211> LENGTH: 10
<212> TYPE: DNA
<213> ORGANISM: Glycine max

<400> SEQUENCE: 351
taacaaagtt                                                          10

<210> SEQ ID NO 352
<211> LENGTH: 10
<212> TYPE: DNA
<213> ORGANISM: Glycine max

<400> SEQUENCE: 352
taagagagca                                                          10

<210> SEQ ID NO 353
<211> LENGTH: 10
<212> TYPE: DNA
<213> ORGANISM: Glycine max

<400> SEQUENCE: 353
ccagaaatct                                                          10
```

<210> SEQ ID NO 354
<211> LENGTH: 10
<212> TYPE: DNA
<213> ORGANISM: Glycine max

<400> SEQUENCE: 354
ccggaaatct                                                                10

<210> SEQ ID NO 355
<211> LENGTH: 10
<212> TYPE: DNA
<213> ORGANISM: Glycine max

<400> SEQUENCE: 355
ccacaaggta                                                                10

<210> SEQ ID NO 356
<211> LENGTH: 10
<212> TYPE: DNA
<213> ORGANISM: Glycine max

<400> SEQUENCE: 356
taggagagct                                                                10

<210> SEQ ID NO 357
<211> LENGTH: 10
<212> TYPE: DNA
<213> ORGANISM: Glycine max

<400> SEQUENCE: 357
ccggagatca                                                                10

<210> SEQ ID NO 358
<211> LENGTH: 10
<212> TYPE: DNA
<213> ORGANISM: Glycine max

<400> SEQUENCE: 358
tcggaggtct                                                                10

<210> SEQ ID NO 359
<211> LENGTH: 10
<212> TYPE: DNA
<213> ORGANISM: Glycine max

<400> SEQUENCE: 359
ccaggaggca                                                                10

<210> SEQ ID NO 360
<211> LENGTH: 10
<212> TYPE: DNA
<213> ORGANISM: Glycine max

<400> SEQUENCE: 360
taacaaggta                                                                10

<210> SEQ ID NO 361
<211> LENGTH: 10
<212> TYPE: DNA
<213> ORGANISM: Glycine max

<400> SEQUENCE: 361
tcacggggta                                                          10

<210> SEQ ID NO 362
<211> LENGTH: 10
<212> TYPE: DNA
<213> ORGANISM: Glycine max

<400> SEQUENCE: 362
tcaggaggta                                                          10

<210> SEQ ID NO 363
<211> LENGTH: 10
<212> TYPE: DNA
<213> ORGANISM: Glycine max

<400> SEQUENCE: 363
taatcagcag                                                          10

<210> SEQ ID NO 364
<211> LENGTH: 10
<212> TYPE: DNA
<213> ORGANISM: Glycine max

<400> SEQUENCE: 364
taatcaccag                                                          10

<210> SEQ ID NO 365
<211> LENGTH: 10
<212> TYPE: DNA
<213> ORGANISM: Glycine max

<400> SEQUENCE: 365
tgggtgccag                                                          10

<210> SEQ ID NO 366
<211> LENGTH: 10
<212> TYPE: DNA
<213> ORGANISM: Glycine max

<400> SEQUENCE: 366
taagtggcaa                                                          10

<210> SEQ ID NO 367
<211> LENGTH: 10
<212> TYPE: DNA
<213> ORGANISM: Glycine max

<400> SEQUENCE: 367
taatcaggag                                                          10

<210> SEQ ID NO 368
<211> LENGTH: 10
<212> TYPE: DNA
<213> ORGANISM: Glycine max

<400> SEQUENCE: 368
taatcaggcg                                                          10

<210> SEQ ID NO 369
<211> LENGTH: 10
<212> TYPE: DNA
<213> ORGANISM: Glycine max

<400> SEQUENCE: 369

-continued tgggtgccaa                                                    10

<210> SEQ ID NO 370
<211> LENGTH: 10
<212> TYPE: DNA
<213> ORGANISM: Glycine max

<400> SEQUENCE: 370
tagtcacgcg                                                    10

<210> SEQ ID NO 371
<211> LENGTH: 10
<212> TYPE: DNA
<213> ORGANISM: Glycine max

<400> SEQUENCE: 371
caatcagcag                                                    10

<210> SEQ ID NO 372
<211> LENGTH: 10
<212> TYPE: DNA
<213> ORGANISM: Glycine max

<400> SEQUENCE: 372
caatcaggcg                                                    10

<210> SEQ ID NO 373
<211> LENGTH: 10
<212> TYPE: DNA
<213> ORGANISM: Glycine max

<400> SEQUENCE: 373
caatcagcaa                                                    10

<210> SEQ ID NO 374
<211> LENGTH: 10
<212> TYPE: DNA
<213> ORGANISM: Glycine max

<400> SEQUENCE: 374
tagtcaccag                                                    10

<210> SEQ ID NO 375
<211> LENGTH: 10
<212> TYPE: DNA
<213> ORGANISM: Glycine max

<400> SEQUENCE: 375
caatcaggag                                                    10

<210> SEQ ID NO 376
<211> LENGTH: 10
<212> TYPE: DNA
<213> ORGANISM: Glycine max

<400> SEQUENCE: 376
tgggcgcgcg                                                    10

<210> SEQ ID NO 377
<211> LENGTH: 10
<212> TYPE: DNA
<213> ORGANISM: Glycine max

```
<400> SEQUENCE: 377
cagttgccaa                                                          10

<210> SEQ ID NO 378
<211> LENGTH: 10
<212> TYPE: DNA
<213> ORGANISM: Glycine max

<400> SEQUENCE: 378
tagttgccaa                                                          10

<210> SEQ ID NO 379
<211> LENGTH: 10
<212> TYPE: DNA
<213> ORGANISM: Glycine max

<400> SEQUENCE: 379
tagtcagcag                                                          10

<210> SEQ ID NO 380
<211> LENGTH: 10
<212> TYPE: DNA
<213> ORGANISM: Glycine max

<400> SEQUENCE: 380
caggtgccaa                                                          10

<210> SEQ ID NO 381
<211> LENGTH: 10
<212> TYPE: DNA
<213> ORGANISM: Glycine max

<400> SEQUENCE: 381
tggttggcag                                                          10

<210> SEQ ID NO 382
<211> LENGTH: 10
<212> TYPE: DNA
<213> ORGANISM: Glycine max

<400> SEQUENCE: 382
taatcagccg                                                          10

<210> SEQ ID NO 383
<211> LENGTH: 10
<212> TYPE: DNA
<213> ORGANISM: Glycine max

<400> SEQUENCE: 383
caattggcag                                                          10

<210> SEQ ID NO 384
<211> LENGTH: 10
<212> TYPE: DNA
<213> ORGANISM: Glycine max

<400> SEQUENCE: 384
tggtcaccag                                                          10

<210> SEQ ID NO 385
<211> LENGTH: 10
<212> TYPE: DNA
<213> ORGANISM: Glycine max
```

```
<400> SEQUENCE: 385
taatcagcaa                                                          10

<210> SEQ ID NO 386
<211> LENGTH: 10
<212> TYPE: DNA
<213> ORGANISM: Glycine max

<400> SEQUENCE: 386
caatcacgcg                                                          10

<210> SEQ ID NO 387
<211> LENGTH: 10
<212> TYPE: DNA
<213> ORGANISM: Glycine max

<400> SEQUENCE: 387
tgagcaccaa                                                          10

<210> SEQ ID NO 388
<211> LENGTH: 10
<212> TYPE: DNA
<213> ORGANISM: Glycine max

<400> SEQUENCE: 388
cagttggcaa                                                          10

<210> SEQ ID NO 389
<211> LENGTH: 10
<212> TYPE: DNA
<213> ORGANISM: Glycine max

<400> SEQUENCE: 389
taatcacgag                                                          10

<210> SEQ ID NO 390
<211> LENGTH: 10
<212> TYPE: DNA
<213> ORGANISM: Glycine max

<400> SEQUENCE: 390
cccgtcctag                                                          10

<210> SEQ ID NO 391
<211> LENGTH: 10
<212> TYPE: DNA
<213> ORGANISM: Glycine max

<400> SEQUENCE: 391
cccgtcctaa                                                          10

<210> SEQ ID NO 392
<211> LENGTH: 10
<212> TYPE: DNA
<213> ORGANISM: Glycine max

<400> SEQUENCE: 392
cccgctatga                                                          10

<210> SEQ ID NO 393
<211> LENGTH: 10
<212> TYPE: DNA
```

```
<213> ORGANISM: Glycine max

<400> SEQUENCE: 393
tttgctagga                                                          10

<210> SEQ ID NO 394
<211> LENGTH: 10
<212> TYPE: DNA
<213> ORGANISM: Glycine max

<400> SEQUENCE: 394
cccgctatgg                                                          10

<210> SEQ ID NO 395
<211> LENGTH: 10
<212> TYPE: DNA
<213> ORGANISM: Glycine max

<400> SEQUENCE: 395
cccgctctaa                                                          10

<210> SEQ ID NO 396
<211> LENGTH: 10
<212> TYPE: DNA
<213> ORGANISM: Glycine max

<400> SEQUENCE: 396
cccgtcataa                                                          10

<210> SEQ ID NO 397
<211> LENGTH: 10
<212> TYPE: DNA
<213> ORGANISM: Glycine max

<400> SEQUENCE: 397
cttgctagga                                                          10

<210> SEQ ID NO 398
<211> LENGTH: 10
<212> TYPE: DNA
<213> ORGANISM: Glycine max

<400> SEQUENCE: 398
tccgtcctaa                                                          10

<210> SEQ ID NO 399
<211> LENGTH: 10
<212> TYPE: DNA
<213> ORGANISM: Glycine max

<400> SEQUENCE: 399
cccgccataa                                                          10

<210> SEQ ID NO 400
<211> LENGTH: 10
<212> TYPE: DNA
<213> ORGANISM: Glycine max

<400> SEQUENCE: 400
tctgctagga                                                          10

<210> SEQ ID NO 401
<211> LENGTH: 10
```

```
<212> TYPE: DNA
<213> ORGANISM: Glycine max

<400> SEQUENCE: 401
cccgccagga                                                          10

<210> SEQ ID NO 402
<211> LENGTH: 10
<212> TYPE: DNA
<213> ORGANISM: Glycine max

<400> SEQUENCE: 402
cccgctctga                                                          10

<210> SEQ ID NO 403
<211> LENGTH: 10
<212> TYPE: DNA
<213> ORGANISM: Glycine max

<400> SEQUENCE: 403
ttgcggggtc                                                          10

<210> SEQ ID NO 404
<211> LENGTH: 10
<212> TYPE: DNA
<213> ORGANISM: Glycine max

<400> SEQUENCE: 404
gtacacgctt                                                          10

<210> SEQ ID NO 405
<211> LENGTH: 10
<212> TYPE: DNA
<213> ORGANISM: Glycine max

<400> SEQUENCE: 405
gtgcaggctc                                                          10

<210> SEQ ID NO 406
<211> LENGTH: 10
<212> TYPE: DNA
<213> ORGANISM: Glycine max

<400> SEQUENCE: 406
ttacacgctt                                                          10

<210> SEQ ID NO 407
<211> LENGTH: 10
<212> TYPE: DNA
<213> ORGANISM: Glycine max

<400> SEQUENCE: 407
tcatacccat                                                          10

<210> SEQ ID NO 408
<211> LENGTH: 10
<212> TYPE: DNA
<213> ORGANISM: Glycine max

<400> SEQUENCE: 408
tcatacgctt                                                          10

<210> SEQ ID NO 409
```

```
<211> LENGTH: 10
<212> TYPE: DNA
<213> ORGANISM: Glycine max

<400> SEQUENCE: 409
ttgcacggtc                                                          10

<210> SEQ ID NO 410
<211> LENGTH: 10
<212> TYPE: DNA
<213> ORGANISM: Glycine max

<400> SEQUENCE: 410
gtgcacggtc                                                          10

<210> SEQ ID NO 411
<211> LENGTH: 10
<212> TYPE: DNA
<213> ORGANISM: Glycine max

<400> SEQUENCE: 411
gtatacgctt                                                          10

<210> SEQ ID NO 412
<211> LENGTH: 10
<212> TYPE: DNA
<213> ORGANISM: Glycine max

<400> SEQUENCE: 412
ttatacgctt                                                          10

<210> SEQ ID NO 413
<211> LENGTH: 10
<212> TYPE: DNA
<213> ORGANISM: Glycine max

<400> SEQUENCE: 413
ttgcggcgac                                                          10

<210> SEQ ID NO 414
<211> LENGTH: 10
<212> TYPE: DNA
<213> ORGANISM: Glycine max

<400> SEQUENCE: 414
ttgcagggtc                                                          10

<210> SEQ ID NO 415
<211> LENGTH: 10
<212> TYPE: DNA
<213> ORGANISM: Glycine max

<400> SEQUENCE: 415
gtacacggtc                                                          10

<210> SEQ ID NO 416
<211> LENGTH: 10
<212> TYPE: DNA
<213> ORGANISM: Glycine max

<400> SEQUENCE: 416
ttacacgctc                                                          10
```

```
<210> SEQ ID NO 417
<211> LENGTH: 10
<212> TYPE: DNA
<213> ORGANISM: Glycine max

<400> SEQUENCE: 417
gtacagggtc                                                          10

<210> SEQ ID NO 418
<211> LENGTH: 10
<212> TYPE: DNA
<213> ORGANISM: Glycine max

<400> SEQUENCE: 418
tcatacggtc                                                          10

<210> SEQ ID NO 419
<211> LENGTH: 10
<212> TYPE: DNA
<213> ORGANISM: Glycine max

<400> SEQUENCE: 419
ttacgggctt                                                          10

<210> SEQ ID NO 420
<211> LENGTH: 10
<212> TYPE: DNA
<213> ORGANISM: Glycine max

<400> SEQUENCE: 420
tcacacgctt                                                          10

<210> SEQ ID NO 421
<211> LENGTH: 10
<212> TYPE: DNA
<213> ORGANISM: Glycine max

<400> SEQUENCE: 421
ttgcacccac                                                          10

<210> SEQ ID NO 422
<211> LENGTH: 10
<212> TYPE: DNA
<213> ORGANISM: Glycine max

<400> SEQUENCE: 422
tcatacggtt                                                          10

<210> SEQ ID NO 423
<211> LENGTH: 10
<212> TYPE: DNA
<213> ORGANISM: Glycine max

<400> SEQUENCE: 423
ttacagggtc                                                          10

<210> SEQ ID NO 424
<211> LENGTH: 10
<212> TYPE: DNA
<213> ORGANISM: Glycine max

<400> SEQUENCE: 424
tcataccctt                                                          10
```

```
<210> SEQ ID NO 425
<211> LENGTH: 10
<212> TYPE: DNA
<213> ORGANISM: Glycine max

<400> SEQUENCE: 425
ttagcacagt                                                          10

<210> SEQ ID NO 426
<211> LENGTH: 10
<212> TYPE: DNA
<213> ORGANISM: Glycine max

<400> SEQUENCE: 426
tgagcacagt                                                          10

<210> SEQ ID NO 427
<211> LENGTH: 10
<212> TYPE: DNA
<213> ORGANISM: Glycine max

<400> SEQUENCE: 427
agttaatatc                                                          10

<210> SEQ ID NO 428
<211> LENGTH: 10
<212> TYPE: DNA
<213> ORGANISM: Glycine max

<400> SEQUENCE: 428
agataatatc                                                          10

<210> SEQ ID NO 429
<211> LENGTH: 10
<212> TYPE: DNA
<213> ORGANISM: Glycine max

<400> SEQUENCE: 429
agtgaatatc                                                          10

<210> SEQ ID NO 430
<211> LENGTH: 10
<212> TYPE: DNA
<213> ORGANISM: Glycine max

<400> SEQUENCE: 430
tttgcacagt                                                          10

<210> SEQ ID NO 431
<211> LENGTH: 10
<212> TYPE: DNA
<213> ORGANISM: Glycine max

<400> SEQUENCE: 431
agttaatagt                                                          10

<210> SEQ ID NO 432
<211> LENGTH: 10
<212> TYPE: DNA
<213> ORGANISM: Glycine max

<400> SEQUENCE: 432
tgagcatagt                                                          10
```

<210> SEQ ID NO 433
<211> LENGTH: 10
<212> TYPE: DNA
<213> ORGANISM: Glycine max

<400> SEQUENCE: 433
tgttaatagc                                                            10

<210> SEQ ID NO 434
<211> LENGTH: 10
<212> TYPE: DNA
<213> ORGANISM: Glycine max

<400> SEQUENCE: 434
ttataacatc                                                            10

<210> SEQ ID NO 435
<211> LENGTH: 10
<212> TYPE: DNA
<213> ORGANISM: Glycine max

<400> SEQUENCE: 435
cgctgatgat                                                            10

<210> SEQ ID NO 436
<211> LENGTH: 10
<212> TYPE: DNA
<213> ORGANISM: Glycine max

<400> SEQUENCE: 436
aatggatgat                                                            10

<210> SEQ ID NO 437
<211> LENGTH: 10
<212> TYPE: DNA
<213> ORGANISM: Glycine max

<400> SEQUENCE: 437
cgttgctaag                                                            10

<210> SEQ ID NO 438
<211> LENGTH: 10
<212> TYPE: DNA
<213> ORGANISM: Glycine max

<400> SEQUENCE: 438
aattaccagg                                                            10

<210> SEQ ID NO 439
<211> LENGTH: 10
<212> TYPE: DNA
<213> ORGANISM: Glycine max

<400> SEQUENCE: 439
cgctgatgag                                                            10

<210> SEQ ID NO 440
<211> LENGTH: 10
<212> TYPE: DNA
<213> ORGANISM: Glycine max

<400> SEQUENCE: 440

-continued aatgaccagg 10

<210> SEQ ID NO 441
<211> LENGTH: 10
<212> TYPE: DNA
<213> ORGANISM: Glycine max

<400> SEQUENCE: 441
aatggccggt 10

<210> SEQ ID NO 442
<211> LENGTH: 10
<212> TYPE: DNA
<213> ORGANISM: Glycine max

<400> SEQUENCE: 442
aacgaccagg 10

<210> SEQ ID NO 443
<211> LENGTH: 10
<212> TYPE: DNA
<213> ORGANISM: Glycine max

<400> SEQUENCE: 443
cgcggccggt 10

<210> SEQ ID NO 444
<211> LENGTH: 10
<212> TYPE: DNA
<213> ORGANISM: Glycine max

<400> SEQUENCE: 444
aacggatgat 10

<210> SEQ ID NO 445
<211> LENGTH: 10
<212> TYPE: DNA
<213> ORGANISM: Glycine max

<400> SEQUENCE: 445
aacgaacagg 10

<210> SEQ ID NO 446
<211> LENGTH: 10
<212> TYPE: DNA
<213> ORGANISM: Glycine max

<400> SEQUENCE: 446
acaccggctt 10

<210> SEQ ID NO 447
<211> LENGTH: 10
<212> TYPE: DNA
<213> ORGANISM: Glycine max

<400> SEQUENCE: 447
accttagttt 10

<210> SEQ ID NO 448
<211> LENGTH: 10
<212> TYPE: DNA
<213> ORGANISM: Glycine max

<400> SEQUENCE: 448

-continued cacctagtct        10

<210> SEQ ID NO 449
<211> LENGTH: 10
<212> TYPE: DNA
<213> ORGANISM: Glycine max

<400> SEQUENCE: 449
cccttagtca        10

<210> SEQ ID NO 450
<211> LENGTH: 10
<212> TYPE: DNA
<213> ORGANISM: Glycine max

<400> SEQUENCE: 450
cacttactca        10

<210> SEQ ID NO 451
<211> LENGTH: 10
<212> TYPE: DNA
<213> ORGANISM: Glycine max

<400> SEQUENCE: 451
accttagtca        10

<210> SEQ ID NO 452
<211> LENGTH: 10
<212> TYPE: DNA
<213> ORGANISM: Glycine max

<400> SEQUENCE: 452
caattaccta        10

<210> SEQ ID NO 453
<211> LENGTH: 10
<212> TYPE: DNA
<213> ORGANISM: Glycine max

<400> SEQUENCE: 453
aacttagtca        10

<210> SEQ ID NO 454
<211> LENGTH: 10
<212> TYPE: DNA
<213> ORGANISM: Glycine max

<400> SEQUENCE: 454
acattagcct        10

<210> SEQ ID NO 455
<211> LENGTH: 10
<212> TYPE: DNA
<213> ORGANISM: Glycine max

<400> SEQUENCE: 455
accccggctt        10

<210> SEQ ID NO 456
<211> LENGTH: 10
<212> TYPE: DNA
<213> ORGANISM: Glycine max

```
<400> SEQUENCE: 456
aacttactca                                                          10

<210> SEQ ID NO 457
<211> LENGTH: 10
<212> TYPE: DNA
<213> ORGANISM: Glycine max

<400> SEQUENCE: 457
cacccgccta                                                          10

<210> SEQ ID NO 458
<211> LENGTH: 10
<212> TYPE: DNA
<213> ORGANISM: Glycine max

<400> SEQUENCE: 458
acattagtca                                                          10

<210> SEQ ID NO 459
<211> LENGTH: 10
<212> TYPE: DNA
<213> ORGANISM: Glycine max

<400> SEQUENCE: 459
caattagtta                                                          10

<210> SEQ ID NO 460
<211> LENGTH: 10
<212> TYPE: DNA
<213> ORGANISM: Glycine max

<400> SEQUENCE: 460
acatcagcct                                                          10

<210> SEQ ID NO 461
<211> LENGTH: 10
<212> TYPE: DNA
<213> ORGANISM: Glycine max

<400> SEQUENCE: 461
acatcagctt                                                          10

<210> SEQ ID NO 462
<211> LENGTH: 10
<212> TYPE: DNA
<213> ORGANISM: Glycine max

<400> SEQUENCE: 462
cccccggcta                                                          10

<210> SEQ ID NO 463
<211> LENGTH: 10
<212> TYPE: DNA
<213> ORGANISM: Glycine max

<400> SEQUENCE: 463
aacttagctt                                                          10

<210> SEQ ID NO 464
<211> LENGTH: 10
<212> TYPE: DNA
<213> ORGANISM: Glycine max
```

```
<400> SEQUENCE: 464
cacccgctta                                                              10

<210> SEQ ID NO 465
<211> LENGTH: 10
<212> TYPE: DNA
<213> ORGANISM: Glycine max

<400> SEQUENCE: 465
cacttagtca                                                              10

<210> SEQ ID NO 466
<211> LENGTH: 10
<212> TYPE: DNA
<213> ORGANISM: Glycine max

<400> SEQUENCE: 466
aaaccggtta                                                              10

<210> SEQ ID NO 467
<211> LENGTH: 10
<212> TYPE: DNA
<213> ORGANISM: Glycine max

<400> SEQUENCE: 467
cccccggctt                                                              10

<210> SEQ ID NO 468
<211> LENGTH: 10
<212> TYPE: DNA
<213> ORGANISM: Glycine max

<400> SEQUENCE: 468
caattactca                                                              10

<210> SEQ ID NO 469
<211> LENGTH: 10
<212> TYPE: DNA
<213> ORGANISM: Glycine max

<400> SEQUENCE: 469 aatgatag gg                                                             10

<210> SEQ ID NO 470
<211> LENGTH: 10
<212> TYPE: DNA
<213> ORGANISM: Glycine max

<400> SEQUENCE: 470
agtaataggg                                                              10

<210> SEQ ID NO 471
<211> LENGTH: 10
<212> TYPE: DNA
<213> ORGANISM: Glycine max

<400> SEQUENCE: 471
agtaatgggg                                                              10

<210> SEQ ID NO 472
<211> LENGTH: 10
<212> TYPE: DNA
```

```
<213> ORGANISM: Glycine max

<400> SEQUENCE: 472
agtaataaag                                                          10

<210> SEQ ID NO 473
<211> LENGTH: 10
<212> TYPE: DNA
<213> ORGANISM: Glycine max

<400> SEQUENCE: 473
taagcggaat                                                          10

<210> SEQ ID NO 474
<211> LENGTH: 10
<212> TYPE: DNA
<213> ORGANISM: Glycine max

<400> SEQUENCE: 474
aataataggg                                                          10

<210> SEQ ID NO 475
<211> LENGTH: 10
<212> TYPE: DNA
<213> ORGANISM: Glycine max

<400> SEQUENCE: 475
aaagaggagg                                                          10

<210> SEQ ID NO 476
<211> LENGTH: 10
<212> TYPE: DNA
<213> ORGANISM: Glycine max

<400> SEQUENCE: 476
agtaataagg                                                          10

<210> SEQ ID NO 477
<211> LENGTH: 10
<212> TYPE: DNA
<213> ORGANISM: Glycine max

<400> SEQUENCE: 477
agtaatagat                                                          10

<210> SEQ ID NO 478
<211> LENGTH: 10
<212> TYPE: DNA
<213> ORGANISM: Glycine max

<400> SEQUENCE: 478
taagcggggg                                                          10

<210> SEQ ID NO 479
<211> LENGTH: 10
<212> TYPE: DNA
<213> ORGANISM: Glycine max

<400> SEQUENCE: 479
agtaatagag                                                          10

<210> SEQ ID NO 480
<211> LENGTH: 10
```

```
<212> TYPE: DNA
<213> ORGANISM: Glycine max

<400> SEQUENCE: 480
taagcgaaag                                                              10

<210> SEQ ID NO 481
<211> LENGTH: 10
<212> TYPE: DNA
<213> ORGANISM: Glycine max

<400> SEQUENCE: 481
aaaaataggg                                                              10

<210> SEQ ID NO 482
<211> LENGTH: 10
<212> TYPE: DNA
<213> ORGANISM: Glycine max

<400> SEQUENCE: 482
taagcggggt                                                              10

<210> SEQ ID NO 483
<211> LENGTH: 10
<212> TYPE: DNA
<213> ORGANISM: Glycine max

<400> SEQUENCE: 483
tatgataggg                                                              10

<210> SEQ ID NO 484
<211> LENGTH: 10
<212> TYPE: DNA
<213> ORGANISM: Glycine max

<400> SEQUENCE: 484
agtgataggg                                                              10

<210> SEQ ID NO 485
<211> LENGTH: 10
<212> TYPE: DNA
<213> ORGANISM: Glycine max

<400> SEQUENCE: 485
tgtaataagg                                                              10

<210> SEQ ID NO 486
<211> LENGTH: 10
<212> TYPE: DNA
<213> ORGANISM: Glycine max

<400> SEQUENCE: 486
tgtaataggg                                                              10

<210> SEQ ID NO 487
<211> LENGTH: 10
<212> TYPE: DNA
<213> ORGANISM: Glycine max

<400> SEQUENCE: 487
taaacggagg                                                              10

<210> SEQ ID NO 488
```

-continued

<210> SEQ ID NO 488
<211> LENGTH: 10
<212> TYPE: DNA
<213> ORGANISM: Glycine max

<400> SEQUENCE: 488
taaataaata                                                            10

<210> SEQ ID NO 489
<211> LENGTH: 10
<212> TYPE: DNA
<213> ORGANISM: Glycine max

<400> SEQUENCE: 489
tatataaccg                                                            10

<210> SEQ ID NO 490
<211> LENGTH: 10
<212> TYPE: DNA
<213> ORGANISM: Glycine max

<400> SEQUENCE: 490
tatataaata                                                            10

<210> SEQ ID NO 491
<211> LENGTH: 10
<212> TYPE: DNA
<213> ORGANISM: Glycine max

<400> SEQUENCE: 491
taaacatata                                                            10

<210> SEQ ID NO 492
<211> LENGTH: 10
<212> TYPE: DNA
<213> ORGANISM: Glycine max

<400> SEQUENCE: 492
tatataacta                                                            10

<210> SEQ ID NO 493
<211> LENGTH: 10
<212> TYPE: DNA
<213> ORGANISM: Glycine max

<400> SEQUENCE: 493
tatataactg                                                            10

<210> SEQ ID NO 494
<211> LENGTH: 10
<212> TYPE: DNA
<213> ORGANISM: Glycine max

<400> SEQUENCE: 494
tatacatata                                                            10

<210> SEQ ID NO 495
<211> LENGTH: 10
<212> TYPE: DNA
<213> ORGANISM: Glycine max

<400> SEQUENCE: 495
atatcgtata                                                            10

```
<210> SEQ ID NO 496
<211> LENGTH: 10
<212> TYPE: DNA
<213> ORGANISM: Glycine max

<400> SEQUENCE: 496
tttataaccg                                                            10

<210> SEQ ID NO 497
<211> LENGTH: 10
<212> TYPE: DNA
<213> ORGANISM: Glycine max

<400> SEQUENCE: 497
atatcgtacg                                                            10

<210> SEQ ID NO 498
<211> LENGTH: 10
<212> TYPE: DNA
<213> ORGANISM: Glycine max

<400> SEQUENCE: 498
taaatatata                                                            10

<210> SEQ ID NO 499
<211> LENGTH: 10
<212> TYPE: DNA
<213> ORGANISM: Glycine max

<400> SEQUENCE: 499
tatataaacg                                                            10

<210> SEQ ID NO 500
<211> LENGTH: 10
<212> TYPE: DNA
<213> ORGANISM: Glycine max

<400> SEQUENCE: 500
ttatcgtata                                                            10

<210> SEQ ID NO 501
<211> LENGTH: 10
<212> TYPE: DNA
<213> ORGANISM: Glycine max

<400> SEQUENCE: 501
attttaaacg                                                            10

<210> SEQ ID NO 502
<211> LENGTH: 10
<212> TYPE: DNA
<213> ORGANISM: Glycine max

<400> SEQUENCE: 502
tatataacca                                                            10

<210> SEQ ID NO 503
<211> LENGTH: 10
<212> TYPE: DNA
<213> ORGANISM: Glycine max

<400> SEQUENCE: 503
taaataaccg                                                            10
```

```
<210> SEQ ID NO 504
<211> LENGTH: 10
<212> TYPE: DNA
<213> ORGANISM: Glycine max

<400> SEQUENCE: 504
tttttaaccg                                                          10

<210> SEQ ID NO 505
<211> LENGTH: 10
<212> TYPE: DNA
<213> ORGANISM: Glycine max

<400> SEQUENCE: 505
acatgaactc                                                          10

<210> SEQ ID NO 506
<211> LENGTH: 10
<212> TYPE: DNA
<213> ORGANISM: Glycine max

<400> SEQUENCE: 506
acacgaaccc                                                          10

<210> SEQ ID NO 507
<211> LENGTH: 10
<212> TYPE: DNA
<213> ORGANISM: Glycine max

<400> SEQUENCE: 507
actcggaccc                                                          10

<210> SEQ ID NO 508
<211> LENGTH: 10
<212> TYPE: DNA
<213> ORGANISM: Glycine max

<400> SEQUENCE: 508
taacgaaccc                                                          10

<210> SEQ ID NO 509
<211> LENGTH: 10
<212> TYPE: DNA
<213> ORGANISM: Glycine max

<400> SEQUENCE: 509
acatgaaccc                                                          10

<210> SEQ ID NO 510
<211> LENGTH: 10
<212> TYPE: DNA
<213> ORGANISM: Glycine max

<400> SEQUENCE: 510
tcacgaaccc                                                          10

<210> SEQ ID NO 511
<211> LENGTH: 10
<212> TYPE: DNA
<213> ORGANISM: Glycine max

<400> SEQUENCE: 511
acacgaactc                                                          10
```

<210> SEQ ID NO 512
<211> LENGTH: 114
<212> TYPE: DNA
<213> ORGANISM: Zea mays

<400> SEQUENCE: 512
ggggttaacc ccggccttcc ccaaccttcc ccttcccctt ttaaggaagg ccaaggggaa    60
ttaaaacccc ctggccttt aaggaaggcc aagggaatt aaaacccct ggcc            114

<210> SEQ ID NO 513
<211> LENGTH: 114
<212> TYPE: DNA
<213> ORGANISM: Zea mays

<400> SEQUENCE: 513
ggggttaacc ccggccttcc ccaaccttcc ccttcccctt ttaaggaagg ccaaggggaa    60
ttaaaacccc ctggccttt aaggaaggcc aagggaatt aaaacccct ggcc            114

<210> SEQ ID NO 514
<211> LENGTH: 122
<212> TYPE: DNA
<213> ORGANISM: Zea mays

<400> SEQUENCE: 514
aaaaccgggg aaccccggaa ccaattccaa ttaaccttt ccttaaccaa ggggaaggaa    60 ttaagggggcc ccttttttcc ttccttaacc aaggggaagg aattaagggg cccctttttt   120
cc                                                                  122

<210> SEQ ID NO 515
<211> LENGTH: 118
<212> TYPE: DNA
<213> ORGANISM: Zea mays

<400> SEQUENCE: 515
aaaaccgggg aaccccggaa ccaattctaa ttaaccttt ccttaaccga ggggaaggaa    60
ttaacgcccc ttttttcctt ccttaaccga ggggaaggaa ttaacgcccc ttttttcc     118

<210> SEQ ID NO 516
<211> LENGTH: 122
<212> TYPE: DNA
<213> ORGANISM: Zea mays

<400> SEQUENCE: 516
ggggttaacc ccggttttcc ttttccttcc ccttggcccc ttaaggaagg ccaaggaagg    60
ccggaaccaa ttccgggggtt ccttaaggaa ggccaaggaa ggccggaacc aattccgggg   120
tt                                                                  122

<210> SEQ ID NO 517
<211> LENGTH: 122
<212> TYPE: DNA
<213> ORGANISM: Zea mays

<400> SEQUENCE: 517
ggggttaacc ccggttttcc ttttccttcc ccttggcccc ttaaggaagg ccaaggaagg    60
ccggaaccaa ttccgggggtt ccttaaggaa ggccaaggaa ggccggaacc aattccgggg   120
tt                                                                  122

<210> SEQ ID NO 518
<211> LENGTH: 431
<212> TYPE: DNA
<213> ORGANISM: Glycine max

<400> SEQUENCE: 518

| | | | | | |
|---|---|---|---|---|---|
| ctttccttgc | tggtttggct | gcatcaggtg | tactaacgtc | tgctttgagg | ttaattacaa | 60 |
| aagcagcatt | tgagaaaact | aagaacggtc | ttcgcaaagg | agccagtaag | ttcagctctc | 120 |
| cagagcttaa | gacatttgat | aattcagagt | ttagccgcat | tcatgtttaa | catagaaaat | 180 |
| tgaaaaaaaa | aatatttagc | ttatgcaatt | gtttaactag | cctttatttc | tattttttca | 240 |
| atgtgtcaga | aacaagtttt | caaattgatt | tttaactctt | ttcatacaac | tcatgaagat | 300 |
| atgaggttta | ttgaagattg | tggaattaat | atgctttaa | taagatattg | acactagcta | 360 |
| cagaccctat | gtgaggtgag | aatcctgtgg | tttatgttgt | agacttcacc | tagtagaata | 420 |
| agactttgtt | a | | | | | 431 |

<210> SEQ ID NO 519
<211> LENGTH: 978
<212> TYPE: DNA
<213> ORGANISM: Glycine max

<400> SEQUENCE: 519

| | | | | | |
|---|---|---|---|---|---|
| atgcatctct | gcctctgaat | atatataaat | atattttcac | tgctatgccg | aaaaaccttt | 60 |
| gatcccacca | gccaccactc | tctctctccg | atggccactg | ttacttcttc | tttctctttc | 120 |
| tccactctca | ctcaatcttc | ttcgccgagg | aacctctcca | cactctcttc | caattcacca | 180 |
| actttcgca | tccgcgttgg | tttctcctgt | cactatgttg | gagttcgagc | ttccaattcc | 240 |
| gcttccaaaa | tagtcgttcg | atgctcctct | gccgtcgcag | gtttgtttgg | ttccccactg | 300 |
| agtgtggggg | acaaaagggt | acaactttat | aagtgttttt | agctcttttc | aactttctga | 360 |
| gaaatgggta | gttttcaatt | tttgtttttt | ttttaaggtt | tggagtttaa | aaaattgata | 420 |
| ttttgattgt | ggatgtatgg | ctgtcaaatt | tttatgtctg | tttttgaaat | ttggtgttgc | 480 |
| aacttgattt | ttgagtgaga | atttgtttta | tggggataat | gtttcaattg | gaagtgtggt | 540 |
| tgatgaggtt | tgatttgaac | cttgttttac | agtttctttt | gtaatcaatt | gatgtagttg | 600 |
| cttgtggctc | tatgtacaat | tgacttgaaa | attctcttga | tcgatgctac | cttgttctgt | 660 |
| tagtgatgaa | attttgtgtg | aatgtggaac | tgaacttgtt | ttgccgctct | ttcttgcaaa | 720 |
| attgaatgta | gtttaaattt | taatattatc | atcatgtgat | ttggtttta | atttgaagat | 780 |
| actgttagaa | ttacatgttg | agggcttaat | tctgttagtg | agcatgtgat | gtagtgtgtg | 840 |
| tgtcaaatgg | tgtgaattgt | tccaaattgg | gttcctttta | ttgttgtaag | attcatagtg | 900 |
| ccaaatgggc | aaaagaaata | aaagatgaaa | tggaatcttg | ttatcaaaag | ttggttatgg | 960 |
| gttgtctaca | tacttgat | | | | | 978 |